(12) United States Patent
Pugh et al.

(10) Patent No.: US 11,149,312 B2
(45) Date of Patent: Oct. 19, 2021

(54) HYBRID-CAPTURE SEQUENCING FOR DETERMINING IMMUNE CELL CLONALITY

(71) Applicant: UNIVERSITY HEALTH NETWORK, Toronto (CA)

(72) Inventors: Trevor John Pugh, Toronto (CA); David Thomas Mulder, Hamilton (CA); Etienne Raymond G. A. Mahe, Calgary (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 65 days.

(21) Appl. No.: 16/093,825

(22) PCT Filed: Apr. 13, 2017

(86) PCT No.: PCT/CA2017/000084
§ 371 (c)(1),
(2) Date: Oct. 15, 2018

(87) PCT Pub. No.: WO2017/177308
PCT Pub. Date: Oct. 19, 2017

(65) Prior Publication Data
US 2019/0390273 A1    Dec. 26, 2019

Related U.S. Application Data

(60) Provisional application No. 62/322,999, filed on Apr. 15, 2016.

(51) Int. Cl.
*C12Q 1/6881* (2018.01)
*C12Q 1/6837* (2018.01)
(Continued)

(52) U.S. Cl.
CPC ......... *C12Q 1/6881* (2013.01); *C12Q 1/6837* (2013.01); *C12Q 1/6855* (2013.01);
(Continued)

(58) Field of Classification Search
CPC .. C12Q 1/6837; C12Q 1/6855; C12Q 1/6869; C12Q 2525/191; C40B 40/06
See application file for complete search history.

(56) References Cited

U.S. PATENT DOCUMENTS 2,392,551 A    1/1946 Roe
6,189,282 B1    2/2001 VanderWerf
(Continued)

FOREIGN PATENT DOCUMENTS

| WO | WO-2016090273 A1 * | 6/2016 | ......... C12N 15/1065 |
| WO | WO 2017/013436 | 1/2017 | |
| WO | WO 2017/177308 | 10/2017 | |

OTHER PUBLICATIONS

Linnemann et al. Nature Medicine. 2013. 19(11):1534-1541 and Supplementary Information. (Year: 2013).*
(Continued)

*Primary Examiner* — Joseph G. Dauner
(74) *Attorney, Agent, or Firm* — Norton Rose Fulbright US LLP

(57) ABSTRACT

A method of capturing a population of T-Cell receptor and/or immunoglobulin sequences with variable regions within a patient sample, the method comprising: extracting and/or preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene
(Continued)

segment within the T cell receptor and/or immunoglobulin genomic loci.

**24 Claims, 21 Drawing Sheets
(16 of 21 Drawing Sheet(s) Filed in Color)
Specification includes a Sequence Listing.**

(51) Int. Cl.
*C12Q 1/6855* (2018.01)
*C12Q 1/6869* (2018.01)
*C40B 40/06* (2006.01)
*C40B 30/04* (2006.01)

(52) U.S. Cl.
CPC .......... *C12Q 1/6869* (2013.01); *C40B 30/04* (2013.01); *C40B 40/06* (2013.01); *C12Q 2525/191* (2013.01); *C12Q 2535/122* (2013.01); *C12Q 2565/514* (2013.01)

(56) References Cited

U.S. PATENT DOCUMENTS

| | | |
|---|---|---|
| 9,453,341 B1 | 9/2016 | Swierad et al. |
| 2007/0292216 A1 | 12/2007 | Hamel |
| 2008/0125333 A1 | 5/2008 | Labgold et al. |
| 2010/0018146 A1 | 1/2010 | Aube et al. |
| 2010/0029498 A1* | 2/2010 | Gnirke .............. C12Q 1/6869 506/9 |
| 2011/0072753 A1 | 3/2011 | MacDonald |
| 2014/0331343 A1 | 11/2014 | Bradley et al. |
| 2015/0218620 A1 | 8/2015 | Behlke et al. |

OTHER PUBLICATIONS

Bashford-Roger et al. BMC Immunology. 2014. 15:29. (Year: 2014).*
Halper-Stromberg et al. BMC Genomics. 2013. 14:565. (Year: 2013).*
Logan et al. PNAS. 2011. 108(52):21194-21199. (Year: 2011).*
Mahe. "Design & Validation of a Hybrid-Capture Next-Generation Sequencing-Based T-cell Clonality Assay". Thesis. 2016. (Year: 2016).*
Parkinson et al. Genome Res. 2015. 25:226-234. (Year: 2015).*
Fisher et al. Clin Cancer Res. 2014. 20(22):5720-5732. (Year: 2014).*
Jiang et al. Genome Biology. 2014. 15:432. (Year: 2014).*
Mamedov et al. EMBO Mol Med. 2011. 3:201-207. (Year: 2011).*
Rosati et al. BMC Biotechnology. 2017. 17:61. (Year: 2017).*
Lin et al. PNAS. 2016. 113(28):7846-7851. (Year: 2016).*
Mulder et al. Blood Advances. 2018. 2(23):3506-3514. (Year: 2018).*
Matsuda et al. J Exp Med. 1998. 188(11):2151-2162 (Year: 1998).*
Jiang et al. Journal of Visualized Experiments. 2015. 106:e53215, 10 pages. (Year: 2015).*
Woodsworth et al. Genome Medicine. 2013. 5:98. (Year: 2013).*
Bolotin et al. Eur J Immunol. 2012. 42:3073-3083. (Year: 2012).*
Mamedov et al. EMBO Molecular Medicine. 2011. 3:201-207. (Year: 2011).*
Bleakley et al. BMC Bioinformatics. 2008. 9:408, 7 pages. (Year: 2008).*
Monod et al. Bioinformatics. 2004. 20(Suppl. 1):i379. (Year: 2004).*
Mamedov et al. Frontiers in Immunology. 2013. 4:456. (Year: 2013).*
Brochet et al., "IMGT/V-QUEST: the Highly customized and integrated system for IG and TR standardized V-J and V-D-J sequence analysis" *Nucleic Acids Res.*, 2008, 36:W503-508.
Camacho et al., "BLAST+: architecture and applications" *BMC Bioinformatics*, 2009, 10:421.
Extended European Search Report issued in corresponding application No. 17781661.8, dated Nov. 18, 2019.
Gazzola et al., "The evolution of clonality testing in the diagnosis and monitoring of hematological malignancies" *Ther Adv Hematol.*, 2014, 5(2):35-47.
Herman et al., "Filter-based hybridization capture of subgenomes enables resequencing and copy-number detection" *Nature Methods* 2009, 6(7), 7 pages.
Li, HD "Fast and accurate short read alignement with Burrows-Wheeler Transform" *Bioinformatics*, 2009, 25:1754-1760.
Liu et al. "Systematic Comparative Evaluation of Methods for Investigating the TCRβ Repertoire" *PLOS One* 2016, 18 pages.
Mamanova et al. "Target-enrichment strategies for next-generation sequencing" *Nat. Methods*, 2010, 7(2):111-118.
Ruggiero et al., "High-resolution analysis of the human T-cell receptor repertoire" *Nature Communications* 2015, 1-7.
Smith et al., "Identification of common molecular subsequences" *J. Mol. Biol.*, 1981, 147(1):195-197.
Gao & Wang, "Ligation-Anchored PCR Unveils Immune Repertoire of TCR-Beta From Whole Blood," *BMC Technology*, 15: 15-39, 2015.
He, et al., "IgH Gene Rearrangements as Plasma Biomarkers in Non-Hodgkins Lymphoma Patients," *Oncotarget*, 2(3): 178-185, 2011.
International Search Report and Written Opinion Issued in Corresponding Application No. PCT/CA2018/000104, dated Sep. 4, 2018.
Partial Supplementary European Search Report Issued in Corresponding EP Patent Application No. 18810749.4, dated Jan. 12, 2021.
Yaari & Kleinstein, "Practical Guidelines for B-Cell Receptor Repertoire Sequencing Analysis," *Genome Medicine*, 7: 121, 2015.

* cited by examiner

FIG. 3D Capture A037 PBMC Beta
FIG. 3E ImmunoSeq A037 PBMC Beta
FIG. 3F Capture-ImmunoSeq Subtractive Comparison
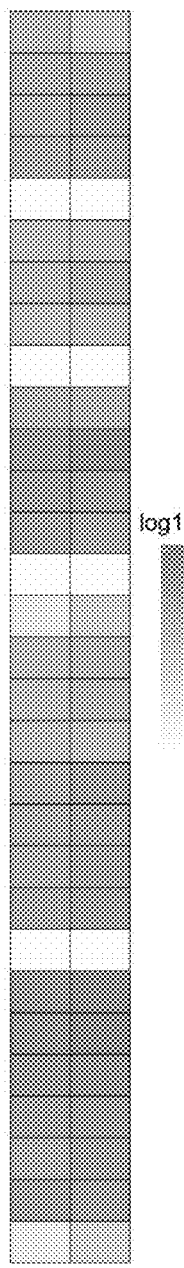
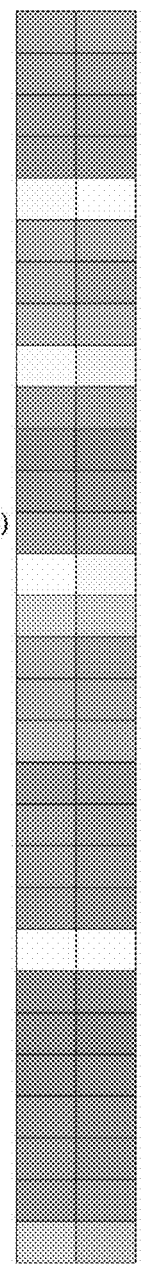
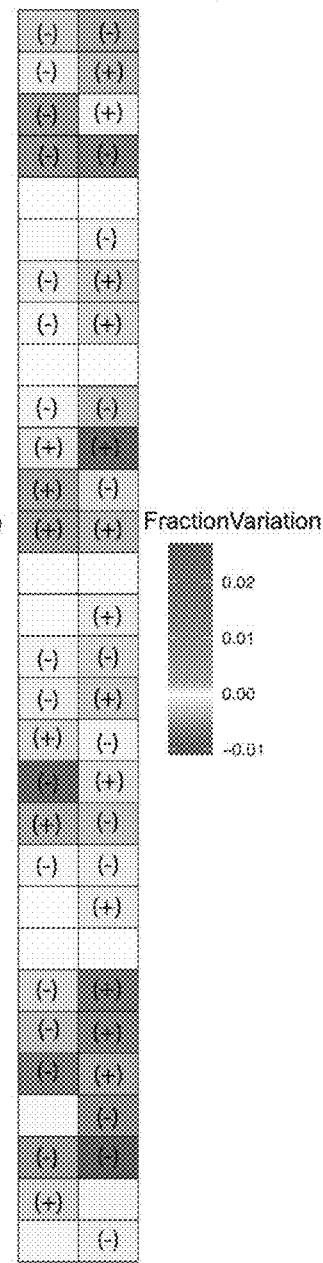

SEQUENCE LISTING

<160> NUMBER OF SEQ ID NOS: 1407

<210> SEQ ID NO 1
<211> LENGTH: 120
<212> TYPE: DNA
<213> ORGANISM: Homo sapiens

<400> SEQUENCE: 1
cccagtgcga caagtcataa catcaaccgc taggatagca gatgagtgag gccgggttgc    60
cctagatgct cctcctggtg cctcaatctg ctgagttgtt ttccagatgc agccaagttt   120

<210> SEQ ID NO 2
<211> LENGTH: 120
<212> TYPE: DNA
<213> ORGANISM: Homo sapiens

<400> SEQUENCE: 2
cctagagtgt tacaggtcat aaaataaacc cccagggaag cagaagtatg actcatggct    60
gccccaggtg cttccactgg tgcctccatc tgctgagagt gtttctcagg tgcagccaag   120

<210> SEQ ID NO 3
<211> LENGTH: 120
<212> TYPE: DNA
<213> ORGANISM: Homo sapiens

<400> SEQUENCE: 3
cactgtgata caagcccgaa cataaaccat ggagggaagt agatgtgtga ggctgggctg    60
ccccagctgc tcctcctggt gccgccctct gctgacagca gttctcagat gcagccaagg   120

<210> SEQ ID NO 4
<211> LENGTH: 120
<212> TYPE: DNA
<213> ORGANISM: Homo sapiens

<400> SEQUENCE: 4
cacagtgtta caaggcataa cataaacccc ccaaggaagc agatgtatgg ggctggcctg    60
ccccagatac tcctcctact gcctccagct gctcagagcg tttctcatat tccagtcaag   120

<210> SEQ ID NO 5
<211> LENGTH: 120
<212> TYPE: DNA
<213> ORGANISM: Homo sapiens

<400> SEQUENCE: 5
cacagtgtta caagtcataa cataaacctc caaggaagca gatgtgtgag gacgagccac    60
cccagatgct cctcctggtg cctccatctg ctgagagcat ttctcaaact cagtcaggtt   120

<210> SEQ ID NO 6
<211> LENGTH: 120
<212> TYPE: DNA
<213> ORGANISM: Homo sapiens

<400> SEQUENCE: 6
cacagtgtta caaaccataa caaccccccc ccaggaaagc agacatgtga cgctgggctg    60
ccccacctgc tcttctttgt gcagccatct ggtgacaaca cttctcagac tcagcctgag   120

<210> SEQ ID NO 7
<211> LENGTH: 120
<212> TYPE: DNA
<213> ORGANISM: Homo sapiens

```
<400> SEQUENCE: 7
cacagtgtta caaacccaat aagctcccca aggaagcaga tatgtgaggg tgggctgccc      60
cagctgcttc tcctgtttcc tccatctgct gagagtgttt ctcagactca gccacactct     120

<210> SEQ ID NO 8
<211> LENGTH: 120
<212> TYPE: DNA
<213> ORGANISM: Homo sapiens

<400> SEQUENCE: 8
caccatgtgg aaacccacat cctgagagtg tcagaaatcc tgatgtggga ggcagctgtg      60
ctgagctgag gcagtgatgc agcagtttcc ttaacttcca tcttatctca ttttgcatcg     120

<210> SEQ ID NO 9
<211> LENGTH: 120
<212> TYPE: DNA
<213> ORGANISM: Homo sapiens

<400> SEQUENCE: 9
cacagtgtga aacccacat cctgagagag tcagaaatcc tgagggaggt ggcagcagtg      60
ctaggcttga gagatgacag ggattttatt tgctttaaag ctttttttta gaaagcgagg     120

<210> SEQ ID NO 10
<211> LENGTH: 120
<212> TYPE: DNA
<213> ORGANISM: Homo sapiens

<400> SEQUENCE: 10
gacacagtgt gaaaacccac atcctgagag tgtcagaaac cctgagggag aaggcagctg      60
tgccgggctg aggagatgac agggtttatt aggtttaagg ctgtttacaa aatgggttat     120

<210> SEQ ID NO 11
<211> LENGTH: 120
<212> TYPE: DNA
<213> ORGANISM: Homo sapiens

<400> SEQUENCE: 11
cacagtgtga aaactcatat cctgagagtg tcagtaaccc tgagggagga agcagctgtc      60
ccagttttca ggatatgaca ggatttatgg ggtttaatgt tgtttagaaa ataggttata     120

<210> SEQ ID NO 12
<211> LENGTH: 120
<212> TYPE: DNA
<213> ORGANISM: Homo sapiens

<400> SEQUENCE: 12
cacaatgtga aacccacat cttgagagtt tcagaaactg cagggaggag gcagctgtgt      60
tcctgcagag gagatgacag ggaagatgag gtttaaagtt gtttagaaaa tgggtcaagt     120

<210> SEQ ID NO 13
<211> LENGTH: 120
<212> TYPE: DNA
<213> ORGANISM: Homo sapiens

<400> SEQUENCE: 13
gacacagagt gaaacccac atcctgagag tgtcagaaac cccaaggagg agcagctgta      60
ctggagctga ggaaatggac aaagattatt cagattgaag actttctacg aaaatgactt     120
```

```
<210> SEQ ID NO 14
<211> LENGTH: 120
<212> TYPE: DNA
<213> ORGANISM: Homo sapiens

<400> SEQUENCE: 14
cacagtgtga aacccacat cctgagagtg tcagaaaccc caggggggaa gcagctgtgc      60
tggcatggag gaaatgacaa agattattag attgaagact ttctcagaaa atgatattaa    120

<210> SEQ ID NO 15
<211> LENGTH: 111
<212> TYPE: DNA
<213> ORGANISM: Homo sapiens

<400> SEQUENCE: 15
gacacagtgc gaaaacccac atcctgagag tgtcagaaac cccaggaagg aggcacctgt     60
gctgacacag agggagatga caaagattat tagattaacg atttctctag a             111

<210> SEQ ID NO 16
<211> LENGTH: 120
<212> TYPE: DNA
<213> ORGANISM: Homo sapiens

<400> SEQUENCE: 16
cacagtgcga aacccacat cctgagagtg tcagaaaccc caggaaggag gcacctgtgc      60
tgacacagag gagatgacaa agattattag attaaagatt ttcttagaaa atgacactaa    120

<210> SEQ ID NO 17
<211> LENGTH: 120
<212> TYPE: DNA
<213> ORGANISM: Homo sapiens

<400> SEQUENCE: 17
cacagtgtga aacccacat cctgagagtg tcagaaagcc tgaggaagga ggcagctgtg      60
ctggggctga ggagatgaca gggattactt gattgaagac tttcttagaa aacgaggtta    120

<210> SEQ ID NO 18
<211> LENGTH: 120
<212> TYPE: DNA
<213> ORGANISM: Homo sapiens

<400> SEQUENCE: 18
cacagtgaga gaaaccagcc ccgagcccgt ctaaaaccct ccacaccgca ggtgcagaat     60
gagctgctag agactcactc cccaggggcc tctctattca tctggggagg aaacactggc    120

<210> SEQ ID NO 19
<211> LENGTH: 120
<212> TYPE: DNA
<213> ORGANISM: Homo sapiens

<400> SEQUENCE: 19
gaccatctaa aaccttccgc ggtgcaggtg cagagtgagc tgccagacac accctccccca    60 ggggcctctc tattcatccg gggaggaaac actggctgtt tgtgtcctca ggagcaaaaa    120

<210> SEQ ID NO 20
<211> LENGTH: 120
<212> TYPE: DNA
<213> ORGANISM: Homo sapiens

<400> SEQUENCE: 20
```

```
gcgaataatg gagaacttga gatatggagt gtgagtggat atgagtgaaa aaacagtgat      60
tctgtgtggc aggttctgac tcagatgtct ctgtgcttgt aggtgtctag tgtggggtgc     120

<210> SEQ ID NO 21
<211> LENGTH: 120
<212> TYPE: DNA
<213> ORGANISM: Homo sapiens

<400> SEQUENCE: 21
cacaggagat atccgtgtgg caacctaaca caggggacac ctgtatttgt gtctgagccc      60
agacacaaac ctccctgcag ggagacagga ggggaccgtg tgacagacac tgctcagaac     120

<210> SEQ ID NO 22
<211> LENGTH: 120
<212> TYPE: DNA
<213> ORGANISM: Homo sapiens

<400> SEQUENCE: 22
ccaagtgaga gctgaggaca tggctgtgca tggctgtaca taaggtccca agtgagcaaa      60
catcggtgtg agtccagaca caacacttcc tgcaaaaaca agaaaggagt ctgggccgaa     120

<210> SEQ ID NO 23
<211> LENGTH: 120
<212> TYPE: DNA
<213> ORGANISM: Homo sapiens

<400> SEQUENCE: 23
acaagagtca gaaaagtgtg caggaggccg ggtgaggctg tagacactgt cagcccacta      60
tgccaatccc accacgagtg ctggagaagg tgggagtctg atgaagctta ctaacaaacc     120

<210> SEQ ID NO 24
<211> LENGTH: 120
<212> TYPE: DNA
<213> ORGANISM: Homo sapiens

<400> SEQUENCE: 24
gccgagattg cgccactgca ctcagcctgg gcgacagagc gagacttcgt ctcaaaaaaa      60
caaaaaaaaa aatcaatcat tggaatactg ttgttcatta caattaatga acgtttgata     120

<210> SEQ ID NO 25
<211> LENGTH: 120
<212> TYPE: DNA
<213> ORGANISM: Homo sapiens

<400> SEQUENCE: 25
cacaggtggg gaagtgggac aaaatctcag cctgctcaga gtcttgttct ctgatgaaat      60
ttagatctta aaataactta tatcacttgt gtgggatgag tgagatatcc cgagctcaca     120

<210> SEQ ID NO 26
<211> LENGTH: 103
<212> TYPE: DNA
<213> ORGANISM: Homo sapiens

<400> SEQUENCE: 26
cacagcgagg ggaagccatt gtgcgctcag aacactctac aaatttttcct ccctagtgtt     60 ttaccaaaac tggtatatat ttcagatact gaaatattta caa                       103

<210> SEQ ID NO 27
```

```
<211> LENGTH: 120
<212> TYPE: DNA
<213> ORGANISM: Homo sapiens

<400> SEQUENCE: 27
agtaagacca aaaccctcct gagattcctg gcttgtgtcc tgacactggg gctgttggga      60
ttcctgtctt tccttcaaga ttgttcaaat aagcaccgac aatcacttcc atgtgagata    120

<210> SEQ ID NO 28
<211> LENGTH: 120
<212> TYPE: DNA
<213> ORGANISM: Homo sapiens

<400> SEQUENCE: 28
aaggcaaagt gaccccagtg aatgaggaag caggacaaaa actgtttttct ctgctccact    60 atgaaggctg ccacgtggcc ctgagaaaca gtgcctgttt tccttactac tcaagaaga    120

<210> SEQ ID NO 29
<211> LENGTH: 120
<212> TYPE: DNA
<213> ORGANISM: Homo sapiens

<400> SEQUENCE: 29
ccgtttgggt aaagcacaga taaatgggga aatgaggcaa aaactgtttt tctactctgc     60
taccaaggtt gaaaaatggc tctcagaacc agtgtctgct gacctgcata ctcaaatatg    120

<210> SEQ ID NO 30
<211> LENGTH: 120
<212> TYPE: DNA
<213> ORGANISM: Homo sapiens

<400> SEQUENCE: 30
taaaataaaa taaatgtaa aaaatgatca ataaatgaaa ttactatcag ttgaaactca      60
ttaaatttaa agacattttc tactcaagta actataagaa catgaatgtc aagtttcaga    120

<210> SEQ ID NO 31
<211> LENGTH: 120
<212> TYPE: DNA
<213> ORGANISM: Homo sapiens

<400> SEQUENCE: 31
cacaggcaga tgagaaagtg agacgaaact cagcctacta agaatggaac tatggctctt     60
tttccaattg tcaaataatt ttcacataca caaactattt tggaagtagc tactgattca    120

<210> SEQ ID NO 32
<211> LENGTH: 120
<212> TYPE: DNA
<213> ORGANISM: Homo sapiens

<400> SEQUENCE: 32
cacagtgaca gacccatgag aggaaccaag acataaacct ccctcggccc ttgtgatgtg     60
gagatcacat gatcagacat gccagatccc aagatagcct acatgtggac cagccataga   120

<210> SEQ ID NO 33
<211> LENGTH: 120
<212> TYPE: DNA
<213> ORGANISM: Homo sapiens

<400> SEQUENCE: 33
cacagtgatt taaacctatg aggaagtgca actaaaacct ctttatatac tgagaacagt     60
``` tcagcccta cagacaggag ggaaagtgag agggtggaaa tggtcaacac ggtgagtgag 120

<210> SEQ ID NO 34
<211> LENGTH: 120
<212> TYPE: DNA
<213> ORGANISM: Homo sapiens

<400> SEQUENCE: 34
tttaaaccca tgaggaggtg caactaaaac ctctttacat actcagaaag attcagccct 60
tagaagcaag agagaagttg agagggtggg aatgtcaaca ccatgagctg ggaacctcct 120

<210> SEQ ID NO 35
<211> LENGTH: 120
<212> TYPE: DNA
<213> ORGANISM: Homo sapiens

<400> SEQUENCE: 35
ttctctgatt atctggatgc tctgtgactc cttctgtgca tctctgggat catcattcag 60
actcacctgc accctgagca gtaacatcaa tgttgtttgc tatgacattt actggaaaca 120

<210> SEQ ID NO 36
<211> LENGTH: 120
<212> TYPE: DNA
<213> ORGANISM: Homo sapiens

<400> SEQUENCE: 36
cacagtgatt ccacaggaaa ccaaacctcc acaagacagc tggtgttttt tcctcaagcc 60
ttctgtttac ttatgggaag ctactatggt ggctgcttag ttattgagag aaaacaatgg 120

<210> SEQ ID NO 37
<211> LENGTH: 120
<212> TYPE: DNA
<213> ORGANISM: Homo sapiens

<400> SEQUENCE: 37
cacagtaatt caacatgaaa caaaaacttt cacaaaacca ttgatttttt ttttctaaaa 60
ccagcagctt tatgggctgc agctatgatg gctgctcagt tttagcaact gtgcctctat 120

<210> SEQ ID NO 38
<211> LENGTH: 120
<212> TYPE: DNA
<213> ORGANISM: Homo sapiens

<400> SEQUENCE: 38
catactgatt caacatgcaa caaaaacctc caggagacct aaggtgttta tttgattata 60
ccacctgctt ccttttttagt catctgatgt ggtgctgctc agttttagca tctctgcttt 120

<210> SEQ ID NO 39
<211> LENGTH: 120
<212> TYPE: DNA
<213> ORGANISM: Homo sapiens

<400> SEQUENCE: 39
cacagtgatt ccacatgaaa caaaaacccc aacaagacca tcagtgttta ctagattatt 60
ataccagctg cttcctttac agacagctag tggggtggcc actcagtgtt agcatctcag 120

<210> SEQ ID NO 40
<211> LENGTH: 120
<212> TYPE: DNA

<213> ORGANISM: Homo sapiens

<400> SEQUENCE: 40

```
cacagagaca cagcccaggg cgcttcctgt acaagaaccc aggtgttttt cagtggtgct    60
ccctccccac ttctgcagaa caggatagtg tggctgagat gccatttcct gcccagggcg   120
```

<210> SEQ ID NO 41
<211> LENGTH: 120
<212> TYPE: DNA
<213> ORGANISM: Homo sapiens

<400> SEQUENCE: 41

```
cacagagaca cagcccaggg cgcctcctgt acaagaaccc aggctgcttc tcagtggtgc    60
tccctcccca cctctgcaga acaggatagt gtggctgaga tgccatttcc tgccagggcc   120
```

<210> SEQ ID NO 42
<211> LENGTH: 120
<212> TYPE: DNA
<213> ORGANISM: Homo sapiens

<400> SEQUENCE: 42

```
agtaagacca aaaccctcct gagattcctg acttgtgtcc tgacaccagg tctgttcttc    60
cctcccctag aataaaacat ctcttaagca caaggctgaa gaaatgtggc ctcctccttt   120
```

<210> SEQ ID NO 43
<211> LENGTH: 120
<212> TYPE: DNA
<213> ORGANISM: Homo sapiens

<400> SEQUENCE: 43

```
cacagcgagg ggaagccatt gtgcgctcag aacactctac aaattttcct ccctagtgtt    60
ttaccaaaac tggtatatat ttcagatact gaaatattta caacctacgt tattatgcta   120
```

<210> SEQ ID NO 44
<211> LENGTH: 120
<212> TYPE: DNA
<213> ORGANISM: Homo sapiens

<400> SEQUENCE: 44

```
caaacaaaac gacacaaaaa attccaaagt tgtgcaccct ctaaaagcat atgtacttaa    60
ttctcatttt taatttatta aacagctcta ataagttcaa tgttcctgcc ttctcagttg   120
```

<210> SEQ ID NO 45
<211> LENGTH: 120
<212> TYPE: DNA
<213> ORGANISM: Homo sapiens

<400> SEQUENCE: 45

```
aaaacttgaa cttccatcaa tgataaatat tccttttgcc tcaagcacat atttgaggaa    60
ttttccattg agtagatcta ccgataaggt cacattttc tgtctgtttt aatctgaata    120
```

<210> SEQ ID NO 46
<211> LENGTH: 120
<212> TYPE: DNA
<213> ORGANISM: Homo sapiens

<400> SEQUENCE: 46

```
tagttatttg agagattttt catacaacat ttattctgta agcaaatttc agggattgtt    60
gaatgaatca tattaacaaa tctgacacag aacttcctct gaatcaatct ttgtaaacat   120
```

<210> SEQ ID NO 47
<211> LENGTH: 120
<212> TYPE: DNA
<213> ORGANISM: Homo sapiens

<400> SEQUENCE: 47
tgcctggccg taagttacca tgtgcttttt aaaaaaatca tagcaaaggg gtgtcttctg    60
gaaatgacat tttgaaatgg tgttattaga ccacccctgg aagggacaca gtaaccacac   120

<210> SEQ ID NO 48
<211> LENGTH: 120
<212> TYPE: DNA
<213> ORGANISM: Homo sapiens

<400> SEQUENCE: 48
agtgatggtg ggggtcctac tagcctgtgg caaatggaag catctctttt ttatcagact    60
gaataatatt gtagtgtttt cttataccac atttacttca tcccttttgtg cattaacact   120

<210> SEQ ID NO 49
<211> LENGTH: 120
<212> TYPE: DNA
<213> ORGANISM: Homo sapiens

<400> SEQUENCE: 49
aaaatccatt gctagtggtg gtgggagtcc atttgtcttg tggaaaatgg cagcatttcc    60
ttattttata aggcataata atgctatgtt gtgtacacat accacattgt ctttatccat   120

<210> SEQ ID NO 50
<211> LENGTH: 120
<212> TYPE: DNA
<213> ORGANISM: Homo sapiens

<400> SEQUENCE: 50
aaaatgcatg gctagtgctg ctggaaaccc attcctactg tggcaaatgg cagcatctct    60
tttaaaaggc taaataatat tctattctgt atacatacca cattgccatt atccttttg   120

<210> SEQ ID NO 51
<211> LENGTH: 120
<212> TYPE: DNA
<213> ORGANISM: Homo sapiens

<400> SEQUENCE: 51
atagatggat aaactaacct aggcctttga aaataaaccc ttatctgaga gtgaaaagat    60
aagccataga tttggagagt ttgcttgcaa atcaaatatt tggaaaagga cttttattac   120

<210> SEQ ID NO 52
<211> LENGTH: 120
<212> TYPE: DNA
<213> ORGANISM: Homo sapiens

<400> SEQUENCE: 52
taggcactgg atggaaagca caggagtggg tcaggtgcat acgtgatgag tggaggatga    60
attccagccc acttatcatg aattcagaca agcccacatg ttcccacatg cactatatct   120

<210> SEQ ID NO 53
<211> LENGTH: 120
<212> TYPE: DNA
<213> ORGANISM: Homo sapiens

<400> SEQUENCE: 53
cactgtgact cgaatccaga gtgaactcag acacaaacct gccctgcagg ggttcttggg    60
accacaaggg gaaggatcag gtcaccaggg tgtacttagg aaccactgaa ctgggtcagg    120

<210> SEQ ID NO 54
<211> LENGTH: 120
<212> TYPE: DNA
<213> ORGANISM: Homo sapiens

<400> SEQUENCE: 54
cgcaatgaag ggccttcatt gtgagcctag acacaaccct ccctgcaggg gtgaatagga    60
gcagcagggg gcattcgggg cagtatgggg gcttaggatg attgttaggg gtcaggatga    120

<210> SEQ ID NO 55
<211> LENGTH: 120
<212> TYPE: DNA
<213> ORGANISM: Homo sapiens

<400> SEQUENCE: 55
cattgtgagc ctagacacaa ccctccctgc aggggtgaat aggagcagca gggggcattc    60
ggggcagtat gggggcttag gatgattgtt aggggtcagg atgagcagga tcaaggcttc    120

<210> SEQ ID NO 56
<211> LENGTH: 120
<212> TYPE: DNA
<213> ORGANISM: Homo sapiens

<400> SEQUENCE: 56
cacaacgagg ggaagtcatt gtgagcccag atacaaacct ccctgcaggg gagctcagaa    60
agagcaggag gcactcagga caccagggaa cactctggac acatcaaggc aggtgcaatg    120

<210> SEQ ID NO 57
<211> LENGTH: 120
<212> TYPE: DNA
<213> ORGANISM: Homo sapiens

<400> SEQUENCE: 57
aacagaagag atgtcagtgt gatcccagac acaaacttcc ctggagaggg gcccaggacc    60
accaaagagc actcaggccc atgaaaacag ggcccaagct ggagaacggg tttcctgtca    120

<210> SEQ ID NO 58
<211> LENGTH: 120
<212> TYPE: DNA
<213> ORGANISM: Homo sapiens

<400> SEQUENCE: 58
cacagaaggg gaggtcattg tgaggccaga cacaaacctc cctgcaggga agctcaggac    60 accaggggggt gctcagacac caagggctct caggacacat caaggcaggt gcaagagggg    120

<210> SEQ ID NO 59
<211> LENGTH: 120
<212> TYPE: DNA
<213> ORGANISM: Homo sapiens

<400> SEQUENCE: 59
cacagtgagg ggaagtcagt gtgagcccag acacaaacct ccctgcaggg atgctcagga    60
ccccagaagg cacccagcac taccagcgca gggcccagac caggagcagg tgtggagtta    120

<210> SEQ ID NO 60
<211> LENGTH: 120
<212> TYPE: DNA
<213> ORGANISM: Homo sapiens

<400> SEQUENCE: 60
cagagtgagg ggaccacggt gcgagctcac acccaaacct tcctggaggg gtgcacagga      60
cagcaggagt cccgatgatg aaggggtg gtctggattc caggtcactc tcaagatcat      120

<210> SEQ ID NO 61
<211> LENGTH: 120
<212> TYPE: DNA
<213> ORGANISM: Homo sapiens

<400> SEQUENCE: 61
cacagtaagg taaccacagt gggaactcac acccaaacct ccctgtgggg gtgcacagga      60
cagccacagt tactcaggac cccaggattc ctcaggacac caaggggcac tcaaggccat      120

<210> SEQ ID NO 62
<211> LENGTH: 120
<212> TYPE: DNA
<213> ORGANISM: Homo sapiens

<400> SEQUENCE: 62
cacagtgagg ggacatcagt gtgagcccag acacaaacct ccctatgcgg gttcacagga      60
cagcatgggg tgctgaggac agaggtgggc actcaggaac cagcagggaa acccaggggg      120

<210> SEQ ID NO 63
<211> LENGTH: 120
<212> TYPE: DNA
<213> ORGANISM: Homo sapiens

<400> SEQUENCE: 63
agtgagagga agtccgtgtg agcccagaca caaacctccc tgcagggggca cgcggggcca      60 ccagagggtg cccaggatcc cctgaagaca gggacagccc aaaggcaggt gcagatggat      120

<210> SEQ ID NO 64
<211> LENGTH: 120
<212> TYPE: DNA
<213> ORGANISM: Homo sapiens

<400> SEQUENCE: 64
cacagtgagg ggaggtcagt gtgagcccag acacaaacct cctgcagggg catctggagc      60
cacaaggggg cgctcaggat acacagagga caggggcagc cccagggcag gtgcaggtgg      120

<210> SEQ ID NO 65
<211> LENGTH: 120
<212> TYPE: DNA
<213> ORGANISM: Homo sapiens

<400> SEQUENCE: 65
cacagtgagg ggaggtcagt gtgagcccgg acacaaacct ccctgcaggg gcgcgcgggg      60
ctaccagggg gcgctcggga ctcactgagg gcgggacagg tcccaggaac aggtgcagcg      120

<210> SEQ ID NO 66
<211> LENGTH: 120
<212> TYPE: DNA
<213> ORGANISM: Homo sapiens

<400> SEQUENCE: 66

-continued

```
cagtgagggg gaggttaacg taggcccata cacaaatctc cctgcagggg cgcgcagggc      60
caactggggg cgctcgggac ccactgagga tgggacaggt cccaggggcg ggtgcagggg     120

<210> SEQ ID NO 67
<211> LENGTH: 120
<212> TYPE: DNA
<213> ORGANISM: Homo sapiens

<400> SEQUENCE: 67
tacggtaagg agaagtcagt gtgagcccag acacaaacct cccttcaggg tacctgggac      60
aaccagggaa agcctgggac actgtgcact gtgctgaccc caggggcaag tgcaggtgct     120

<210> SEQ ID NO 68
<211> LENGTH: 120
<212> TYPE: DNA
<213> ORGANISM: Homo sapiens

<400> SEQUENCE: 68
cacagagtga ggggaagtca gtgagagccc aggcacaaac ctccctgaag gggtcccaga      60
aacgactagg gggcgccagg acactgtgca cggggctgtc tccagggcag gtgcaggtgc     120

<210> SEQ ID NO 69
<211> LENGTH: 120
<212> TYPE: DNA
<213> ORGANISM: Homo sapiens

<400> SEQUENCE: 69
aacagtgaga ggaagtcaat gtgagtccag acataaacct tcctgctgag aacaatggaa      60
agcttttctt ctaagataag gaataagaaa agaatgccca gtcttaataa ttctaatcag     120

<210> SEQ ID NO 70
<211> LENGTH: 120
<212> TYPE: DNA
<213> ORGANISM: Homo sapiens

<400> SEQUENCE: 70
cacagtgagg ggaggtcagt gtgagcccag acacaaacct ccctgcaggg ccatgcgggt      60
ggtttccttt ctcagctgca ggaggcgggc ttattgttgc aggactctgg agacttatta     120

<210> SEQ ID NO 71
<211> LENGTH: 120
<212> TYPE: DNA
<213> ORGANISM: Homo sapiens

<400> SEQUENCE: 71
ctcagtgagg aggtgtcctt atgagccctg acacaaacct gtcagggcac ttaggacctc      60
caggaagact caagaccacc aaggggactc acgaccactg gggaagggca ggttgcagta     120

<210> SEQ ID NO 72
<211> LENGTH: 120
<212> TYPE: DNA
<213> ORGANISM: Homo sapiens

<400> SEQUENCE: 72
cacagcgagg gacatttctg tgagtccaga cagaaacctc cctgcaggga gacaagagag      60
gactttgtga taaatggtgc ttaggacacc aggggggcact caggacagca gagggtgctc    120

<210> SEQ ID NO 73
<211> LENGTH: 120
```

```
<212> TYPE: DNA
<213> ORGANISM: Homo sapiens

<400> SEQUENCE: 73
cacggtgagg ggacatctgt gtgagctcag acacaaacct gcctgcaggg agacacaaac      60
ctccctgcat ggtagatgct tctcagaacc accaggggg gcacaggaaa ccagaaggtg      120

<210> SEQ ID NO 74
<211> LENGTH: 120
<212> TYPE: DNA
<213> ORGANISM: Homo sapiens

<400> SEQUENCE: 74
cataggagca ggaacatctg cgtgagccca gacacaaaat cctctgcagg gagacaggag      60
ggaatcgcat ggtagatgct gattggaact accatgtgtc gctcagaact accaggaggt      120

<210> SEQ ID NO 75
<211> LENGTH: 120
<212> TYPE: DNA
<213> ORGANISM: Homo sapiens

<400> SEQUENCE: 75
cacaggagag agattatctg cacaagccca gacacaaaaa tctgcaggga gacaggaggg      60
aactgcatgg tagatgctgc tcagaagcac caggggcac tcaacacaag ggggcgctca      120

<210> SEQ ID NO 76
<211> LENGTH: 120
<212> TYPE: DNA
<213> ORGANISM: Homo sapiens

<400> SEQUENCE: 76
agacacagga gagggaatat ctgcgtgagc ccagacagaa aaatctctgc aggaagacag      60
gagggagctg catggtagat gctcctcaga accaccaggg caccttgggg acaacctggg      120

<210> SEQ ID NO 77
<211> LENGTH: 120
<212> TYPE: DNA
<213> ORGANISM: Homo sapiens

<400> SEQUENCE: 77
cacaggagag ggaatatctg tgtgagccca gacacaaaaa tctctgcaga gagacaggag      60
ggaactgcat ggtagatgct cctcataacc acaaggggc agtcaggacc atcaggagga      120

<210> SEQ ID NO 78
<211> LENGTH: 120
<212> TYPE: DNA
<213> ORGANISM: Homo sapiens

<400> SEQUENCE: 78
cacatgagga aaggccggtg tgagacacaa acctccagga acacctgggc taatgagctg      60 caggggcgc tcaggaccca ctgatcagtc aaccacagag gggagtgcaa aggttaggac      120

<210> SEQ ID NO 79
<211> LENGTH: 120
<212> TYPE: DNA
<213> ORGANISM: Homo sapiens

<400> SEQUENCE: 79
ccaagtgagg aaacatcggt gtgagtccag acacaaaatt tcctgcagaa agaagaaagg      60
```
attctgggcc aagggaca ctcagcactc acaaaacagg tggagcccca gggcaggtac    120

<210> SEQ ID NO 80
<211> LENGTH: 116
<212> TYPE: DNA
<213> ORGANISM: Homo sapiens

<400> SEQUENCE: 80
gtcaccaggt aagaagacat cagtgtgatc acagacacag aatttcctga aataagggag    60
gagtctgggc taaaagggca ctcaggaccc acagaaaaca gcggaagctc tagggc    116

<210> SEQ ID NO 81
<211> LENGTH: 120
<212> TYPE: DNA
<213> ORGANISM: Homo sapiens

<400> SEQUENCE: 81
caccaggtaa gaagacatca gtgtgaacac agacacagaa tttcctgaaa taaggagga    60 gtctgggcta aaagggcact caggacccac agaaaacagg gaagctcta gggcaggtgc    120

<210> SEQ ID NO 82
<211> LENGTH: 120
<212> TYPE: DNA
<213> ORGANISM: Homo sapiens

<400> SEQUENCE: 82
agaagacatc agtgtgaaca cagacacaga ggttcctgta atgataaggg aggaggctgg    60
gataaaggga gcactcaaga cccacagaaa caggggaag ctctagggca ggtgcagacg    120

<210> SEQ ID NO 83
<211> LENGTH: 120
<212> TYPE: DNA
<213> ORGANISM: Homo sapiens

<400> SEQUENCE: 83
caccaggtaa gaagacatca gtgtgaacac agacacagag tttcctgcaa tgataaggga    60
ggaggctggg ctaaaagggg cactcaggac ccactgaaaa cgggcagctc tagggcaggt    120

<210> SEQ ID NO 84
<211> LENGTH: 120
<212> TYPE: DNA
<213> ORGANISM: Homo sapiens

<400> SEQUENCE: 84
ccaggtaaga agacatcagt gtgaacacag acacagtttc ctgcaatgat aagggaggag    60
gctgggctaa aggggcact caggacccac tgaaaacggg cagctctagg gcaggtacag    120

<210> SEQ ID NO 85
<211> LENGTH: 120
<212> TYPE: DNA
<213> ORGANISM: Homo sapiens

<400> SEQUENCE: 85
cacagtgagg ggaagtcagc gagagcccag acaaaaacct cctgcaggaa gacaggaggg    60
gcctgggctg cagagggcac tcaagacaca ctgaaaacac ggttaacact gggacaagtt    120

<210> SEQ ID NO 86
<211> LENGTH: 120
<212> TYPE: DNA
<213> ORGANISM: Homo sapiens

<400> SEQUENCE: 86
catcgtgatg ggaagtccac gtgggctcag agacagactg ccatgcagga cacaggggggt   60 ggcttggctg aaggggggcac tcagcaccca cagaagacag gagcagccca gggcagggggc   120

<210> SEQ ID NO 87
<211> LENGTH: 120
<212> TYPE: DNA
<213> ORGANISM: Homo sapiens

<400> SEQUENCE: 87
cgcagtgaga agtcagtgtg agcccagaca caaacctcct gcagggtacc tgggacaatc   60
agggaaagcc tgggacactg tatactgggc tgtccccagg ggcaagtcca ggtgatataa   120

<210> SEQ ID NO 88
<211> LENGTH: 120
<212> TYPE: DNA
<213> ORGANISM: Homo sapiens

<400> SEQUENCE: 88
cactgtgaga ggacggaagt gtgagcccag acacaaacct cctgcaggaa cgttggggga   60
aatcagctgc aggggggcgct caagacccac tcatcagagt caaccccaga gcaggtgcac   120

<210> SEQ ID NO 89
<211> LENGTH: 120
<212> TYPE: DNA
<213> ORGANISM: Homo sapiens

<400> SEQUENCE: 89
cacagtgagg agaagtcagt gtgagcccag tcacaaacct cctacaggaa cgctgggagg   60
aaaatcagct acagggctca ctcaaggccc actgatcaga gtccactcca gagggaggtt   120

<210> SEQ ID NO 90
<211> LENGTH: 120
<212> TYPE: DNA
<213> ORGANISM: Homo sapiens

<400> SEQUENCE: 90
catggtgagg ggaaatcagt atgagcccag ccagaaacct ccctgcagga accctggggt   60 gggggggaaat cagctgcagg gggcactcag gacccactga tcagaatcaa ccccagaagg   120

<210> SEQ ID NO 91
<211> LENGTH: 120
<212> TYPE: DNA
<213> ORGANISM: Homo sapiens

<400> SEQUENCE: 91
cacagtgagg ggaagtcatt gtgagcccag acacaaacct ccctgcagga acgatggggg   60
tgaaatcagc ggcaggggggc gctcaggacc cgctgatcag agtcatccgc agaggcaggt   120

<210> SEQ ID NO 92
<211> LENGTH: 120
<212> TYPE: DNA
<213> ORGANISM: Homo sapiens

<400> SEQUENCE: 92
cacagtgagg ggaggccatt gtgcgcccag acacaaacct ccctgcagga acgctgggga   60
aatcagcggc aggggggcgct caggagccac tgatcagagt cagcccccgga ggcaggtgca   120

<210> SEQ ID NO 93
<211> LENGTH: 120
<212> TYPE: DNA
<213> ORGANISM: Homo sapiens

<400> SEQUENCE: 93
cacagtgagg ggaggtgagt gtgagcccag acaaaaacct ccctgcaggg aggctgaggg      60
cgcggtcgca ggtgcagctc agggccagca gggggcgcgc ggagctcacg gaatacaagg     120

<210> SEQ ID NO 94
<211> LENGTH: 120
<212> TYPE: DNA
<213> ORGANISM: Homo sapiens

<400> SEQUENCE: 94
tacacagtga ggggaggtga gtgtgagccc agacacaaac ctccctacag ataggcagag      60
ggggcgggca caggtgctgc tcaggaccaa caggggcgc gcgaggcaca gagcccgagg     120

<210> SEQ ID NO 95
<211> LENGTH: 120
<212> TYPE: DNA
<213> ORGANISM: Homo sapiens

<400> SEQUENCE: 95
cacagtgaga cagatgagga agtcggacaa aaaccaaggt tttaagcttg tcatttttac      60
tgaactggtt aagaacttca gtggttaata aaatcacatt aaatacagga ttgttgttaa     120

<210> SEQ ID NO 96
<211> LENGTH: 120
<212> TYPE: DNA
<213> ORGANISM: Homo sapiens

<400> SEQUENCE: 96
cactgtgctc taggccaatg ggaaaatccc ctctgcttgt gctgcctggg ctcccactag      60 gccctgctg tttgtgacaa cagccagcac tggtggtgac gcttcagcca tgtatgccct     120

<210> SEQ ID NO 97
<211> LENGTH: 120
<212> TYPE: DNA
<213> ORGANISM: Homo sapiens

<400> SEQUENCE: 97
cactgtgcta caacccaaaa caaaaattag ctcagcctgg cggaacagag aaactgaaca      60 atacccgtt tttatgatcc ttgcaggtgc agttggggaa ataatttacc aaataccatc     120

<210> SEQ ID NO 98
<211> LENGTH: 120
<212> TYPE: DNA
<213> ORGANISM: Homo sapiens

<400> SEQUENCE: 98
cacagtgctt taggtctaaa caaaaacctc cccaggcagc tgctccctga ggctcaaatc      60
cctcagatgt ggcttttat gcaggtccat cagcctgctg tcataggctt gtttgaacaa     120

<210> SEQ ID NO 99
<211> LENGTH: 120
<212> TYPE: DNA
<213> ORGANISM: Homo sapiens

<400> SEQUENCE: 99

```
cacaatggtt cagcaccaaa caaaagcctc ctgcttggat tgtcccagct gcccaaatta    60
gttccttcac tgaggagtag acagggtata tgctctaaat ctatgtaaca ggaagatgtt   120
```

<210> SEQ ID NO 100
<211> LENGTH: 120
<212> TYPE: DNA
<213> ORGANISM: Homo sapiens

<400> SEQUENCE: 100

```
cacagtggta caaccctgaa cagaaacctc ccttcttgct gtggttcagc tgcccaaatg    60
tgttgtttat ctggaaagca gacactgtct attatcttgg gagagtaaag agaggaagat   120
```

<210> SEQ ID NO 101
<211> LENGTH: 120
<212> TYPE: DNA
<213> ORGANISM: Homo sapiens

<400> SEQUENCE: 101

```
cacagtggta aaccctgaa cacaaacctc cctacttggg atggcccagc catccacaag     60
tgtttgcacg tggactgtct gcatggcaga ttctgagttg gcttcacagg tagatgttag   120
```

<210> SEQ ID NO 102
<211> LENGTH: 120
<212> TYPE: DNA
<213> ORGANISM: Homo sapiens

<400> SEQUENCE: 102

```
cacagtgcta catcctcgaa cagaaacctc cctgctggtt gacccagctc gcgcatgggc    60
tgcttgtctg agggaacagc tgagcagagt ctttgagtct gcagaggaga aggctgttgg   120
```

<210> SEQ ID NO 103
<211> LENGTH: 120
<212> TYPE: DNA
<213> ORGANISM: Homo sapiens

<400> SEQUENCE: 103

```
cacagtgctt cagcctcgaa cacaaacctc ctccccatac gctgggccag taggtctttg    60
ctgcagcagc tgcttcctct gcacacagcc cccaacatgc atgcttcctc tgtgtgttgg   120
```

<210> SEQ ID NO 104
<211> LENGTH: 120
<212> TYPE: DNA
<213> ORGANISM: Homo sapiens

<400> SEQUENCE: 104

```
gggaggcgga gggggcgggc gcaggtgccg ctcaggacca gcaggggcg cgcggggccc     60 acagagcagg aggccgggtc aggagcaggt gcagggaggg cggggcttcc tcatctgctc   120
```

<210> SEQ ID NO 105
<211> LENGTH: 120
<212> TYPE: DNA
<213> ORGANISM: Homo sapiens

<400> SEQUENCE: 105

```
ctcagcctcc tcactcaggg cacaggtgac acctccaggg aaagggtcac aggggtctct    60
gggctgatcc ttggtctcct gctcctcagg ctcacctggg cccagcactg actcactaga   120
```

<210> SEQ ID NO 106

<211> LENGTH: 120
<212> TYPE: DNA
<213> ORGANISM: Homo sapiens

<400> SEQUENCE: 106
tgcccttggc ctgtcccgag gctgatcact ccatacttgc ctatgacaaa caaagagggt    60
gcctgtggct gatcgtacag tttaagcaag ggaggaagtg agactcagcc acaggcccct   120

<210> SEQ ID NO 107
<211> LENGTH: 120
<212> TYPE: DNA
<213> ORGANISM: Homo sapiens

<400> SEQUENCE: 107
cactgtgctc cagacttacg gggaagtgag attagaacct cccctgcatt ctctctgcct    60
tgtgcaggca acaatacact gtctgggacc gagtgtggct catcagtagc agctttgttg   120

<210> SEQ ID NO 108
<211> LENGTH: 120
<212> TYPE: DNA
<213> ORGANISM: Homo sapiens

<400> SEQUENCE: 108
cacagtgctc cagacccatg aggaagtaag acaaaaccct cccctctact ctcctggtct    60
agtgaaatca cccctgctgg tggctctgac caaatctagc tcaggggtg acatctgttg    120

<210> SEQ ID NO 109
<211> LENGTH: 120
<212> TYPE: DNA
<213> ORGANISM: Homo sapiens

<400> SEQUENCE: 109
tacagtgctc caggcttgca ggggagtgag acaagaaccc ccttcctcct ttcccaggag    60
ggtgagtgcc cagcagctac tgcacaggcc tggcctgtgg cttctgcagt tgctgtttcc   120

<210> SEQ ID NO 110
<211> LENGTH: 120
<212> TYPE: DNA
<213> ORGANISM: Homo sapiens

<400> SEQUENCE: 110
cacagtgctc cagacccatg gggaagtgag acagaaactc cccagagcat ctctacctgg    60
gccagtctca gcctgtctcc accagagagg gtagctctcc catctctcct gtctaagtgc   120

<210> SEQ ID NO 111
<211> LENGTH: 120
<212> TYPE: DNA
<213> ORGANISM: Homo sapiens

<400> SEQUENCE: 111
caccgtggtc caagttcatg gggaattgag acccaaacct gccctgggct ctcagcctct    60
ctcttgttct gaagatgctt cctcaccctg tgcaagggc ttcttgcagc actgccttga   120

<210> SEQ ID NO 112
<211> LENGTH: 120
<212> TYPE: DNA
<213> ORGANISM: Homo sapiens

<400> SEQUENCE: 112
tccacagtga tttaaaccca tgaggaggtg caactaaaac ctctttacat actcagaaag    60

```
attcagccct tagaagcaag agagaagttg agagggtggg aatgtcaaca ccatgagctg    120
```

<210> SEQ ID NO 113
<211> LENGTH: 120
<212> TYPE: DNA
<213> ORGANISM: Homo sapiens

<400> SEQUENCE: 113

```
cacagtgaca cagacagatt ggaaagtgag atctaaagac cttcactgtc tgtatcaccc    60
tctttctcca gccatagcag gactgagcag ggctggcccg ggtcacctgg atcgaagccc   120
```

<210> SEQ ID NO 114
<211> LENGTH: 120
<212> TYPE: DNA
<213> ORGANISM: Homo sapiens

<400> SEQUENCE: 114

```
cactcatggg acagcagtgc tactcacctc acaatgacac agacagattg ggaagtgaga    60
tctaaagacc ttcactgtct gtgtcaccct cttcctccag ccatagcagg actgtggaga   120
```

<210> SEQ ID NO 115
<211> LENGTH: 120
<212> TYPE: DNA
<213> ORGANISM: Homo sapiens

<400> SEQUENCE: 115

```
cacagtgaca gaggcagaca aggaagtaag acacagaccc cttccccatc tgtgctgctg    60
tcgtcctcca gcccggcaac actgtggaca aagccatgag catgcatgac ccagttcacc   120
```

<210> SEQ ID NO 116
<211> LENGTH: 120
<212> TYPE: DNA
<213> ORGANISM: Homo sapiens

<400> SEQUENCE: 116

```
cacagtgata caggcagatg aggaagtggg acaaaatcct caacctgctg aggctattgt    60
tcagtgacaa tttttaattt taaaacattt tctgtatgta aaaaatctat ctggatgcat   120
```

<210> SEQ ID NO 117
<211> LENGTH: 120
<212> TYPE: DNA
<213> ORGANISM: Homo sapiens

<400> SEQUENCE: 117

```
cacagtgcct caggccagtg gggaagtgag ataaaaactc aagagctccc tcggcctcac    60
tgaacaggcc tcacagagca ctgtttaaac tggaccaccc aaaagacaag ggatgcattc   120
```

<210> SEQ ID NO 118
<211> LENGTH: 120
<212> TYPE: DNA
<213> ORGANISM: Homo sapiens

<400> SEQUENCE: 118

```
cacagcgcct caggggaagt gagacgaaaa ctcaggagct cccctagctt cactcggtat    60
gcgggggcgt catagagcac tgtttaaact aaaccaaaaa tgacaagggc tggtttccac   120
```

<210> SEQ ID NO 119
<211> LENGTH: 120
<212> TYPE: DNA

<213> ORGANISM: Homo sapiens

<400> SEQUENCE: 119
aacagtgctg cagtctggga aagtgagatg agaacacgcc aggtctccta ggagcatgac    60
cttccaatgg caccacccac aaccaggaca cgctggtctt gttttaccat ttgtgtggat   120

<210> SEQ ID NO 120
<211> LENGTH: 120
<212> TYPE: DNA
<213> ORGANISM: Homo sapiens

<400> SEQUENCE: 120
cacagtggac ataagattga ttctcaggct ccaagtctgg ccagtgagct tctttgagac    60
tccctgggat cccagcagtg acactgatca ctattgctgt cccacacatc ccaagtgatg   120

<210> SEQ ID NO 121
<211> LENGTH: 120
<212> TYPE: DNA
<213> ORGANISM: Homo sapiens

<400> SEQUENCE: 121
cagcactcca gacccactgg gaggttacaa aaacctcttc tctgatctcc tggcctggtg    60
tagtcactcc tgctggtggc tctaataaag tctatctcac tgggtgactt atattttaga   120

<210> SEQ ID NO 122
<211> LENGTH: 120
<212> TYPE: DNA
<213> ORGANISM: Homo sapiens

<400> SEQUENCE: 122
cacagtgctc cgggttgaag taagtcagac caaaacacac agtgtgccca gccatgaagc    60
tctcccatgc accccctact ctgcagctaa gtcaatgtgt tctctcactt gtttgtccta   120

<210> SEQ ID NO 123
<211> LENGTH: 120
<212> TYPE: DNA
<213> ORGANISM: Homo sapiens

<400> SEQUENCE: 123
ggcagtactt caggccagtg gggaagtggg agaaaaagct gctgcccatc cagcaatgga    60
gcttctctgt gcagccccca cttcttgggc aagtcagctg attaacgttg cttttcattt   120

<210> SEQ ID NO 124
<211> LENGTH: 120
<212> TYPE: DNA
<213> ORGANISM: Homo sapiens

<400> SEQUENCE: 124
acacctggcc tcttcgtttt tattcatata ttccttcagc agccactatg tcttcccact    60
gatttcttca gttctgcct tttccttttg aataaggctg ttactcctga gggaagatgg   120

<210> SEQ ID NO 125
<211> LENGTH: 120
<212> TYPE: DNA
<213> ORGANISM: Homo sapiens

<400> SEQUENCE: 125
ggcaggccac caagtccagc taattttgt attttagta gacactgggt ttcacaatat    60
tggtctggct ggtctcaaac tcctgatctc agcctcccaa agtgctggga ttaaagccgt   120

<210> SEQ ID NO 126
<211> LENGTH: 120
<212> TYPE: DNA
<213> ORGANISM: Homo sapiens

<400> SEQUENCE: 126
attgtgtgca tcccttgttt aggtacatgc agagatgctg ctttggtgtg ttcaggggct    60
cctgttttgg ggacaccaat tttggagttt gcagtatcct tgagtccagt acgttcatgg   120

<210> SEQ ID NO 127
<211> LENGTH: 120
<212> TYPE: DNA
<213> ORGANISM: Homo sapiens

<400> SEQUENCE: 127
atggtctcac tgatatcttt acttctttta tcacttttgt tatgtaaatc acaatgaata    60
gtgtattcct catctattat acatttgtta agtctttttt ggtgtcttta aaaaaactga   120

<210> SEQ ID NO 128
<211> LENGTH: 120
<212> TYPE: DNA
<213> ORGANISM: Homo sapiens

<400> SEQUENCE: 128
cacaatgaat agtgtattcc tcatctatta tacatttgtt aagtctttttt tggtgtcttt    60 aaaaaaactg ataactttat agtatgtaat atccttaagt cctgaaagtg tttttttgatg   120

<210> SEQ ID NO 129
<211> LENGTH: 120
<212> TYPE: DNA
<213> ORGANISM: Homo sapiens

<400> SEQUENCE: 129
cttcatctat tatacacttg ttaagtcttt tttggcatct tttaaaaaac tggtaacttt    60
atcctgtgta atatccctgt taagtcctaa aagtcttttt tgatgtctat ttttcttaa   120

<210> SEQ ID NO 130
<211> LENGTH: 120
<212> TYPE: DNA
<213> ORGANISM: Homo sapiens

<400> SEQUENCE: 130
tacctaaatg tgtgtggggg aagcagggg tgttattctg ttgttctgtg ttctctgaga     60
tgcatggatt caccatttac tctgcctcca ttttggggaa cacagttaga aaaatgtca   120

<210> SEQ ID NO 131
<211> LENGTH: 120
<212> TYPE: DNA
<213> ORGANISM: Homo sapiens

<400> SEQUENCE: 131
tggttttcag cagtttttaat aagattcacc taaatgtgtg tgtgtgtgtc gagggtgtt    60 atgctattgt tctgtgttct ctgagatgca tggattcacc gtttactctg tctccatttt   120

<210> SEQ ID NO 132
<211> LENGTH: 120
<212> TYPE: DNA
<213> ORGANISM: Homo sapiens

<400> SEQUENCE: 132
cacagtgatt cagacactga aaatctgcct gtggttgctt ctggtacaca agatagacca    60
gccaactctc atttcctgcc ctgaatttac tgtattctgt acaaagagaa acacagctta   120

<210> SEQ ID NO 133
<211> LENGTH: 120
<212> TYPE: DNA
<213> ORGANISM: Homo sapiens

<400> SEQUENCE: 133
cacagtgatt cagatccgcc ctacaccaca ctgaaaacct gccttgtggc tgcttctggt    60
acacaagata gagctgcccc ctctcatttc ctgccaccaa atttaccgtg tgctgaacaa   120

<210> SEQ ID NO 134
<211> LENGTH: 120
<212> TYPE: DNA
<213> ORGANISM: Homo sapiens

<400> SEQUENCE: 134
cacagcagca gacagtttga gccatcccat tcaataaatg tttattgagt ctttgtttat    60
aattacgaat tgggaagcca cagttaccac cagtgtgctt gtaaacagtt tttaagataa   120

<210> SEQ ID NO 135
<211> LENGTH: 120
<212> TYPE: DNA
<213> ORGANISM: Homo sapiens

<400> SEQUENCE: 135
cgcagccttg catgctgccc cagccctaca caaaaggact cttcctcccg atccaacaag    60
gccttgggca ttttcactta ctcttggtcc cttgggtttc cctgtggcat agaagaaaaa   120

<210> SEQ ID NO 136
<211> LENGTH: 120
<212> TYPE: DNA
<213> ORGANISM: Homo sapiens

<400> SEQUENCE: 136
caataatggc aatgtggcag tttccataca tatgtttgtg ctagcttttt tattattata    60
tagtaaactt ctttgcctct ttttatagtt attgtcttga aatatatttt atctgatata   120

<210> SEQ ID NO 137
<211> LENGTH: 120
<212> TYPE: DNA
<213> ORGANISM: Homo sapiens

<400> SEQUENCE: 137
cacaatggaa gcacaaccat tgtctctctg tgcggaaatg tgtcctcacc ctacagcccc    60
caccacatcc tctagcttaa ttttttcatt tttaatattt tcttgagatt ttactatgtc   120

<210> SEQ ID NO 138
<211> LENGTH: 120
<212> TYPE: DNA
<213> ORGANISM: Homo sapiens

<400> SEQUENCE: 138
cacagtgact atgaggcctc cttaactgtg ccaaaattca aaagacaatc agtggagtac    60
aggtgggctt gagaagttct agaacttcct gagtgtatct ttgcttaccg tctaatttta   120

```
<210> SEQ ID NO 139
<211> LENGTH: 120
<212> TYPE: DNA
<213> ORGANISM: Homo sapiens

<400> SEQUENCE: 139
cacggtgact atgaggcctc tttagctgca ccaaaattca aaaggcaacc acagcagcga    60
gaagctgtat ttcctgagtg tatgcctgct gtgagttaag actggggact ttggaaccag   120

<210> SEQ ID NO 140
<211> LENGTH: 120
<212> TYPE: DNA
<213> ORGANISM: Homo sapiens

<400> SEQUENCE: 140
tcaggaccct gtgataattg tgttaactgc acaaattata gagcatgtgt gttcaaacaa    60
tatgaaatct gggcaccttg aaaaaagaac aggataacag caatgttcag ggaataagag   120

<210> SEQ ID NO 141
<211> LENGTH: 120
<212> TYPE: DNA
<213> ORGANISM: Homo sapiens

<400> SEQUENCE: 141
cacagtgccg aatgttagcc cttcttagaa cacaaactca ttatggaccc agctcaggaa    60
ataagtgtat gtcaggttgg tacacactat aataacagaa agccaacttg aaagacaata   120

<210> SEQ ID NO 142
<211> LENGTH: 120
<212> TYPE: DNA
<213> ORGANISM: Homo sapiens

<400> SEQUENCE: 142
cacaatgtta aatattagct aatcttagga cacagactca tcacggactc agctcaggaa    60
gcaggtggta tactaggttg gaaggaaata acagaaacta gagctagctt aagccaaagg   120

<210> SEQ ID NO 143
<211> LENGTH: 120
<212> TYPE: DNA
<213> ORGANISM: Homo sapiens

<400> SEQUENCE: 143
cacagcactg aaatgtcagt tcctcttagc acacaaactt gtcacagacc cagctcagga    60
agcaggtgat gtattaggct ggaagggagt aacagaaaat aactggagcc agcttaagcc   120

<210> SEQ ID NO 144
<211> LENGTH: 120
<212> TYPE: DNA
<213> ORGANISM: Homo sapiens

<400> SEQUENCE: 144
cactgtgtta aaagcacagt gggagctata caaaaacctc aaaggctcag aggaagtatg    60
tagtgaggct ggaaaaccca ggttgtagag ccctgttctc tctttcacag acagtcctgt   120

<210> SEQ ID NO 145
<211> LENGTH: 120
<212> TYPE: DNA
<213> ORGANISM: Homo sapiens

<400> SEQUENCE: 145
```

```
cactatgatg caggtgccca ggaagtcata acacaaactc ctggggcaca gctcagcaga    60
gctgcctctt agggcaggtc atgtctggga cttggcatcc ttctcttagc cattttgggt   120
```

<210> SEQ ID NO 146
<211> LENGTH: 120
<212> TYPE: DNA
<213> ORGANISM: Homo sapiens

<400> SEQUENCE: 146

```
cacagaggca gggaacccat gaagagctga acagaaacag agatcacagc ctttgcagga    60
ggcaaaacag agatgagcaa taacttttc ctccttaatt cagtattacc caagcttttt   120
```

<210> SEQ ID NO 147
<211> LENGTH: 120
<212> TYPE: DNA
<213> ORGANISM: Homo sapiens

<400> SEQUENCE: 147

```
cacagtagct ggttttgcaa ggaagcagaa cacaaaccct ttaaatacag gaaatatttc    60
tttgcaaact ctctgtatgg ccacagcagg gcattctttc tccagaaaatt aatattgagt   120
```

<210> SEQ ID NO 148
<211> LENGTH: 120
<212> TYPE: DNA
<213> ORGANISM: Homo sapiens

<400> SEQUENCE: 148

```
gactgtgcct gggactgcag gaggagctga acacaaactt cctgagacac tgaggttttc    60
aggaactcaa gggcacagcc tgacctattt gtagcaaggt ctctcatttg atgaaagtga   120
```

<210> SEQ ID NO 149
<211> LENGTH: 120
<212> TYPE: DNA
<213> ORGANISM: Homo sapiens

<400> SEQUENCE: 149

```
cacagtgcct gagactgcag gagagctgaa cacaaacctc ctgagatgct gagactttct    60
gtgactcaag aactcaacct gtggagcttt caagagggtc ccttttttct gtgcccgttt   120
```

<210> SEQ ID NO 150
<211> LENGTH: 120
<212> TYPE: DNA
<213> ORGANISM: Homo sapiens

<400> SEQUENCE: 150

```
cacactgata ggggctgcag ggggagcaga acacaaactc ttgagtctgg taaagcccat    60
tttcttgaag tctttgttcc ttcacatgag aacggtgtgc ttccaggata tgtcacttat   120
```

<210> SEQ ID NO 151
<211> LENGTH: 120
<212> TYPE: DNA
<213> ORGANISM: Homo sapiens

<400> SEQUENCE: 151

```
cacagtgtct gggactgcaa agggagctga acacaaactt cctaaggtgc tagggagaat    60
aactgcctct gaaagatttt ggattctgtc acagtagaaa ccatgatgtt agtattttta   120
```

<210> SEQ ID NO 152
<211> LENGTH: 120

-continued

```
<212> TYPE: DNA
<213> ORGANISM: Homo sapiens

<400> SEQUENCE: 152
cagagtggga gggactgcag cgagagccca gcacaaaccc tggggaacgc aggtggggcc      60
tgggtgtgag ccgctttggg agatgaatga atatggactc ttgttcgctg ggaccccaaa     120

<210> SEQ ID NO 153
<211> LENGTH: 120
<212> TYPE: DNA
<213> ORGANISM: Homo sapiens

<400> SEQUENCE: 153
cacagtgaca gggactgcag gggaagctga gcacaaactc tgagcagcac gaggggcctg      60
gctgctgagt gtaagccact gtgatcccct ctggttaggg accaggaact actctactat     120

<210> SEQ ID NO 154
<211> LENGTH: 120
<212> TYPE: DNA
<213> ORGANISM: Homo sapiens

<400> SEQUENCE: 154
cactgtgaag aacatgttag aagagcctta caaaaagatc ggaactcaac ctgaggcaat      60
tgcctattcc cacattctca ggaaaaactc acaaacctta cccaggcatt tgttagcagc     120

<210> SEQ ID NO 155
<211> LENGTH: 120
<212> TYPE: DNA
<213> ORGANISM: Homo sapiens

<400> SEQUENCE: 155
cacaatgaga tgagcagcag ggagaggctt acagaaacct cagacctcag catctgtgca      60
aaggtcacag ggtgagaggg aagtggtagg gtaataggta tagaaaatca ttgacttctc     120

<210> SEQ ID NO 156
<211> LENGTH: 120
<212> TYPE: DNA
<213> ORGANISM: Homo sapiens

<400> SEQUENCE: 156
cacagtgaga tgggtgcctg tgggagccct acaaaaacct caacaagagg cagggctcct      60
ggggagagac tctgtcacag acaggaagaa gcaaggaggg tctgtgtcag cacaggtggt     120

<210> SEQ ID NO 157
<211> LENGTH: 114
<212> TYPE: DNA
<213> ORGANISM: Homo sapiens

<400> SEQUENCE: 157
cacagtgaca gaactgtcgg agggaggtgt acaaaagccc tggggacctg cttgagacct      60
ccacctgctg gagaaccaag gcgggaaatc aacatcacag acaggaagtg gcta           114

<210> SEQ ID NO 158
<211> LENGTH: 120
<212> TYPE: DNA
<213> ORGANISM: Homo sapiens

<400> SEQUENCE: 158
cacagaagta gaaatgacag tggaagataa acaaaaacct tagcactcca taaggaagc       60
```
cacctgctca ggagcttagg gaaaatacat gaagcacaga caggaagaag gcacattagt      120

<210> SEQ ID NO 159
<211> LENGTH: 120
<212> TYPE: DNA
<213> ORGANISM: Homo sapiens

<400> SEQUENCE: 159
cacagtgttt gaagtgatag taaaagcaaa acaaaaaccc tagggctcaa taagagaacc      60
cctctactcc ccatcctttg ctacaggagc caatctgaaa tgcacacctg cagatctcag     120

<210> SEQ ID NO 160
<211> LENGTH: 120
<212> TYPE: DNA
<213> ORGANISM: Homo sapiens

<400> SEQUENCE: 160
caccctgctg cagctctact tctgagcagc tcaaaaacca ctgaccaggc gcggtggctc      60
acacctgtaa tcccagcact ttgggaggcc gaggtgggtg gatcacgagg tcaggagatc     120

<210> SEQ ID NO 161
<211> LENGTH: 120
<212> TYPE: DNA
<213> ORGANISM: Homo sapiens

<400> SEQUENCE: 161
cacactgagc tgggtggggc agacatctgt gcaaaaaccc caccctctcc tgagccctaa      60
ccatactccc caggggcctt cacttaggga ctgggtggag gatatttgta agtaggtttc     120

<210> SEQ ID NO 162
<211> LENGTH: 120
<212> TYPE: DNA
<213> ORGANISM: Homo sapiens

<400> SEQUENCE: 162
cacagcgcca ggaggggatc agacaccgcg gcaagaaccc ctgcagctgc cctccgcccc      60
agcgggcccc ctgagtgctg agaggggaag cgtggagaat ggaaaaccac agctttcctg     120

<210> SEQ ID NO 163
<211> LENGTH: 120
<212> TYPE: DNA
<213> ORGANISM: Homo sapiens

<400> SEQUENCE: 163
cacagtgcag ggcacagatc aaagatctaa gcaagaacct cagctcccTT ctacccagct      60
cccctcacat gaacctgagg gccctgtcaa ggtgggacag aagaggaaac cacagctctt     120

<210> SEQ ID NO 164
<211> LENGTH: 120
<212> TYPE: DNA
<213> ORGANISM: Homo sapiens

<400> SEQUENCE: 164
gccacacaca ctcaagatgc cccagacacc ctgcactccg atcttactcg ttcctttact      60
gttttcatcc taattgccct cttacacatt tgaccacaca ttttggtct tggtggttgt     120

<210> SEQ ID NO 165
<211> LENGTH: 120
<212> TYPE: DNA
<213> ORGANISM: Homo sapiens

```
<400> SEQUENCE: 165
accatactag aactgttgaa acaacatgca caaaatcccc tcccagggtc tgtgcccacc    60
acatccttcc caacaggggc aaccacagcc agtccccagc tgggctccca gactcaggct   120

<210> SEQ ID NO 166
<211> LENGTH: 120
<212> TYPE: DNA
<213> ORGANISM: Homo sapiens

<400> SEQUENCE: 166
cacagcatca gtgccacact gtcccacaca acaacctctg ttgggtctct gcccaaccac    60
atccttccca tgggagcaaa ctctatggac tcctagctgg gctcccaccc tcagccttgc   120

<210> SEQ ID NO 167
<211> LENGTH: 120
<212> TYPE: DNA
<213> ORGANISM: Homo sapiens

<400> SEQUENCE: 167
cacagtgtta gagttgtcaa gataacctac acagaaacta tctccgagtc tgtgcctgtc    60
cacatccttc tccatgtggg caaccacagc ggtttgctca gctgggtgcc cagccggagc   120

<210> SEQ ID NO 168
<211> LENGTH: 120
<212> TYPE: DNA
<213> ORGANISM: Homo sapiens

<400> SEQUENCE: 168
ctcgtgggtg acacacagtg agacagatgg gcctgcacct gtgccgtttt cctctgtggg    60
gtgggagtca cagcctagaa agaagtccaa aagtgctttc taaaatttttt attttcaaaa   120

<210> SEQ ID NO 169
<211> LENGTH: 120
<212> TYPE: DNA
<213> ORGANISM: Homo sapiens

<400> SEQUENCE: 169
cacactggga cagatggggc tgcacctgtg caatatctcc ctggtggcaa gtgaggagga    60
gggtagcatt cacctagagc aaaatgtcga taggagtcaa aaagtaacaa gaaaagagga   120

<210> SEQ ID NO 170
<211> LENGTH: 120
<212> TYPE: DNA
<213> ORGANISM: Homo sapiens

<400> SEQUENCE: 170
cacagtggga cagatggggc tgcagctgtg caatatctcc ctggtgatga agggaaggc    60 atctaacgag gccactgcac aagaaggagc agaagtttaa tagaggaaga agaaaattta   120

<210> SEQ ID NO 171
<211> LENGTH: 120
<212> TYPE: DNA
<213> ORGANISM: Homo sapiens

<400> SEQUENCE: 171
cacagtgctg cacagctgcc tcctctctgc acataaaggg cagttagaat gactgaggtt    60
gcctgtgctc ccaagtccca gccttcacag gagtcggaga gccctggcta gcctgggggc   120
```

<210> SEQ ID NO 172
<211> LENGTH: 120
<212> TYPE: DNA
<213> ORGANISM: Homo sapiens

<400> SEQUENCE: 172
cacagtgctg cacagctgcc tcctctctgc acggaaacgg cagttagaaa aactgaggtt    60
gcctgtgcac ccaagtctgg gccccaccct gggacgtctc agcccccata ggagtcacag   120

<210> SEQ ID NO 173
<211> LENGTH: 120
<212> TYPE: DNA
<213> ORGANISM: Homo sapiens

<400> SEQUENCE: 173
cacagtgctg catggctgcc tcctctctgc acgtaaacag cagttagaaa gactgaggtt    60
gctctgtgtc tatccccacc cttggaagtc caggcctcca tagaagtcag agggccctgg   120

<210> SEQ ID NO 174
<211> LENGTH: 120
<212> TYPE: DNA
<213> ORGANISM: Homo sapiens

<400> SEQUENCE: 174
cacagcgcag cacagctgca tcctctctgc acaaaaagag cggacgtaag agagaagggg    60
ccctaactca gggctggtgc tggctccgat ggcacattcg tgctaaatag aaaaaaagcg   120

<210> SEQ ID NO 175
<211> LENGTH: 120
<212> TYPE: DNA
<213> ORGANISM: Homo sapiens

<400> SEQUENCE: 175
cacagtgctg cacggctgtc tcctctctgc acagaaaggc aagggaaggt gctgccctcc    60
tccgcagcac agattcagcg atgcccttgg tcctagcacc gaaaactttg gagccccaat   120

<210> SEQ ID NO 176
<211> LENGTH: 120
<212> TYPE: DNA
<213> ORGANISM: Homo sapiens

<400> SEQUENCE: 176
cacagtgctg cacagccatc tcctctctgt acataaatgc aggggaggct ctgccctcct    60
ccccgacccc agactcaacc atgtccttgg cagagttctc agcactggga atcttggaag   120

<210> SEQ ID NO 177
<211> LENGTH: 120
<212> TYPE: DNA
<213> ORGANISM: Homo sapiens

<400> SEQUENCE: 177
cacagcgctg caagcctgtc tcctctctgc acataaaggc acagaggctc tgccctcctc    60
ccacccaaga ctcaaggatg ccctgggcag agttctctgc accaggaacc ttggaaccca   120

<210> SEQ ID NO 178
<211> LENGTH: 120
<212> TYPE: DNA
<213> ORGANISM: Homo sapiens

<400> SEQUENCE: 178
cacagcgctg caaggctgtc tcctctctgc acataaaggc aagggaaggt gctgccctcc    60
tcccccaccc aagactcaag gatgccctgt gcagagatct ctgcaccagg aaccttggaa   120

<210> SEQ ID NO 179
<211> LENGTH: 120
<212> TYPE: DNA
<213> ORGANISM: Homo sapiens

<400> SEQUENCE: 179
cacagcgcta caaggccgtc tcctctctgc acataaaggc agggaggttc tgccctcctc    60
ccccacccaa gactcaggga tgccctgggc agagatctct gcgccaggaa ccttggaacc   120

<210> SEQ ID NO 180
<211> LENGTH: 112
<212> TYPE: DNA
<213> ORGANISM: Homo sapiens

<400> SEQUENCE: 180
gccagtagta tagacacagt gaagcacgga tgtcgcctct ctgtgcataa atgtgcccag    60
tcctgcttcc ccgaccaggt ggcagggctc ctctgcactc tatgatggca gg           112

<210> SEQ ID NO 181
<211> LENGTH: 120
<212> TYPE: DNA
<213> ORGANISM: Homo sapiens

<400> SEQUENCE: 181
cacagtgaag cacggatgtc gcctctctgt gcataaatgt gcccagtcct gcttccccga    60
ccaggtgaca gggctcctct gcactctatg atggcaggaa acgccactca gccactaagc   120

<210> SEQ ID NO 182
<211> LENGTH: 120
<212> TYPE: DNA
<213> ORGANISM: Homo sapiens

<400> SEQUENCE: 182
cacagcactg cacaggcatg tgctcacctc acaaaatggc agtctcaaag ggaggagtgc    60
ccacccacaa gaggctccac cctattctga gaaagaactt ctttcagagg aggagagaat   120

<210> SEQ ID NO 183
<211> LENGTH: 120
<212> TYPE: DNA
<213> ORGANISM: Homo sapiens

<400> SEQUENCE: 183
cacagcactg catagctgcc acatcctctc acataaaaaa aaggtgcata ccaaagagga    60
aaagcctgcc ctcaaaattc ctcaccgcaa ataagagaag ttacctcaca ggtattgaca   120

<210> SEQ ID NO 184
<211> LENGTH: 120
<212> TYPE: DNA
<213> ORGANISM: Homo sapiens

<400> SEQUENCE: 184
cacagtgcta catagatacc gacactctgc acagaaaggg tcgcctctaa ggtgaggaca    60
tcttgccttc agaaacctta tcttaaacta cagaaacccc tgcaaatctt cccagactcc   120

<210> SEQ ID NO 185

```
<211> LENGTH: 120
<212> TYPE: DNA
<213> ORGANISM: Homo sapiens

<400> SEQUENCE: 185
cacagtgttg cacagccagc tgctctctgc acaaaaacag agggtagctg caagaacaag      60
gagactcctc cttcaggaga cccctcaccg accaacagga taaacttcct ccatcatccc     120

<210> SEQ ID NO 186
<211> LENGTH: 120
<212> TYPE: DNA
<213> ORGANISM: Homo sapiens

<400> SEQUENCE: 186
cgcagccctg cacagccagc tgccctctgc acaaaagggg cagtcacagg ctggaggtgg      60
gcactcctta tggaagcccg tgtctcaacc agaagaaaaa gctgcccttt ctgaagctct     120

<210> SEQ ID NO 187
<211> LENGTH: 120
<212> TYPE: DNA
<213> ORGANISM: Homo sapiens

<400> SEQUENCE: 187
cacagtgctt cttggccacc tgctctctac acagaaagac agacacatgg gtgagttgtt      60
tgctctgaag ggtacctgga tgtgggttgt gggatgtggg gtgtttagag ctttcagtgg     120

<210> SEQ ID NO 188
<211> LENGTH: 120
<212> TYPE: DNA
<213> ORGANISM: Homo sapiens

<400> SEQUENCE: 188
cacagccttg caaagacaac tccagcctgt gcaaaatccc tcacagagct gcctccctcc      60
cagccgccag ctcccacttc ctgcctaaga aaaggaagtc tctggttggg tttgttcttg     120

<210> SEQ ID NO 189
<211> LENGTH: 120
<212> TYPE: DNA
<213> ORGANISM: Homo sapiens

<400> SEQUENCE: 189
cacagcgttg cagagacttt ctctcctgtg cacaaaactc cagggctctc tccgctctac      60
tcagctcaca gcagcctttc cttattcctc atcctctcag ggaagaagtg agttttcaga     120

<210> SEQ ID NO 190
<211> LENGTH: 120
<212> TYPE: DNA
<213> ORGANISM: Homo sapiens

<400> SEQUENCE: 190
cacagtgtag cagagacact tccctcctgt gcagaaaacc agaaaccgc aggactctct      60 cctctctact cagctcacag cagcctttcc ttattcctca tcctcccaag gaagaagtga     120

<210> SEQ ID NO 191
<211> LENGTH: 120
<212> TYPE: DNA
<213> ORGANISM: Homo sapiens

<400> SEQUENCE: 191
cacagtgtag cagagacact tccctcctgt gcagaaaacc gcaggactct ctcctctcta      60
```
ctcagctcac agcagccttt ccttattcct catcctccca ggaaagaagt gagtttcag    120

<210> SEQ ID NO 192
<211> LENGTH: 120
<212> TYPE: DNA
<213> ORGANISM: Homo sapiens

<400> SEQUENCE: 192
cacagagctg cagtgcttcc tgctctctgt tcataaacct cattgtttcc cagatccagg    60
tgctttctct aggacttctc cctcaccacc tcttacaaca ataggaagtg ggttggtggc    120

<210> SEQ ID NO 193
<211> LENGTH: 120
<212> TYPE: DNA
<213> ORGANISM: Homo sapiens

<400> SEQUENCE: 193
cacagcgctg cagaatcacc tgctccctgt gcagaaaccc tggtgcttcc tcttctcctc    60
cagtacccag cagctctcag cagcctttct tgctcctccc ctagcacagg aagtacatag    120

<210> SEQ ID NO 194
<211> LENGTH: 120
<212> TYPE: DNA
<213> ORGANISM: Homo sapiens

<400> SEQUENCE: 194
cacagcactg cagaatctcc ccatctctgt gcagaaaccc tggtgcttcc tcttctcccc    60
acagctctca gcagtcgtca gcaaagtctt tcctgctctc tgctcaccat ggctcacgcc    120

<210> SEQ ID NO 195
<211> LENGTH: 120
<212> TYPE: DNA
<213> ORGANISM: Homo sapiens

<400> SEQUENCE: 195
cacagcatga cacaatcgcc tccttcctgc tcataaacct cctcctctct ctccttgctt    60
ccttatgata ctattttgca ccaggggatc ctcatctcac accactccac tgcctcttcc    120

<210> SEQ ID NO 196
<211> LENGTH: 120
<212> TYPE: DNA
<213> ORGANISM: Homo sapiens

<400> SEQUENCE: 196
cacagcatgg cacagtcgcc tccttcctgc tcacaaaccc tcaggcactt acttctcctt    60
ccagctctca gaagccctga acaaaggagc tgccctgctc tttcctcagc aaggagaatg    120

<210> SEQ ID NO 197
<211> LENGTH: 120
<212> TYPE: DNA
<213> ORGANISM: Homo sapiens

<400> SEQUENCE: 197
cacagcatgg cacagtcgcc tccttcctgc tcataaacct catccttctc tctccttgca    60
gctcctagac acccttaaca gaggcttctc tttgcttctc cctccccatg ggaaacaagt    120

<210> SEQ ID NO 198
<211> LENGTH: 120
<212> TYPE: DNA

<213> ORGANISM: Homo sapiens

<400> SEQUENCE: 198
cacagtgtgg catagtcgcc tccttcctgt tcacaaacct catccttctc tctccttgca     60
cctcctagag acccttaaca gaggcctctc tttgctcctc acttttgatg ggaaagaagt    120

<210> SEQ ID NO 199
<211> LENGTH: 120
<212> TYPE: DNA
<213> ORGANISM: Homo sapiens

<400> SEQUENCE: 199
cacagcatgg ctgagtcagt tccctccagg gtgcaaaccc tctggctgct cttctcccag     60
ttgaactcca agaaaacatt tgaaaaagcc tcttccttat cttcctaccc cagaagaaag    120

<210> SEQ ID NO 200
<211> LENGTH: 120
<212> TYPE: DNA
<213> ORGANISM: Homo sapiens

<400> SEQUENCE: 200
cacagcccag cagagtcact gacattctgt atataaactt ccgccttagc tttgacttga     60
gaactgcagg ccccacccag gttttcactcc ttcaagggaa gcttttagtt gtttggaagg    120

<210> SEQ ID NO 201
<211> LENGTH: 120
<212> TYPE: DNA
<213> ORGANISM: Homo sapiens

<400> SEQUENCE: 201
cacagcccat cagagtcact gacgttctgt atataaactt cctgccttag ctttgccttg     60
agagctgcag gccccaccca gatttcactc cttcaaggga agcttttagt tgtttggaag    120

<210> SEQ ID NO 202
<211> LENGTH: 120
<212> TYPE: DNA
<213> ORGANISM: Homo sapiens

<400> SEQUENCE: 202
cacagcccta caaagccaac cacattctgt gcacaaacct ccctggccca atgtggagca     60
acctcagccc tgacatatct gtgagaacct ggggactgca gggagaaaga aaggcaattt    120

<210> SEQ ID NO 203
<211> LENGTH: 120
<212> TYPE: DNA
<213> ORGANISM: Homo sapiens

<400> SEQUENCE: 203
cacagccctg cagagtcact ggaactctgt gcactaatct ctctgcttcc gtgtacagca     60
gtctcagacc agacagctgt gagaacctgg ggccttcagg gggaaagata aacaatttca    120

<210> SEQ ID NO 204
<211> LENGTH: 120
<212> TYPE: DNA
<213> ORGANISM: Homo sapiens

<400> SEQUENCE: 204
atgcaggcct gcagagccaa gaacattctg tgtacaaaca tccctgcccc agtgtggaga     60
acttcagccc taacatatct gtgagaactt gaggactgta gtgggaaaga aaagcagttt    120

<210> SEQ ID NO 205
<211> LENGTH: 120
<212> TYPE: DNA
<213> ORGANISM: Homo sapiens

<400> SEQUENCE: 205
cacagccttg cagagtcacc gctttcctgt gcagaaacct tcggggcctg ccaggaagcc      60
gtgggggcca cggagggctc gggtgaacat ttcctccaag agccccgaag aagcttcaga     120

<210> SEQ ID NO 206
<211> LENGTH: 120
<212> TYPE: DNA
<213> ORGANISM: Homo sapiens

<400> SEQUENCE: 206
cacagccctg cagagtcacc gcctccctgt gcacaaacct cctggatcta atcagaaaac      60
cgtgggggca acgcatccag ctgagcctca gcactcggtt cagcattctg taagacctca     120

<210> SEQ ID NO 207
<211> LENGTH: 120
<212> TYPE: DNA
<213> ORGANISM: Homo sapiens

<400> SEQUENCE: 207
acacagcctt acagagccac tgcatccctg tgcacaaacc tcccggctca gccaggaagc      60
tgtgggccgt gtgtgcacct gcacccaagg ctccagtctc cattccctga tggcctctga     120

<210> SEQ ID NO 208
<211> LENGTH: 120
<212> TYPE: DNA
<213> ORGANISM: Homo sapiens

<400> SEQUENCE: 208
cacattgatg cagagccaca tcctctcagt ccacaaacat cctccagacc tgccttggaa      60
acagcggtgg gccaggaagg gaaacgcgtt acctgtacag tgaacaggtc agctctacgg     120

<210> SEQ ID NO 209
<211> LENGTH: 120
<212> TYPE: DNA
<213> ORGANISM: Homo sapiens

<400> SEQUENCE: 209
cacagccctg catgagcatc agccttctgt gcaataacat tcctgcccca ctcaggaagt      60
gacggtgagg ggagggctgc cagccagagg ggctcaggcc ctggagagtg acaggcctt     120

<210> SEQ ID NO 210
<211> LENGTH: 120
<212> TYPE: DNA
<213> ORGANISM: Homo sapiens

<400> SEQUENCE: 210
cacagaccct ggagaattac tggctttctg tacccaaacc ctcctatctc acttgaggat      60
gtaataggga gaaggaggtg ggggctgcca cacaacttta gccaagcccc agagatgctt     120

<210> SEQ ID NO 211
<211> LENGTH: 120
<212> TYPE: DNA
<213> ORGANISM: Homo sapiens

```
<400> SEQUENCE: 211
cacagcgatc ttcaggcctc tatcagctgt ctccaaacct gcagctgggc cacatatgct    60
cttctgacat ggggctcctg agatgtggct gggacctttg ccaagacatg aagtctcaga   120

<210> SEQ ID NO 212
<211> LENGTH: 120
<212> TYPE: DNA
<213> ORGANISM: Homo sapiens

<400> SEQUENCE: 212
cacagtgata cccaggcctc caagacctgt actcaaacct aaagctgagc cgcagatgct    60
cccctagcac agatgcccac acaggagta tggggaactt accagaaggt tcatccatga   120

<210> SEQ ID NO 213
<211> LENGTH: 120
<212> TYPE: DNA
<213> ORGANISM: Homo sapiens

<400> SEQUENCE: 213
cacagtactc cctaggcacc tgcaacctgt atccaaacat gcagctgggt agaagtacca    60
taacagaagc atcagcaata ggggccctga gcctgagtag acgtgaagaa ctaaggcatg   120

<210> SEQ ID NO 214
<211> LENGTH: 120
<212> TYPE: DNA
<213> ORGANISM: Homo sapiens

<400> SEQUENCE: 214
cacagtgctc cccaggcacc tgcggcctgt acacaaaccc tcatccgggc tcggttcctc    60
taccagtaac aaccacatca cgaggccacc gcagcagcat tttgcacagc ttaatattcc   120

<210> SEQ ID NO 215
<211> LENGTH: 120
<212> TYPE: DNA
<213> ORGANISM: Homo sapiens

<400> SEQUENCE: 215
cacagtagtg ccctggcagc tgcttcctgc acccaaactc tgctaactct cacaatcaga    60
gctcatggct gtgctgtctc ccaaaggcta atcacagctc ctgacagaat gggggggtgt   120

<210> SEQ ID NO 216
<211> LENGTH: 120
<212> TYPE: DNA
<213> ORGANISM: Homo sapiens

<400> SEQUENCE: 216
cacagtgctc ttgaggcacc tgctgcctgc acccaaaccc tgctgccagc cccagtcacg    60
aggctgccac atgcctccag ctccgcctcg cacagcttat ggcatgaata gagagaacaa   120

<210> SEQ ID NO 217
<211> LENGTH: 120
<212> TYPE: DNA
<213> ORGANISM: Homo sapiens

<400> SEQUENCE: 217
cacagcgttc cccaggcacc tgcaacttgt atcaaaaccc tgcagctgag gatctgaaat    60
gatggcagag gtatctctgc tgttcttcct cttgaaggag tatttattta atgcccagga   120
```

```
<210> SEQ ID NO 218
<211> LENGTH: 120
<212> TYPE: DNA
<213> ORGANISM: Homo sapiens

<400> SEQUENCE: 218
cacagtgctc cctagtcacc tgcagcctgt actcaaattc tacagctgag gctctgcaac      60
tgtaagatgg ggaacttgct acattgagca agccctcaaa ataaactat acggaaaagc     120

<210> SEQ ID NO 219
<211> LENGTH: 120
<212> TYPE: DNA
<213> ORGANISM: Homo sapiens

<400> SEQUENCE: 219
cacagtgcac aacaggcacc tgcaaccaat acccaaactc tatagctggg gctctaactg      60
catgttttat cttgagactg agcaatgttt ttgcattaag aggacttcta aattgacact     120

<210> SEQ ID NO 220
<211> LENGTH: 120
<212> TYPE: DNA
<213> ORGANISM: Homo sapiens

<400> SEQUENCE: 220
cacagtgctc cccaggcacc tggagcccgt acctaaactc taaagttgag gcatcatttc      60
ttactcctgt ctttcagact tgtctgtctc tatccttggt cagatgatgt aaaatgttta     120

<210> SEQ ID NO 221
<211> LENGTH: 120
<212> TYPE: DNA
<213> ORGANISM: Homo sapiens

<400> SEQUENCE: 221
cacagtgccc acagtcacct gcacccggta cctaaagctt gctgaggggc ctgggcacac      60
ctcctttttat aagggccctg ggcactgac tataactctg ctgcatacaa agggaaatat     120

<210> SEQ ID NO 222
<211> LENGTH: 120
<212> TYPE: DNA
<213> ORGANISM: Homo sapiens

<400> SEQUENCE: 222
agtagtgtct ccccagcacc tgcagcctgt accataacct gcagccggga cccttgacac      60
aggctagcct tgcaggtggg agtgaagatt ttttttttt ttttgtatag agggaacttt      120

<210> SEQ ID NO 223
<211> LENGTH: 120
<212> TYPE: DNA
<213> ORGANISM: Homo sapiens

<400> SEQUENCE: 223
cacagggtcc ccaagcacct gcagcctgta ccacaacctg catccgggac ccttgacaca      60
gccttgcctt gcaggtggga gtgaaggtgt tgtctttata tgtagagaga acttcttttat    120

<210> SEQ ID NO 224
<211> LENGTH: 120
<212> TYPE: DNA
<213> ORGANISM: Homo sapiens

<400> SEQUENCE: 224
```

```
cacagtgttc cccaggaacc tgcagcctct acgcaaaccc tgccaaagca gcttcttaga      60
agccctaata gtgggtagaa ttagtggtta tgtctttcag tcaagaagag tctacaaaca     120
```

<210> SEQ ID NO 225
<211> LENGTH: 120
<212> TYPE: DNA
<213> ORGANISM: Homo sapiens

<400> SEQUENCE: 225

```
cactgtgctc cacaggcact tgaagccagt atgcaaacct gcacctggag gttatcaagg      60
aggcatagga gttagagtag accgttattt tttatgcaga atatgatttc actagtgaat     120
```

<210> SEQ ID NO 226
<211> LENGTH: 120
<212> TYPE: DNA
<213> ORGANISM: Homo sapiens

<400> SEQUENCE: 226

```
cacagcacta ctgctccagt gtcagcttgg ttccctagga aatggggttt ctagaacctg      60
aatgctgaca ataagagtt gtatatgtgt ataccatgca acctgcgttt aaaaatgtat     120
```

<210> SEQ ID NO 227
<211> LENGTH: 120
<212> TYPE: DNA
<213> ORGANISM: Homo sapiens

<400> SEQUENCE: 227

```
cacagtgctg ttcaggcacc tgcagcccat acgcaaacct gtgtctggtg ttgcactgtt      60
accagcattg acaaagaacc atgagtagga tggaaaagac aagttcgttg aattacagtt     120
```

<210> SEQ ID NO 228
<211> LENGTH: 120
<212> TYPE: DNA
<213> ORGANISM: Homo sapiens

<400> SEQUENCE: 228

```
cacagtgctc ccctgacgcc accagtctgt acccaaacct gcagctggtg ggcccactcc      60
tcctgcagga actatgactg tgaggcttcg ttcactgtct gtacatttct ttctgcaagg     120
```

<210> SEQ ID NO 229
<211> LENGTH: 120
<212> TYPE: DNA
<213> ORGANISM: Homo sapiens

<400> SEQUENCE: 229

```
cacagtgctc cccaaacacc tgcagcctgt actcaaactt gcagctggaa ctctagtctc      60
tatgctgcct tcagctctta gtcctcttgg catgaaatgt gattatgcat gccacctttg     120
```

<210> SEQ ID NO 230
<211> LENGTH: 120
<212> TYPE: DNA
<213> ORGANISM: Homo sapiens

<400> SEQUENCE: 230

```
cacagtgctc cccagacacc tgcagtctgt acccaaacct gccatgcccc aggaatgcct      60
gatgtagagc ttagactgca gggtagtgaa actccccttg ctctctagtt tcaagtggaa     120
```

<210> SEQ ID NO 231
<211> LENGTH: 120

```
<212> TYPE: DNA
<213> ORGANISM: Homo sapiens

<400> SEQUENCE: 231
cacagtgctc tccaggcacc tgcagcccgt actcaaacct gctttgggga ctcagactgg      60
gagacacata gactcgcttc catttacaca tgccaatatg agagattatg ctttgaagta     120

<210> SEQ ID NO 232
<211> LENGTH: 120
<212> TYPE: DNA
<213> ORGANISM: Homo sapiens

<400> SEQUENCE: 232
cacagtgctc cccaggcacc tgaagcctgt acccaaacct gcagttgagg ttccagccaa      60 acccacagt gggagcttac gtaggcagag atgtagccta gttttcatct gcatatgcaa     120

<210> SEQ ID NO 233
<211> LENGTH: 120
<212> TYPE: DNA
<213> ORGANISM: Homo sapiens

<400> SEQUENCE: 233
cactgtgctc ttcagacacc tgcagcctat acatgaaacc atagctgaag gcctaaccca      60
tccccgagag tggcagtagg tcccgatgtg attagcattg cattcccact gcctacatct     120

<210> SEQ ID NO 234
<211> LENGTH: 120
<212> TYPE: DNA
<213> ORGANISM: Homo sapiens

<400> SEQUENCE: 234
cacagtgctc cccaagcacc tgctgcctgt ctccaaatct gccctgggt cttcaggagc      60 agatcatcct actctcccca aagagcgggc gccagagaaa gccaaagtca caatgtctgt     120

<210> SEQ ID NO 235
<211> LENGTH: 120
<212> TYPE: DNA
<213> ORGANISM: Homo sapiens

<400> SEQUENCE: 235
cacagaactc ttcaggcacc tgcaacctgt actcaaacct gcaactggga gtccagtcac      60
attctttgtc tttgaacggg ttttgggtta gaatggttta ccataatgtg cttgtttcta     120

<210> SEQ ID NO 236
<211> LENGTH: 120
<212> TYPE: DNA
<213> ORGANISM: Homo sapiens

<400> SEQUENCE: 236
cacattgctt ctcaggcacc tgtatcctgt acccaaacct gcacctggga ctaaagccac      60
actctatttc ctttaccttt aagtcaggga ttttgctgta aggtattttt aatgtacgga     120

<210> SEQ ID NO 237
<211> LENGTH: 120
<212> TYPE: DNA
<213> ORGANISM: Homo sapiens

<400> SEQUENCE: 237
cacattgctt tccaggcatc tgtaaccatc acccaaacct gagatgggag gtgaagcagc      60
```

```
atcccttcc tttgcaataa attttagtta tagcacttgt cattttgttt gttcataagt    120

<210> SEQ ID NO 238
<211> LENGTH: 120
<212> TYPE: DNA
<213> ORGANISM: Homo sapiens

<400> SEQUENCE: 238
gcagcaagta cacattgctt cccaggcacc tgctacccgt acacaaacct gagactggag    60
ctgaagctgc accccctttc ctttgtcata gatcgtcaat tatagcattt gtcatattgt    120

<210> SEQ ID NO 239
<211> LENGTH: 120
<212> TYPE: DNA
<213> ORGANISM: Homo sapiens

<400> SEQUENCE: 239
cacacttcag cccagccttt ctgggccaac tctccatctg tagagacaca tccaaggccc    60
agttatccct gcagctgagc tccgtgatgg ccaagggcag ggccgcacat tcccgtggga    120

<210> SEQ ID NO 240
<211> LENGTH: 120
<212> TYPE: DNA
<213> ORGANISM: Homo sapiens

<400> SEQUENCE: 240
gcttgttgct catgtagctc agccatagga agagctgccc cggcggacat agatctggag    60
gtggcgactg gactcttgag gagtgggttg gaattttgc tgccttcatg acctgtgcac     120

<210> SEQ ID NO 241
<211> LENGTH: 120
<212> TYPE: DNA
<213> ORGANISM: Homo sapiens

<400> SEQUENCE: 241
aatccaaccc actcctcaag agtccagtca ccatctccag atccacatcc aaaaaacagt    60
ttctcctaca gctgagctac cttaacaagg agtacacaac catgattttt atacaaaga    120

<210> SEQ ID NO 242
<211> LENGTH: 120
<212> TYPE: DNA
<213> ORGANISM: Homo sapiens

<400> SEQUENCE: 242
catcatgcac cctccaccca ggtccatgtc cccatcaaca gtgactcaac caagagccag    60
ttctctgtga agctcagctc catgaccacc taggacacgg ctgagtatta ctgtgaaaga    120

<210> SEQ ID NO 243
<211> LENGTH: 120
<212> TYPE: DNA
<213> ORGANISM: Homo sapiens

<400> SEQUENCE: 243
gtgaagggag cacaaattac aacccactgc tcaagagtcc atatccagat ccaagaaaca    60
gttcttacag ctgagctctg tgcccagtga acacacaact acgcattttt aagcaaaaga    120

<210> SEQ ID NO 244
<211> LENGTH: 120
<212> TYPE: DNA
<213> ORGANISM: Homo sapiens
```

```
<400> SEQUENCE: 244
ttactcccct cttctcaaga gtccagtcac catctccaga tccatgtcca aaaagtagtt      60
cttcttacag ctgaactatg tgaggaacaa acacatagcc atgtatttta gagcaaaaga     120

<210> SEQ ID NO 245
<211> LENGTH: 120
<212> TYPE: DNA
<213> ORGANISM: Homo sapiens

<400> SEQUENCE: 245
ttacaaccca cttctcaaga gtccatatcc ggatccaaga aacagttctt acagctgagc      60
tctgtgccca gtgaacacac aactacgcat tttgaagcaa aagatgcaat gaagggcctt    120

<210> SEQ ID NO 246
<211> LENGTH: 120
<212> TYPE: DNA
<213> ORGANISM: Homo sapiens

<400> SEQUENCE: 246
ttacaaccca ctgctcaaga gtccatatcc agatccaaga aacagttctt acagctgagc      60
tctgtgccca gtgaacacac aactacgcat ttttaagcaa aagacgcaat gaagggcctt    120

<210> SEQ ID NO 247
<211> LENGTH: 120
<212> TYPE: DNA
<213> ORGANISM: Homo sapiens

<400> SEQUENCE: 247
ttactcccct cttctcaaga gtccagtcac catctccaga tccatgtcca aaaagtactt      60
cttcttacag gtgaactatg tgagcaacaa acacatagcc atgtatttta gagcaaaaga    120

<210> SEQ ID NO 248
<211> LENGTH: 120
<212> TYPE: DNA
<213> ORGANISM: Homo sapiens

<400> SEQUENCE: 248
ttacatccca cttctcaaga gtccatatcc agatccaaga aacagttctt acagctgagc      60
tctgtgccca gtgaacacac aactacacat tttgaagcaa aagacgcaat gaagggcctt    120

<210> SEQ ID NO 249
<211> LENGTH: 77
<212> TYPE: DNA
<213> ORGANISM: Homo sapiens

<400> SEQUENCE: 249
agcctggtga agcccttgca aacccctca ctcacctgtg ctgcctctgg attctctgtc      60
acaatcagtg cttcctg                                                    77

<210> SEQ ID NO 250
<211> LENGTH: 120
<212> TYPE: DNA
<213> ORGANISM: Homo sapiens

<400> SEQUENCE: 250
catgaaggga gcacaaattc taacccactc ctcaagagtc cagtcaccac ctccagatct      60
atgtccaaaa acagctcttc gtatggctga gtgacattag caacaagcac acagccatgt    120
```

<210> SEQ ID NO 251
<211> LENGTH: 120
<212> TYPE: DNA
<213> ORGANISM: Homo sapiens

<400> SEQUENCE: 251
catgaaggga gcacaaattc taacccactc ctcaagagtc cagtcaccac ctccagatct     60
atgtccaaaa acagctcttc gtatggctga gtgacattag caacaagcac acaaccatgt    120

<210> SEQ ID NO 252
<211> LENGTH: 120
<212> TYPE: DNA
<213> ORGANISM: Homo sapiens

<400> SEQUENCE: 252
acgatgatcc atctctgcag agccaactct ccttctccag agattcatcc aagaaacaat     60
tttgactata cctgagctct gtgacatctg aggacatggt ttgtattact gtgcaagaca    120

<210> SEQ ID NO 253
<211> LENGTH: 120
<212> TYPE: DNA
<213> ORGANISM: Homo sapiens

<400> SEQUENCE: 253
gacctgaata gcacacactt accctctgcc tcacctacac tgttactggc cactccgtca     60
caaccagtcc ttactagtgg acctggatct gccggctctc agggaggggc tgcaatggat    120

<210> SEQ ID NO 254
<211> LENGTH: 120
<212> TYPE: DNA
<213> ORGANISM: Homo sapiens

<400> SEQUENCE: 254
acgcaaccca cgcctcaaga gtccagtcac catctccaga tccacatcca aaacacagtt     60
tcttctacag ctgagctacc tgagcaacga gtacacaacc atgaattttt acacaaaaga    120

<210> SEQ ID NO 255
<211> LENGTH: 120
<212> TYPE: DNA
<213> ORGANISM: Homo sapiens

<400> SEQUENCE: 255
aattctaacc cactcctcat gagctcagtc accatctcca gatccacgtc caagaaccaa     60
attttctttt agctgagttc tgtgaccaac aatgccacaa ccttgtatta ctgtgagagg    120

<210> SEQ ID NO 256
<211> LENGTH: 120
<212> TYPE: DNA
<213> ORGANISM: Homo sapiens

<400> SEQUENCE: 256
attccaaccc actcctcaag agtccagtca ccatctccag atccatgtcc aaaaagcagt     60
tcttcctaca gccgagctaa gtgagtcaca agcacacagc catgtatttt taacaaaaga    120

<210> SEQ ID NO 257
<211> LENGTH: 120
<212> TYPE: DNA
<213> ORGANISM: Homo sapiens

<400> SEQUENCE: 257
aaattcccac ccactcctta tgaatccagt caccatctcc aaattcgggt ccaaaaaaca    60
cttgttttta cagtggagct atgtgagcaa caagctcaca gccatgtttt aaagaagaga   120

<210> SEQ ID NO 258
<211> LENGTH: 120
<212> TYPE: DNA
<213> ORGANISM: Homo sapiens

<400> SEQUENCE: 258
attactcccc tttcctcaag agtccagtca ccatccccag atccatgtcc aaaaacagtt    60
cttcctacag ctgagctaca tgagcaacaa tcacatagcc atatatttt cagcaataga   120

<210> SEQ ID NO 259
<211> LENGTH: 120
<212> TYPE: DNA
<213> ORGANISM: Homo sapiens

<400> SEQUENCE: 259
ttccaaccca ctcctcaaga gtccagtcac tatctccaga tccacatcca aaaacagtg    60 tttcctgtag ctgagctacc tgagcaacaa gtacacaacc atgaattta atacaaaaga   120

<210> SEQ ID NO 260
<211> LENGTH: 120
<212> TYPE: DNA
<213> ORGANISM: Homo sapiens

<400> SEQUENCE: 260
atgcctaggt gtgaagatca cacactgacc tcacccatgc tgtctctggc cacttcatca    60
caaccaatgc ttaatattgg acgtggatct gccagtcccc ggggaatggg ttgaatggat   120

<210> SEQ ID NO 261
<211> LENGTH: 120
<212> TYPE: DNA
<213> ORGANISM: Homo sapiens

<400> SEQUENCE: 261
ggcagcaaca gggagaaatt caagaggaag ttcttacatg cacccttacg tgcacggtct    60
cactgagatc tttacttcct ttatcacgtt tgttctgtaa atcacaacga atggtgcatt   120

<210> SEQ ID NO 262
<211> LENGTH: 120
<212> TYPE: DNA
<213> ORGANISM: Homo sapiens

<400> SEQUENCE: 262
tgggactctc cttgagtaaa aagatgatta acaatcctca aatacactca gttcaggaga    60 ttctcttta agatgattaa cctgagagct caggaaaagt ccgtgtatta ctttgaggga   120

<210> SEQ ID NO 263
<211> LENGTH: 120
<212> TYPE: DNA
<213> ORGANISM: Homo sapiens

<400> SEQUENCE: 263
tcagagttac tctccatgag tacaaataaa ttaacagtcc caagcgacac cttttcatgt    60
gcagtctacc ttaaagggac caaactgaaa gtcaaggaca aggccttgta atactgtgag   120

<210> SEQ ID NO 264

```
<211> LENGTH: 120
<212> TYPE: DNA
<213> ORGANISM: Homo sapiens

<400> SEQUENCE: 264
accagaagaa tgctatcatc atctttctg ttcttttgga aggaatgccc cctctactca      60
cctccacttg cctgcatata tttctatttg tctttgcttt tcagcagttt taataagatt     120

<210> SEQ ID NO 265
<211> LENGTH: 120
<212> TYPE: DNA
<213> ORGANISM: Homo sapiens

<400> SEQUENCE: 265
gggttacttt ccatgagtac aaataaatta acaatctcaa gcaacaccct tttaagtgca      60
gtctgcctta caatgaccaa tctgaaagcc aaggacaagg tcatgtatta ctgtgagtga     120

<210> SEQ ID NO 266
<211> LENGTH: 120
<212> TYPE: DNA
<213> ORGANISM: Homo sapiens

<400> SEQUENCE: 266
gcaagctcca ggaccagggt tgatgtgggc agcaacaggg agaaattgaa gaggaagctc      60
tcagtggtgc cctccatgaa tacaaagaat cttcacagtc cccaggacac ccttacgtgc     120

<210> SEQ ID NO 267
<211> LENGTH: 120
<212> TYPE: DNA
<213> ORGANISM: Homo sapiens

<400> SEQUENCE: 267
agaggaagct ctcagtggtg ccctccatga atacaaagaa tcttcacagt ccccaggaca      60
cccttacgtg catggtctca ctgatatctt tacttccttt atcacttttg ttatgtaaat     120

<210> SEQ ID NO 268
<211> LENGTH: 120
<212> TYPE: DNA
<213> ORGANISM: Homo sapiens

<400> SEQUENCE: 268
gggttactct ccatgagtac agataaatca acattcccaa gtgacaccct ttcaagtgca      60
gtctaccttA caaggaccaa cctgaaagcc aagggcaagg ccgtatatta cagtgaggga     120

<210> SEQ ID NO 269
<211> LENGTH: 120
<212> TYPE: DNA
<213> ORGANISM: Homo sapiens

<400> SEQUENCE: 269
aatgggactc gccttcagta caaagaagat taacagtcct cagagacact gttcagaaga      60
ttctctttta agataataaa actgagagcc caagacaagt ctgtgtatta ctgtgaggga     120

<210> SEQ ID NO 270
<211> LENGTH: 120
<212> TYPE: DNA
<213> ORGANISM: Homo sapiens

<400> SEQUENCE: 270
aatgggactc gccttcagta caaagaagat taacagtcct cagagacact gttcagaaga      60
```

```
ttctctttta agataataaa accgagagcc caagacaagt ctgtgtatta ctgtgaggga      120
```

<210> SEQ ID NO 271
<211> LENGTH: 120
<212> TYPE: DNA
<213> ORGANISM: Homo sapiens

<400> SEQUENCE: 271

```
agtgggactc tccttcagta caaagaagat taacagtcct cagagacact gttcagaaga       60
ttctctttta agataattaa accaagagcc caggacaagt ctgtgtatta ctgtgaggga      120
```

<210> SEQ ID NO 272
<211> LENGTH: 120
<212> TYPE: DNA
<213> ORGANISM: Homo sapiens
<220> FEATURE:
<221> NAME/KEY: misc_feature
<222> LOCATION: (80)..(80)
<223> OTHER INFORMATION: n is a, c, g, or t

<400> SEQUENCE: 272

```
tttaggaaga atgccccctc aactcatctc cacttgtctg catgtatttc tatttgtctt       60
ggacgttccc aacagcctcn cgaacactca cctcacccta caatgctgct cgaggggtc      120
```

<210> SEQ ID NO 273
<211> LENGTH: 120
<212> TYPE: DNA
<213> ORGANISM: Homo sapiens

<400> SEQUENCE: 273

```
attttcctct tgcttataag gttttaacca gaagaatgct gtcatcatct ttcctgttct       60
tttagaagga atgccccctc aactcatctc cacttgtctg catgtatttc tatttgtctt      120
```

<210> SEQ ID NO 274
<211> LENGTH: 99
<212> TYPE: DNA
<213> ORGANISM: Homo sapiens

<400> SEQUENCE: 274

```
gatttatcat ctcaagagac aatgtcaaga agatgctgtt tctgcaaatg ggcaatctgc       60
aaaccaagga cacgtcacta cattactgtg caagagaag                              99
```

<210> SEQ ID NO 275
<211> LENGTH: 120
<212> TYPE: DNA
<213> ORGANISM: Homo sapiens

<400> SEQUENCE: 275

```
caatgcagac tatgttaggg gcagactcac cacttccaga acaacacca agtacatgct       60 gtacatgcaa atgaacagcc tgagaaccca gaacatggca gcatttaact gtgcaggaaa      120
```

<210> SEQ ID NO 276
<211> LENGTH: 118
<212> TYPE: DNA
<213> ORGANISM: Homo sapiens

<400> SEQUENCE: 276

```
tacactttg gccaggggac caagctggaa atcagacgta agtactttt tccactgatt       60 cttcactgtt gctaattagt ttactttgtg ttcctttgtg tggattttca ttagtcgg       118
```

<210> SEQ ID NO 277
<211> LENGTH: 120
<212> TYPE: DNA
<213> ORGANISM: Homo sapiens

<400> SEQUENCE: 277
gatcaccttc ggccaaggga cacgactgga gattaaacgt aagtaatttt tcactattgt    60
cttctgaaat ttgggtctga tggccagtat tgacttttag aggcttaaat aggagtttgg   120

<210> SEQ ID NO 278
<211> LENGTH: 120
<212> TYPE: DNA
<213> ORGANISM: Homo sapiens

<400> SEQUENCE: 278
gctcactttc ggcggaggga ccaaggtgga gatcaaacgt aagtgcactt tcctaatgct    60
ttttcttata aggttttaaa tttggagcgt ttttgtgttt gagatattag ctcaggtcaa   120

<210> SEQ ID NO 279
<211> LENGTH: 120
<212> TYPE: DNA
<213> ORGANISM: Homo sapiens

<400> SEQUENCE: 279
attcactttc ggccctggga ccaaagtgga tatcaaacgt aagtacatct gtctcaatta    60
ttcgtgagat tttagtgcca ttgtatcatt tgtgcaagtt tgtgatatt tggttgaat    120

<210> SEQ ID NO 280
<211> LENGTH: 120
<212> TYPE: DNA
<213> ORGANISM: Homo sapiens

<400> SEQUENCE: 280
tgtacacttt tggccagggg accaagctgg agatcaaacg taagtacttt tttccactga    60
ttcttcactg ttgctaatta gtttactttg tgttcctttg tgtggatttt cattagtcgg   120

<210> SEQ ID NO 281
<211> LENGTH: 120
<212> TYPE: DNA
<213> ORGANISM: Homo sapiens

<400> SEQUENCE: 281
gtggacgttc ggccaaggga ccaaggtgga aatcaaacgt gagtagaatt taaactttgc    60
ttcctcagtt gtctgtgtct tctgttccct gtgtctatga agtgatctat aaggtgactc   120

<210> SEQ ID NO 282
<211> LENGTH: 120
<212> TYPE: DNA
<213> ORGANISM: Homo sapiens

<400> SEQUENCE: 282
ggacgttcgg ccaagggacc aaggtggaaa tcaaacgtga gtagaattta actttgctt    60 cctcagttgt ctgtgtcttc tgttccctgt gtctatgaag tgatctataa ggtgactctg   120

<210> SEQ ID NO 283
<211> LENGTH: 120
<212> TYPE: DNA
<213> ORGANISM: Homo sapiens

<400> SEQUENCE: 283

```
ggctcctgct ccagcccagc ccccagagag cagaccccag gtgctggccc cgggggtttt      60
ggtctgagcc tcagtcactg tgttatgtct tcggaactgg gaccaaggtc accgtcctag     120

<210> SEQ ID NO 284
<211> LENGTH: 120
<212> TYPE: DNA
<213> ORGANISM: Homo sapiens

<400> SEQUENCE: 284
ttatgtcttc ggaactggga ccaaggtcac cgtcctaggt aagtggctct caacctttcc      60
cagcctgtct caccctctgc tgtccctgga aaatctgttt tctctctctg gggcttcctc     120

<210> SEQ ID NO 285
<211> LENGTH: 120
<212> TYPE: DNA
<213> ORGANISM: Homo sapiens

<400> SEQUENCE: 285
cagcttcctc cttcacagct gcagtgggGG ctggggctgg ggcatcccag ggagggtttt      60
tgtatgagcc tgtgtcacag tgtgtggtat tcggcggagg gaccaagctg accgtcctag     120

<210> SEQ ID NO 286
<211> LENGTH: 120
<212> TYPE: DNA
<213> ORGANISM: Homo sapiens

<400> SEQUENCE: 286
tgtggtattc ggcggaggga ccaagctgac cgtcctaggt gagtctcttc tcccctctcc      60
ttccccactc ttgggacaat ttctgctgtt tttgtttgtt tctgtatctt gtctcaactt     120

<210> SEQ ID NO 287
<211> LENGTH: 120
<212> TYPE: DNA
<213> ORGANISM: Homo sapiens

<400> SEQUENCE: 287
cagcttcctc cttcacagct gcagtgggGG ctggggctgg ggcatcccag ggagggtttt      60
tgtatgagcc tgtgtcacag tgttgggtgt tcggcggagg gaccaagctg accgtcctag     120

<210> SEQ ID NO 288
<211> LENGTH: 120
<212> TYPE: DNA
<213> ORGANISM: Homo sapiens

<400> SEQUENCE: 288
ttgggtgttc ggcggaggga ccaagctgac cgtcctaggt gagtctcttc tcccctctcc      60
ttccccgctc ttgggacaat ttctgctgtt tttgtttgtt tctgtatctt gtctcaactt     120

<210> SEQ ID NO 289
<211> LENGTH: 120
<212> TYPE: DNA
<213> ORGANISM: Homo sapiens

<400> SEQUENCE: 289
agcttcctcc ttcacagctg cagtgggggc tggggctagg ggcatcccag ggagggtttt      60
tgtatgagcc tgtgtcacag tgttgggtgt tcggcggagg gaccaagctg accgtcctag     120

<210> SEQ ID NO 290
```

```
<211> LENGTH: 120
<212> TYPE: DNA
<213> ORGANISM: Homo sapiens

<400> SEQUENCE: 290
ttgggtgttc ggcggaggga ccaagctgac cgtcctaggt gagtctcttc tccctctcc      60 ttccccgctc ttgggacaat ttctgctgtt tttgtttgtt tctgtatctt gtctcaactt    120

<210> SEQ ID NO 291
<211> LENGTH: 120
<212> TYPE: DNA
<213> ORGANISM: Homo sapiens

<400> SEQUENCE: 291
agcttcctcc ttcacagctg cagtgggggc tggggctagg ggcatcccag ggagggtttt     60
tgtatgagcc tgtgtcacag tgtgtggtat cggcggagg gaccaagctg accgtcctag    120

<210> SEQ ID NO 292
<211> LENGTH: 120
<212> TYPE: DNA
<213> ORGANISM: Homo sapiens

<400> SEQUENCE: 292
tgtggtattc ggcggaggga ccaagctgac cgtcctaggt gagtctcttc tccctctcc      60 ttccccgctc ttgggacaat ttctgctgtt tttgtttgtt tctgtatctt gtctcaactt    120

<210> SEQ ID NO 293
<211> LENGTH: 120
<212> TYPE: DNA
<213> ORGANISM: Homo sapiens

<400> SEQUENCE: 293
gtatttggtg gaggaaccca gctgatcatt ttagatgagt ctcttcttcc ctttctttcc     60
ctgccaagtt ggtgacaatt ttattctgat ttcgatcttt gtctgtgact tgccacagcc    120

<210> SEQ ID NO 294
<211> LENGTH: 120
<212> TYPE: DNA
<213> ORGANISM: Homo sapiens

<400> SEQUENCE: 294
ttttgtattt ggtggaggaa cccagctgat cattttagat gagtctcttc ttccctttct     60
ttccctgcca agttggtgac aattttattc tgatttcgat ctttgtctgt gacttgccac    120

<210> SEQ ID NO 295
<211> LENGTH: 120
<212> TYPE: DNA
<213> ORGANISM: Homo sapiens

<400> SEQUENCE: 295
cagagagggt ttttgtatga gcctgtgtca cagcactggg tgtttggtga ggggacggag     60
ctgaccgtcc tagatgagtc ttttcccccct ccttccctgg tctccccaag gtactgggaa   120

<210> SEQ ID NO 296
<211> LENGTH: 120
<212> TYPE: DNA
<213> ORGANISM: Homo sapiens

<400> SEQUENCE: 296
ctgggtgttt ggtgagggga cggagctgac cgtcctagga tgagtctttt ccccctcctt     60
```

```
cctggtctc cccaaggtac tgggaaattt tctgctgctt ttgttctttt ctgtatcttg    120
```

<210> SEQ ID NO 297
<211> LENGTH: 120
<212> TYPE: DNA
<213> ORGANISM: Homo sapiens

<400> SEQUENCE: 297

```
ggagggtttg tgtgcagggt tatatcacag tgtaatgtgt tcggcagtgg caccaaggtg    60
accgtcctcg gtgagtcccc ttttctattc ttttgggtct agggtgagat ctggggagac   120
```

<210> SEQ ID NO 298
<211> LENGTH: 120
<212> TYPE: DNA
<213> ORGANISM: Homo sapiens

<400> SEQUENCE: 298

```
taatgtgttc ggcagtggca ccaaggtgac cgtcctcggt gagtcccctt ttctattctt    60
ttgggtctag ggtgagatct ggggagactt ttctgtcctt tctgttctct ctagggtaga   120
```

<210> SEQ ID NO 299
<211> LENGTH: 120
<212> TYPE: DNA
<213> ORGANISM: Homo sapiens

<400> SEQUENCE: 299

```
tcactgtgtg ctgtgttcgg aggaggcacc cagctgaccg tcctcggtaa gtctccccgc    60
ttctctcctc tttgagatcc caagttaaac acggggagtt tttcccttttc ctgtctgtcg   120
```

<210> SEQ ID NO 300
<211> LENGTH: 120
<212> TYPE: DNA
<213> ORGANISM: Homo sapiens

<400> SEQUENCE: 300

```
tgctgtgttc ggaggaggca cccagctgac cgtcctcggt aagtctcccc gcttctctcc    60
tctttgagat cccaagttaa acacggggag ttttcccctt tcctgtctgt cgaaggctaa   120
```

<210> SEQ ID NO 301
<211> LENGTH: 120
<212> TYPE: DNA
<213> ORGANISM: Homo sapiens

<400> SEQUENCE: 301

```
tcactgtgtg ctgtgttcgg aggaggcacc cagctgaccg ccctcggtaa gtctccccgc    60
ttctctcctc tttgagatcc caagttaaac acggggagtt tttcccttttc ctgtctgtcg   120
```

<210> SEQ ID NO 302
<211> LENGTH: 120
<212> TYPE: DNA
<213> ORGANISM: Homo sapiens

<400> SEQUENCE: 302

```
tgctgtgttc ggaggaggca cccagctgac cgccctcggt aagtctcccc gcttctctcc    60
tctttgagat cccaagttaa acacggggag ttttcccctt tcctgtctgt cgaaggctaa   120
```

<210> SEQ ID NO 303
<211> LENGTH: 120
<212> TYPE: DNA

<213> ORGANISM: Homo sapiens

<400> SEQUENCE: 303

```
tactactact actactacat ggacgtctgg ggcaaaggga ccacggtcac cgtctcctca    60
ggtaagaatg ccactctag ggcctttgtt ttctgctact gcctgtgggg tttcctgagc   120
```

<210> SEQ ID NO 304
<211> LENGTH: 117
<212> TYPE: DNA
<213> ORGANISM: Homo sapiens

<400> SEQUENCE: 304

```
attactacta ctactactac atggacgtct ggggcaaagg gaccacggtc accgtctcct    60
caggtaagaa tggccactct agggccttttg ttttctgcta ctgcctgtgg ggaattc     117
```

<210> SEQ ID NO 305
<211> LENGTH: 120
<212> TYPE: DNA
<213> ORGANISM: Homo sapiens

<400> SEQUENCE: 305

```
attactacta ctactacggt atggacgtct ggggcaaagg gaccacggtc accgtctcct    60
caggtaagaa tggccactct agggccttttg ttttctgcta ctgcctgtgg ggtttcctga  120
```

<210> SEQ ID NO 306
<211> LENGTH: 120
<212> TYPE: DNA
<213> ORGANISM: Homo sapiens

<400> SEQUENCE: 306

```
tgatgctttt gatatctggg gccaagggac aatggtcacc gtctcttcag gtaagatggc    60
tttccttctg cctcctttct ctgggcccag cgtcctctgt cctggagctg ggagataatg   120
```

<210> SEQ ID NO 307
<211> LENGTH: 120
<212> TYPE: DNA
<213> ORGANISM: Homo sapiens

<400> SEQUENCE: 307

```
cttgcagttg gacttcccag gccgacagtg gtctggcttc tgaggggtca ggccagaatg    60
tggggtacgt gggaggccag cagagggttc catgagaagg gcaggacagg gccacggaca   120
```

<210> SEQ ID NO 308
<211> LENGTH: 120
<212> TYPE: DNA
<213> ORGANISM: Homo sapiens

<400> SEQUENCE: 308

```
gactattggg gccagggaac cctggtcacc gtctcctcag gtgagtcctc acaagctctc    60
tcctacttta actcagaaga ctctcactgc attttttgggg ggagataagg gtgctgggtc  120
```

<210> SEQ ID NO 309
<211> LENGTH: 120
<212> TYPE: DNA
<213> ORGANISM: Homo sapiens

<400> SEQUENCE: 309

```
actactttga ctactggggc cagggaaccc tggtcaccgt ctcctcaggt gagtcctcac    60
aacctctctc ctgctttaac tctgaagggt tttgctgcat ttttgggggg aaataagggt   120
```

<210> SEQ ID NO 310
<211> LENGTH: 120
<212> TYPE: DNA
<213> ORGANISM: Homo sapiens

<400> SEQUENCE: 310
aactggttcg acccctgggg ccagggaacc ctggtcaccg tctcctcagg tgagtcctca    60
ccaccccctc tctgagtcca cttagggaga ctcagcttgc cagggtctca gggtcagagt   120

<210> SEQ ID NO 311
<211> LENGTH: 120
<212> TYPE: DNA
<213> ORGANISM: Homo sapiens

<400> SEQUENCE: 311
cagtgcttcg accctgggg ccagggaacc ctggtcaccg tctcctcagg agattcctca    60
ccaccccctc tctgagtcct cttagtgaga ctcagtttgc cggactctca gggtcagagt   120

<210> SEQ ID NO 312
<211> LENGTH: 120
<212> TYPE: DNA
<213> ORGANISM: Homo sapiens

<400> SEQUENCE: 312
acaactggtt cgaccctgg ggccagggaa ccctggtcac cgtctcctca ggtgagtcct    60
caccaccccc tctctgagtc cacttaggga gactcagctt gccagggtct cagggtcaga   120

<210> SEQ ID NO 313
<211> LENGTH: 120
<212> TYPE: DNA
<213> ORGANISM: Homo sapiens

<400> SEQUENCE: 313
tactttgact actggggcca gggaaccctg gtcaccgtct cctcaggtga gtcctcacaa    60
cctctctcct gctttaactc tgaagggttt tgctgcattt ctgggggaa ataagggtgc    120

<210> SEQ ID NO 314
<211> LENGTH: 120
<212> TYPE: DNA
<213> ORGANISM: Homo sapiens

<400> SEQUENCE: 314
tttgactgct ggggcaggg aaccctggtc accgtctcct caggtgagcc ctcacaacct    60
ctctcctggg ttaactctga agggttttgc tgcattttg gggggaaata agggtgctgg   120

<210> SEQ ID NO 315
<211> LENGTH: 120
<212> TYPE: DNA
<213> ORGANISM: Homo sapiens

<400> SEQUENCE: 315
tgatgctttt gatgtctggg gccaagggac aatggtcacc gtctcttcag gtaagatggg    60
ctttccttct gcctcctttc tctggcccca gcgtcctctg tcctggagct gggagataat   120

<210> SEQ ID NO 316
<211> LENGTH: 120
<212> TYPE: DNA
<213> ORGANISM: Homo sapiens

```
<400> SEQUENCE: 316
tgatgctttt gatatctggg gccaagggac aatggtcacc gtctcttcag gtaagatggc      60
tttccttctg cctcctttct ctgggcccag cgtcctctgt cctggagctg ggagataatg     120

<210> SEQ ID NO 317
<211> LENGTH: 120
<212> TYPE: DNA
<213> ORGANISM: Homo sapiens

<400> SEQUENCE: 317 gatgctttg atatctgggg ccaagggaca atggtcaccg tctcttcagg taagatggct       60
ttccttctgc ctcctttctc tgggcccagc gtcctctgtc ctggagctgg gagataatgt    120

<210> SEQ ID NO 318
<211> LENGTH: 120
<212> TYPE: DNA
<213> ORGANISM: Homo sapiens

<400> SEQUENCE: 318
gctacaagtg cttggagcac tggggccagg gcagcccggc caccgtctcc ctgggaacgt     60
caccctcccc tgcctgggtc tcagcccggg ggtctgtgtg gctggggaca gggacgccgg   120

<210> SEQ ID NO 319
<211> LENGTH: 120
<212> TYPE: DNA
<213> ORGANISM: Homo sapiens

<400> SEQUENCE: 319
ctactggtac ttcgatctct ggggccgtgg caccctggtc actgtctcct caggtgagtc     60
ccactgcagc cccctcccag tcttctctgt ccaggcacca ggccaggtat ctggggtctg   120

<210> SEQ ID NO 320
<211> LENGTH: 120
<212> TYPE: DNA
<213> ORGANISM: Homo sapiens

<400> SEQUENCE: 320
gctgaatact tccagcactg gggccagggc accctggtca ccgtctcctc aggtgagtct     60
gctgtctggg gatagcgggg agccaggtgt actgggccag gcaagggctt tggcttcaga   120

<210> SEQ ID NO 321
<211> LENGTH: 120
<212> TYPE: DNA
<213> ORGANISM: Homo sapiens

<400> SEQUENCE: 321
aaaggtgctg ggggcccctg gacccgaccc gccctggaga ccgcagccac atcaagcccc     60
cagccccaca ggcccctac cagccgcagg gttttggctg agctgagaac cactgtgcta    120

<210> SEQ ID NO 322
<211> LENGTH: 100
<212> TYPE: DNA
<213> ORGANISM: Homo sapiens

<400> SEQUENCE: 322
ggacaaagcc ttgagcagcc ctctgaagtg acagctgtgg aaggagccat tgtccagata     60
aactgcacgt accagacatc tgggttttat gggctgtcct                          100
```

```
<210> SEQ ID NO 323
<211> LENGTH: 100
<212> TYPE: DNA
<213> ORGANISM: Homo sapiens

<400> SEQUENCE: 323
gtttttcttc attccttagt cgctctgata gttatggtta cctccttcta caggagctcc      60
agatgaaaga ctctgcctct tacttctgcg ctgtgagaga                           100

<210> SEQ ID NO 324
<211> LENGTH: 100
<212> TYPE: DNA
<213> ORGANISM: Homo sapiens

<400> SEQUENCE: 324
ggacaaagcc ttgagcagcc ctctgaagtg acagctgtgg aaggagccat tgtccagata      60
aactgcacgt accagacatc tgggttttat gggctgtcct                           100

<210> SEQ ID NO 325
<211> LENGTH: 100
<212> TYPE: DNA
<213> ORGANISM: Homo sapiens

<400> SEQUENCE: 325
caggtcgttt ttcttcattc cttagtcgct ctgatagtta tggttacctc cttctacagg      60
agctccagat gaaagactct gcctcttact tctgcgctgt                           100

<210> SEQ ID NO 326
<211> LENGTH: 100
<212> TYPE: DNA
<213> ORGANISM: Homo sapiens

<400> SEQUENCE: 326
ggacaaaaca ttgaccagcc cactgagatg acagctacgg aaggtgccat tgtccagatc      60
aactgcacgt accagacatc tgggttcaac gggctgttct                           100

<210> SEQ ID NO 327
<211> LENGTH: 100
<212> TYPE: DNA
<213> ORGANISM: Homo sapiens

<400> SEQUENCE: 327
gtttttcttc attccttagt cggtctaaag ggtacagtta cctccttttg aaggagctcc      60
agatgaaaga ctctgcctct tacctctgtg ctgtgagaga                           100

<210> SEQ ID NO 328
<211> LENGTH: 100
<212> TYPE: DNA
<213> ORGANISM: Homo sapiens

<400> SEQUENCE: 328
ggacaaaaca ttgaccagcc cactgagatg acagctacgg aaggtgccat tgtccagatc      60
aactgcacgt accagacatc tgggttcaac gggctgttct                           100

<210> SEQ ID NO 329
<211> LENGTH: 100
<212> TYPE: DNA
<213> ORGANISM: Homo sapiens

<400> SEQUENCE: 329
```

```
catctgggtt caacgggctg ttctggtacc agcaacatgc tggcgaagca cccacatttc    60
tgtcttacaa tgttctggat ggtctggagg agaaaggtcg                         100

<210> SEQ ID NO 330
<211> LENGTH: 100
<212> TYPE: DNA
<213> ORGANISM: Homo sapiens

<400> SEQUENCE: 330
aaaaaccaag tggagcagag tcctcagtcc ctgatcatcc tggagggaaa gaactgcact    60
cttcaatgca attatacagt gagccccttc agcaacttaa                         100

<210> SEQ ID NO 331
<211> LENGTH: 100
<212> TYPE: DNA
<213> ORGANISM: Homo sapiens

<400> SEQUENCE: 331
agatatacag caactctgga tgcagacaca aagcaaagct ctctgcacat cacagcctcc    60
cagctcagcg attcagcctc ctacatctgt gtggtgagcg                         100

<210> SEQ ID NO 332
<211> LENGTH: 100
<212> TYPE: DNA
<213> ORGANISM: Homo sapiens

<400> SEQUENCE: 332
ctacatacac tggagcagag tccttcattc ctgaatattc aggagggaat gcatgccgtt    60
cttaattgta cttatcagga gagaacactc ttcaatttcc                         100

<210> SEQ ID NO 333
<211> LENGTH: 100
<212> TYPE: DNA
<213> ORGANISM: Homo sapiens

<400> SEQUENCE: 333
caaatatttt aaagaactgc ttggaaaaga aaaattttat agtgtttgga atatcgcagc    60
ctctcatctg ggagattcag ccacctactt ctgtgctttg                         100

<210> SEQ ID NO 334
<211> LENGTH: 100
<212> TYPE: DNA
<213> ORGANISM: Homo sapiens

<400> SEQUENCE: 334
cggaaggagg tggagcagga tcctggaccc ttcaatgttc cagagggagc cactgtcgct    60
ttcaactgta cttacagcaa cagtgcttct cagtctttct                         100

<210> SEQ ID NO 335
<211> LENGTH: 100
<212> TYPE: DNA
<213> ORGANISM: Homo sapiens

<400> SEQUENCE: 335
aggtttacag cacagctcaa tagagccagc cagtatattt ccctgctcat cagagactcc    60
aagctcagtg attcagccac ctacctctgt gtggtgaaca                         100

<210> SEQ ID NO 336
<211> LENGTH: 100
```

```
<212> TYPE: DNA
<213> ORGANISM: Homo sapiens

<400> SEQUENCE: 336
cggaaggagg tggagcagga tcctggaccc ttcaatgttc cagagggagc cactgtcgct      60
ttcaactgta cttacagcaa cagtgcttct cagtctttct                          100

<210> SEQ ID NO 337
<211> LENGTH: 100
<212> TYPE: DNA
<213> ORGANISM: Homo sapiens

<400> SEQUENCE: 337
acagcacacg tcaatagagc cagccagtat atttccctgc tcatcagaga ctccaagctc      60
agtgattcag ccacctacct ctgtgtggtg aacattcgcc                          100

<210> SEQ ID NO 338
<211> LENGTH: 100
<212> TYPE: DNA
<213> ORGANISM: Homo sapiens

<400> SEQUENCE: 338
cagaaggagg tggagcagaa ttctggaccc ctcagtgttc cagagggagc cattgcctct      60
ctcaactgca cttacagtga ccgaggttcc cagtccttct                          100

<210> SEQ ID NO 339
<211> LENGTH: 100
<212> TYPE: DNA
<213> ORGANISM: Homo sapiens

<400> SEQUENCE: 339
aggtttacag cacagctcaa taaagccagc cagtatgttt ctctgctcat cagagactcc      60
cagcccagtg attcagccac ctacctctgt gccgtgaaca                          100

<210> SEQ ID NO 340
<211> LENGTH: 100
<212> TYPE: DNA
<213> ORGANISM: Homo sapiens

<400> SEQUENCE: 340
cagaaggagg tggagcagaa ttctggaccc ctcagtgttc cagagggagc cattgcctct      60
ctcaactgca cttacagtga ccgaggttcc cagtccttct                          100

<210> SEQ ID NO 341
<211> LENGTH: 100
<212> TYPE: DNA
<213> ORGANISM: Homo sapiens

<400> SEQUENCE: 341
gtttacagca cagctcaata aagccagcca gtatgtttct ctgctcatca gagactccca      60
gcccagtgat tcagccacct acctctgtgc cgtgtaccac                          100

<210> SEQ ID NO 342
<211> LENGTH: 100
<212> TYPE: DNA
<213> ORGANISM: Homo sapiens

<400> SEQUENCE: 342
ggacccctca gtgttccaga gggagccatt gcctctctca actgcactta cagtgaccga      60
```

```
gtttcccagt ccttcttctg gtacagacaa tattctggga                          100

<210> SEQ ID NO 343
<211> LENGTH: 100
<212> TYPE: DNA
<213> ORGANISM: Homo sapiens

<400> SEQUENCE: 343
aaggtttaca gcacagctca ataaagccag ccagtatgtt tctctgctca tcagagactc    60
ccagcccagt gattcagcca cctacctctg tgccgtgaac                         100

<210> SEQ ID NO 344
<211> LENGTH: 100
<212> TYPE: DNA
<213> ORGANISM: Homo sapiens

<400> SEQUENCE: 344
cagaaggagg tggagcagga tcctggacca ctcagtgttc cagagggagc cattgtttct    60
ctcaactgca cttacagcaa cagtgctttt caatacttca                         100

<210> SEQ ID NO 345
<211> LENGTH: 100
<212> TYPE: DNA
<213> ORGANISM: Homo sapiens

<400> SEQUENCE: 345
aggtttacag cacaggtcga taaatccagc aagtatatct ccttgttcat cagagactca    60
cagcccagtg attcagccac ctacctctgt gcaatgagcg                         100

<210> SEQ ID NO 346
<211> LENGTH: 100
<212> TYPE: DNA
<213> ORGANISM: Homo sapiens

<400> SEQUENCE: 346
cagaaggagg tggagcagga tcctggacca ctcagtgttc cagagggagc cattgtttct    60
ctcaactgca cttacagcaa cagtgctttt caatacttca                         100

<210> SEQ ID NO 347
<211> LENGTH: 100
<212> TYPE: DNA
<213> ORGANISM: Homo sapiens

<400> SEQUENCE: 347
aggtttacag cacaggtcga taaatccagc aagtatatct ccttgttcat cagagactca    60
cagcccagtg attcagccac ctacctctgt gcaatgagcg                         100

<210> SEQ ID NO 348
<211> LENGTH: 100
<212> TYPE: DNA
<213> ORGANISM: Homo sapiens

<400> SEQUENCE: 348
ggagagaatg tggagcagca tccttcaacc ctgagtgtcc aggagggaga cagcgctgtt    60
atcaagtgta cttattcaga cagtgcctca aactacttcc                         100

<210> SEQ ID NO 349
<211> LENGTH: 100
<212> TYPE: DNA
<213> ORGANISM: Homo sapiens
```

<400> SEQUENCE: 349
cgaattgctg ttacattgaa caagacagcc aaacatttct ccctgcacat cacagagacc     60
caacctgaag actcggctgt ctacttctgt gcagcaagta                          100

<210> SEQ ID NO 350
<211> LENGTH: 100
<212> TYPE: DNA
<213> ORGANISM: Homo sapiens

<400> SEQUENCE: 350
ggagagaatg tggagcagca tccttcaacc ctgagtgtcc aggagggaga cagcgctgtt     60
atcaagtgta cttattcaga cagtgcctca aactacttcc                          100

<210> SEQ ID NO 351
<211> LENGTH: 100
<212> TYPE: DNA
<213> ORGANISM: Homo sapiens

<400> SEQUENCE: 351
tgttacattg aacaagacag ccaaacattt ctccctgcac atcacagaga cccaacctga     60
agactcggct gtctacttct gtgcagcaag taggaaggac                          100

<210> SEQ ID NO 352
<211> LENGTH: 100
<212> TYPE: DNA
<213> ORGANISM: Homo sapiens

<400> SEQUENCE: 352
ggagagaatg tggagcagca tccttcaacc ctgagtgtcc aggagggaga cagcgctgtt     60
atcaagtgta cttattcaga cagtgcctca aactacttcc                          100

<210> SEQ ID NO 353
<211> LENGTH: 100
<212> TYPE: DNA
<213> ORGANISM: Homo sapiens

<400> SEQUENCE: 353
gcttattata gacattcgtt caaatgtggg cgaaaagaaa gaccaacgaa ttgctgttac     60
attgaacaag acagccaaac atttctcccT gcagatcaca                          100

<210> SEQ ID NO 354
<211> LENGTH: 100
<212> TYPE: DNA
<213> ORGANISM: Homo sapiens

<400> SEQUENCE: 354
ggagagagtg tggggctgca tcttcctacc ctgagtgtcc aggagggtga caactctatt     60
atcaactgtg cttattcaaa cagcgcctca gactacttca                          100

<210> SEQ ID NO 355
<211> LENGTH: 100
<212> TYPE: DNA
<213> ORGANISM: Homo sapiens

<400> SEQUENCE: 355
agagtcaccg ttttattgaa taagacagtg aaacatctct ctctgcaaat tgcagctact     60
caacctggag actcagctgt ctactttTgt gcagagaata                          100

<210> SEQ ID NO 356
<211> LENGTH: 100
<212> TYPE: DNA
<213> ORGANISM: Homo sapiens

<400> SEQUENCE: 356
ggagagagtg tggggctgca tcttcctacc ctgagtgtcc aggagggtga caactctatt    60
atcaactgtg cttattcaaa cagcgcctca gactacttca                         100

<210> SEQ ID NO 357
<211> LENGTH: 100
<212> TYPE: DNA
<213> ORGANISM: Homo sapiens

<400> SEQUENCE: 357
caaagagtca ccgttttatt gaataagaca gtgaaacatc tctctctgca aattgcagct    60
actcaacctg gagactcagc tgtctacttt tgtgcagaga                         100

<210> SEQ ID NO 358
<211> LENGTH: 100
<212> TYPE: DNA
<213> ORGANISM: Homo sapiens

<400> SEQUENCE: 358
gcccagaaga taactcaaac ccaaccagga atgttcgtgc aggaaaagga ggctgtgact    60
ctggactgca catatgacac cagtgatcca agttatggtc                         100

<210> SEQ ID NO 359
<211> LENGTH: 100
<212> TYPE: DNA
<213> ORGANISM: Homo sapiens

<400> SEQUENCE: 359
actcattgaa tttccagaag gcaagaaaat ccgccaacct tgtcatctcc gcttcacaac    60
tgggggactc agcaatgtac ttctgtgcaa tgagagaggg                         100

<210> SEQ ID NO 360
<211> LENGTH: 100
<212> TYPE: DNA
<213> ORGANISM: Homo sapiens

<400> SEQUENCE: 360
gcccagaaga taactcaaac ccaaccagga atgttcgtgc aggaaaagga ggctgtgact    60
ctggactgca catatgacac cagtgatcaa agttatggtc                         100

<210> SEQ ID NO 361
<211> LENGTH: 100
<212> TYPE: DNA
<213> ORGANISM: Homo sapiens

<400> SEQUENCE: 361
actcattgaa tttccagaag gcaagaaaat ccgccaacct tgtcatctcc gcttcacaac    60
tgggggactc agcaatgtat ttctgtgcaa tgagagaggg                         100

<210> SEQ ID NO 362
<211> LENGTH: 100
<212> TYPE: DNA
<213> ORGANISM: Homo sapiens

<400> SEQUENCE: 362

```
gcccagaaga taactcaaac ccaaccagga atgttcgtgc aggaaaagga ggctgtgact    60
ctggactgca catatgacac cagtgatcca agttatggtc                         100

<210> SEQ ID NO 363
<211> LENGTH: 100
<212> TYPE: DNA
<213> ORGANISM: Homo sapiens

<400> SEQUENCE: 363
aggtcgctac tcattgaatt tccagaaggc aagaaaatcc gccaaccttg tcatctccgc    60
ttcacaactg ggggactcag caatgtattt ctgtgcaatg                         100

<210> SEQ ID NO 364
<211> LENGTH: 100
<212> TYPE: DNA
<213> ORGANISM: Homo sapiens

<400> SEQUENCE: 364
cagaagataa ctcaaaccca accaggaatg ttcgtgcagg aaaaggaggc tgtgactctg    60
gactgcacat atgacaccag tgatcaaagt tatggtctct                         100

<210> SEQ ID NO 365
<211> LENGTH: 100
<212> TYPE: DNA
<213> ORGANISM: Homo sapiens

<400> SEQUENCE: 365
gcaacagaag gtcgctactc attgaatttc cagaaggcaa gaaaatccgc caaccttgtc    60
atctccgctt cacaactggg ggactcagca atgtacttct                         100

<210> SEQ ID NO 366
<211> LENGTH: 100
<212> TYPE: DNA
<213> ORGANISM: Homo sapiens

<400> SEQUENCE: 366
ctccatattc tggagtagag tccttcattc attcctgagt atccgggagg gaatgcacaa    60
cattcttaat tgcacttatg aggagagaac gttctcttaa                         100

<210> SEQ ID NO 367
<211> LENGTH: 100
<212> TYPE: DNA
<213> ORGANISM: Homo sapiens

<400> SEQUENCE: 367
acattttaaa gaagcgcttg gaaaagagaa gttttatagt gttttgaata tgctggtctc    60
tcatcctgga gattcaggca cctacttctg tgctttgagg                         100

<210> SEQ ID NO 368
<211> LENGTH: 100
<212> TYPE: DNA
<213> ORGANISM: Homo sapiens

<400> SEQUENCE: 368
gcccagagag tgactcagcc cgagaagctc ctctctgtct ttaaaggggc cccagtggag    60
ctgaagtgca actattccta ttctgggagt cctgaactct                         100

<210> SEQ ID NO 369
```

```
<211> LENGTH: 100
<212> TYPE: DNA
<213> ORGANISM: Homo sapiens

<400> SEQUENCE: 369
gcttcactgc tgaccttaac aaaggcgaga catctttcca cctgaagaaa ccatttgctc    60
aagaggaaga ctcagccatg tattactgtg ctctaagtgg                          100

<210> SEQ ID NO 370
<211> LENGTH: 100
<212> TYPE: DNA
<213> ORGANISM: Homo sapiens

<400> SEQUENCE: 370
agtcaacagg gagaagagga tcctcaggcc ttgagcatcc aggagggtga aaatgccacc    60
atgaactgca gttacaaaac tagtataaac aatttacagt                          100

<210> SEQ ID NO 371
<211> LENGTH: 100
<212> TYPE: DNA
<213> ORGANISM: Homo sapiens

<400> SEQUENCE: 371
agattaagag tcacgcttga cacttccaag aaaagcagtt ccttgttgat cacggcttcc    60
cgggcagcag acactgcttc ttacttctgt gctacggacg                          100

<210> SEQ ID NO 372
<211> LENGTH: 100
<212> TYPE: DNA
<213> ORGANISM: Homo sapiens

<400> SEQUENCE: 372
ggagactcgg ttacccagac agaaggccca gttaccctcc ctgagagggc agctctgaca    60
ttaaactgca cttatcagtc cagctattca acttttctat                          100

<210> SEQ ID NO 373
<211> LENGTH: 100
<212> TYPE: DNA
<213> ORGANISM: Homo sapiens

<400> SEQUENCE: 373
gttttcaggc cagtcctatc aagagtgaca gttccttcca cctggagaag ccctcggtgc    60
agctgtcgga ctctgccgtg tactactgcg ctctgagaga                          100

<210> SEQ ID NO 374
<211> LENGTH: 100
<212> TYPE: DNA
<213> ORGANISM: Homo sapiens

<400> SEQUENCE: 374
gctcagaagg taactcaagc gcagactgaa atttctgtgg tggagaagga ggatgtgacc    60
ttggactgtg tgtatgaaac ccgtgatact acttattact                          100

<210> SEQ ID NO 375
<211> LENGTH: 100
<212> TYPE: DNA
<213> ORGANISM: Homo sapiens

<400> SEQUENCE: 375
attcttggaa cttccagaaa tccaccagtt ccttcaactt caccatcaca gcctcacaag    60
```
tcgtggactc agcagtatac ttctgtgctc tgagtgaggc 100

<210> SEQ ID NO 376
<211> LENGTH: 100
<212> TYPE: DNA
<213> ORGANISM: Homo sapiens

<400> SEQUENCE: 376
aaggaccaag tgtttcagcc ttccacagtg gcatcttcag agggagctgt ggtggaaatc 60
ttctgtaatc actctgtgtc caatgcttac aacttcttct 100

<210> SEQ ID NO 377
<211> LENGTH: 100
<212> TYPE: DNA
<213> ORGANISM: Homo sapiens

<400> SEQUENCE: 377
agggacgata caacatgacc tatgaacggt tctcttcatc gctgctcatc ctccaggtgc 60
gggaggcaga tgctgctgtt tactactgtg ctgtggagga 100

<210> SEQ ID NO 378
<211> LENGTH: 100
<212> TYPE: DNA
<213> ORGANISM: Homo sapiens

<400> SEQUENCE: 378
aaggaccaag tgtttcagcc ttccacagtg gcatcttcag agggagctgt ggtggaaatc 60
ttctgtaatc actctgtgtc caatgcttac aacttcttct 100

<210> SEQ ID NO 379
<211> LENGTH: 100
<212> TYPE: DNA
<213> ORGANISM: Homo sapiens

<400> SEQUENCE: 379
gggacgatac aacatgacct atgaacggtt ctcttcatcg ctgctcatcc tccaggtgcg 60
ggaggcagat gctgctgttt actactgtgc tgtggcctgg 100

<210> SEQ ID NO 380
<211> LENGTH: 100
<212> TYPE: DNA
<213> ORGANISM: Homo sapiens

<400> SEQUENCE: 380
gaagaccagg tgacgcagag tcccgaggcc ctgagactcc aggagggaga gagtagcagt 60
cttaactgca gttacacagt cagcggttta agagggctgt 100

<210> SEQ ID NO 381
<211> LENGTH: 100
<212> TYPE: DNA
<213> ORGANISM: Homo sapiens

<400> SEQUENCE: 381
aaagaaaggc taaaagccac attaacaaag aaggaaagct tctgcacat cacagcccct 60 aaacctgaag actcagccac ttatctctgt gctgtgcagg 100

<210> SEQ ID NO 382
<211> LENGTH: 100
<212> TYPE: DNA

-continued

<213> ORGANISM: Homo sapiens

<400> SEQUENCE: 382
gaagaccagg tgacgcagag tcccgaggcc ctgagactcc aggagggaga gagtagcagt    60
ctcaactgca gttacacagt cagcggttta agagggctgt    100

<210> SEQ ID NO 383
<211> LENGTH: 100
<212> TYPE: DNA
<213> ORGANISM: Homo sapiens

<400> SEQUENCE: 383
aaaggagaaa gaaaggctaa aagccacatt aacaaagaag gaaagctttc tgcacatcac    60
agcccctaaa cctgaagact cagccactta tctctgtgct    100

<210> SEQ ID NO 384
<211> LENGTH: 100
<212> TYPE: DNA
<213> ORGANISM: Homo sapiens

<400> SEQUENCE: 384
gaagaccagg tgacgcagag tcccgaggcc ctgagactcc aggagggaga gagtcgcagt    60
ctcaactgca gttacacagt cagcggttta agagggctgt    100

<210> SEQ ID NO 385
<211> LENGTH: 100
<212> TYPE: DNA
<213> ORGANISM: Homo sapiens

<400> SEQUENCE: 385
agaaaaggag aaagaaaggc taaaagccac attaacaaag aaggaaagct ttctgcacat    60
cacagcccct aaacctgaag actcagccac ttatctctgt    100

<210> SEQ ID NO 386
<211> LENGTH: 100
<212> TYPE: DNA
<213> ORGANISM: Homo sapiens

<400> SEQUENCE: 386
gaagaccagg tgacgcagag tcccgaggcc ctgagactcc aggagggaga gagtagcagt    60
ctcaactgca gttgcacagt cagcggttta agagggctgt    100

<210> SEQ ID NO 387
<211> LENGTH: 100
<212> TYPE: DNA
<213> ORGANISM: Homo sapiens

<400> SEQUENCE: 387
aaaggagaaa gaaaggctaa aagccacatt aacaaagaag gaaagctttc tgcacatcac    60
agcccctaaa cctgaagact cagccactta tctctgtgct    100

<210> SEQ ID NO 388
<211> LENGTH: 100
<212> TYPE: DNA
<213> ORGANISM: Homo sapiens

<400> SEQUENCE: 388
aaacaggagg tgacgcagat tcctgcagct ctgagtgtcc cagaaggaga aaacttggtt    60
ctcaactgca gtttcactga tagcgctatt tacaacctcc    100

<210> SEQ ID NO 389
<211> LENGTH: 100
<212> TYPE: DNA
<213> ORGANISM: Homo sapiens

<400> SEQUENCE: 389
aagacttaat gcctcgctgg ataaatcatc aggacgtagt actttataca ttgcagcttc     60
tcagcctggt gactcagcca cctacctctg tgctgtgagg                          100

<210> SEQ ID NO 390
<211> LENGTH: 100
<212> TYPE: DNA
<213> ORGANISM: Homo sapiens

<400> SEQUENCE: 390
aaacaggagg tgacacagat tcctgcagct ctgagtgtcc cagaaggaga aaacttggtt     60
ctcaactgca gtttcactga tagcgctatt tacaacctcc                          100

<210> SEQ ID NO 391
<211> LENGTH: 100
<212> TYPE: DNA
<213> ORGANISM: Homo sapiens

<400> SEQUENCE: 391
aagtggaaga cttaatgcct cgctggataa atcatcagga cgtagtactt tatacattgc     60
agcttctcag cctggtgact cagccaccta cctctgtgct                          100

<210> SEQ ID NO 392
<211> LENGTH: 100
<212> TYPE: DNA
<213> ORGANISM: Homo sapiens

<400> SEQUENCE: 392
ggaatacaag tggagcagag tcctccagac ctgattctcc aggagggagc caattccacg     60
ctgcggtgca attttctga ctctgtgaac aatttgcagt                           100

<210> SEQ ID NO 393
<211> LENGTH: 100
<212> TYPE: DNA
<213> ORGANISM: Homo sapiens

<400> SEQUENCE: 393
agattaagcg ccacgactgt cgctacggaa cgctacagct tattgtacat ttcctcttcc     60
cagaccacag actcaggcgt ttatttctgt gctgtggagc                          100

<210> SEQ ID NO 394
<211> LENGTH: 100
<212> TYPE: DNA
<213> ORGANISM: Homo sapiens

<400> SEQUENCE: 394
cagcagcagg tgaaacaaag tcctcaatct ttgatagtcc agaaaggagg gatttcaatt     60
ataaactgtg cttatgagaa cactgcgttt gactactttc                          100

<210> SEQ ID NO 395
<211> LENGTH: 100
<212> TYPE: DNA
<213> ORGANISM: Homo sapiens

```
<400> SEQUENCE: 395
agattcacaa tctccttcaa taaaagtgcc aagcagttct cattgcatat catggattcc      60
cagcctggag actcagccac ctacttctgt gcagcaagca                           100

<210> SEQ ID NO 396
<211> LENGTH: 100
<212> TYPE: DNA
<213> ORGANISM: Homo sapiens

<400> SEQUENCE: 396
cagcagcagg tgaaacaaag tcctcaatct ttgatagtcc agaaaggagg gattccaatt      60
ataaactgtg cttatgagaa cactgcgttt gactactttc                           100

<210> SEQ ID NO 397
<211> LENGTH: 100
<212> TYPE: DNA
<213> ORGANISM: Homo sapiens

<400> SEQUENCE: 397
agattcacaa tctccttcaa taaaagtgcc aagcagttct cattgcatat catggattcc      60
cagcctggag actcagccac ctacttctgt gcagcaagcg                           100

<210> SEQ ID NO 398
<211> LENGTH: 100
<212> TYPE: DNA
<213> ORGANISM: Homo sapiens

<400> SEQUENCE: 398
cagcagcagg tgaaacaaag tcctcaatct ttgatagtcc agaaaggagg gatttcaatt      60
ataaactgtg cttatgagaa cactgcgttt gactactttc                           100

<210> SEQ ID NO 399
<211> LENGTH: 100
<212> TYPE: DNA
<213> ORGANISM: Homo sapiens

<400> SEQUENCE: 399
agattcacaa tctccttcaa taaaagtgcc aagcagttct cattgcatat catggattcc      60
cagcctggag actcagccac ctacttctgt gcagcaagca                           100

<210> SEQ ID NO 400
<211> LENGTH: 100
<212> TYPE: DNA
<213> ORGANISM: Homo sapiens

<400> SEQUENCE: 400
cagcaggtga acaaagtcc tcaatctttg atagtccaga aaggagggat ttcaattata      60
aactgtgctt atgagaacac tgcgtttgac tactttccat                           100

<210> SEQ ID NO 401
<211> LENGTH: 100
<212> TYPE: DNA
<213> ORGANISM: Homo sapiens

<400> SEQUENCE: 401
gaaagaagga agattcacaa tctccttcaa taaaagtgcc aagcagttct cattgcatat      60
catggattcc cagcctggag actcagccac ctacttctgt                           100
```

```
<210> SEQ ID NO 402
<211> LENGTH: 100
<212> TYPE: DNA
<213> ORGANISM: Homo sapiens

<400> SEQUENCE: 402
aggacgaata agtgccactc ttaataccaa ggagggttac agctatttgt acatcaaagg      60
atcccagcct gaagactcag ccacatacct ctgtgccttt                          100

<210> SEQ ID NO 403
<211> LENGTH: 100
<212> TYPE: DNA
<213> ORGANISM: Homo sapiens

<400> SEQUENCE: 403
ggacgaataa gtgccactct taataccaag gagggttaca gctatttgta catcaaagga      60
tcccagcctg aagactcagc cacatacctc tgtgccttta                          100

<210> SEQ ID NO 404
<211> LENGTH: 100
<212> TYPE: DNA
<213> ORGANISM: Homo sapiens

<400> SEQUENCE: 404
atactgaacg tggaacaagg tcctcagtca ctgcatgttc aggagggaga cagcaccaat      60
ttcacctgca gcttcccttc cagcaatttt tatgccttac                          100

<210> SEQ ID NO 405
<211> LENGTH: 100
<212> TYPE: DNA
<213> ORGANISM: Homo sapiens

<400> SEQUENCE: 405
ggacgaataa gtgccactct taataccaag gagggttaca gctatttgta catcaaagga      60
tcccagcctg aagattcagc cacatacctc tgtgccttta                          100

<210> SEQ ID NO 406
<211> LENGTH: 100
<212> TYPE: DNA
<213> ORGANISM: Homo sapiens

<400> SEQUENCE: 406
ggacaacagg taatgcaaat tcctcagtac cagcatgtac aagaaggaga ggacttcacc      60
acgtactgca attcctcaac tactttaagc aatatacagt                          100

<210> SEQ ID NO 407
<211> LENGTH: 100
<212> TYPE: DNA
<213> ORGANISM: Homo sapiens

<400> SEQUENCE: 407
gaaaagactg acatttcagt ttggagaagc aaaaaagaac agctccctgc acatcacagc      60
cacccagact acagatgtag gaacctactt ctgtgcaggg                          100

<210> SEQ ID NO 408
<211> LENGTH: 100
<212> TYPE: DNA
<213> ORGANISM: Homo sapiens

<400> SEQUENCE: 408
```

```
gatgctaaga ccacccagcc ccctccatg gattgcgctg aaggaagagc tgcaaacctg    60
ccttgtaatc actctaccat cagtggaaat gagtatgtgt                       100
```

<210> SEQ ID NO 409
<211> LENGTH: 100
<212> TYPE: DNA
<213> ORGANISM: Homo sapiens

<400> SEQUENCE: 409

```
gcctctctga tcatcacaga agacagaaag tccagcacct tgatcctgcc ccacgctacg    60
ctgagagaca ctgctgtgta ctattgcatc gtcagagtcg                        100
```

<210> SEQ ID NO 410
<211> LENGTH: 100
<212> TYPE: DNA
<213> ORGANISM: Homo sapiens

<400> SEQUENCE: 410

```
gatgctaaga ccacccagcc cacctccatg gattgcgctg aaggaagagc tgcaaacctg    60
ccttgtaatc actctaccat cagtggaaat gagtatgtgt                       100
```

<210> SEQ ID NO 411
<211> LENGTH: 100
<212> TYPE: DNA
<213> ORGANISM: Homo sapiens

<400> SEQUENCE: 411

```
ctctgatcat cacagaagac agaaagtcca gcaccttgat cctgcccac gctacgctga    60 gagacactgc tgtgtactat tgcatcgtca gagattgggt                        100
```

<210> SEQ ID NO 412
<211> LENGTH: 100
<212> TYPE: DNA
<213> ORGANISM: Homo sapiens

<400> SEQUENCE: 412

```
gatgctaaga ccacccagcc ccctccatg gattgcgctg aaggaagagc tgcaaacctg    60
ccttgtaatc actctaccat cagtggaaat gagtatgtgt                       100
```

<210> SEQ ID NO 413
<211> LENGTH: 100
<212> TYPE: DNA
<213> ORGANISM: Homo sapiens

<400> SEQUENCE: 413

```
caatgaaatg gcctctctga tcatcacaga agacagaaag tccagcacct tgatcctgcc    60
ccacgctacg ctgagagaca ctgctgtgta ctattgcatc                       100
```

<210> SEQ ID NO 414
<211> LENGTH: 100
<212> TYPE: DNA
<213> ORGANISM: Homo sapiens

<400> SEQUENCE: 414

```
gatgctaaga ccacacagcc aaattcaatg gagagtaacg aagaagagcc tgttcacttg    60
ccttgtaacc actccacaat cagtggaact gattacatac                       100
```

<210> SEQ ID NO 415
<211> LENGTH: 100

```
<212> TYPE: DNA
<213> ORGANISM: Homo sapiens

<400> SEQUENCE: 415
ggcctctctg gcaatcgctg aagacagaaa gtccagtacc ttgatcctgc accgtgctac    60
cttgagagat gctgctgtgt actactgcat cctgagagac                         100

<210> SEQ ID NO 416
<211> LENGTH: 100
<212> TYPE: DNA
<213> ORGANISM: Homo sapiens

<400> SEQUENCE: 416
gatgctaaga ccacacagcc aaattcaatg gagagtaacg aagaagagcc tgttcacttg    60
ccttgtaacc actccacaat cagtggaact gattacatac                         100

<210> SEQ ID NO 417
<211> LENGTH: 100
<212> TYPE: DNA
<213> ORGANISM: Homo sapiens

<400> SEQUENCE: 417
ccctcccagg gtccagagta cgtgattcat ggtcttacaa gcaatgtgaa caacagaatg    60
gcctgtgtgg caatcgctga agacagaaag tccagtacct                         100

<210> SEQ ID NO 418
<211> LENGTH: 100
<212> TYPE: DNA
<213> ORGANISM: Homo sapiens

<400> SEQUENCE: 418
acccagctgc tggagcagag ccctcagttt ctaagcatcc aagagggaga aaatctcact    60
gtgtactgca actcctcaag tgttttttcc agcttacaat                         100

<210> SEQ ID NO 419
<211> LENGTH: 100
<212> TYPE: DNA
<213> ORGANISM: Homo sapiens

<400> SEQUENCE: 419
aagagactaa cctttcagtt tggtgatgca agaaaggaca gttctctcca catcactgca    60
gcccagcctg gtgatacagg cctctacctc tgtgcaggag                         100

<210> SEQ ID NO 420
<211> LENGTH: 100
<212> TYPE: DNA
<213> ORGANISM: Homo sapiens

<400> SEQUENCE: 420
acccagctgc tggagcagag ccctcagttt ctaagcatcc aagagggaga aaatctcact    60
gtgtactgca actcctcaag tgttttttcc agcttacaat                         100

<210> SEQ ID NO 421
<211> LENGTH: 100
<212> TYPE: DNA
<213> ORGANISM: Homo sapiens

<400> SEQUENCE: 421
tgaagagact aacctttcag tttggtgatg caagaaagga cagttctctc cacatcactg    60
```
cggcccagcc tggtgataca ggccactacc tctgtgcagg 100

<210> SEQ ID NO 422
<211> LENGTH: 100
<212> TYPE: DNA
<213> ORGANISM: Homo sapiens

<400> SEQUENCE: 422
acccagctgc tggagcagag ccctcagttt ctaagcatcc aagagggaga aaatctcact 60
gtgtactgca actcctcaag tgttttttcc agcttacaat 100

<210> SEQ ID NO 423
<211> LENGTH: 100
<212> TYPE: DNA
<213> ORGANISM: Homo sapiens

<400> SEQUENCE: 423
gctgaagaga ctaacctttc agtttggtga tgcaagaaag gacagttctc tccacatcac 60
tgcagcccag actggtgata caggcctcta cctctgtgca 100

<210> SEQ ID NO 424
<211> LENGTH: 100
<212> TYPE: DNA
<213> ORGANISM: Homo sapiens

<400> SEQUENCE: 424
aaagtggagc agagtcctca ggtcctgatc ctccaagagg gaagaaattc attcctggtg 60
tgcagttgtt ctatttacat gatccgtgtg cagtggtttc 100

<210> SEQ ID NO 425
<211> LENGTH: 100
<212> TYPE: DNA
<213> ORGANISM: Homo sapiens

<400> SEQUENCE: 425
gaagactaaa atccgcagtc aaagctgagg aactttatgg ccacctatac atcagattcc 60
cagcctgagg actcagctat ttacttctgt gctgtgggga 100

<210> SEQ ID NO 426
<211> LENGTH: 100
<212> TYPE: DNA
<213> ORGANISM: Homo sapiens

<400> SEQUENCE: 426
gaccagcaag ttaagcaaaa ttcaccatcc ctgagcgtcc aggaaggaag aatttctatt 60
ctgaactgtg actatactaa cagcatgttt gattatttcc 100

<210> SEQ ID NO 427
<211> LENGTH: 100
<212> TYPE: DNA
<213> ORGANISM: Homo sapiens

<400> SEQUENCE: 427
agattcactg tcttcttaaa caaaagtgcc aagcacctct ctctgcacat tgtgccctcc 60
cagcctggag actctgcagt gtacttctgt gcagcaagcg 100

<210> SEQ ID NO 428
<211> LENGTH: 100
<212> TYPE: DNA
<213> ORGANISM: Homo sapiens

```
<400> SEQUENCE: 428
gaccagcaag ttaagcaaaa ttcaccatcc ctgagcgtcc aggaaggaag aatttctatt      60
ctgaactgtg actatactaa cagcatgttt gattatttcc                          100

<210> SEQ ID NO 429
<211> LENGTH: 100
<212> TYPE: DNA
<213> ORGANISM: Homo sapiens

<400> SEQUENCE: 429
aagattcact gttttcttaa acaaaagtgc caagcacctc tctctcgaca ttgtgccctc      60
ccagcctgga gactctgcag tgtacttctg tgcagcaagc                          100

<210> SEQ ID NO 430
<211> LENGTH: 100
<212> TYPE: DNA
<213> ORGANISM: Homo sapiens

<400> SEQUENCE: 430
gaccagcaag ttaagcaaaa ttcaccatcc ctgagcgtcc aggaaggaag aatttctatt      60
ctgaactgtg actatactaa cagcatgttt gattatttcc                          100

<210> SEQ ID NO 431
<211> LENGTH: 100
<212> TYPE: DNA
<213> ORGANISM: Homo sapiens

<400> SEQUENCE: 431
agattcactg ttttcttaaa caaaagtgcc aagcacctct ctctgcacat tgtgccctcc      60
cagcctggag actctgcagt gtacttctgt gcagcaagcg                          100

<210> SEQ ID NO 432
<211> LENGTH: 100
<212> TYPE: DNA
<213> ORGANISM: Homo sapiens

<400> SEQUENCE: 432
gctcagtcag tggctcagcc ggaagatcag gtcaacgttg ctgaagggaa tcctctgact      60
gtgaaatgca cctattcagt ctctggaaac ccttatcttt                          100

<210> SEQ ID NO 433
<211> LENGTH: 100
<212> TYPE: DNA
<213> ORGANISM: Homo sapiens

<400> SEQUENCE: 433
tttgaagctg aatttaacaa gagccaaacc tccttccacc tgaagaaacc atctgccctt      60
gtgagcgact ccgctttgta cttctgtgct gtgagagaca                          100

<210> SEQ ID NO 434
<211> LENGTH: 100
<212> TYPE: DNA
<213> ORGANISM: Homo sapiens

<400> SEQUENCE: 434
gctcagtcag tggctcagcg gaagatcagg tcaacgttgc tgaagggaat cctctgactg      60
tgaaatgcac ctattcagtc tctggaaacc cttatctttt                          100
```

<210> SEQ ID NO 435
<211> LENGTH: 100
<212> TYPE: DNA
<213> ORGANISM: Homo sapiens

<400> SEQUENCE: 435
ctttgaagct gaatttaaca agagccaaac ctccttccac ctgaagaaac catctgccct    60
tgtgagcgac tccgctttgt acttctgtgc tgtgagaccc                         100

<210> SEQ ID NO 436
<211> LENGTH: 100
<212> TYPE: DNA
<213> ORGANISM: Homo sapiens

<400> SEQUENCE: 436
caacaaccag tgcagagtcc tcaagccgtg atcctccgag aaggggaaga tgctgtcatc    60
aactgcagtt cctccaaggc tttatattct gtacactggt                         100

<210> SEQ ID NO 437
<211> LENGTH: 100
<212> TYPE: DNA
<213> ORGANISM: Homo sapiens

<400> SEQUENCE: 437
aaaatatctg cttcatttaa tgaaaaaaag cagcaaagct ccctgtacct tacggcctcc    60
cagctcagtt actcaggaac ctacttctgc ggcacagaga                         100

<210> SEQ ID NO 438
<211> LENGTH: 100
<212> TYPE: DNA
<213> ORGANISM: Homo sapiens

<400> SEQUENCE: 438
caacaaccag tgcagagtcc tcaagccgtg atcctccgag aaggggaaga tgctgtcacc    60
aactgcagtt cctccaaggc tttatattct gtacactggt                         100

<210> SEQ ID NO 439
<211> LENGTH: 100
<212> TYPE: DNA
<213> ORGANISM: Homo sapiens

<400> SEQUENCE: 439
tcgtgaaaaa atatctgctt catttaatga aaaaaagcag caaagctccc tgtaccttac    60
ggcctcccag ctcagttact caggaaccta cttctgcggg                         100

<210> SEQ ID NO 440
<211> LENGTH: 100
<212> TYPE: DNA
<213> ORGANISM: Homo sapiens

<400> SEQUENCE: 440
caacaaccag tgcagagtcc tcaagccgtg atcctccgag aaggggaaga tgctgtcatc    60
aactgcagtt cctccaaggc tttatattct gtacactggt                         100

<210> SEQ ID NO 441
<211> LENGTH: 100
<212> TYPE: DNA
<213> ORGANISM: Homo sapiens

<400> SEQUENCE: 441

```
tcatgaaaaa atatctgctt catttaatga aaaaaagcgg caaagctccc tgtaccttac    60
ggcctcccag ctcagttact caggaaccta cttctgcggc                         100

<210> SEQ ID NO 442
<211> LENGTH: 100
<212> TYPE: DNA
<213> ORGANISM: Homo sapiens

<400> SEQUENCE: 442
caacaaccag tgcagagtcc tcaagccgtg atcctccgag aaggggaaga tgctgtcatc    60
aactgcagtt cctccaaggc tttatattct gtacactggt                         100

<210> SEQ ID NO 443
<211> LENGTH: 100
<212> TYPE: DNA
<213> ORGANISM: Homo sapiens

<400> SEQUENCE: 443
tcctgatgat attactgaag ggtggagaac agaagcgtca tgaaaaaata tctgcttcat    60
ttaatgaaaa aaagcagcaa agctccctgt accttacggc                         100

<210> SEQ ID NO 444
<211> LENGTH: 100
<212> TYPE: DNA
<213> ORGANISM: Homo sapiens

<400> SEQUENCE: 444
cagagggtca ttcaatccca accagcaata tctacgcagg agggtgagac cgtgaaactg    60
gactgtgcat acaaaactaa tattgtatat tacatattgt                         100

<210> SEQ ID NO 445
<211> LENGTH: 100
<212> TYPE: DNA
<213> ORGANISM: Homo sapiens

<400> SEQUENCE: 445
tattctgtga gcttccagaa aacaactaaa actattcagc ttatcatatc atcatcacag    60
ccagaagacc tgcaacatat ttctgttgtc tcaaagagcc                         100

<210> SEQ ID NO 446
<211> LENGTH: 100
<212> TYPE: DNA
<213> ORGANISM: Homo sapiens

<400> SEQUENCE: 446
aaggatgtga tacagagtta ttcaaatcta aatgtctagg agagagaaat ggccgttatt    60
aatgacagtt atacagatgg agctttgaat tatttctgtt                         100

<210> SEQ ID NO 447
<211> LENGTH: 100
<212> TYPE: DNA
<213> ORGANISM: Homo sapiens

<400> SEQUENCE: 447
aggctcactg tactgttgaa taaaaatgct aaacatgtct ccctgcatat tacagccacc    60
caaccaggag actcattcct gtacttctgt gcagtgagaa                         100

<210> SEQ ID NO 448
```

```
<211> LENGTH: 100
<212> TYPE: DNA
<213> ORGANISM: Homo sapiens

<400> SEQUENCE: 448
gctcagaaag taacccaagt tcagaccaca gtaactaggc agaaaggagt agctgtgacc      60
ttggactgca tgtttgaaac cagatagaat tcgtacactt                          100

<210> SEQ ID NO 449
<211> LENGTH: 100
<212> TYPE: DNA
<213> ORGANISM: Homo sapiens

<400> SEQUENCE: 449
gcaaagcctg tgaactttga aaaaagaaa aagttcatca acctcaccat caattcctta      60
aaactgactc agccaagtac ttctgtgctc tcaggaatcc                          100

<210> SEQ ID NO 450
<211> LENGTH: 100
<212> TYPE: DNA
<213> ORGANISM: Homo sapiens

<400> SEQUENCE: 450
agccaagaac tggagcagag tcctcagtcc ttgatcgtcc aagagggaaa gaatctcacc      60
ataaactgca cgtcatcaaa gacgttatat ggcttatact                          100

<210> SEQ ID NO 451
<211> LENGTH: 100
<212> TYPE: DNA
<213> ORGANISM: Homo sapiens

<400> SEQUENCE: 451
aagataactg ccaagttgga tgagaaaaag cagcaaagtt ccctgcatat cacagcctcc      60
cagcccagcc atgcaggcat ctacctctgt ggagcagaca                          100

<210> SEQ ID NO 452
<211> LENGTH: 100
<212> TYPE: DNA
<213> ORGANISM: Homo sapiens

<400> SEQUENCE: 452
ggtcaacagc tgaatcagag tcctcaatct atgtttatcc aggaaggaga agatgtctcc      60
atgaactgca cttcttcaag catatttaac acctggctat                          100

<210> SEQ ID NO 453
<211> LENGTH: 100
<212> TYPE: DNA
<213> ORGANISM: Homo sapiens

<400> SEQUENCE: 453
aagactgact gctcagtttg gtataaccag aaaggacagc ttcctgaata tctcagcatc      60
catacctagt gatgtaggca tctacttctg tgctgggcag                          100

<210> SEQ ID NO 454
<211> LENGTH: 100
<212> TYPE: DNA
<213> ORGANISM: Homo sapiens

<400> SEQUENCE: 454
ggtcaacagc tgaatcagag tcctcaatct atgtttatcc aggaaggaga agatgtctcc      60
```

```
atgaactgca cttcttcaag catatttaac acctggctat                    100
```

<210> SEQ ID NO 455
<211> LENGTH: 100
<212> TYPE: DNA
<213> ORGANISM: Homo sapiens

<400> SEQUENCE: 455

```
aaatggaaga ctgactgctc agtttggtat aaccagaaag gacagcttcc tgaatatctc    60
agcatccata cctagtgatg taggcatcta cttctgtgct                        100
```

<210> SEQ ID NO 456
<211> LENGTH: 100
<212> TYPE: DNA
<213> ORGANISM: Homo sapiens

<400> SEQUENCE: 456

```
gaagacaagg tggtacaaag ccctctatct ctggttgtcc acgagggaga caccgtaact    60
ctcaattgca gttatgaagt gactaacttt cgaagcctac                        100
```

<210> SEQ ID NO 457
<211> LENGTH: 100
<212> TYPE: DNA
<213> ORGANISM: Homo sapiens

<400> SEQUENCE: 457

```
agactaagta gcatattaga taagaaagaa ctttccagca tcctgaacat cacagccacc    60
cagaccggag actcggccat ctacctctgt gctgtggagg                        100
```

<210> SEQ ID NO 458
<211> LENGTH: 100
<212> TYPE: DNA
<213> ORGANISM: Homo sapiens

<400> SEQUENCE: 458

```
gaagacaagg tggtacaaag ccctcaatct ctggttgtcc acgagggaga cactgtaact    60
ctcaattgca gttatgaaat gactaacttt cgaagcctac                        100
```

<210> SEQ ID NO 459
<211> LENGTH: 100
<212> TYPE: DNA
<213> ORGANISM: Homo sapiens

<400> SEQUENCE: 459

```
ggaagactaa gtagcatatt agataagaaa gaacttttca gcatcctgaa catcacagcc    60
acccagaccg gagactcggc cgtctacctc tgtgctgtgg                        100
```

<210> SEQ ID NO 460
<211> LENGTH: 100
<212> TYPE: DNA
<213> ORGANISM: Homo sapiens

<400> SEQUENCE: 460

```
gaagacaagg tggtacaaag ccctctatct ctggttgtcc acgagggaga cactgtaact    60
cccaattgca gttatgaagt gactaacttt cgaagcctac                        100
```

<210> SEQ ID NO 461
<211> LENGTH: 100
<212> TYPE: DNA

<213> ORGANISM: Homo sapiens

<400> SEQUENCE: 461
gtcaggaaga ctaagtagca tattagataa gaaagaactt ttcagcatcc tgaacatcac    60
agccacccag accggagact cggccgtcta cctctgtgct                         100

<210> SEQ ID NO 462
<211> LENGTH: 100
<212> TYPE: DNA
<213> ORGANISM: Homo sapiens

<400> SEQUENCE: 462
gaagacaagg tggtacaaag ccctctatct ctggttgtcc acgagggaga cactgtaact    60
ctcaattgca gttatgaagt gactaacttt cgaagcctac                         100

<210> SEQ ID NO 463
<211> LENGTH: 100
<212> TYPE: DNA
<213> ORGANISM: Homo sapiens

<400> SEQUENCE: 463
tcaggaagac taagtagcat attagataag aaagaactttt tcagcatcct gaacatcaca   60
gccacccaga ccggagactc ggccgtctac ctctgtgctg                         100

<210> SEQ ID NO 464
<211> LENGTH: 100
<212> TYPE: DNA
<213> ORGANISM: Homo sapiens

<400> SEQUENCE: 464
caactgccag tggaacagaa tgctccttcc ctgaaagtca aggaaggtga cagcgtcaca    60
ctgaactgca gttacagaga cagcccttca gatttcttca                         100

<210> SEQ ID NO 465
<211> LENGTH: 100
<212> TYPE: DNA
<213> ORGANISM: Homo sapiens

<400> SEQUENCE: 465
agattcacag ccaggcttaa aaaaggagac cagcacattt ccctgcacat acaggattcc    60
cagctccatg actcaaccac attcttctgc gcagcaagca                         100

<210> SEQ ID NO 466
<211> LENGTH: 100
<212> TYPE: DNA
<213> ORGANISM: Homo sapiens

<400> SEQUENCE: 466
gcccagacag tcactcagtc tcaaccagag atgtctgtgc aggaggcaga gactgtgacc    60
ctgagttgca catatgacac cagtgagaat aattattatt                         100

<210> SEQ ID NO 467
<211> LENGTH: 100
<212> TYPE: DNA
<213> ORGANISM: Homo sapiens

<400> SEQUENCE: 467
tctctgtgaa cttccagaaa gcagccaaat ccttcagtct caagatctca gactcacagc    60
tgggggacac tgcgatgtat ttctgtgctt tcatgaagca                         100

<210> SEQ ID NO 468
<211> LENGTH: 100
<212> TYPE: DNA
<213> ORGANISM: Homo sapiens

<400> SEQUENCE: 468
gcccagacag tcactcagtc tcaaccagag atgtctgtgc aggaggcaga gactgtgacc      60
ctgagttgca catatgacac cagtgagaat gattattatt                          100

<210> SEQ ID NO 469
<211> LENGTH: 100
<212> TYPE: DNA
<213> ORGANISM: Homo sapiens

<400> SEQUENCE: 469
gagaatcgtt tctctgtgaa cttccagaaa gcagccaaat ccttcagtct caagatctca      60
gactcacagc tgggggacac tgcgatgtat ttctgtgctt                          100

<210> SEQ ID NO 470
<211> LENGTH: 100
<212> TYPE: DNA
<213> ORGANISM: Homo sapiens

<400> SEQUENCE: 470
gcccagacag tcactcagtc tcaaccagag atgtctgtgc aggaggcaga gactgtgacc      60
ctgagttgca catatgacac cagtgagagt aattattatt                          100

<210> SEQ ID NO 471
<211> LENGTH: 100
<212> TYPE: DNA
<213> ORGANISM: Homo sapiens

<400> SEQUENCE: 471
aatcgtttct ctgtgaactt ccagaaagca gccaaatcct tcagtctcaa gatctcagac      60
tcacagctgg gggacactgc gatgtatttc tgtgctttca                          100

<210> SEQ ID NO 472
<211> LENGTH: 100
<212> TYPE: DNA
<213> ORGANISM: Homo sapiens

<400> SEQUENCE: 472
gcccagacag tcactcagtc ccagccagag atgtctgtgc aggaggcaga gactgtgacc      60
ctgagttgca catatgacac cagtgagaat aattattatt                          100

<210> SEQ ID NO 473
<211> LENGTH: 100
<212> TYPE: DNA
<213> ORGANISM: Homo sapiens

<400> SEQUENCE: 473
ggagaatcgt ttctctgtga acttccagaa agcagccaaa tccttcagtc tcaagatctc      60
agactcacag ctgggggaca ctgcgatgta tttctgtgca                          100

<210> SEQ ID NO 474
<211> LENGTH: 100
<212> TYPE: DNA
<213> ORGANISM: Homo sapiens

```
<400> SEQUENCE: 474
gctcagacag tcactcagtc tcaaccagag atgtctgtgc aggaggcaga gaccgtgacc    60
ctgagctgca catatgacac cagtgagagt gattattatt                         100

<210> SEQ ID NO 475
<211> LENGTH: 100
<212> TYPE: DNA
<213> ORGANISM: Homo sapiens

<400> SEQUENCE: 475
ttctctgtga acttccagaa agcagccaaa tccttcagtc tcaagatctc agactcacag    60
ctgggggatg ccgcgatgta tttctgtgct tataggagcg                         100

<210> SEQ ID NO 476
<211> LENGTH: 100
<212> TYPE: DNA
<213> ORGANISM: Homo sapiens

<400> SEQUENCE: 476
gagctgaaag tggaacaaaa ccctctgttc ctgagcatgc aggagggaaa aaactatacc    60
atctactgca attattcaac cacttcagac agactgtatt                         100

<210> SEQ ID NO 477
<211> LENGTH: 100
<212> TYPE: DNA
<213> ORGANISM: Homo sapiens

<400> SEQUENCE: 477
cgattaatgg cctcacttga taccaaagcc cgtctcagca ccctccacat cacagctgcc    60
gtgcatgacc tctctgccac ctacttctgt gccgtggaca                         100

<210> SEQ ID NO 478
<211> LENGTH: 100
<212> TYPE: DNA
<213> ORGANISM: Homo sapiens

<400> SEQUENCE: 478
cttgctaaga ccacccagcc catctccatg gactcatatg aaggacaaga agtgaacata    60
acctgtagcc acaacaacat tgctacaaat gattatatca                         100

<210> SEQ ID NO 479
<211> LENGTH: 100
<212> TYPE: DNA
<213> ORGANISM: Homo sapiens

<400> SEQUENCE: 479
gcctccctgt ttatccctgc cgacagaaag tccagcactc tgagcctgcc ccgggtttcc    60
ctgagcgaca ctgctgtgta ctactgcctc gtgggtgaca                         100

<210> SEQ ID NO 480
<211> LENGTH: 100
<212> TYPE: DNA
<213> ORGANISM: Homo sapiens

<400> SEQUENCE: 480
agcaattcag tcaagcagac gggccaaata accgtctcgg agggagcatc tgtgactatg    60
aactgcacat acacatccac gggggtaccct acccttttct                         100
```

```
<210> SEQ ID NO 481
<211> LENGTH: 100
<212> TYPE: DNA
<213> ORGANISM: Homo sapiens

<400> SEQUENCE: 481
aaaacttcgg aggcggaaat attaaagaca aaaactcccc cattgtgaaa tattcagtcc      60
aggtatcaga ctcagccgtg tactactgtc ttctgggaga                          100

<210> SEQ ID NO 482
<211> LENGTH: 100
<212> TYPE: DNA
<213> ORGANISM: Homo sapiens

<400> SEQUENCE: 482
aaaaatgaag tggagcagag tcctcagaac ctgactgccc aggaaggaga atttatcaca      60
atcaactgca gttactcggt aggaataagt gccttacact                          100

<210> SEQ ID NO 483
<211> LENGTH: 100
<212> TYPE: DNA
<213> ORGANISM: Homo sapiens

<400> SEQUENCE: 483
aagattaatt gccacaataa acatacagga aaagcacagc tccctgcaca tcacagcctc      60
ccatcccaga gactctgccg tctacatctg tgctgtcaga                          100

<210> SEQ ID NO 484
<211> LENGTH: 100
<212> TYPE: DNA
<213> ORGANISM: Homo sapiens

<400> SEQUENCE: 484
ggagaggatg tggagcagag tcttttcctg agtgtccgag agggagacag ctccgttata      60
aactgcactt acacagacag ctcctccacc tacttatact                          100

<210> SEQ ID NO 485
<211> LENGTH: 100
<212> TYPE: DNA
<213> ORGANISM: Homo sapiens

<400> SEQUENCE: 485
agactcactg ttctattgaa taaaaaggat aaacatctgt ctctgcgcat tgcagacacc      60
cagactgggg actcagctat ctacttctgt gcagagagta                          100

<210> SEQ ID NO 486
<211> LENGTH: 100
<212> TYPE: DNA
<213> ORGANISM: Homo sapiens

<400> SEQUENCE: 486
agccaaaaga tagaacagaa ttccgaggcc ctgaacattc aggagggtaa aacggccacc      60
ctgacctgca actatacaaa ctattcccca gcatacttac                          100

<210> SEQ ID NO 487
<211> LENGTH: 100
<212> TYPE: DNA
<213> ORGANISM: Homo sapiens

<400> SEQUENCE: 487
```

```
agactgaagg tcacctttga taccacccTT aaacagagtt tgtttcatat cacagcctcc    60
cagcctgcag actcagctac ctacctctgt gctctagaca                        100
```

<210> SEQ ID NO 488
<211> LENGTH: 100
<212> TYPE: DNA
<213> ORGANISM: Homo sapiens

<400> SEQUENCE: 488

```
agccaaaaga tagaacagaa ttccgaggcc ctgaacattc aggagggtaa aacggccacc    60
ctgacctgca actatacaaa ctattctcca gcatacttac                        100
```

<210> SEQ ID NO 489
<211> LENGTH: 100
<212> TYPE: DNA
<213> ORGANISM: Homo sapiens

<400> SEQUENCE: 489

```
gaaagaaaga ctgaaggtca cctttgatac caccctTaaa cagagtttgt ttcatatcac    60
agcctcccag cctgcagact cagctaccta cctctgtgct                        100
```

<210> SEQ ID NO 490
<211> LENGTH: 100
<212> TYPE: DNA
<213> ORGANISM: Homo sapiens

<400> SEQUENCE: 490

```
gaggccctga acattcagga gggtaaaacg gccaccctga cctgcaacta tacaaactat    60
tctccagcat acttacagtg gtaccgacaa gatccaggaa                        100
```

<210> SEQ ID NO 491
<211> LENGTH: 100
<212> TYPE: DNA
<213> ORGANISM: Homo sapiens

<400> SEQUENCE: 491

```
gaaagaaaga ctgaaggtca cctttgatac caccctTaaa cagagtttgt ttcatatcac    60
agcctcccag cctgcagact cagctaccta cctctgtgct                        100
```

<210> SEQ ID NO 492
<211> LENGTH: 100
<212> TYPE: DNA
<213> ORGANISM: Homo sapiens

<400> SEQUENCE: 492

```
gaggccctga acattcagga gggtaaaacg gccaccctga cctgcaacta tacaaactat    60
tctccagcat acttacagtg gtaccgacaa gatccaggaa                        100
```

<210> SEQ ID NO 493
<211> LENGTH: 100
<212> TYPE: DNA
<213> ORGANISM: Homo sapiens

<400> SEQUENCE: 493

```
gaaagaaaga ctgaaggtca cctttgatac caccctTaaa cagagtttgt ttcatgtcac    60
agcctcccag cctgcagact cagctaccta cctctgtgct                        100
```

<210> SEQ ID NO 494
<211> LENGTH: 100

```
<212> TYPE: DNA
<213> ORGANISM: Homo sapiens

<400> SEQUENCE: 494
gaggccctga acattcagga gggtaaaacg gccaccctga cctgcaacta tacgaactat    60
tctccagcat acttacagtg gtaccgacaa gatccaggaa                         100

<210> SEQ ID NO 495
<211> LENGTH: 100
<212> TYPE: DNA
<213> ORGANISM: Homo sapiens

<400> SEQUENCE: 495
gaaagaaaga ctgaaggtca cctttgatac caccccttaaa cagagtttgt ttcatatcac   60
agcctcccag cctgcagact cagctaccta cctctgtgct                         100

<210> SEQ ID NO 496
<211> LENGTH: 100
<212> TYPE: DNA
<213> ORGANISM: Homo sapiens

<400> SEQUENCE: 496
agccaaaaga tagaacagaa ttccgaggcc ctgaacattc aggagggtaa aacgccacc    60 ctgacctgca actatacaaa ctattctcca gcatacttac                         100

<210> SEQ ID NO 497
<211> LENGTH: 100
<212> TYPE: DNA
<213> ORGANISM: Homo sapiens

<400> SEQUENCE: 497
ccaggaagag gccctgtttt cttgctactc atacgtgaaa atgagaaaga aaaaggaaa    60 gaaagactga aggtcacctt tgataccacc cttaaccaga                         100

<210> SEQ ID NO 498
<211> LENGTH: 100
<212> TYPE: DNA
<213> ORGANISM: Homo sapiens

<400> SEQUENCE: 498
gaaaaccagg tggagcacag ccctcatttt ctgggacccc agcagggaga cgttgcctcc   60
atgagctgca cgtactctgt cagtcgtttt aacaatttgc                         100

<210> SEQ ID NO 499
<211> LENGTH: 100
<212> TYPE: DNA
<213> ORGANISM: Homo sapiens

<400> SEQUENCE: 499
aaaggaagac taaatgctac attactgaag aatggaagca gcttgtacat tacagccgtg    60
cagcctgaag attcagccac ctatttctgt gctgtagatg                         100

<210> SEQ ID NO 500
<211> LENGTH: 100
<212> TYPE: DNA
<213> ORGANISM: Homo sapiens

<400> SEQUENCE: 500
gcccagtctg tgagccagca taaccaccac gtaattctct ctgaagcagc ctcactggag    60
```

```
ttgggatgca actattccta tgtgggaact gttaatctct                        100
```

<210> SEQ ID NO 501
<211> LENGTH: 100
<212> TYPE: DNA
<213> ORGANISM: Homo sapiens

<400> SEQUENCE: 501

```
gctttgaggc tgaatttata aagagtaaat tctcctttaa tctgaggaaa ccctctgtgc   60
agtggagtga cacagctgag tacttctgtg ccgtgaatgc                        100
```

<210> SEQ ID NO 502
<211> LENGTH: 100
<212> TYPE: DNA
<213> ORGANISM: Homo sapiens

<400> SEQUENCE: 502

```
gcccagtctg tgagccagca taaccaccac gtaattctct ctgaagcagc ctcactggag   60
ttgggatgca actattccta tgtgggaact gttaatctct                        100
```

<210> SEQ ID NO 503
<211> LENGTH: 100
<212> TYPE: DNA
<213> ORGANISM: Homo sapiens

<400> SEQUENCE: 503

```
ttttcagggg atccactggt taaaggcatc aagggcgttg aggctgaatt tataaagagt   60
aaattctcct ttaatctgag gaaaccctct gtgcagtgga                        100
```

<210> SEQ ID NO 504
<211> LENGTH: 100
<212> TYPE: DNA
<213> ORGANISM: Homo sapiens

<400> SEQUENCE: 504

```
gcccagtcgg tgacccagct tgacagccac gtctctgtct ctgaaggaac cccggtgctg   60
ctgaggtgca actactcatc ttcttattca ccatctctct                        100
```

<210> SEQ ID NO 505
<211> LENGTH: 100
<212> TYPE: DNA
<213> ORGANISM: Homo sapiens

<400> SEQUENCE: 505

```
gttttgaggc tgaatttaag aagagtgaaa cctccttcca cctgacgaaa ccctcagccc   60
atatgagcga cgcggctgag tacttctgtg ttgtgagtga                        100
```

<210> SEQ ID NO 506
<211> LENGTH: 100
<212> TYPE: DNA
<213> ORGANISM: Homo sapiens

<400> SEQUENCE: 506

```
gcccagtcgg tgacccagct tagcagccac gtctctgtct ctgaaggaac cccggtgctg   60
ctgaggtgca actactcatc ttcttattca ccatctctct                        100
```

<210> SEQ ID NO 507
<211> LENGTH: 100
<212> TYPE: DNA
<213> ORGANISM: Homo sapiens

<400> SEQUENCE: 507
tttaagaaga gtgaaacctc cttccacctg acgaaaccct cagcccatat gagcgacgcg    60
gctgagtact tctgtgttgt gacccgtcac gagctttcag                         100

<210> SEQ ID NO 508
<211> LENGTH: 100
<212> TYPE: DNA
<213> ORGANISM: Homo sapiens

<400> SEQUENCE: 508
gcccagtcag tgacccagcc tgacatccac atcactgtct ctgaaggagc ctcactggag    60
ttgagatgta actattccta tggggcaaca ccttatctct                         100

<210> SEQ ID NO 509
<211> LENGTH: 100
<212> TYPE: DNA
<213> ORGANISM: Homo sapiens

<400> SEQUENCE: 509
gctttgaggc tgaatttaag aggagtcaat cttccttcaa tctgaggaaa ccctctgtgc    60
attggagtga tgctgctgag tacttctgtg ctgtgggtgc                         100

<210> SEQ ID NO 510
<211> LENGTH: 100
<212> TYPE: DNA
<213> ORGANISM: Homo sapiens

<400> SEQUENCE: 510
gcccagtcag tgacccagcc tgacatccac atcactgtct ctgaaggagc ctcactggag    60
ttgagatgta actattccta tggggcaaca ccttatctct                         100

<210> SEQ ID NO 511
<211> LENGTH: 100
<212> TYPE: DNA
<213> ORGANISM: Homo sapiens

<400> SEQUENCE: 511
aggctttgag gctgaattta agaggagtca atcttccttc aacctgagga aaccctctgt    60
gcattggagt gatgctgctg agtacttctg tgctgtggtt                         100

<210> SEQ ID NO 512
<211> LENGTH: 100
<212> TYPE: DNA
<213> ORGANISM: Homo sapiens

<400> SEQUENCE: 512
gcccagtcag tgacccagcc tgacatccac atcactgtct ctgaaggagc ctcactggag    60
ttgagatgta actattccta tggggcaaca ccttatctct                         100

<210> SEQ ID NO 513
<211> LENGTH: 100
<212> TYPE: DNA
<213> ORGANISM: Homo sapiens

<400> SEQUENCE: 513
tattaaaggc tttgaggctg aatttaagag gagtcaatct tccttcaatc tgaggaaacc    60
ctctgtgcat tggagtgatg cgtctgagta cttctgtgct                         100

<210> SEQ ID NO 514
<211> LENGTH: 100
<212> TYPE: DNA
<213> ORGANISM: Homo sapiens

<400> SEQUENCE: 514
gcccagtcgg tgacccagct tggcagccac gtctctgtct ctgaaggagc cctggttctg     60
ctgaggtgca actactcatc gtctgttcca ccatatctct                         100

<210> SEQ ID NO 515
<211> LENGTH: 100
<212> TYPE: DNA
<213> ORGANISM: Homo sapiens

<400> SEQUENCE: 515
gttttgaggc tgaatttaag aagagtgaaa cctccttcca cctgacgaaa ccctcagccc     60
atatgagcga cgcggctgag tacttctgtg ctgtgagtga                         100

<210> SEQ ID NO 516
<211> LENGTH: 100
<212> TYPE: DNA
<213> ORGANISM: Homo sapiens

<400> SEQUENCE: 516
gcccagtcgg tgacccagct tggcagccac gtctctgtct ctgaaggagc cctggttctg     60
ctgaggtgca actactcatc gtctgttcca ccatatctct                         100

<210> SEQ ID NO 517
<211> LENGTH: 100
<212> TYPE: DNA
<213> ORGANISM: Homo sapiens

<400> SEQUENCE: 517
gaatttaaga agagtgaaac ctccttccac ctgacaaaac cctcagccca tatgagcgac     60
gcggctgagt acttctgtgc tgtgagtgat ctcgaaccga                         100

<210> SEQ ID NO 518
<211> LENGTH: 100
<212> TYPE: DNA
<213> ORGANISM: Homo sapiens

<400> SEQUENCE: 518
gcccagtcgg tgacccagct tggcagccac gtctctgtct ctgagggagc cctggttctg     60
ctgaggtgca actactcatc gtctgttcca ccatatctct                         100

<210> SEQ ID NO 519
<211> LENGTH: 100
<212> TYPE: DNA
<213> ORGANISM: Homo sapiens

<400> SEQUENCE: 519
catcaacggt tttgaggctg aatttaagaa gagtgaaacc tccttccacc tgacgaaacc     60
ctcagcccat atgagcgacg cggctgagta cttctgtgct                         100

<210> SEQ ID NO 520
<211> LENGTH: 100
<212> TYPE: DNA
<213> ORGANISM: Homo sapiens

<400> SEQUENCE: 520

```
gcccagtcgg tgacccagct tggcagccac gtctctgtct ctgaacgagc cctggttctg    60
ctgaggtgca actactcatc gtctgttcca ccatatctct                         100

<210> SEQ ID NO 521
<211> LENGTH: 100
<212> TYPE: DNA
<213> ORGANISM: Homo sapiens

<400> SEQUENCE: 521
aggcatcaac ggttttgagg ctgaatttaa gaagagtgaa acctccttcc acctgacgaa    60
accctcagcc catatgagcg acgcggctga gtacttctgt                         100

<210> SEQ ID NO 522
<211> LENGTH: 100
<212> TYPE: DNA
<213> ORGANISM: Homo sapiens

<400> SEQUENCE: 522
gcccagtcgg tgacccagct tggcagccac gtctctgtct ctgaaggagc cctggttctg    60
ctgaggtgca actactcatc gtctgttcca ccatatctct                         100

<210> SEQ ID NO 523
<211> LENGTH: 100
<212> TYPE: DNA
<213> ORGANISM: Homo sapiens

<400> SEQUENCE: 523
ggctgaattt aagaagagtg aaacctcctt ccacctgacg aaaccctcag cccatatgag    60
cgacgcggct gagtacttct gtgctgtgag tgagtctcca                         100

<210> SEQ ID NO 524
<211> LENGTH: 100
<212> TYPE: DNA
<213> ORGANISM: Homo sapiens

<400> SEQUENCE: 524
ctcttctggt atgtgcaata ccccaaccaa ggactccagc ttctcctgaa gtacacatca    60
gcggccaccc tggttaaagg catcaacggt tttgaggctg                         100

<210> SEQ ID NO 525
<211> LENGTH: 100
<212> TYPE: DNA
<213> ORGANISM: Homo sapiens

<400> SEQUENCE: 525
gaatttaaga agagtgaaac ctccttccac ctgacgaaac ccgcagccca tatgagcgac    60
gcggctgagt acttctgtgc tgtgagtgat ctcgaaccga                         100

<210> SEQ ID NO 526
<211> LENGTH: 100
<212> TYPE: DNA
<213> ORGANISM: Homo sapiens

<400> SEQUENCE: 526
gttgaaccat atctcttctg gtatgtgcaa taccccaacc aaggactcca gcttctcctg    60
aagtacacaa caggggccac cctggttaaa ggcatcaacg                         100

<210> SEQ ID NO 527
```

```
<211> LENGTH: 100
<212> TYPE: DNA
<213> ORGANISM: Homo sapiens

<400> SEQUENCE: 527 acgttttga ggctgaattt aaaaagagtg aaacctcctt ccacctgacg aaaccctcag    60
cccatatgac cgacccggct gagtacttct gtgctgtgag                        100

<210> SEQ ID NO 528
<211> LENGTH: 100
<212> TYPE: DNA
<213> ORGANISM: Homo sapiens

<400> SEQUENCE: 528
gcccagtcag tgacccagcc tgacatccgc atcactgtct ctgaaggagc ctcactggag    60
ttgagatgta actattccta tggggcgatg ttgtgggaag                          100

<210> SEQ ID NO 529
<211> LENGTH: 100
<212> TYPE: DNA
<213> ORGANISM: Homo sapiens

<400> SEQUENCE: 529
tggacactta tcacttcccc aatcaatacc cctgtgattt cctatgcctg tctttacttt    60
aatctcttaa tcctgtcagc tgaggaggat gtatgtcacc                          100

<210> SEQ ID NO 530
<211> LENGTH: 100
<212> TYPE: DNA
<213> ORGANISM: Homo sapiens

<400> SEQUENCE: 530
gcccagtctg tgacccagct tgacagccaa gtccctgtct ttgaagaagc ccctgtggag    60
ctgaggtgca actactcatc gtctgtttca gtgtatctct                          100

<210> SEQ ID NO 531
<211> LENGTH: 100
<212> TYPE: DNA
<213> ORGANISM: Homo sapiens

<400> SEQUENCE: 531
gttttgaggc tgaatttaac aagagtcaaa cttccttcca cttgaggaaa ccctcagtcc    60
atataagcga cacggctgag tacttctgtg ctgtgagtga                          100

<210> SEQ ID NO 532
<211> LENGTH: 100
<212> TYPE: DNA
<213> ORGANISM: Homo sapiens

<400> SEQUENCE: 532
gcccagtctg tgacccagct tgacagccaa gtccctgtct ttgaagaagc ccctgtggag    60
ctgaggtgca actactcatc gtctgtttca gtgtatctct                          100

<210> SEQ ID NO 533
<211> LENGTH: 100
<212> TYPE: DNA
<213> ORGANISM: Homo sapiens

<400> SEQUENCE: 533
gttttgaggc tgaatttaac aagagtcaaa cttccttcca cttgaggaaa ccctcagtcc    60
```

```
atataagcga cacggctgag tacttctgtg ctgtgagtga                          100
```

<210> SEQ ID NO 534
<211> LENGTH: 100
<212> TYPE: DNA
<213> ORGANISM: Homo sapiens

<400> SEQUENCE: 534

```
acccagtcgg tgacccagct tgatggccac atcactgtct ctgaagaagc ccctctggaa    60
ctgaagtgca actattccta tagtggagtt ccttctctct                          100
```

<210> SEQ ID NO 535
<211> LENGTH: 100
<212> TYPE: DNA
<213> ORGANISM: Homo sapiens

<400> SEQUENCE: 535

```
aggctgaatt taagaagagc gaaacctcct tctacctgag gaaaccatca acccatgtga    60
gtgatgctgc tgagtacttc tgtgctgtgg gtgacaggag                          100
```

<210> SEQ ID NO 536
<211> LENGTH: 100
<212> TYPE: DNA
<213> ORGANISM: Homo sapiens

<400> SEQUENCE: 536

```
ggagattcag tggtccagac agaaggccaa gtgctcccct ctgaagggga ttccctgatt    60
gtgaactgct cctatgaaac cacacagtac ccttcccttt                          100
```

<210> SEQ ID NO 537
<211> LENGTH: 100
<212> TYPE: DNA
<213> ORGANISM: Homo sapiens

<400> SEQUENCE: 537

```
gttttgaagc catgtaccgt aaagaaacca cttctttcca cttggagaaa gactcagttc    60
aagagtcaga ctccgctgtg tacttctgtg ctctgagtga                          100
```

<210> SEQ ID NO 538
<211> LENGTH: 100
<212> TYPE: DNA
<213> ORGANISM: Homo sapiens

<400> SEQUENCE: 538

```
ggaaattcag tgacccagat ggaagggcca gtgactctct cagaagaggc cttcctgact    60
ataaactgca cgtacacagc cacaggatac ccttcccttt                          100
```

<210> SEQ ID NO 539
<211> LENGTH: 100
<212> TYPE: DNA
<213> ORGANISM: Homo sapiens

<400> SEQUENCE: 539

```
gttttgaagc cacataccgt aaagaaacca cttctttcca cttggagaaa ggctcagttc    60
aagtgtcaga ctcagcggtg tacttctgtg ctctgagtga                          100
```

<210> SEQ ID NO 540
<211> LENGTH: 100
<212> TYPE: DNA

<213> ORGANISM: Homo sapiens

<400> SEQUENCE: 540

```
ggagattcag tgacccagat ggaagggcca gtgactctct cagaagaggc cttcctgact    60
ataaactgca cgtacacagc cacaggatac ccttcccttt                        100
```

<210> SEQ ID NO 541
<211> LENGTH: 100
<212> TYPE: DNA
<213> ORGANISM: Homo sapiens

<400> SEQUENCE: 541

```
caacaaaggt tttgaagcca cataccgtaa agaaaccact tctttccact tggagaaagg    60
ctcagttcaa gtgtcagact cagcggtgta cttctgtgct                        100
```

<210> SEQ ID NO 542
<211> LENGTH: 100
<212> TYPE: DNA
<213> ORGANISM: Homo sapiens

<400> SEQUENCE: 542

```
ggagattcag tgacccagat ggaagggcca gtgactctct cagaagaggc cttcctgact    60
ataaactgca cgtacacagc cacaggatac ccttcccttt                        100
```

<210> SEQ ID NO 543
<211> LENGTH: 100
<212> TYPE: DNA
<213> ORGANISM: Homo sapiens

<400> SEQUENCE: 543

```
caacaaaggt tttgaagcca cataccgtaa ggaaaccact tctttccact tggagaaagg    60
ctcagttcaa gtgtcagact cagcggtgta cttctgtgct                        100
```

<210> SEQ ID NO 544
<211> LENGTH: 100
<212> TYPE: DNA
<213> ORGANISM: Homo sapiens

<400> SEQUENCE: 544

```
ggaaattcag tgacccagat ggaagggcca gtgactctct cagaagaggc cttcctgact    60
ataaactgca cgtacacagc cacaggatac ccttcccttt                        100
```

<210> SEQ ID NO 545
<211> LENGTH: 100
<212> TYPE: DNA
<213> ORGANISM: Homo sapiens

<400> SEQUENCE: 545

```
caacaaaggt tttgaagcca cataccgtaa ggaaaccact tctttccact tggagaaagg    60
ctcagttcaa gtgtcagact cagcggtgta cttctgtgct                        100
```

<210> SEQ ID NO 546
<211> LENGTH: 100
<212> TYPE: DNA
<213> ORGANISM: Homo sapiens

<400> SEQUENCE: 546

```
gatactggaa ttacccagac accaaaatac ctggtcacag caatgggggag taaaaggaca    60
atgaaacgtg agcatctggg acatgattct atgtattggt                        100
```

<210> SEQ ID NO 547
<211> LENGTH: 100
<212> TYPE: DNA
<213> ORGANISM: Homo sapiens

<400> SEQUENCE: 547
acttcacacc tgaatgccct gacagctctc gcttatacct tcatgtggtc gcactgcagc    60
aagaagactc agctgcgtat ctctgcacca gcagccaaga                          100

<210> SEQ ID NO 548
<211> LENGTH: 100
<212> TYPE: DNA
<213> ORGANISM: Homo sapiens

<400> SEQUENCE: 548
gatgctgaaa tcacccagag cccaagacac aagatcacag agacaggaag gcaggtgacc    60
ttggcgtgtc accagacttg gaaccacaac aatatgttct                          100

<210> SEQ ID NO 549
<211> LENGTH: 100
<212> TYPE: DNA
<213> ORGANISM: Homo sapiens

<400> SEQUENCE: 549
gctacagtgt ctctagatca aacacagagg acctcccct cactctggag tctgctgcct     60
cctcccagac atctgtatat ttctgcgcca gcagtgagtc                          100

<210> SEQ ID NO 550
<211> LENGTH: 100
<212> TYPE: DNA
<213> ORGANISM: Homo sapiens

<400> SEQUENCE: 550
gatgctgaaa tcacccagag cccaagacac aagatcacag agacaggaag gcaggtgacc    60
ttggcgtgtc accagacttg gaaccacaac aatatgttct                          100

<210> SEQ ID NO 551
<211> LENGTH: 100
<212> TYPE: DNA
<213> ORGANISM: Homo sapiens

<400> SEQUENCE: 551
agatggctac agtgtctcta gatcaaacac agaggacctc cccctcactc tggagtctgc    60
tgcctcctcc cagacatctg tatatttctg cgccagcagt                          100

<210> SEQ ID NO 552
<211> LENGTH: 100
<212> TYPE: DNA
<213> ORGANISM: Homo sapiens

<400> SEQUENCE: 552
aggcaggtga ccttggcgtg tcaccagact tggaaccaca acaatatgtt ctggtatcga    60
caagacctgg acatgggct gaggctgatc cattactcat                           100

<210> SEQ ID NO 553
<211> LENGTH: 100
<212> TYPE: DNA
<213> ORGANISM: Homo sapiens

```
<400> SEQUENCE: 553
ctaacaaagg agaagtctca gatggctaca gtgtctctag atcaaacaca gaggacctcc      60
ccctcactct gtagtctgct gcctcctccc agacatctgt                           100

<210> SEQ ID NO 554
<211> LENGTH: 100
<212> TYPE: DNA
<213> ORGANISM: Homo sapiens

<400> SEQUENCE: 554
gatgctggaa tcacccagag cccaagatac aagatcacag agacaggaag gcaggtgacc      60
ttgatgtgtc accagacttg gagccacagc tatatgttct                           100

<210> SEQ ID NO 555
<211> LENGTH: 100
<212> TYPE: DNA
<213> ORGANISM: Homo sapiens

<400> SEQUENCE: 555
gctatgttgt ctccagatcc aagacagaga atttccccct cactctggag tcagctaccc      60
gctcccagac atctgtgtat ttctgcgcca gcagtgagtc                           100

<210> SEQ ID NO 556
<211> LENGTH: 100
<212> TYPE: DNA
<213> ORGANISM: Homo sapiens

<400> SEQUENCE: 556
aaggcaggtg accttgatgt gtcaccagac ttggagccac agctatatgt tctggtatcg      60
acaagacctg ggacatgggc tgaggctgat ctattactca                           100

<210> SEQ ID NO 557
<211> LENGTH: 100
<212> TYPE: DNA
<213> ORGANISM: Homo sapiens

<400> SEQUENCE: 557
agataaagga gaagtccccg atggctacgt tgtctccaga tccaagacag agaatttccc      60
cctcactctg gagtcagcta cccgctccca gacatctgtg                           100

<210> SEQ ID NO 558
<211> LENGTH: 100
<212> TYPE: DNA
<213> ORGANISM: Homo sapiens

<400> SEQUENCE: 558
gatgctggaa tcacccagag cccaagacac aaggtcacag agacaggaac accagtgact      60
ctgagatgtc accagactga gaaccaccgc tatatgtact                           100

<210> SEQ ID NO 559
<211> LENGTH: 100
<212> TYPE: DNA
<213> ORGANISM: Homo sapiens

<400> SEQUENCE: 559
gctatagtgt ctctagatca aagacagagg atttcctcct cactctggag tccgctacca      60
gctcccagac atctgtgtac ttctgtgcca tcagtgagtc                           100
```

```
<210> SEQ ID NO 560
<211> LENGTH: 100
<212> TYPE: DNA
<213> ORGANISM: Homo sapiens

<400> SEQUENCE: 560
gatgctggaa tcacccagag cccaagacac aaggtcacag agacaggaac accagtgact      60
ctgagatgtc atcagactga gaaccaccgc tatatgtact                          100

<210> SEQ ID NO 561
<211> LENGTH: 100
<212> TYPE: DNA
<213> ORGANISM: Homo sapiens

<400> SEQUENCE: 561
gctatagtgt ctctagatca aagacagagg atttcctcct cactctggag tccgctacca      60
gctcccagac atctgtgtac ttctgtgcca tcagtgagtc                          100

<210> SEQ ID NO 562
<211> LENGTH: 100
<212> TYPE: DNA
<213> ORGANISM: Homo sapiens

<400> SEQUENCE: 562
gatgctggaa tcacccagag cccaagacac aaggtcacag agacaggaac accagtgact      60
ctgagatgtc accagactga gaaccaccgc tacatgtact                          100

<210> SEQ ID NO 563
<211> LENGTH: 100
<212> TYPE: DNA
<213> ORGANISM: Homo sapiens

<400> SEQUENCE: 563
agaagtctca gatggctata gtgtctctag atcaaagaca gaggatttcc tcctcactct      60
ggagtccgct accagctccc agacatctgt gtacttctgt                          100

<210> SEQ ID NO 564
<211> LENGTH: 100
<212> TYPE: DNA
<213> ORGANISM: Homo sapiens

<400> SEQUENCE: 564
gatgctggaa tcacccagag cccaagacac aaggtcacag agacaggaac accagtgact      60
ctgagatgtc accagactga gaaccaccgc tacatgtact                          100

<210> SEQ ID NO 565
<211> LENGTH: 100
<212> TYPE: DNA
<213> ORGANISM: Homo sapiens

<400> SEQUENCE: 565
agaagtctca gatggctata gtgtctctag atcaaagaca gaggatttcc tcctcactct      60
ggagtccgct accagctccc agacatctgt gtacttctgt                          100

<210> SEQ ID NO 566
<211> LENGTH: 100
<212> TYPE: DNA
<213> ORGANISM: Homo sapiens

<400> SEQUENCE: 566
```

```
gaagctgaag ttgcccagtc ccccagatat aagattacag agaaaagcca ggctgtggct    60
ttttggtgtg atcctatttc tggccatgct acccttact                          100

<210> SEQ ID NO 567
<211> LENGTH: 100
<212> TYPE: DNA
<213> ORGANISM: Homo sapiens

<400> SEQUENCE: 567
gattttctgc agagaggctc aaaggagtag actccactct caagatccag cctgcagagc    60
ttggggactc ggccatgtat ctctgtgcca gcagcttagc                          100

<210> SEQ ID NO 568
<211> LENGTH: 100
<212> TYPE: DNA
<213> ORGANISM: Homo sapiens

<400> SEQUENCE: 568
gaagctggag ttgcccagtc tcccagatat aagattatag agaaaaggca gagtgtggct    60
ttttggtgca atcctatatc tggccatgct acccttact                          100

<210> SEQ ID NO 569
<211> LENGTH: 100
<212> TYPE: DNA
<213> ORGANISM: Homo sapiens

<400> SEQUENCE: 569
gattttctgc agagaggctc aaaggagtag actccactct caagatccag cctgcaaagc    60
ttgaggactc ggccgtgtat ctctgtgcca gcagcttaga                          100

<210> SEQ ID NO 570
<211> LENGTH: 100
<212> TYPE: DNA
<213> ORGANISM: Homo sapiens

<400> SEQUENCE: 570
gaagctggag ttgcccagtc tcccagatat aagattatag agaaaaggca gagtgtggct    60
ttttggtgca atcctatatc tggccatgct acccttact                          100

<210> SEQ ID NO 571
<211> LENGTH: 100
<212> TYPE: DNA
<213> ORGANISM: Homo sapiens

<400> SEQUENCE: 571
ggatcgattt tctgcagaga ggctcaaagg agtagactcc actctcaaga tccagcctgc    60
aaagcttgag aactcggccg tgtatctctg tgccagcagt                          100

<210> SEQ ID NO 572
<211> LENGTH: 100
<212> TYPE: DNA
<213> ORGANISM: Homo sapiens

<400> SEQUENCE: 572
gaagctggag ttgcccagtc tcccagatat aagattatag agaaaaggca gagtgtggct    60
ttttggtgca atcctatatc tggccatgct acccttact                          100

<210> SEQ ID NO 573
<211> LENGTH: 100
```

```
<212> TYPE: DNA
<213> ORGANISM: Homo sapiens

<400> SEQUENCE: 573
ggatcgattt tctgcagaga ggctcaaagg agtagactcc actctcaaga tccaacctgc      60
aaagcttgag gactcggccg tgtatctctg tgccagcagc                           100

<210> SEQ ID NO 574
<211> LENGTH: 100
<212> TYPE: DNA
<213> ORGANISM: Homo sapiens

<400> SEQUENCE: 574
gaagctggag tggttcagtc tcccagatat aagattatag agaaaaaaca gcctgtggct      60
ttttggtgca atcctatttc tggccacaat acccttact                            100

<210> SEQ ID NO 575
<211> LENGTH: 100
<212> TYPE: DNA
<213> ORGANISM: Homo sapiens

<400> SEQUENCE: 575
gattttctgc agagaggctc aaaggagtag actccactct caagatccag cctgcagagc      60
ttggggactc ggccgtgtat ctctgtgcca gcagcttaga                           100

<210> SEQ ID NO 576
<211> LENGTH: 100
<212> TYPE: DNA
<213> ORGANISM: Homo sapiens

<400> SEQUENCE: 576
gaagctggag tggttcagtc tcccagatat aagattatag agaaaaagca gcctgtggct      60
ttttggtgca atcctatttc tggccacaat acccttact                            100

<210> SEQ ID NO 577
<211> LENGTH: 100
<212> TYPE: DNA
<213> ORGANISM: Homo sapiens

<400> SEQUENCE: 577
ggatcgattt tctgcagaga ggctcaaagg agtagactcc actctcaaga tccagcctgc      60
agagcttggg gactcggccg tgtatctctg tgccagcagc                           100

<210> SEQ ID NO 578
<211> LENGTH: 100
<212> TYPE: DNA
<213> ORGANISM: Homo sapiens

<400> SEQUENCE: 578
ggtctcccag atataagatt atagagaaga acagcctgt ggcttttgg tgcaatccaa        60
tttctggcca caatacccct tactggtacc tgcagaactt                           100

<210> SEQ ID NO 579
<211> LENGTH: 100
<212> TYPE: DNA
<213> ORGANISM: Homo sapiens

<400> SEQUENCE: 579
ggatcgattt tctgcagaga ggctcaaagg agtagactcc actctcaaga tccagccagc      60
```
agagcttggg gactcggcca tgtatctctg tgccagcagc    100

<210> SEQ ID NO 580
<211> LENGTH: 100
<212> TYPE: DNA
<213> ORGANISM: Homo sapiens

<400> SEQUENCE: 580
gatgctggtg ttatccagtc acccaggcac aaagtgacag agatgggaca atcagtaact    60
ctgagatgcg aaccaatttc aggccacaat gatcttctct    100

<210> SEQ ID NO 581
<211> LENGTH: 100
<212> TYPE: DNA
<213> ORGANISM: Homo sapiens

<400> SEQUENCE: 581
gattctcagc acagatgcct gatgtatcat tctccactct gaggatccag cccatggaac    60
ccagggactt gggcctatat ttctgtgcca gcagctttgc    100

<210> SEQ ID NO 582
<211> LENGTH: 100
<212> TYPE: DNA
<213> ORGANISM: Homo sapiens

<400> SEQUENCE: 582
gatgctggca ttatccagtc acccaagcat gaggtgacag aaatgggaca aacagtgact    60
ctgagatgtg agccaatttt tggccacaat ttccttttct    100

<210> SEQ ID NO 583
<211> LENGTH: 100
<212> TYPE: DNA
<213> ORGANISM: Homo sapiens

<400> SEQUENCE: 583
gattctcagc tgagaggcct gatggatcat tctctactct gaagatccag cctgcagagc    60 aggggactc ggccgtgtat gtctgtgcaa gtcgcttagc    100

<210> SEQ ID NO 584
<211> LENGTH: 100
<212> TYPE: DNA
<213> ORGANISM: Homo sapiens

<400> SEQUENCE: 584
gatgctggag ttatccagtc accccgccat gaggtgacag agatgggaca agaagtgact    60
ctgagatgta aaccaatttc aggccacaac tccctttcct    100

<210> SEQ ID NO 585
<211> LENGTH: 100
<212> TYPE: DNA
<213> ORGANISM: Homo sapiens

<400> SEQUENCE: 585
gattctcagc taagatgcct aatgcatcat tctccactct gaagatccag ccctcagaac    60
ccagggactc agctgtgtac ttctgtgcca gcagtttagc    100

<210> SEQ ID NO 586
<211> LENGTH: 100
<212> TYPE: DNA
<213> ORGANISM: Homo sapiens

<400> SEQUENCE: 586
gatgctggag ttatccagtc accccggcac gaggtgacag agatgggaca agaagtgact    60
ctgagatgta aaccaatttc aggacacgac tacctttct                          100

<210> SEQ ID NO 587
<211> LENGTH: 100
<212> TYPE: DNA
<213> ORGANISM: Homo sapiens

<400> SEQUENCE: 587
gattctcagc taagatgcct aatgcatcat tctccactct gaagatccag ccctcagaac    60
ccagggactc agctgtgtac ttctgtgcca gcagtttagc                         100

<210> SEQ ID NO 588
<211> LENGTH: 100
<212> TYPE: DNA
<213> ORGANISM: Homo sapiens

<400> SEQUENCE: 588
gatgctggag ttatccagtc accccggcac gaggtgacag agatgggaca agaagtgact    60
ctgagatgta aaccaatttc aggacatgac tacctttct                          100

<210> SEQ ID NO 589
<211> LENGTH: 100
<212> TYPE: DNA
<213> ORGANISM: Homo sapiens

<400> SEQUENCE: 589
tcgattctca gctaagatgc ctaatgcatc attctccact ctgaggatcc agccctcaga    60
acccagggac tcagctgtgt acttctgtgc cagcagttta                         100

<210> SEQ ID NO 590
<211> LENGTH: 100
<212> TYPE: DNA
<213> ORGANISM: Homo sapiens

<400> SEQUENCE: 590
gatgctagag tcacccagac accaaggcac aaggtgacag agatgggaca agaagtaaca    60
atgagatgtc agccaatttt aggccacaat actgttttct                         100

<210> SEQ ID NO 591
<211> LENGTH: 100
<212> TYPE: DNA
<213> ORGANISM: Homo sapiens

<400> SEQUENCE: 591
gattctcagc agagatgcct gatgcaactt tagccactct gaagatccag ccctcagaac    60
ccagggactc agctgtgtat ttttgtgcta gtggtttggt                         100

<210> SEQ ID NO 592
<211> LENGTH: 100
<212> TYPE: DNA
<213> ORGANISM: Homo sapiens

<400> SEQUENCE: 592
gctgctggag tcatccagtc cccaagacat ctgatcaaag aaaagaggga aacagccact    60
ctgaaatgct atcctatccc tagacacgac actgtctact                         100

<210> SEQ ID NO 593
<211> LENGTH: 100
<212> TYPE: DNA
<213> ORGANISM: Homo sapiens

<400> SEQUENCE: 593
gattctcagc tcaacagttc agtgactatc attctgaact gaacatgagc tccttggagc    60
tgggggactc agccctgtac ttctgtgcca gcagcttagg                          100

<210> SEQ ID NO 594
<211> LENGTH: 100
<212> TYPE: DNA
<213> ORGANISM: Homo sapiens

<400> SEQUENCE: 594
gctgctggag tcatccagtc cccaagacat ctgatcagag aaaagaggga aacagccact    60
ctgaaatgct atcctatccc tagacacgac actgtctact                          100

<210> SEQ ID NO 595
<211> LENGTH: 100
<212> TYPE: DNA
<213> ORGANISM: Homo sapiens

<400> SEQUENCE: 595
tgatcgattc tcagctcaac agttcagtga ctatcattct gaactgaaca tgagctcctt    60
ggagctgggg gactcagccc tgtacttctg tgccagcagc                          100

<210> SEQ ID NO 596
<211> LENGTH: 100
<212> TYPE: DNA
<213> ORGANISM: Homo sapiens

<400> SEQUENCE: 596
gaagctggag ttactcagtt ccccagccac agcgtaatag agaagggcca gactgtgact    60
ctgagatgtg acccaatttc tggacatgat aatctttatt                          100

<210> SEQ ID NO 597
<211> LENGTH: 100
<212> TYPE: DNA
<213> ORGANISM: Homo sapiens

<400> SEQUENCE: 597
gattcttagc tgaaaggact ggagggacgt attctactct gaaggtgcag cctgcagaac    60
tggaggattc tggagtttat ttctgtgcca gcagccaaga                          100

<210> SEQ ID NO 598
<211> LENGTH: 100
<212> TYPE: DNA
<213> ORGANISM: Homo sapiens

<400> SEQUENCE: 598
gaagctggag ttactcagtt ccccagccac agcgtaatag agaagggcca gactgtgact    60
ctgagatgtg acccaatttc tggacatgat aatctttatt                          100

<210> SEQ ID NO 599
<211> LENGTH: 100
<212> TYPE: DNA
<213> ORGANISM: Homo sapiens

<400> SEQUENCE: 599

```
caatcgattc ttagctgaaa ggactggagg gacgtattct actctgaagg tgcagcctgc    60
agaactggag gattctggag tttatttctg tgccagcagc                         100

<210> SEQ ID NO 600
<211> LENGTH: 100
<212> TYPE: DNA
<213> ORGANISM: Homo sapiens

<400> SEQUENCE: 600
gatgccatgg tcatccagaa cccaagatac caggttaccc agtttggaaa gccagtgacc    60
ctgagttgtt ctcagacttt gaaccataac gtcatgtact                         100

<210> SEQ ID NO 601
<211> LENGTH: 100
<212> TYPE: DNA
<213> ORGANISM: Homo sapiens

<400> SEQUENCE: 601
acttccaatc caggaggccg aacacttctt tctgctttct tgacatccgc tcaccaggcc    60
tgggggacac agccatgtac ctgtgtgcca ccagcagaga                         100

<210> SEQ ID NO 602
<211> LENGTH: 100
<212> TYPE: DNA
<213> ORGANISM: Homo sapiens

<400> SEQUENCE: 602
gatgccatgg tcatccagaa cccaagatac caggttaccc agtttggaaa gccagtgacc    60
ctgagttgtt ctcagacttt gaaccataac gtcatgtact                         100

<210> SEQ ID NO 603
<211> LENGTH: 100
<212> TYPE: DNA
<213> ORGANISM: Homo sapiens

<400> SEQUENCE: 603
tgataacttc caatccagga ggccgaacac ttctttctgc tttcttgaca tccgctcacc    60
aggcctgggg gacgcagcca tgtacctgtg tgccaccagc                         100

<210> SEQ ID NO 604
<211> LENGTH: 100
<212> TYPE: DNA
<213> ORGANISM: Homo sapiens

<400> SEQUENCE: 604
gatgccatgg tcatccagaa cccaagatac cgggttaccc agtttggaaa gccagtgacc    60
ctgagttgtt ctcagacttt gaaccataac gtcatgtact                         100

<210> SEQ ID NO 605
<211> LENGTH: 100
<212> TYPE: DNA
<213> ORGANISM: Homo sapiens

<400> SEQUENCE: 605
tgataacttc caatccagga ggccgaacac ttctttctgc tttctagaca tccgctcacc    60
aggcctgggg gacgcagcca tgtaccagtg tgccaccagc                         100

<210> SEQ ID NO 606
```

```
<211> LENGTH: 100
<212> TYPE: DNA
<213> ORGANISM: Homo sapiens

<400> SEQUENCE: 606
ggtgaagaag tcgcccagac tccaaaacat cttgtcagag gggaaggaca gaaagcaaaa      60
ttatattgtg ccccaataaa aggacacagt tatgtttttt                          100

<210> SEQ ID NO 607
<211> LENGTH: 100
<212> TYPE: DNA
<213> ORGANISM: Homo sapiens

<400> SEQUENCE: 607
gattttcagc taagtgcctc ccaaattcac cctgtagcct tgagatccag gctacgaagc      60
ttgaggattc agcagtgtat ttttgtgcca gcagccaatc                          100

<210> SEQ ID NO 608
<211> LENGTH: 100
<212> TYPE: DNA
<213> ORGANISM: Homo sapiens

<400> SEQUENCE: 608
ggtgaagaag tcgcccagac tccaaaacat cttgtcagag gggaaggaca gaaagcaaaa      60
ttatattgtg ccccaataaa aggacacagt taggtttttt                          100

<210> SEQ ID NO 609
<211> LENGTH: 100
<212> TYPE: DNA
<213> ORGANISM: Homo sapiens

<400> SEQUENCE: 609
gattttcagc taagtgcctc ccaaattcac cctgtagcct tgagatccag gctacgaagc      60
ttgaggattc agcagtgtat ttttgtgcca gcagccaatc                          100

<210> SEQ ID NO 610
<211> LENGTH: 100
<212> TYPE: DNA
<213> ORGANISM: Homo sapiens

<400> SEQUENCE: 610
ggtgaagaag tcgcccagac tccaaaacat cttgtcagag gggaaggaca gaaagcaaaa      60
ttatattgtg ccccaataaa aggacacagt tatgtttttt                          100

<210> SEQ ID NO 611
<211> LENGTH: 100
<212> TYPE: DNA
<213> ORGANISM: Homo sapiens

<400> SEQUENCE: 611
ggaaagattt tcagctaagt gcctcccaaa ttcaccctgt agccttgaga tccaggctac      60
gaagcttgag gattcagcag tgtattttig tgccagcagc                          100

<210> SEQ ID NO 612
<211> LENGTH: 100
<212> TYPE: DNA
<213> ORGANISM: Homo sapiens

<400> SEQUENCE: 612
gagcctggag tcagccagac ccccagacac aaggtcacca acatgggaca ggaggtgatt      60
```
ctgaggtgcg atccatcttc tggtcacatg tttgttcact    100

<210> SEQ ID NO 613
<211> LENGTH: 100
<212> TYPE: DNA
<213> ORGANISM: Homo sapiens

<400> SEQUENCE: 613
aacgattcac agctgaaaga cctaacggaa cgtcttccac gctgaagatc catcccgcag    60
agccgaggga ctcagccgtg tatctctaca gtagcggtgg    100

<210> SEQ ID NO 614
<211> LENGTH: 100
<212> TYPE: DNA
<213> ORGANISM: Homo sapiens

<400> SEQUENCE: 614
aatgccggcg tcatgcagaa cccaagacac ctggtcagga ggaggggaca ggaggcaaga    60
ctgagatgca gcccaatgaa aggacacagt catgtttact    100

<210> SEQ ID NO 615
<211> LENGTH: 100
<212> TYPE: DNA
<213> ORGANISM: Homo sapiens

<400> SEQUENCE: 615
gattttctgc tgaatttccc aaagagggcc ccagcatcct gaggatccag caggtagtgc    60
gaggagattc ggcagcttat ttctgtgcca gctcaccacc    100

<210> SEQ ID NO 616
<211> LENGTH: 100
<212> TYPE: DNA
<213> ORGANISM: Homo sapiens

<400> SEQUENCE: 616
gatggtggaa tcactcagtc cccaaagtac ctgttcagaa aggaaggaca gaatgtgacc    60
ctgagttgtg aacagaattt gaaccacgat gccatgtact    100

<210> SEQ ID NO 617
<211> LENGTH: 100
<212> TYPE: DNA
<213> ORGANISM: Homo sapiens

<400> SEQUENCE: 617
ggtacagcgt ctctcgggag aagaaggaat cctttcctct cactgtgaca tcggcccaaa    60
agaacccgac agctttctat ctctgtgcca gtagtataga    100

<210> SEQ ID NO 618
<211> LENGTH: 100
<212> TYPE: DNA
<213> ORGANISM: Homo sapiens

<400> SEQUENCE: 618
gatggtggaa tcactcagtc cccaaagtac ctgttcagaa aggaaggaca gaatgtgacc    60
ctgagttgtg aacagaattt gaaccacgat gccatgtact    100

<210> SEQ ID NO 619
<211> LENGTH: 100
<212> TYPE: DNA

<213> ORGANISM: Homo sapiens

<400> SEQUENCE: 619
ggtacagcgt ctctcgggag aagaaggaat cctttcctct cactgtgaca tcggcccaaa    60
agaacccgac agctttctat ctctgtgcca gtagtataga                          100

<210> SEQ ID NO 620
<211> LENGTH: 100
<212> TYPE: DNA
<213> ORGANISM: Homo sapiens

<400> SEQUENCE: 620
gatggtggaa tcactcagtc cccaaagtac ctgttcagaa aggaaggaca gaatgtgacc    60
ctgagttgtg aacagaattt gaaccacgat gccatgtact                          100

<210> SEQ ID NO 621
<211> LENGTH: 100
<212> TYPE: DNA
<213> ORGANISM: Homo sapiens

<400> SEQUENCE: 621
tgaagggtac agcgtctctc gggagaagaa ggaatccttt cctctcactg tgacatcggc    60
ccaaaagaac ccgacagctt tctatctctg tgccagtagc                          100

<210> SEQ ID NO 622
<211> LENGTH: 100
<212> TYPE: DNA
<213> ORGANISM: Homo sapiens

<400> SEQUENCE: 622
gaacctgaag tcacccagac tcccagccat caggtcacac agatgggaca ggaagtgatc    60
ttgcgctgtg tccccatctc taatcactta tacttctatt                          100

<210> SEQ ID NO 623
<211> LENGTH: 100
<212> TYPE: DNA
<213> ORGANISM: Homo sapiens

<400> SEQUENCE: 623
aattctcagt tgaaaggcct gatggatcaa atttcactct gaagatccgg tccacaaagc    60
tggaggactc agccatgtac ttctgtgcca gcagtgaagc                          100

<210> SEQ ID NO 624
<211> LENGTH: 100
<212> TYPE: DNA
<213> ORGANISM: Homo sapiens

<400> SEQUENCE: 624
gaacctgaag tcacccagac tcccagccat caggtcacac agatgggaca ggaagtgatc    60
ttgcactgtg tccccatctc taatcactta tacttctatt                          100

<210> SEQ ID NO 625
<211> LENGTH: 100
<212> TYPE: DNA
<213> ORGANISM: Homo sapiens

<400> SEQUENCE: 625
tgatcaattc tcagttgaaa ggcctgatgg atcaaatttc actctgaaga tccggtccac    60
aaagctggag gactcagcca tgtacttctg tgccagcagt                          100

<210> SEQ ID NO 626
<211> LENGTH: 100
<212> TYPE: DNA
<213> ORGANISM: Homo sapiens

<400> SEQUENCE: 626
gaacctgaag tcacccagac tcccagccat caggtcacac agatgggaca ggaagtgatc    60
ttgcgctgtg tccccatctc taatcactta tacttctatt                        100

<210> SEQ ID NO 627
<211> LENGTH: 100
<212> TYPE: DNA
<213> ORGANISM: Homo sapiens

<400> SEQUENCE: 627
tcaattctca gttgagaggc ctgatggatc aaatttcact ctgaagatcc ggtccacaaa    60
gctggaggac tcagccatgt acttctgtgc cagcagtgaa                        100

<210> SEQ ID NO 628
<211> LENGTH: 100
<212> TYPE: DNA
<213> ORGANISM: Homo sapiens

<400> SEQUENCE: 628
ggtgctgtcg tctctcaaca tccgagctgg gttatctgta agagtggaac ctctgtgaag    60
atcgagtgcc gttccctgga ctttcaggcc acaactatgt                        100

<210> SEQ ID NO 629
<211> LENGTH: 100
<212> TYPE: DNA
<213> ORGANISM: Homo sapiens

<400> SEQUENCE: 629
acaagtttct catcaaccat gcaagcctga ccttgtccac tctgacagtg accagtgccc    60
atcctgaaga cagcagcttc tacatctgca gtgctagaga                        100

<210> SEQ ID NO 630
<211> LENGTH: 100
<212> TYPE: DNA
<213> ORGANISM: Homo sapiens

<400> SEQUENCE: 630
ggtgctgtcg tctctcaaca tccgagcagg gttatctgta agagtggaac ctctgtgaag    60
atcgagtgcc gttccctgga ctttcaggcc acaactatgt                        100

<210> SEQ ID NO 631
<211> LENGTH: 100
<212> TYPE: DNA
<213> ORGANISM: Homo sapiens

<400> SEQUENCE: 631
gaaggacaag tttctcatca accatgcaag cctgaccttg tccactctga cagtgaccag    60
tgcccatcct gaagacagca gcttctacat ctgcagtgct                        100

<210> SEQ ID NO 632
<211> LENGTH: 100
<212> TYPE: DNA
<213> ORGANISM: Homo sapiens

```
<400> SEQUENCE: 632
ggtgctgtcg tctctcaaca tccgagctgg gttatctgta agagtggaac ctctgtgaag    60
atcgagtgcc gttccctgga ctttcaggcc acaactatgt                         100

<210> SEQ ID NO 633
<211> LENGTH: 100
<212> TYPE: DNA
<213> ORGANISM: Homo sapiens

<400> SEQUENCE: 633
gaaggacaag tttctcatca accatgcaag cctgaccttg tccactctga cagtgaccag    60
tgcccatcct gaagacagca gcttctacat ctgcagtgct                         100

<210> SEQ ID NO 634
<211> LENGTH: 100
<212> TYPE: DNA
<213> ORGANISM: Homo sapiens

<400> SEQUENCE: 634
ggtgctgtcg tctctcaaca tccgagcagg gttatctgta agagtggaac ctctgtgaag    60
atcgagtgcc gttccttgga ctttcaggcc acaactatgt                         100

<210> SEQ ID NO 635
<211> LENGTH: 100
<212> TYPE: DNA
<213> ORGANISM: Homo sapiens

<400> SEQUENCE: 635
ggacaagttt ctcatcaacc atgcaagcct gaccttgtcc actctgacag tgaccagtgc    60
ccatcctgaa gacagcagct tctacatctg cagtgctagt                         100

<210> SEQ ID NO 636
<211> LENGTH: 100
<212> TYPE: DNA
<213> ORGANISM: Homo sapiens

<400> SEQUENCE: 636
ggtgctgtcg tctctcaaca tccgagcagg gttatctgta agagtggaac ctctgtgaag    60
atcgagtgcc gttccctgga ctttcaggcc acaactatgt                         100

<210> SEQ ID NO 637
<211> LENGTH: 100
<212> TYPE: DNA
<213> ORGANISM: Homo sapiens

<400> SEQUENCE: 637
ggacaagttt ctcatcaacc atgcaagcct gaccttgtcc actctgacag tgaccagtgc    60
ccatcctgaa gacagcagct tctacatctg cagtgctaga                         100

<210> SEQ ID NO 638
<211> LENGTH: 100
<212> TYPE: DNA
<213> ORGANISM: Homo sapiens

<400> SEQUENCE: 638
ggtgctgtcg tctctcaaca tccgagtagg gttatctgta agagtggaac ctctgtgaag    60
atcgagtgcc gttccctgga ctttcaggcc acaactatgt                         100
```

```
<210> SEQ ID NO 639
<211> LENGTH: 100
<212> TYPE: DNA
<213> ORGANISM: Homo sapiens

<400> SEQUENCE: 639
gaaggacaag tttctcatca accatgcaag cctgaccttg tccactctga cagtgaccag      60
tgcccatcct gaagacagca gcttctacat ctgcagtgct                           100

<210> SEQ ID NO 640
<211> LENGTH: 100
<212> TYPE: DNA
<213> ORGANISM: Homo sapiens

<400> SEQUENCE: 640
ggtgctgtcg tctctcaaca tccgagcagg gttatctgta agagtggaac ctctgtgaag      60
atcgagtgcc gttccctgga ctttcaggcc acaactatgt                           100

<210> SEQ ID NO 641
<211> LENGTH: 100
<212> TYPE: DNA
<213> ORGANISM: Homo sapiens

<400> SEQUENCE: 641
ggacaagttt ctcatcaacc atgcaagcct gaccttgtcc actctgacag tgaccagtgc      60
ccatcctgaa gacagcagct ctacatctg cagtgctaga                            100

<210> SEQ ID NO 642
<211> LENGTH: 100
<212> TYPE: DNA
<213> ORGANISM: Homo sapiens

<400> SEQUENCE: 642
agtgctgtcg tctctcaaca tccgagcagg gttatctgta agagtggaac ctctgtgaac      60
atcgagtgcc gttccctgga ctttcaggcc acaactatgt                           100

<210> SEQ ID NO 643
<211> LENGTH: 100
<212> TYPE: DNA
<213> ORGANISM: Homo sapiens

<400> SEQUENCE: 643
acaagtttcc catcaaccat ccaaacctga ccttctccgc tctgacagtg accagtgccc      60
atcctgaaga cagcagcttc tacatctgca gtgctagaga                           100

<210> SEQ ID NO 644
<211> LENGTH: 100
<212> TYPE: DNA
<213> ORGANISM: Homo sapiens

<400> SEQUENCE: 644
ggtgctgtcg tctctcaaca tccgagcagg gttatctgta agagtggaac ctctgtgaac      60
atcgagtgcc gttccctgga ctttcaggcc acaactatgt                           100

<210> SEQ ID NO 645
<211> LENGTH: 100
<212> TYPE: DNA
<213> ORGANISM: Homo sapiens

<400> SEQUENCE: 645
```

```
gaaggacaag tttcccatca accatccaaa cctgaccttc tccgctctga cagtgacctg    60
tgcccatcct gaagacagca gcttctacat ctgcagtgct                         100
```

<210> SEQ ID NO 646
<211> LENGTH: 100
<212> TYPE: DNA
<213> ORGANISM: Homo sapiens

<400> SEQUENCE: 646

```
agtgctgtcg tctctcaaca tccgagcagg gttatctgta agagtggaac ctctgtgaac    60
atcgagtgcc gttccctgga ctttcaggcc acaactatgt                         100
```

<210> SEQ ID NO 647
<211> LENGTH: 100
<212> TYPE: DNA
<213> ORGANISM: Homo sapiens

<400> SEQUENCE: 647

```
acaagtttcc catcaaccat ccaaacctga ccttctccgc tctgacagtg accagtgccc    60
atcctgaaga cagcagcttc tacatctgca gtgctagaga                         100
```

<210> SEQ ID NO 648
<211> LENGTH: 100
<212> TYPE: DNA
<213> ORGANISM: Homo sapiens

<400> SEQUENCE: 648

```
gacaccaagg tcacccagag acctagactt ctggtcaaag caagtgaaca gaaagcaaag    60
atggattgtg ttcctataaa agcacatagt tatgtttact                         100
```

<210> SEQ ID NO 649
<211> LENGTH: 100
<212> TYPE: DNA
<213> ORGANISM: Homo sapiens

<400> SEQUENCE: 649

```
gattttagc ccaatgctcc aaaaactcat cctgtacctt ggagatccag tccacggagt     60 cagggacac agcactgtat ttctgtgcca gcagcaaagc                          100
```

<210> SEQ ID NO 650
<211> LENGTH: 100
<212> TYPE: DNA
<213> ORGANISM: Homo sapiens

<400> SEQUENCE: 650

```
gacaccaagg tcacccagag acctagattt ctggtcaaag caaatgaaca gaaagcaaag    60
atggactgtg ttcctataaa aagcacatagt tatgtttact                        100
```

<210> SEQ ID NO 651
<211> LENGTH: 100
<212> TYPE: DNA
<213> ORGANISM: Homo sapiens

<400> SEQUENCE: 651

```
gattttcagc ccaatgcccc caaaactcac cctgtaccttg gagatccag tccacggagt    60 caggagacac agcacggtat ttctgtgcca acagcaaagc                         100
```

<210> SEQ ID NO 652
<211> LENGTH: 100

```
<212> TYPE: DNA
<213> ORGANISM: Homo sapiens

<400> SEQUENCE: 652
gatgctgaca tctatcagat gccattccag ctcactgggg ctggatggga tgtgactctg    60
gagtggaaac ggaatttgag acacaatgac atgtactgct                         100

<210> SEQ ID NO 653
<211> LENGTH: 100
<212> TYPE: DNA
<213> ORGANISM: Homo sapiens

<400> SEQUENCE: 653
aggctacgtg tctgccaaga ggagaagggg ctatttcttc tcagggtgaa gttggcccac    60
accagccaaa cagctttgta cttctgtcct gggagcgcac                         100

<210> SEQ ID NO 654
<211> LENGTH: 100
<212> TYPE: DNA
<213> ORGANISM: Homo sapiens

<400> SEQUENCE: 654
gatgctgaca tctatcagac gccattccag ctcactgggg ctggatggga tgtgaccctg    60
gagtagaaac aatttgagac acaatgacat gtactggtac                         100

<210> SEQ ID NO 655
<211> LENGTH: 100
<212> TYPE: DNA
<213> ORGANISM: Homo sapiens

<400> SEQUENCE: 655
ggctacggtg tctcccgaga ggagaagggg ctgtttcttc tcatggtgaa gctggcccac    60
accagccaaa cagctctgta cttctgtcct gggagtgcac                         100

<210> SEQ ID NO 656
<211> LENGTH: 100
<212> TYPE: DNA
<213> ORGANISM: Homo sapiens

<400> SEQUENCE: 656
catgccaaag tcacacagac tccaggacat ttggtcaaag gaaaaggaca gaaaacaaag    60
atggattgta cccccgaaaa aggacatact tttgtttatt                         100

<210> SEQ ID NO 657
<211> LENGTH: 100
<212> TYPE: DNA
<213> ORGANISM: Homo sapiens

<400> SEQUENCE: 657
gattctcatc tcaatgcccc aagaacgcac cctgcagcct ggcaatcctg tcctcagaac    60
cgggagacac ggcactgtat ctctgcgcca gcagtcaatc                         100

<210> SEQ ID NO 658
<211> LENGTH: 100
<212> TYPE: DNA
<213> ORGANISM: Homo sapiens

<400> SEQUENCE: 658
catgccaaag tcacacagac tccaggatat ttggtcaaag gaaaaggaag gaaaacaaag    60
```

```
atgtattgta cccccaaaaa cggacatact tttgtttgtt                           100

<210> SEQ ID NO 659
<211> LENGTH: 100
<212> TYPE: DNA
<213> ORGANISM: Homo sapiens

<400> SEQUENCE: 659
gatgcacaag aagcgattct catctcaatg ccccaagaac ccaccctgca gcctggcaat      60
cctgtcctcg gaaccgggag acaccgcact gtatctctgt                          100

<210> SEQ ID NO 660
<211> LENGTH: 100
<212> TYPE: DNA
<213> ORGANISM: Homo sapiens

<400> SEQUENCE: 660
catgccaaag tcacacagac tccaggatat ttggtcaaag gaaaggaag gaaaacaaag       60 atgtattgta cccccaaaaa cggacatact tttgtttgtt                          100

<210> SEQ ID NO 661
<211> LENGTH: 100
<212> TYPE: DNA
<213> ORGANISM: Homo sapiens

<400> SEQUENCE: 661
gtttttgatt tcctttcaga atgaacaagt tcttcaagaa atggagatgc acaagaagcg      60
attctcatct caatgccccca agaacgcacc ctgcagcctg                         100

<210> SEQ ID NO 662
<211> LENGTH: 100
<212> TYPE: DNA
<213> ORGANISM: Homo sapiens

<400> SEQUENCE: 662
gatgctgatg ttacccagac cccaaggaat aggatcacaa agacaggaaa gaggattatg      60
ctggaatgtt ctcagactaa gggtcatgat agaatgtact                          100

<210> SEQ ID NO 663
<211> LENGTH: 100
<212> TYPE: DNA
<213> ORGANISM: Homo sapiens

<400> SEQUENCE: 663
atacagtgtc tctcgacagg cacaggctaa attctccctg tccctagagt ctgccatccc      60
caaccagaca gctctttact tctgtgccac cagtgatttg                          100

<210> SEQ ID NO 664
<211> LENGTH: 100
<212> TYPE: DNA
<213> ORGANISM: Homo sapiens

<400> SEQUENCE: 664
gatgctgatg ttacccagac cccaaggaat aggatcacaa agacaggaaa gaggattatg      60
ctggaatgtt ctcagactaa gggtcatgat agaatgtact                          100

<210> SEQ ID NO 665
<211> LENGTH: 100
<212> TYPE: DNA
```

```
<400> SEQUENCE: 665
atacagtgtc tctcgacagg cacaggctaa attctccctg tccctagagt ctgccatccc      60
caaccagaca gctctttact tctgtgccac cagtgatttg                             100

<210> SEQ ID NO 666
<211> LENGTH: 100
<212> TYPE: DNA
<213> ORGANISM: Homo sapiens

<400> SEQUENCE: 666
gatgctgatg ttatccagac cccaaggaat aggatcacaa agacaggaaa gaggattatg      60
ctggcatgtt ctcagactaa gggtcatgat ggaatgtact                             100

<210> SEQ ID NO 667
<211> LENGTH: 100
<212> TYPE: DNA
<213> ORGANISM: Homo sapiens

<400> SEQUENCE: 667
cagttgatct attgctcctt tgatgtcaaa atatataaac aaaagagaga tctctgatgg      60
atacagtgtc tcttgacagg aacaggctaa attctccctg                             100

<210> SEQ ID NO 668
<211> LENGTH: 100
<212> TYPE: DNA
<213> ORGANISM: Homo sapiens

<400> SEQUENCE: 668
gatgctgatg ttatccagac cccaaggaat aggatcacaa agacaggaaa gaggattatg      60
ctggaatgtt ctcagactaa gggtcatgat ggaatgtact                             100

<210> SEQ ID NO 669
<211> LENGTH: 100
<212> TYPE: DNA
<213> ORGANISM: Homo sapiens

<400> SEQUENCE: 669
agtgtctctt gacaggaaca ggctaaattc tccctgtccc tagagcctgc cacccccaac      60
cagacagctt ctaggttact tcagtgccac cagtgatttc                             100

<210> SEQ ID NO 670
<211> LENGTH: 100
<212> TYPE: DNA
<213> ORGANISM: Homo sapiens

<400> SEQUENCE: 670
gaagctgaca tctaccagac cccaagatac cttgttatag ggacaggaaa gaagatcact      60
ctggaatgtt ctcaaaccat gggccatgac aaaatgtact                             100

<210> SEQ ID NO 671
<211> LENGTH: 100
<212> TYPE: DNA
<213> ORGANISM: Homo sapiens

<400> SEQUENCE: 671
agtcaacagt ctccagaata aggacggagc attttcccct gaccctggag tctgccaggc      60
cctcacatac ctctcagtac ctctgtgcca gcagtgaata                             100
```

<210> SEQ ID NO 672
<211> LENGTH: 100
<212> TYPE: DNA
<213> ORGANISM: Homo sapiens

<400> SEQUENCE: 672
gaagctgaaa tctaccagac cccaagacac cgtgttatag gggcaggaaa gaagatcact      60
ctggaatgtt ctcaaaccat gggccatgac aaaatgtact                          100

<210> SEQ ID NO 673
<211> LENGTH: 100
<212> TYPE: DNA
<213> ORGANISM: Homo sapiens

<400> SEQUENCE: 673
agtcaacagt ctccagaata aggatagagc gttttcccct gaccctggag tctgccagcc      60
cctcacatac ctctcagtac ctctgtgcca gcagtgaata                          100

<210> SEQ ID NO 674
<211> LENGTH: 100
<212> TYPE: DNA
<213> ORGANISM: Homo sapiens

<400> SEQUENCE: 674
gaagctgaaa tctaccagac cccaagacac cgtgttatag gggcaggaaa gaagatcact      60
ctggaatgtt ctcaaaccat gggccatgac aaaatgtact                          100

<210> SEQ ID NO 675
<211> LENGTH: 100
<212> TYPE: DNA
<213> ORGANISM: Homo sapiens

<400> SEQUENCE: 675
gagttaattc cacagagaag ggagatcttt gctctgagtc aacagtctcc agaataagga      60
tagagcgttt tcccctgacc ctggagtctg ccagcccctc                          100

<210> SEQ ID NO 676
<211> LENGTH: 100
<212> TYPE: DNA
<213> ORGANISM: Homo sapiens

<400> SEQUENCE: 676
gatgctgtag ttacacaatt cccaagacac agaatcattg ggacaggaaa ggaattcatt      60
ctacagtgtt cccagaatat gaatcatgtt acaatgtact                          100

<210> SEQ ID NO 677
<211> LENGTH: 100
<212> TYPE: DNA
<213> ORGANISM: Homo sapiens

<400> SEQUENCE: 677
ggtatcatgt ttcttgaaat actatagcat cttttcccct gaccctgaag tctgccagca      60
ccaaccagac atctgtgtat ctctatgcca gcagttcatc                          100

<210> SEQ ID NO 678
<211> LENGTH: 100
<212> TYPE: DNA
<213> ORGANISM: Homo sapiens

<400> SEQUENCE: 678

```
gatgctgtag ttacacaatt ctcaagacac agaatcattg ggacaggaaa ggaattcatt    60
ctactgtgtc cccagaatat gaatcatgtt gcaatgtact                         100
```

<210> SEQ ID NO 679
<211> LENGTH: 100
<212> TYPE: DNA
<213> ORGANISM: Homo sapiens

<400> SEQUENCE: 679

```
ggtatcatgt ttcttgaaat actatagcat cttttctcct gaccctgaag tctgctagca    60
ccaaccagac atgtgtgtat ctctgcgcca gcagttcatc                         100
```

<210> SEQ ID NO 680
<211> LENGTH: 100
<212> TYPE: DNA
<213> ORGANISM: Homo sapiens

<400> SEQUENCE: 680

```
gatgctgtag ttacacaatt cccaagacac agaatcattg ggacaggaaa ggaattcatt    60
ctactgtgtc cccagaatat gaatcatgtt gcaatgtact                         100
```

<210> SEQ ID NO 681
<211> LENGTH: 100
<212> TYPE: DNA
<213> ORGANISM: Homo sapiens

<400> SEQUENCE: 681

```
ggtatcatgt ttcttgaaat actatagcat cttttctcct gaccctgaag tctgctagca    60
ccaaccagac atgtgtgtat ctctgcgcca gcagttcatc                         100
```

<210> SEQ ID NO 682
<211> LENGTH: 100
<212> TYPE: DNA
<213> ORGANISM: Homo sapiens

<400> SEQUENCE: 682

```
gaagcccaag tgacccagaa cccaagatac ctcatcacag tgactggaaa gaagttaaca    60
gtgacttgtt ctcagaatat gaaccatgag tatatgtcct                         100
```

<210> SEQ ID NO 683
<211> LENGTH: 100
<212> TYPE: DNA
<213> ORGANISM: Homo sapiens

<400> SEQUENCE: 683

```
ggtacaaagt ctctcgaaaa gagaagagga atttccccct gatcctggag tcgcccagcc    60
ccaaccagac ctctctgtac ttctgtgcca gcagtttatc                         100
```

<210> SEQ ID NO 684
<211> LENGTH: 100
<212> TYPE: DNA
<213> ORGANISM: Homo sapiens

<400> SEQUENCE: 684

```
gatgtgaaag taacccagag ctcgagatat ctagtcaaaa ggacgggaga gaaagttttt    60
ctggaatgtg tccaggatat ggaccatgaa aatatgttct                         100
```

<210> SEQ ID NO 685

```
<211> LENGTH: 100
<212> TYPE: DNA
<213> ORGANISM: Homo sapiens

<400> SEQUENCE: 685
ggtacagtgt ctctagagag aagaaggagc gcttctccct gattctggag tccgccagca      60
ccaaccagac atctatgtac ctctgtgcca gcagtttatg                           100

<210> SEQ ID NO 686
<211> LENGTH: 100
<212> TYPE: DNA
<213> ORGANISM: Homo sapiens

<400> SEQUENCE: 686
agtgctgtca tctctcaaaa gccaagcagg gatatctgtc aacgtggaac ctccctgacg      60
atccagtgtc aagtcgatag ccaagtcacc atgatgttct                           100

<210> SEQ ID NO 687
<211> LENGTH: 100
<212> TYPE: DNA
<213> ORGANISM: Homo sapiens

<400> SEQUENCE: 687
acaagtttcc catcagccgc ccaaacctaa cattctcaac tctgactgtg agcaacatga      60
gccctgaaga cagcagcata tatctctgca gcgttgaaga                           100

<210> SEQ ID NO 688
<211> LENGTH: 99
<212> TYPE: DNA
<213> ORGANISM: Homo sapiens

<400> SEQUENCE: 688
agtgctgtca tctctcaaaa gccaagcagg gatatctgtc aacgtggaac ctccctgacg      60
atccagtgtc aagtcgatag ccaagtcacc atgatgttc                            99

<210> SEQ ID NO 689
<211> LENGTH: 100
<212> TYPE: DNA
<213> ORGANISM: Homo sapiens

<400> SEQUENCE: 689
tgacaagttt cccatcagcc gcccaaacct aacattctca gtctgactg tgagcaacat       60 gagccctgaa gacagcagca tatatctctg cagcgttgaa                           100

<210> SEQ ID NO 690
<211> LENGTH: 100
<212> TYPE: DNA
<213> ORGANISM: Homo sapiens

<400> SEQUENCE: 690
acgatccagt gtcaagtcga tagccaagtc accatgatat tctggtaccg tcagcaacct      60
ggacagagcc tgacactgat cgcaactgca aatcagggct                           100

<210> SEQ ID NO 691
<211> LENGTH: 100
<212> TYPE: DNA
<213> ORGANISM: Homo sapiens

<400> SEQUENCE: 691
tgacaagttt cccatcagcc gcccaaacct aacattctca actctgactg tgagcaacat      60
```

```
gagccctgaa gacagcagca tatatctctg cagcgcgggc                          100

<210> SEQ ID NO 692
<211> LENGTH: 100
<212> TYPE: DNA
<213> ORGANISM: Homo sapiens

<400> SEQUENCE: 692
agtgctgtca tctctcaaaa gccaagcagg gatatctgtc aacgtggaac ctccatgatg    60
atccagtgtc aagtcgacag ccaagtcacc atgatgttct                         100

<210> SEQ ID NO 693
<211> LENGTH: 100
<212> TYPE: DNA
<213> ORGANISM: Homo sapiens

<400> SEQUENCE: 693
acaagtttcc catcagccgc ccaaacctaa cattctcaac tctgactgtg agcaacagga    60
gacctgaaga cagcagcata tacctctgca gcgttgaaga                         100

<210> SEQ ID NO 694
<211> LENGTH: 100
<212> TYPE: DNA
<213> ORGANISM: Homo sapiens

<400> SEQUENCE: 694
agtgctgtca tctctcaaaa gccaagcagg gatatctgtc aacgtggaac ctccatgatg    60
atccagtgtc aagtcgacag ccaagtcacc atgatgttct                         100

<210> SEQ ID NO 695
<211> LENGTH: 100
<212> TYPE: DNA
<213> ORGANISM: Homo sapiens

<400> SEQUENCE: 695
acaagtttcc catcagccgc ccaaacctaa cattctcaac tctgactgtg agcaacagga    60
gacctgaaga cagcagcata tacctctgca gcgttgaaga                         100

<210> SEQ ID NO 696
<211> LENGTH: 100
<212> TYPE: DNA
<213> ORGANISM: Homo sapiens

<400> SEQUENCE: 696
gacacagctg tttcccagac tccaaaatac ctggtcacac agatgggaaa cgacaagtcc    60
attaaatgtg aacaaaatct gggccatgat actatgtatt                         100

<210> SEQ ID NO 697
<211> LENGTH: 100
<212> TYPE: DNA
<213> ORGANISM: Homo sapiens

<400> SEQUENCE: 697
gcttctcacc taaatctcca gacaaagctc acttaaatct tcacatcaat tccctggagc    60
ttggtgactc tgctgtgtat ttctgtgcca gcagccaaga                         100

<210> SEQ ID NO 698
<211> LENGTH: 100
<212> TYPE: DNA
```

<213> ORGANISM: Homo sapiens

<400> SEQUENCE: 698
gacacagctg tttcccagac tccaaaatac ctggtcacac agatgggaaa cgacaagtcc    60
attaaatgtg aacaaaatct gggccatgat actatgtatt                          100

<210> SEQ ID NO 699
<211> LENGTH: 100
<212> TYPE: DNA
<213> ORGANISM: Homo sapiens

<400> SEQUENCE: 699
tccaaatcga ttctcaccta aatctccaga caaagctaaa ttaaatcttc acatcaattc    60
cctggagctt ggtgactctg ctgtgtattt ctgtgccagc                          100

<210> SEQ ID NO 700
<211> LENGTH: 100
<212> TYPE: DNA
<213> ORGANISM: Homo sapiens

<400> SEQUENCE: 700
gacacagccg tttcccagac tccaaaatac ctggtcacac agatgggaaa aaaggagtct    60
cttaaatgag aacaaaatct gggccataat gctatgtatt                          100

<210> SEQ ID NO 701
<211> LENGTH: 100
<212> TYPE: DNA
<213> ORGANISM: Homo sapiens

<400> SEQUENCE: 701
gcttctcacc tgactctcca gacaaagctc atttaaatct tcacatcaat tccctggagc    60
ttggtgactc tgctgtgtat ttctgtgcca gcagccaaga                          100

<210> SEQ ID NO 702
<211> LENGTH: 100
<212> TYPE: DNA
<213> ORGANISM: Homo sapiens

<400> SEQUENCE: 702
gacacagccg tttcccagac tccaaaatac ctggtcacac agatgggaaa aaaggagtct    60
cttaaatgag aacaaaatct gggccataat gctatgtatt                          100

<210> SEQ ID NO 703
<211> LENGTH: 100
<212> TYPE: DNA
<213> ORGANISM: Homo sapiens

<400> SEQUENCE: 703
gcttctcacc tgactctcca gacaaagttc atttaaatct tcacatcaat tccctggagc    60
ttggtgactc tgctgtgtat ttctgtgcca gcagccaaga                          100

<210> SEQ ID NO 704
<211> LENGTH: 100
<212> TYPE: DNA
<213> ORGANISM: Homo sapiens

<400> SEQUENCE: 704
gacacagccg tttcccagac tccaaaatac ctggtcacac agacgggaaa aaaggagtct    60
cttaaatgag aacaaaatct gggccataat gctatgtatt                          100

<210> SEQ ID NO 705
<211> LENGTH: 100
<212> TYPE: DNA
<213> ORGANISM: Homo sapiens

<400> SEQUENCE: 705
tcgcttctca cctgactctc cagacaaagt tcatttaaat cttcacatca attccctgga    60
gcttggtgac tctgctgtgt atttctgtgc cagcagccaa                         100

<210> SEQ ID NO 706
<211> LENGTH: 100
<212> TYPE: DNA
<213> ORGANISM: Homo sapiens

<400> SEQUENCE: 706
tctcagacta ttcatcaatg ccagcgacc ctggtgcagc ctgtgggcag cccgctctct    60
ctggagtgca ctgtggaggg aacatcaaac cccaacctat                         100

<210> SEQ ID NO 707
<211> LENGTH: 100
<212> TYPE: DNA
<213> ORGANISM: Homo sapiens

<400> SEQUENCE: 707
agaatctctc agcctccaga ccccaggacc ggcagttcat cctgagttct aagaagctcc    60
ttctcagtga ctctggcttc tatctctgtg cctggagtgt                         100

<210> SEQ ID NO 708
<211> LENGTH: 100
<212> TYPE: DNA
<213> ORGANISM: Homo sapiens

<400> SEQUENCE: 708
tctcagacta ttcatcaatg ccagcgacc ctggtgcagc ctgtgggcag cccgctctct    60
ctggagtgca ctgtggaggg aacatcaaac cccaacctat                         100

<210> SEQ ID NO 709
<211> LENGTH: 100
<212> TYPE: DNA
<213> ORGANISM: Homo sapiens

<400> SEQUENCE: 709
agaatctctc agcctccaga ccccaggacc ggcagttcat cctgagttct aagaagctcc    60
tcctcagtga ctctggcttc tatctctgtg cctggagtgt                         100

<210> SEQ ID NO 710
<211> LENGTH: 100
<212> TYPE: DNA
<213> ORGANISM: Homo sapiens

<400> SEQUENCE: 710
actattcatc aatggccagc gaccctggtg cagcctgtgg gcagcccgct ctctctggag    60
tgcactgtgg agggaacatc aaaccccaac ctatactggt                         100

<210> SEQ ID NO 711
<211> LENGTH: 100
<212> TYPE: DNA
<213> ORGANISM: Homo sapiens

<400> SEQUENCE: 711
ccagaatctc tcagcctcca gaccccagga ccggcagttc attctgagtt ctaagaagct    60
cctcctcagt gactctggct tctatctctg tgcctggagt                          100

<210> SEQ ID NO 712
<211> LENGTH: 100
<212> TYPE: DNA
<213> ORGANISM: Homo sapiens

<400> SEQUENCE: 712
tctcagacta ttcatcaatg gccagcgacc ctggtgcagc ctgtgggcag cccgctctcc    60
ctggagtgca ctgtggaggg aacatcaaac cccaacctat                          100

<210> SEQ ID NO 713
<211> LENGTH: 100
<212> TYPE: DNA
<213> ORGANISM: Homo sapiens

<400> SEQUENCE: 713
ccagaatctc tcagcctcca gaccccagga ccggcagttc atcctgagtt ctaagaagct    60
ccttctcagt gactctggct tctatctctg tgcctgggga                          100

<210> SEQ ID NO 714
<211> LENGTH: 100
<212> TYPE: DNA
<213> ORGANISM: Homo sapiens

<400> SEQUENCE: 714
gacactgaag ttacccagac accaaaacac ctggtcatgg gaatgacaaa taagaagtct    60
ttgaaatgtg aacaacatat ggggcacagg gctatgtatt                          100

<210> SEQ ID NO 715
<211> LENGTH: 100
<212> TYPE: DNA
<213> ORGANISM: Homo sapiens

<400> SEQUENCE: 715
gcttctcacc tgaatgcccc aacagctctc tcttaaacct tcacctacac gccctgcagc    60
cagaagactc agccctgtat ctctgcgcca gcagccaaga                          100

<210> SEQ ID NO 716
<211> LENGTH: 100
<212> TYPE: DNA
<213> ORGANISM: Homo sapiens

<400> SEQUENCE: 716
cacctggtca tgggaatgac aaataagaag tctttgaaat gtgaacaaca tatggggcac    60
agggcaatgt attggtacaa gcagaaagct aagaagccac                          100

<210> SEQ ID NO 717
<211> LENGTH: 100
<212> TYPE: DNA
<213> ORGANISM: Homo sapiens

<400> SEQUENCE: 717
tcgcttctca cctgaatgcc caacagctc tcttaaac cttcacctac acgccctgca       60
gccagaagac tcagccctgt atctctgcgc cagcagccaa                          100

<210> SEQ ID NO 718
<211> LENGTH: 100
<212> TYPE: DNA
<213> ORGANISM: Homo sapiens

<400> SEQUENCE: 718
gaaacgggag ttacgcagac accaagacac ctggtcatgg gaatgacaaa taagaagtct      60
ttgaaatgtg aacaacatct ggggcataac gctatgtatt                          100

<210> SEQ ID NO 719
<211> LENGTH: 100
<212> TYPE: DNA
<213> ORGANISM: Homo sapiens

<400> SEQUENCE: 719
gcttctcacc tgaatgcccc aacagctctc acttattcct tcacctacac accctgcagc      60
cagaagactc ggccctgtat ctctgtgcca gcagccaaga                          100

<210> SEQ ID NO 720
<211> LENGTH: 100
<212> TYPE: DNA
<213> ORGANISM: Homo sapiens

<400> SEQUENCE: 720
gaaacgggag ttacgcagac accaagacac ctggtcatgg gaatgacaaa taagaagtct      60
ttgaaatgtg aacaacatct ggggcataac gctatgtatt                          100

<210> SEQ ID NO 721
<211> LENGTH: 100
<212> TYPE: DNA
<213> ORGANISM: Homo sapiens

<400> SEQUENCE: 721
aagtcgcttc tcacctgaat gccccaacag ctctcactta tgccttcacc tacacaccct      60
gcagccagaa gactcggccc tgtatctctg tgccagcacc                          100

<210> SEQ ID NO 722
<211> LENGTH: 100
<212> TYPE: DNA
<213> ORGANISM: Homo sapiens

<400> SEQUENCE: 722
gaaacgggag ttacgcagac accaagacac ctggtcatgg gaatgacaaa taagaagtct      60
ttgaaatgtg aacaacatct gggtcataac gctatgtatt                          100

<210> SEQ ID NO 723
<211> LENGTH: 100
<212> TYPE: DNA
<213> ORGANISM: Homo sapiens

<400> SEQUENCE: 723
gcttctcacc tgaatgcccc aacagctctc acttattcct tcacctacac accctgcagc      60
cagaagactc ggccctgtat ctctgcgcca gcagccaaga                          100

<210> SEQ ID NO 724
<211> LENGTH: 100
<212> TYPE: DNA
<213> ORGANISM: Homo sapiens

<400> SEQUENCE: 724

```
gaaacgggag ttacgcagac accaagacac ctggtcatgg gaatgacaaa taagaagtct    60
ttgaaatgtg aacaacatct gggtcataac gctatgtatt                         100

<210> SEQ ID NO 725
<211> LENGTH: 100
<212> TYPE: DNA
<213> ORGANISM: Homo sapiens

<400> SEQUENCE: 725
aagtcgcttc tcacctgaat gccccaacag ctctcactta tcccttcacc tacacaccct    60
gcagccagaa gactcggccc tgtatctctg cgccagcagc                         100

<210> SEQ ID NO 726
<211> LENGTH: 100
<212> TYPE: DNA
<213> ORGANISM: Homo sapiens

<400> SEQUENCE: 726
gaaacgggag ttacgcagac accaagacac ctggtcatgg gaatgacaaa taagaagtct    60
ttgaaatgtg aacaacatct gggtcataac gctatgtatt                         100

<210> SEQ ID NO 727
<211> LENGTH: 100
<212> TYPE: DNA
<213> ORGANISM: Homo sapiens

<400> SEQUENCE: 727
aagtcgcttc tcacctgaat gccccaacag ctctcactta ttccttcacc tacacaccct    60
gcagccagaa gactcggccc tgtatctctg cgccagcagc                         100

<210> SEQ ID NO 728
<211> LENGTH: 100
<212> TYPE: DNA
<213> ORGANISM: Homo sapiens

<400> SEQUENCE: 728
aagaagtctt tgaaatgtga acaacatctg gggcataacg ctatgtattg gtacaagcaa    60
agtgctaaga agccactgga gctcatgttt gtctacagtc                         100

<210> SEQ ID NO 729
<211> LENGTH: 100
<212> TYPE: DNA
<213> ORGANISM: Homo sapiens

<400> SEQUENCE: 729
aagtcgcttc tcacctgaat gccccaacag ctctcactta ttccttcacc tacacaccct    60
gcagccagaa gactcggccc tgtatctctg cgccagcagc                         100

<210> SEQ ID NO 730
<211> LENGTH: 100
<212> TYPE: DNA
<213> ORGANISM: Homo sapiens

<400> SEQUENCE: 730
aaggctggag tcactcaaac tccaagatat ctgatcaaaa cgagaggaca gcaagtgaca    60
ctgagctgct cccctatctc tgggcatagg agtgtatcct                         100

<210> SEQ ID NO 731
<211> LENGTH: 100
```

```
<212> TYPE: DNA
<213> ORGANISM: Homo sapiens

<400> SEQUENCE: 731
cgattctcag ggcgccagtt ctctaactct cgctctgaga tgaatgtgag caccttggag      60
ctgggggact cggcccttta tctttgcgcc agcagcttgg                           100

<210> SEQ ID NO 732
<211> LENGTH: 100
<212> TYPE: DNA
<213> ORGANISM: Homo sapiens

<400> SEQUENCE: 732
agggctgggg tcactcaaac tccaagacat ctgatcaaaa cgagaggaca gcaagtgaca      60
ctgggctgct cccctatctc tgggcatagg agtgtatcct                           100

<210> SEQ ID NO 733
<211> LENGTH: 100
<212> TYPE: DNA
<213> ORGANISM: Homo sapiens

<400> SEQUENCE: 733
tcgattctca gggcgccagt tctctaactc tcgctctgag atgaatgtga gcaccttgga      60
gctggggac tcggcccttt atctttgcgc cagcgcttgc                            100

<210> SEQ ID NO 734
<211> LENGTH: 100
<212> TYPE: DNA
<213> ORGANISM: Homo sapiens

<400> SEQUENCE: 734
gaggctggaa tcacccaagc tccaagacac ctgatcaaaa caagagacca gcaagtgaca      60
ctgagatgct cccctgcctc tgggcataac tgtgtgtcct                           100

<210> SEQ ID NO 735
<211> LENGTH: 100
<212> TYPE: DNA
<213> ORGANISM: Homo sapiens

<400> SEQUENCE: 735
aacttgccta attgattctc agctcaccac gtccataact attactgagt caaacacgga      60
gctaggggac tcagccctgt atctctgtgc cagcaacttg                           100

<210> SEQ ID NO 736
<211> LENGTH: 100
<212> TYPE: DNA
<213> ORGANISM: Homo sapiens

<400> SEQUENCE: 736
gaggctggag tcacccaaag tcccacacac ctgatcaaaa cgagaggaca gcaagtgact      60
ctgagatgct ctcctatctc tgggcacagc agtgtgtcct                           100

<210> SEQ ID NO 737
<211> LENGTH: 100
<212> TYPE: DNA
<213> ORGANISM: Homo sapiens

<400> SEQUENCE: 737
cgattctcag ggcgccagtt ccatgactgt tgctctgaga tgaatgtgag tgccttggag      60
```

```
ctgggggact cggccctgta tctctgtgcc agaagcttgg                           100
```

<210> SEQ ID NO 738
<211> LENGTH: 100
<212> TYPE: DNA
<213> ORGANISM: Homo sapiens

<400> SEQUENCE: 738

```
gaggctggag tcacccaaag tcccacacac ctgatcaaaa cgagaggaca gcaagtgact    60
ctgagatgct ctcctatctc tgggcacagc agtgtgtcct                         100
```

<210> SEQ ID NO 739
<211> LENGTH: 100
<212> TYPE: DNA
<213> ORGANISM: Homo sapiens

<400> SEQUENCE: 739

```
cgattctcag ggcgccagtt ccatgactat tgctctgaga tgaatgtgag tgccttggag    60
ctgggggact cggccctgta tctctgtgcc agaagcttgg                         100
```

<210> SEQ ID NO 740
<211> LENGTH: 100
<212> TYPE: DNA
<213> ORGANISM: Homo sapiens

<400> SEQUENCE: 740

```
gagactggag tcacccaaag tcccacacac ctgatcaaaa cgagaggaca gcaagtgact    60
ctgagatgct cttctcagtc tgggcacaac actgtgtcct                         100
```

<210> SEQ ID NO 741
<211> LENGTH: 100
<212> TYPE: DNA
<213> ORGANISM: Homo sapiens

<400> SEQUENCE: 741

```
agattctcag gtctccagtt ccctaattat agctctgagc tgaatgtgaa cgccttggag    60
ctggacgact cggccctgta tctctgtgcc agcagcttgg                         100
```

<210> SEQ ID NO 742
<211> LENGTH: 100
<212> TYPE: DNA
<213> ORGANISM: Homo sapiens

<400> SEQUENCE: 742

```
gagactggag tcacccaaag tcccacacac ctgatcaaaa cgagaggaca gcaagtgact    60
ctgagatgct cttctcagtc tgggcacaac actgtgtcct                         100
```

<210> SEQ ID NO 743
<211> LENGTH: 100
<212> TYPE: DNA
<213> ORGANISM: Homo sapiens

<400> SEQUENCE: 743

```
tcctagattc tcaggtctcc agttccctaa ttataactct gagctgaatg tgaacgcctt    60
ggagctggac gactcggccc tgtatctctg tgccagcagc                         100
```

<210> SEQ ID NO 744
<211> LENGTH: 100
<212> TYPE: DNA
<213> ORGANISM: Homo sapiens

```
<400> SEQUENCE: 744
cagcaagtga cactgagatg ctcttctcag tctgggcaca acactgtgtc ctggtaccaa        60
caggccctgg gtcaggggcc ccagtttatc tttcagtatt                             100

<210> SEQ ID NO 745
<211> LENGTH: 100
<212> TYPE: DNA
<213> ORGANISM: Homo sapiens

<400> SEQUENCE: 745
tcctagattc tcaggtctcc agttccctaa ttatagctct gagctgaatg tgaacgcctt        60
ggagctggac gactcggccc tgtatctctg tgccagcagc                             100

<210> SEQ ID NO 746
<211> LENGTH: 100
<212> TYPE: DNA
<213> ORGANISM: Homo sapiens

<400> SEQUENCE: 746
actgtgtcct ggtaccaaca ggccctgggt caggggcccc agtttatctt tcagtattat        60
agggaggaag agaatggcag aggaaactcc cctcctagat                             100

<210> SEQ ID NO 747
<211> LENGTH: 100
<212> TYPE: DNA
<213> ORGANISM: Homo sapiens

<400> SEQUENCE: 747
tcctagattc tcaggtctcc agttccctaa ttatagctct gagctgaatg tgaacgcctt        60
ggagctggac gactcggccc tgtatctctg tgccagcagc                             100

<210> SEQ ID NO 748
<211> LENGTH: 100
<212> TYPE: DNA
<213> ORGANISM: Homo sapiens

<400> SEQUENCE: 748
gacgctggag tcacccaaag tcccacacac ctgatcaaaa cgagaggaca gcaagtgact        60
ctgagatgct ctcctatctc tgggcacaag agtgtgtcct                             100

<210> SEQ ID NO 749
<211> LENGTH: 100
<212> TYPE: DNA
<213> ORGANISM: Homo sapiens

<400> SEQUENCE: 749
cgattctcag ctcgccagtt ccctaactat agctctgagc tgaatgtgaa cgccttgttg        60
ctgggggact cggccctgta tctctgtgcc agcagcttgg                             100

<210> SEQ ID NO 750
<211> LENGTH: 100
<212> TYPE: DNA
<213> ORGANISM: Homo sapiens

<400> SEQUENCE: 750
gacgctggag tcacccaaag tcccacacac ctgatcaaaa cgagaggaca gcacgtgact        60
ctgagatgct ctcctatctc tgggcacaag agtgtgtcct                             100
```

<210> SEQ ID NO 751
<211> LENGTH: 100
<212> TYPE: DNA
<213> ORGANISM: Homo sapiens

<400> SEQUENCE: 751
tgatcgattc tcagctcgcc agttccctaa ctatagctct gagctgaatg tgaacgcctt    60
gttgctgggg gactcggccc tgtatctctg tgccagcagc                         100

<210> SEQ ID NO 752
<211> LENGTH: 100
<212> TYPE: DNA
<213> ORGANISM: Homo sapiens

<400> SEQUENCE: 752
gacgctggag tcacccaaag tcccacacac ctgatcaaaa cgagaggaca gcaagtgact    60
ctgagatgct ctcctatctc tgagcacaag agtgtgtcct                         100

<210> SEQ ID NO 753
<211> LENGTH: 100
<212> TYPE: DNA
<213> ORGANISM: Homo sapiens

<400> SEQUENCE: 753
tgatcgattc tcagctcgcc agttccctaa ctatagctct gagctgaatg tgaacgcctt    60
gttgctgggg gactcggccc tgtatctctg tgccagcagc                         100

<210> SEQ ID NO 754
<211> LENGTH: 100
<212> TYPE: DNA
<213> ORGANISM: Homo sapiens

<400> SEQUENCE: 754
gacgctggag tcacccaaag tcccacacac ctgatcaaaa cgagaggaca gcaagtgact    60
ctgagatgct ctcctaagtc tgggcatgac actgtgtcct                         100

<210> SEQ ID NO 755
<211> LENGTH: 100
<212> TYPE: DNA
<213> ORGANISM: Homo sapiens

<400> SEQUENCE: 755
cgattctcag gtcaccagtt ccctaactat agctctgagc tgaatgtgaa cgccttgttg    60
ctgggggact cggccctcta tctctgtgcc agcagcttgg                         100

<210> SEQ ID NO 756
<211> LENGTH: 100
<212> TYPE: DNA
<213> ORGANISM: Homo sapiens

<400> SEQUENCE: 756
gacgctggag tcacccaaag tcccacacac ctgatcaaaa cgagaggaca gcacgtgact    60
ctgagatgct ctcctatctc tgggcacacc agtgtgtcct                         100

<210> SEQ ID NO 757
<211> LENGTH: 100
<212> TYPE: DNA
<213> ORGANISM: Homo sapiens

<400> SEQUENCE: 757
caattctcag gtcaccagtt ccctaactat agctctgagc tgaatgtgaa cgccttgttg    60
ctaggggact cggccctcta tctctgtgcc agcagcttgg    100

<210> SEQ ID NO 758
<211> LENGTH: 100
<212> TYPE: DNA
<213> ORGANISM: Homo sapiens

<400> SEQUENCE: 758
gaggctggag tcacacaaag tcccacacac ctgatcaaaa cgagaggaca gcaagcgact    60
ctgagatgct ctcctatctc tgggcacacc agtgtgtact    100

<210> SEQ ID NO 759
<211> LENGTH: 100
<212> TYPE: DNA
<213> ORGANISM: Homo sapiens

<400> SEQUENCE: 759
agattttcag gtcgccagtt ccctaattat agctctgagc tgaatgtgaa cgccttggag    60
ctggaggact cggccctgta tctctgtgcc agcagcttgg    100

<210> SEQ ID NO 760
<211> LENGTH: 100
<212> TYPE: DNA
<213> ORGANISM: Homo sapiens

<400> SEQUENCE: 760
aggacagcaa gcgactctga gatgctctcc tatctctggg cacaccagtg tgtactggta    60
ccaacaggcc ctgggtctgg gcctccagct cctcctttgg    100

<210> SEQ ID NO 761
<211> LENGTH: 100
<212> TYPE: DNA
<213> ORGANISM: Homo sapiens

<400> SEQUENCE: 761
tcctagattt tcaggtcgcc agttccctaa ttatagctct gagctgaatg tgaacgcctt    60
ggagctggag gactcggccc tgtatctctg tgccagcagc    100

<210> SEQ ID NO 762
<211> LENGTH: 100
<212> TYPE: DNA
<213> ORGANISM: Homo sapiens

<400> SEQUENCE: 762
aatgctggtg tcactcagac cccaaaattc caggtcctga agacaggaca gagcatgaca    60
ctgcagtgtg cccaggatat gaaccataac tccatgtact    100

<210> SEQ ID NO 763
<211> LENGTH: 100
<212> TYPE: DNA
<213> ORGANISM: Homo sapiens

<400> SEQUENCE: 763
gctacaatgt ctccagatta aacaaacggg agttctcgct caggctggag tcggctgctc    60
cctcccagac atctgtgtac ttctgtgcca gcagtgaagc    100

<210> SEQ ID NO 764

```
<211> LENGTH: 100
<212> TYPE: DNA
<213> ORGANISM: Homo sapiens

<400> SEQUENCE: 764
aatgctggtg tcactcagac cccaaaattc cggtcctga agacaggaca gagcatgaca    60
ctgctgtgtg cccaggatat gaaccatgaa tacatgtact                        100

<210> SEQ ID NO 765
<211> LENGTH: 100
<212> TYPE: DNA
<213> ORGANISM: Homo sapiens

<400> SEQUENCE: 765
gctacaatgt ctccagatta aaaaaacaga atttcctgct ggggttggag tcggctgctc    60
cctcccaaac atctgtgtac ttctgtgcca gcagttactc                         100

<210> SEQ ID NO 766
<211> LENGTH: 100
<212> TYPE: DNA
<213> ORGANISM: Homo sapiens

<400> SEQUENCE: 766
aatgctggtg tcactcagac cccaaaattc cgggtcctga agacaggaca gagcatgaca    60
ctgctgtgtg cccaggatat gaaccatgaa tacatgtact                        100

<210> SEQ ID NO 767
<211> LENGTH: 100
<212> TYPE: DNA
<213> ORGANISM: Homo sapiens

<400> SEQUENCE: 767
tggctacaat gtctccagat taaaaaaaca gaatttcctg ctggggttgg agtcggctgc    60
tccctcccaa acatctgtgt acttctgtgc cagcagccct                         100

<210> SEQ ID NO 768
<211> LENGTH: 100
<212> TYPE: DNA
<213> ORGANISM: Homo sapiens

<400> SEQUENCE: 768
aatgctggtg tcactcagac cccaaaattc cgggtcctga agacaggaca gagcatgaca    60
ctgctgtgtg cccaggatat gaaccatgaa tacatgtact                        100

<210> SEQ ID NO 769
<211> LENGTH: 100
<212> TYPE: DNA
<213> ORGANISM: Homo sapiens

<400> SEQUENCE: 769
gctacaatgt ctccagatta aaaaaacaga atttcctgct ggggttggag tcggctgctc    60
cctcccaaac atctgtgtac ttctgtgcca gcagttactc                         100

<210> SEQ ID NO 770
<211> LENGTH: 100
<212> TYPE: DNA
<213> ORGANISM: Homo sapiens

<400> SEQUENCE: 770
attgctggga tcacccaggc accaacatct cagatcctgg cagcaggacg gcgcatgaca    60
```

```
ctgagatgta cccaggatat gagacataat gccatgtact                           100
```

<210> SEQ ID NO 771
<211> LENGTH: 100
<212> TYPE: DNA
<213> ORGANISM: Homo sapiens

<400> SEQUENCE: 771

```
gttatagtgt ctccagagca aacacagatg atttccccct cacgttggcg tctgctgtac     60
cctctcagac atctgtgtac ttctgtgcca gcagtgactc                          100
```

<210> SEQ ID NO 772
<211> LENGTH: 100
<212> TYPE: DNA
<213> ORGANISM: Homo sapiens

<400> SEQUENCE: 772

```
actgctggga tcacccaggc accaacatct cagatcctgg cagcaggacg gagcatgaca     60
ctgagatgta cccaggatat gagacataat gccatgtact                          100
```

<210> SEQ ID NO 773
<211> LENGTH: 100
<212> TYPE: DNA
<213> ORGANISM: Homo sapiens

<400> SEQUENCE: 773

```
gttatagtgt ctccagagca aacacagatg atttccccct cacgttggcg tctgctgtac     60
cctctcagac atctgtgtac ttctgtgcca gcagtgactc                          100
```

<210> SEQ ID NO 774
<211> LENGTH: 100
<212> TYPE: DNA
<213> ORGANISM: Homo sapiens

<400> SEQUENCE: 774

```
aatgctggtg tcactcagac cccaaaattc caggtcctga agacaggaca gagcatgaca     60
ctgcagtgtg cccaggatat gaaccatgaa tacatgtcct                          100
```

<210> SEQ ID NO 775
<211> LENGTH: 100
<212> TYPE: DNA
<213> ORGANISM: Homo sapiens

<400> SEQUENCE: 775

```
gctacaatgt ctccagatca accacagagg atttcccgct caggctgctg tcggctgctc     60
cctcccagac atctgtgtac ttctgtgcca gcagttactc                          100
```

<210> SEQ ID NO 776
<211> LENGTH: 100
<212> TYPE: DNA
<213> ORGANISM: Homo sapiens

<400> SEQUENCE: 776

```
aatgctggtg tcactcagac cccaaaattc cgcatcctga agataggaca gagcatgaca     60
ctgcagtgta cccaggatat gaaccataac tacatgtact                          100
```

<210> SEQ ID NO 777
<211> LENGTH: 100
<212> TYPE: DNA

<213> ORGANISM: Homo sapiens

<400> SEQUENCE: 777
gctacaacgt ctccagatca accacagagg atttcccgct caggctggag ttggctgctc    60
cctcccagac atctgtgtac ttctgtgcca gcagttactc                          100

<210> SEQ ID NO 778
<211> LENGTH: 100
<212> TYPE: DNA
<213> ORGANISM: Homo sapiens

<400> SEQUENCE: 778
aatgctggtg tcactcagac cccaaaattc cgcatcctga agataggaca gagcatgaca    60
ctgcagtgtg cccaggatat gaaccataac tacatgtact                          100

<210> SEQ ID NO 779
<211> LENGTH: 100
<212> TYPE: DNA
<213> ORGANISM: Homo sapiens

<400> SEQUENCE: 779
gaatggctac aacgtctcca gatcaaccac agaggatttc cgctcaggc tggagttggc     60 tgctccctcc cagacatctg tgtacttctg tgccagcagt                          100

<210> SEQ ID NO 780
<211> LENGTH: 100
<212> TYPE: DNA
<213> ORGANISM: Homo sapiens

<400> SEQUENCE: 780
aatgctggtg tcactcagac cccaaaattc cgcatcctga agataggaca gagcatgaca    60
ctgcagtgtg cccaggatat gaaccataac tacatgtact                          100

<210> SEQ ID NO 781
<211> LENGTH: 100
<212> TYPE: DNA
<213> ORGANISM: Homo sapiens

<400> SEQUENCE: 781
gaatggctac aacgtctcca gatcaaccac agaggatttc cgctcaggc tggagttggc     60 tgctccctcc cagacatctg tgtacttctg tgccagcagt                          100

<210> SEQ ID NO 782
<211> LENGTH: 100
<212> TYPE: DNA
<213> ORGANISM: Homo sapiens

<400> SEQUENCE: 782
aatgctggtg tcactcagac cccaaaattc cgcatcctga agataggaca gagcatgaca    60
ctgcagtgta cccaggatat gaaccatgaa tacatgtact                          100

<210> SEQ ID NO 783
<211> LENGTH: 100
<212> TYPE: DNA
<213> ORGANISM: Homo sapiens

<400> SEQUENCE: 783
tggctacaat gtctccagat caaccacaga ggatttcccg ctcaggctgg agttggctgc    60
tccctcccag acatctgtgt acttctgtgc cagcagtcga                          100

<210> SEQ ID NO 784
<211> LENGTH: 100
<212> TYPE: DNA
<213> ORGANISM: Homo sapiens

<400> SEQUENCE: 784
aatgctggtg tcactcagac cccaaaattc cgcatcctga agataggaca gagcatgaca     60
ctgcagtgtg cccaggatat gaaccataac tacatgtact                         100

<210> SEQ ID NO 785
<211> LENGTH: 100
<212> TYPE: DNA
<213> ORGANISM: Homo sapiens

<400> SEQUENCE: 785
gaatggctac aacgtctcca gatcaaccac agaggattcc ccgctcaggc tggagttggc     60
tgctgcctcc cagacatctg tgtacttctg tgccagcagc                         100

<210> SEQ ID NO 786
<211> LENGTH: 100
<212> TYPE: DNA
<213> ORGANISM: Homo sapiens

<400> SEQUENCE: 786
aatgctggtg tcactcagac cccaaaattc cacgtcctga agacaggaca gagcatgact     60
ctgctgtgtg cccaggatat gaaccatgaa tacatgtatc                         100

<210> SEQ ID NO 787
<211> LENGTH: 100
<212> TYPE: DNA
<213> ORGANISM: Homo sapiens

<400> SEQUENCE: 787
gctacaatgt ctccagatca aacacagagg atttcccct caagctggag tcagctgctc      60
cctctcagac ttctgtttac ttctgtgcca gcagttactc                         100

<210> SEQ ID NO 788
<211> LENGTH: 100
<212> TYPE: DNA
<213> ORGANISM: Homo sapiens

<400> SEQUENCE: 788
aatgctggtg tcactcagac cccaaaattc cacatcctga agacaggaca gagcatgaca     60
ctgcagtgtg cccaggatat gaaccatgga tacatgtcct                         100

<210> SEQ ID NO 789
<211> LENGTH: 100
<212> TYPE: DNA
<213> ORGANISM: Homo sapiens

<400> SEQUENCE: 789
gctacaatgt ctctagatta aacacagagg atttcccact caggctggtg tcggctgctc     60
cctcccagac atctgtgtac ttgtgtgcca gcagttactc                         100

<210> SEQ ID NO 790
<211> LENGTH: 100
<212> TYPE: DNA
<213> ORGANISM: Homo sapiens

<400> SEQUENCE: 790
aatgctggtg tcactcagac cccaaaattc cacatcctga agacaggaca gagcatgaca    60
ctgcagtgtg cccaggatat gaaccatgga tacttgtcct                          100

<210> SEQ ID NO 791
<211> LENGTH: 100
<212> TYPE: DNA
<213> ORGANISM: Homo sapiens

<400> SEQUENCE: 791
gctacaatgt atccagatca aacacagagg atttcccgct caggctggag tcagctgctc    60
cctcccagac atctgtatac ttctgtgcca gcagttattc                          100

<210> SEQ ID NO 792
<211> LENGTH: 100
<212> TYPE: DNA
<213> ORGANISM: Homo sapiens

<400> SEQUENCE: 792
ggtgctggag tctcccagtc cctgagacac aaggtagcaa agaagggaaa ggatgtagct    60
ctcagatatg atccaatttc aggtcataat gccctttatt                          100

<210> SEQ ID NO 793
<211> LENGTH: 100
<212> TYPE: DNA
<213> ORGANISM: Homo sapiens

<400> SEQUENCE: 793
ggttctctgc acagaggtct gagggatcca tctccactct gaagttccag cgcacacagc    60 aggggggactt ggctgtgtat ctctgtgcca gcagctcagc                         100

<210> SEQ ID NO 794
<211> LENGTH: 100
<212> TYPE: DNA
<213> ORGANISM: Homo sapiens

<400> SEQUENCE: 794
ggagctggag tctcccagtc ccccagtaac aaggtcacag agaagggaaa ggatgtagag    60
ctcaggtgtg atccaatttc aggtcatact gccctttact                          100

<210> SEQ ID NO 795
<211> LENGTH: 100
<212> TYPE: DNA
<213> ORGANISM: Homo sapiens

<400> SEQUENCE: 795
gcttctctgc agagaggact gggggatccg tctccactct gacgatccag cgcacacagc    60
aggaggactc ggccgtgtat ctctgtgcca gcagcttagc                          100

<210> SEQ ID NO 796
<211> LENGTH: 100
<212> TYPE: DNA
<213> ORGANISM: Homo sapiens

<400> SEQUENCE: 796
ggagctggag tctcccagtc ccccagtaac aaggtcacag agaagggaaa ggatgtagag    60
ctcaggtgtg atccaatttc aggtcatact gccctttact                          100

```
<210> SEQ ID NO 797
<211> LENGTH: 100
<212> TYPE: DNA
<213> ORGANISM: Homo sapiens

<400> SEQUENCE: 797
gcttctctgc agagaggact ggggaatccg tctccactct gacgatccag cgcacacagc    60
aggaggactc ggccgtgtat ctctgtgcca gcagcttagc                         100

<210> SEQ ID NO 798
<211> LENGTH: 100
<212> TYPE: DNA
<213> ORGANISM: Homo sapiens

<400> SEQUENCE: 798
ggagctggag tctcccagtc ccccagtaac aaggtcacag agaagggaaa ggatgtagag    60
ctcaggtgtg atccaatttc aggtcatact gcccttact                          100

<210> SEQ ID NO 799
<211> LENGTH: 100
<212> TYPE: DNA
<213> ORGANISM: Homo sapiens

<400> SEQUENCE: 799
gcttctctgc agagaggact ggggaatccg tctccactct gacgatccag cgcacacagc    60
aggaggactc ggccgtgtat ctctgtacca gcagcttagc                         100

<210> SEQ ID NO 800
<211> LENGTH: 100
<212> TYPE: DNA
<213> ORGANISM: Homo sapiens

<400> SEQUENCE: 800
ggagctggag tttcccagtc ccccagtaac aaggtcacag agaagggaaa ggatgtagag    60
ctcaggtgtg atccaatttc aggtcatact gcccttact                          100

<210> SEQ ID NO 801
<211> LENGTH: 100
<212> TYPE: DNA
<213> ORGANISM: Homo sapiens

<400> SEQUENCE: 801
tcgcttctct gcagagagga ctgggggatc cgtctccact ctgacgatcc agcgcacaca    60
gcaggaggac tcggccgtgt atctctgtgc cagcagctta                         100

<210> SEQ ID NO 802
<211> LENGTH: 100
<212> TYPE: DNA
<213> ORGANISM: Homo sapiens

<400> SEQUENCE: 802
ggtgctggag tctcccagac ccccagtaac aaggtcacag agaagggaaa atatgtagag    60
ctcaggtgtg atccaatttc aggtcatact gcccttact                          100

<210> SEQ ID NO 803
<211> LENGTH: 100
<212> TYPE: DNA
<213> ORGANISM: Homo sapiens

<400> SEQUENCE: 803
```

```
ggttctttgc agtcaggcct gagggatccg tctctactct gaagatccag cgcacagagc    60 gggggggactc agccgtgtat ctctgtgcca gcagcttaac                        100

<210> SEQ ID NO 804
<211> LENGTH: 100
<212> TYPE: DNA
<213> ORGANISM: Homo sapiens

<400> SEQUENCE: 804
ggtgctggag tctcccagac ccccagtaac aaggtcacag agaagggaaa agatgtagag    60
ctcaggtgtg atccaatttc aggtcatact gcccttact                          100

<210> SEQ ID NO 805
<211> LENGTH: 100
<212> TYPE: DNA
<213> ORGANISM: Homo sapiens

<400> SEQUENCE: 805
ggttctttgc agtcaggcct gagggatccg tctctactct gaagatccag cgcacagagc    60 aggggggactc agccgtgtat ctccgtgcca gcagcttaac                        100

<210> SEQ ID NO 806
<211> LENGTH: 100
<212> TYPE: DNA
<213> ORGANISM: Homo sapiens

<400> SEQUENCE: 806
ggtgctggag tctcccagac ccccagtaac aaggtcacag agaagggaaa agatgtagag    60
ctcaggtgtg atccaatttc aggtcatact gcccttact                          100

<210> SEQ ID NO 807
<211> LENGTH: 100
<212> TYPE: DNA
<213> ORGANISM: Homo sapiens

<400> SEQUENCE: 807
ggttctttgc agtcaggcct gagggatccg tctctactct gaagatccag cgcacagagc    60 aggggggactc agccgcgtat ctccgtgcca gcagcttaac                        100

<210> SEQ ID NO 808
<211> LENGTH: 100
<212> TYPE: DNA
<213> ORGANISM: Homo sapiens

<400> SEQUENCE: 808
ggtgctggag tctcccagac ccccagtaac aaggtcacag agaagggaaa atatgtagag    60
ctcaggtgtg atccaatttc aggtcatact gcccttact                          100

<210> SEQ ID NO 809
<211> LENGTH: 100
<212> TYPE: DNA
<213> ORGANISM: Homo sapiens

<400> SEQUENCE: 809
cgatcggttc tttgcagtca ggcctgaggg atccgtctct actctgaaga tccagcgcac    60
agagcggggg gactctgccg tgtatctctg tgccagcagc                         100

<210> SEQ ID NO 810
<211> LENGTH: 100
```

```
<212> TYPE: DNA
<213> ORGANISM: Homo sapiens

<400> SEQUENCE: 810
tgggagctca ggtgtgatcc aatttcaggt catactgccc tttactggta ccgacaaagc    60
ctggggcagg gcccagagct tctaatttac ttccaaggca                         100

<210> SEQ ID NO 811
<211> LENGTH: 100
<212> TYPE: DNA
<213> ORGANISM: Homo sapiens

<400> SEQUENCE: 811
cgatcggttc tttgcagtca ggcctgaggg atccgtctct actctgaaga tccagcgcac    60
agagcggggg gactcagccg tgtatctctg tgccagcagc                         100

<210> SEQ ID NO 812
<211> LENGTH: 100
<212> TYPE: DNA
<213> ORGANISM: Homo sapiens

<400> SEQUENCE: 812
ggtgctggag tctcccagtc cccaaggtac aaagtcgcaa agaggggacg ggatgtagct    60
ctcaggtgtg attcaatttc gggtcatgta acccttatt                         100

<210> SEQ ID NO 813
<211> LENGTH: 100
<212> TYPE: DNA
<213> ORGANISM: Homo sapiens

<400> SEQUENCE: 813
ggttctctgc agagaggcct gagagatccg tctccactct gaagatccag cgcacagagc    60 aggggactc agctgtgtat ctctgtgcca gcagcttagc                          100

<210> SEQ ID NO 814
<211> LENGTH: 100
<212> TYPE: DNA
<213> ORGANISM: Homo sapiens

<400> SEQUENCE: 814
ggtgctggag tctcccagtc cccaaggtac aaagtcgcaa agaggggacg ggatgtagct    60
ctcaggtgtg attcaatttc gggtcatgta acccttatt                         100

<210> SEQ ID NO 815
<211> LENGTH: 100
<212> TYPE: DNA
<213> ORGANISM: Homo sapiens

<400> SEQUENCE: 815
aacgagacaa atcagggcgg cccagtggtc ggttctctgc agagaggcct gagagatcgt    60
ctccactccg aagatccagc gcacagagca gggggactca                         100

<210> SEQ ID NO 816
<211> LENGTH: 100
<212> TYPE: DNA
<213> ORGANISM: Homo sapiens

<400> SEQUENCE: 816
ggtgctggag tctcccagtc cccaaggtac gaagtcacac agaggggaca ggatgtagct    60
```
cccaggtgtg atccaatttc gggtcaggta acccttatt 100

<210> SEQ ID NO 817
<211> LENGTH: 100
<212> TYPE: DNA
<213> ORGANISM: Homo sapiens

<400> SEQUENCE: 817
tcaattctcc acagagaggt ctgaggatct ttctccacct gaagatccag cgcacagagc    60
aagggcgact cggctgtgta tctctgtgcc agaagcttag                          100

<210> SEQ ID NO 818
<211> LENGTH: 100
<212> TYPE: DNA
<213> ORGANISM: Homo sapiens

<400> SEQUENCE: 818
ggtgctggag tctcccagtc cccaaggtac gaagtcacac agaggggaca ggatgtagct    60
cccaggtgtg atccaatttc gggtcaggta acccttatt                          100

<210> SEQ ID NO 819
<211> LENGTH: 100
<212> TYPE: DNA
<213> ORGANISM: Homo sapiens

<400> SEQUENCE: 819
caattctcca cagagaggtc tgaggatctt tctccacctg aagatccagc gcacagagca    60
agggcgactc ggctgtgtat ctctgtgtca gaagcttagc                          100

<210> SEQ ID NO 820
<211> LENGTH: 100
<212> TYPE: DNA
<213> ORGANISM: Homo sapiens

<400> SEQUENCE: 820
ggtgctggag tctcccagtc tcccaggtac aaagtcacaa agaggggaca ggatgtagct    60
ctcaggtgtg atccaatttc gggtcatgta tcccttatt                          100

<210> SEQ ID NO 821
<211> LENGTH: 100
<212> TYPE: DNA
<213> ORGANISM: Homo sapiens

<400> SEQUENCE: 821
ggttctctgc agagaggcct gagggatcca tctccactct gacgatccag cgcacagagc    60
agcgggactc ggccatgtat cgctgtgcca gcagcttagc                          100

<210> SEQ ID NO 822
<211> LENGTH: 100
<212> TYPE: DNA
<213> ORGANISM: Homo sapiens

<400> SEQUENCE: 822
ggtgctggag tctcccagtc tcccaggtac aaagtcacaa agaggggaca ggatgtagct    60
ctcaggtgtg atccaatctc gggtcatgta tcccttatt                          100

<210> SEQ ID NO 823
<211> LENGTH: 100
<212> TYPE: DNA
<213> ORGANISM: Homo sapiens

<400> SEQUENCE: 823
tgatcggttc tctgcagaga ggcctgaggg atccatctcc actctgacga tccagcgcac     60
agagcagcgg gactcggcca tgtatcgctg tgccagcagc     100

<210> SEQ ID NO 824
<211> LENGTH: 100
<212> TYPE: DNA
<213> ORGANISM: Homo sapiens

<400> SEQUENCE: 824
ggtgctggag tctcccagtc tcccaggtac aaagtcacaa agaggggaca ggatgtaact     60
ctcaggtgtg atccaatttc gagtcatgca acccttatt     100

<210> SEQ ID NO 825
<211> LENGTH: 100
<212> TYPE: DNA
<213> ORGANISM: Homo sapiens

<400> SEQUENCE: 825
ggttctctgc agagaggcct gagggatcca tctccactct gacgattcag cgcacagagc     60
agcgggactc agccatgtat cgctgtgcca gcagcttagc     100

<210> SEQ ID NO 826
<211> LENGTH: 100
<212> TYPE: DNA
<213> ORGANISM: Homo sapiens

<400> SEQUENCE: 826
ggtgctggag tctcccagtc tcccaggtac aaagtcacaa agaggggaca ggatgtaact     60
ctcaggtgtg atccaatttc gagtcatgta acccttatt     100

<210> SEQ ID NO 827
<211> LENGTH: 100
<212> TYPE: DNA
<213> ORGANISM: Homo sapiens

<400> SEQUENCE: 827
tgatcggttc tctgcagaga ggcctgaggg atccatctcc actctgacga ttcagcgcac     60
agagcagcgg gactcagcca tgtatcgctg tgccagcagc     100

<210> SEQ ID NO 828
<211> LENGTH: 100
<212> TYPE: DNA
<213> ORGANISM: Homo sapiens

<400> SEQUENCE: 828
ggtgctggag tctcccagtc ccctaggtac aaagtcgcaa agagaggaca ggatgtagct     60
ctcaggtgtg atccaatttc gggtcatgta tcccttttt     100

<210> SEQ ID NO 829
<211> LENGTH: 100
<212> TYPE: DNA
<213> ORGANISM: Homo sapiens

<400> SEQUENCE: 829
gcttctttgc agaaaggcct gagggatccg tctccactct gaagatccag cgcacacagc     60
aggaggactc cgccgtgtat ctctgtgcca gcagcttagc     100

<210> SEQ ID NO 830
<211> LENGTH: 100
<212> TYPE: DNA
<213> ORGANISM: Homo sapiens

<400> SEQUENCE: 830
ggtgctggag tctcccagtc ccctaggtac aaagtcgcaa agagaggaca ggatgtagct    60
ctcaggtgtg atccaatttc gggtcatgta tccctttttt                        100

<210> SEQ ID NO 831
<211> LENGTH: 100
<212> TYPE: DNA
<213> ORGANISM: Homo sapiens

<400> SEQUENCE: 831
gcttctttgc agaaaggcct gagggatccg tctccactct gaagatccag cgcacacaga    60
aggaggactc cgccgtgtat ctctgtgcca gcagcttagc                        100

<210> SEQ ID NO 832
<211> LENGTH: 100
<212> TYPE: DNA
<213> ORGANISM: Homo sapiens

<400> SEQUENCE: 832
ggtgctggag tctcccagtc ccctaggtac aaagtcgcaa agagaggaca ggatgtagct    60
ctcaggtgtg atccaatttc gggtcatgta tccctttttt                        100

<210> SEQ ID NO 833
<211> LENGTH: 100
<212> TYPE: DNA
<213> ORGANISM: Homo sapiens

<400> SEQUENCE: 833
tcgcttcttt gcagaaaggc ctgagggatc cgtctccact ctgaagatcc agcgcacaca    60
gcaggaggac tccgccgtgt atctctgtgc cagcagccga                        100

<210> SEQ ID NO 834
<211> LENGTH: 100
<212> TYPE: DNA
<213> ORGANISM: Homo sapiens

<400> SEQUENCE: 834
gatactggag tctcccagaa ccccagacac aagatcacaa agaggggaca gaatgtaact    60
ttcaggtgtg atccaatttc tgaacacaac cgcctttatt                        100

<210> SEQ ID NO 835
<211> LENGTH: 100
<212> TYPE: DNA
<213> ORGANISM: Homo sapiens

<400> SEQUENCE: 835
ggttctctgc agagaggcct aagggatctt tctccacctt ggagatccag cgcacagagc    60
agggggactc ggccatgtat ctctgtgcca gcagcttagc                        100

<210> SEQ ID NO 836
<211> LENGTH: 100
<212> TYPE: DNA
<213> ORGANISM: Homo sapiens

<400> SEQUENCE: 836
gatactggag tctcccagaa ccccagacac aacatcacaa agaggggaca gaatgtaact    60
ttcaggtgtg atccaatttc tgaacacaac cgcctttatt                        100

<210> SEQ ID NO 837
<211> LENGTH: 100
<212> TYPE: DNA
<213> ORGANISM: Homo sapiens

<400> SEQUENCE: 837
tcggttctct gcagagaggc ctaagggatc tttctccacc ttggagatcc agcgcacaga    60 gcaggggac tcggccatgt atctctgtgc cagcagctta                         100

<210> SEQ ID NO 838
<211> LENGTH: 100
<212> TYPE: DNA
<213> ORGANISM: Homo sapiens

<400> SEQUENCE: 838
gatactggag tctcccagga ccccagacac aagatcacaa agaggggaca gaatgtaact    60
ttcaggtgtg atccaatttc tgaacacaac cgcctttatt                        100

<210> SEQ ID NO 839
<211> LENGTH: 100
<212> TYPE: DNA
<213> ORGANISM: Homo sapiens

<400> SEQUENCE: 839
tgatcggttc tctgcagaga ggcctaaggg atctttctcc accttggaga tccagcgcac    60
agagcagggg gactcggcca tgtatctctg tgccagcagc                        100

<210> SEQ ID NO 840
<211> LENGTH: 100
<212> TYPE: DNA
<213> ORGANISM: Homo sapiens

<400> SEQUENCE: 840
atatctggag tctcccacaa ccccagacac aagatcacaa agaggggaca gaatgtaact    60
ttcaggtgtg atccaatttc tgaacacaac cgcctttatt                        100

<210> SEQ ID NO 841
<211> LENGTH: 100
<212> TYPE: DNA
<213> ORGANISM: Homo sapiens

<400> SEQUENCE: 841
tcggatctct gcagagaggc ctaagggatc tttctccacc ttggagatcc agcgcacaga    60 gcaggggac tcggccatgt atctctgtgc cagcagctct                         100

<210> SEQ ID NO 842
<211> LENGTH: 100
<212> TYPE: DNA
<213> ORGANISM: Homo sapiens

<400> SEQUENCE: 842
gatactggag tctcccagaa ccccagacac aagatcacaa agaggggaca gaatgtaact    60
ttcaggtgtg atccaatttc tgaacacaac cgcctttatt                        100

<210> SEQ ID NO 843

```
<211> LENGTH: 100
<212> TYPE: DNA
<213> ORGANISM: Homo sapiens

<400> SEQUENCE: 843
tcggttctct gcagagaggc ctaagggatc tctctccacc ttggagatcc agcgcacaga      60 gcaggggac tcggccatgt atctctgtgc cagcaccaaa                           100

<210> SEQ ID NO 844
<211> LENGTH: 100
<212> TYPE: DNA
<213> ORGANISM: Homo sapiens

<400> SEQUENCE: 844
gatactggag tctcccagaa ccccagacac aagatcacaa agagggaca gaatgtaact      60 ttcaggtgtg atccaatttc tgaacacaac cgcctttatt                          100

<210> SEQ ID NO 845
<211> LENGTH: 100
<212> TYPE: DNA
<213> ORGANISM: Homo sapiens

<400> SEQUENCE: 845
tcggttctct gcagagaggc ctaagggatc tctttccacc ttggagatcc agcgcacaga      60 gcaggggac tcggccatgt atctctgtgc cagcacgttg                          100

<210> SEQ ID NO 846
<211> LENGTH: 100
<212> TYPE: DNA
<213> ORGANISM: Homo sapiens

<400> SEQUENCE: 846
cacaaccgcc tttattggta ccgacagacc ctggggcagg cccagagtt tctgacttac      60 ttccagaatg aagctcaact agaaaaatca aggctgctca                          100

<210> SEQ ID NO 847
<211> LENGTH: 100
<212> TYPE: DNA
<213> ORGANISM: Homo sapiens

<400> SEQUENCE: 847
gttctctgca gagaggccta agggatcttt ctccaccttg gagatccagc gcacagagga      60
gggggactcg gccatgtatc tctgtgccag cagcagcagt                          100

<210> SEQ ID NO 848
<211> LENGTH: 100
<212> TYPE: DNA
<213> ORGANISM: Homo sapiens

<400> SEQUENCE: 848
gaggcaggga tcagccagat accaagatat cacagacaca cagggaaaaa gatcatcctg      60
aaatatgctc agattaggaa ccattattca gtgttctgtt                          100

<210> SEQ ID NO 849
<211> LENGTH: 100
<212> TYPE: DNA
<213> ORGANISM: Homo sapiens

<400> SEQUENCE: 849
ggaagggtac aatgtctctg gaaacaagct caagcatttt ccctcaaccc tggagtctac      60
```

```
tagcaccagc cagacctctg tacctctgtg gcagtgcatc                          100

<210> SEQ ID NO 850
<211> LENGTH: 100
<212> TYPE: DNA
<213> ORGANISM: Homo sapiens

<400> SEQUENCE: 850
gatgctggga tcacccagat gccaagatat cacattgtac agaagaaaga gatgatcctg    60
gaatgtgctc aggttaggaa cagtgttctg atatcgacag                         100

<210> SEQ ID NO 851
<211> LENGTH: 100
<212> TYPE: DNA
<213> ORGANISM: Homo sapiens

<400> SEQUENCE: 851
agaggggtac tgtgtttctt gaaacaagct tgagcatttc cccaatcctg gcatccacca    60
gcaccagcca gacctatctg taccactgtg gcagcacatc                         100

<210> SEQ ID NO 852
<211> LENGTH: 100
<212> TYPE: DNA
<213> ORGANISM: Homo sapiens

<400> SEQUENCE: 852
gattctggag tcacacaaac cccaaagcac ctgatcacag caactggaca gcgagtgacg    60
ctgagatgct cccctaggtc tggagacctc tctgtgtact                         100

<210> SEQ ID NO 853
<211> LENGTH: 100
<212> TYPE: DNA
<213> ORGANISM: Homo sapiens

<400> SEQUENCE: 853
cgattctccg cacaacagtt ccctgacttg cactctgaac taaacctgag ctctctggag    60
ctgggggact cagctttgta tttctgtgcc agcagcgtag                         100

<210> SEQ ID NO 854
<211> LENGTH: 100
<212> TYPE: DNA
<213> ORGANISM: Homo sapiens

<400> SEQUENCE: 854
gattctggag tcacacaaac cccaaagcac ctgatcacag caactggaca gcgagtgacg    60
ctgagatgct cccctaggtc tggagacctc tctgtgtact                         100

<210> SEQ ID NO 855
<211> LENGTH: 100
<212> TYPE: DNA
<213> ORGANISM: Homo sapiens

<400> SEQUENCE: 855
cgattctccg cacaacagtt ccctgacttg cactctgaac taaacctgag ctctctggag    60
ctgggggact cagctttgta tttctgtgcc agcagcgtag                         100

<210> SEQ ID NO 856
<211> LENGTH: 100
<212> TYPE: DNA
```

```
<213> ORGANISM: Homo sapiens

<400> SEQUENCE: 856
gattctggag tcacacaaac cccaaagcac ctgatcacag caactggaca gcgagtgacg    60
ctgagatgct cccctaggtc tggagacctc tctgtgtact                        100

<210> SEQ ID NO 857
<211> LENGTH: 100
<212> TYPE: DNA
<213> ORGANISM: Homo sapiens

<400> SEQUENCE: 857
tgaacgattc tccgcacaac agttccctga cttgcactct gaactaaacc tgagctctct    60
ggagctgggg gactcagctt tgtatttctg tgccagcagc                        100

<210> SEQ ID NO 858
<211> LENGTH: 100
<212> TYPE: DNA
<213> ORGANISM: Homo sapiens

<400> SEQUENCE: 858
gaagctgaag ccacctagac tctaagacac ctgattgcag agacaggaaa ggagttctca    60
agataagtgc caagatttca tactggtttt cacaagaatc                        100

<210> SEQ ID NO 859
<211> LENGTH: 100
<212> TYPE: DNA
<213> ORGANISM: Homo sapiens

<400> SEQUENCE: 859
tccctattga aaatatttcc tggcaaaaaa tagaagttct ctttggctct gaaatctgca    60
actccctttc aggtgtccct gtgtccttgt accgtcactc                        100

<210> SEQ ID NO 860
<211> LENGTH: 100
<212> TYPE: DNA
<213> ORGANISM: Homo sapiens

<400> SEQUENCE: 860
gaagctgaag tcacctagac tccaagacac ctgattgtag agacaggaaa ggagttctca    60
ggatatgtgc cataatttca tactggtttc tacaagaatc                        100

<210> SEQ ID NO 861
<211> LENGTH: 100
<212> TYPE: DNA
<213> ORGANISM: Homo sapiens

<400> SEQUENCE: 861
tccctgttga aaatatttcc cggcaaaaaa cagaagttcc ctttggctct gaaatctgca    60 aagcccttc agatgtccct gtgtccttgt gccgtcactc                         100

<210> SEQ ID NO 862
<211> LENGTH: 100
<212> TYPE: DNA
<213> ORGANISM: Homo sapiens

<400> SEQUENCE: 862
aatgtcaaag taacacagac cctgagatga ggcaggaaag ttgtatcgga atgttttcag    60
actatcaacc agaccaaacg ttctggaatc cataagatcc                        100
```

<210> SEQ ID NO 863
<211> LENGTH: 100
<212> TYPE: DNA
<213> ORGANISM: Homo sapiens

<400> SEQUENCE: 863
gactctgaga ccctctgcag cagcagccta tcagtgcagc cacatcctct ctgagcggat    60
atgacaaacc ccagggttga agcgacctaa cctatgagcc                         100

<210> SEQ ID NO 864
<211> LENGTH: 100
<212> TYPE: DNA
<213> ORGANISM: Homo sapiens

<400> SEQUENCE: 864
agtgacttct aaattggtct atgaaggaga atctccccca ttcctggagt cgcccagtcc    60
agacctctct gtacatttgc accagcagtt tatccacagt                         100

<210> SEQ ID NO 865
<211> LENGTH: 100
<212> TYPE: DNA
<213> ORGANISM: Homo sapiens

<400> SEQUENCE: 865
gcccagaagg ttactcaagc ccagtcatca gtatccatgc cagtgaggaa agcagtcacc    60
ctgaactgcc tgtatgaaac aagttggtgg tcatattata                         100

<210> SEQ ID NO 866
<211> LENGTH: 100
<212> TYPE: DNA
<213> ORGANISM: Homo sapiens

<400> SEQUENCE: 866
attctgtcaa cttcaagaaa gcagcgaaat ccgtcgcctt aaccatttca gccttacagc    60
tagaagattc agcaaagtac ttttgtgctc ttggggaact                         100

<210> SEQ ID NO 867
<211> LENGTH: 100
<212> TYPE: DNA
<213> ORGANISM: Homo sapiens

<400> SEQUENCE: 867
gccattgagt tggtgcctga acaccaaaca gtgcctgtgt caatagggt ccctgccacc     60 ctcaggtgct ccatgaaagg agaagcgatc ggtaactact                         100

<210> SEQ ID NO 868
<211> LENGTH: 100
<212> TYPE: DNA
<213> ORGANISM: Homo sapiens

<400> SEQUENCE: 868
tttccaaggt gacattgata ttgcaaagaa cctggctgta cttaagatac ttgcaccatc    60
agagagagat gaagggtctt actactgtgc ctgtgacacc                         100

<210> SEQ ID NO 869
<211> LENGTH: 100
<212> TYPE: DNA
<213> ORGANISM: Homo sapiens

<400> SEQUENCE: 869
attgagttgg tgcctgaaca ccaaacagtg cctgtgtcaa tagggatccc tgccaccctc    60
aggtgctcca tgaaaggaga agcgatcggt aactactata                         100

<210> SEQ ID NO 870
<211> LENGTH: 100
<212> TYPE: DNA
<213> ORGANISM: Homo sapiens

<400> SEQUENCE: 870
aatttccaag gtgacattga tattgcaaag aacctggctg tacttaagat acttgcacca    60
tcagagagag atgaagggtc ttactactgt gcctgtgaca                         100

<210> SEQ ID NO 871
<211> LENGTH: 100
<212> TYPE: DNA
<213> ORGANISM: Homo sapiens

<400> SEQUENCE: 871
gccattgagt tggtgcctga acaccaaaca gtgcctgtgt caatagggt ccctgccacc    60 ctcaggtgct ccatgaaagg agaagcgatc ggtaactact                         100

<210> SEQ ID NO 872
<211> LENGTH: 100
<212> TYPE: DNA
<213> ORGANISM: Homo sapiens

<400> SEQUENCE: 872
tttccaaggt gacattgata ttgcaaagaa cctggctgta cttaagatac ttgcaccatc    60
agagagagat gaagggtctt actactgtgc ctgtgacacc                         100

<210> SEQ ID NO 873
<211> LENGTH: 100
<212> TYPE: DNA
<213> ORGANISM: Homo sapiens

<400> SEQUENCE: 873
tgtgacaaag taacccagag ttccccggac cagacggtgg cgagtggcag tgaggtggta    60
ctgctctgca cttacgacac tgtatattca aatccagatt                         100

<210> SEQ ID NO 874
<211> LENGTH: 100
<212> TYPE: DNA
<213> ORGANISM: Homo sapiens

<400> SEQUENCE: 874
gacggttttc tgtgaaacac attctgaccc agaaagcctt tcacttggtg atctctccag    60
taaggactga agacagtgcc acttactact gtgcctttag                         100

<210> SEQ ID NO 875
<211> LENGTH: 100
<212> TYPE: DNA
<213> ORGANISM: Homo sapiens

<400> SEQUENCE: 875
tgtgacaaag taacccagag ttccccggac cagacggtgg cgagtggcag tgaggtggta    60
ctgctctgca cttacgacac tgtatattca aatccagatt                         100

```
<210> SEQ ID NO 876
<211> LENGTH: 100
<212> TYPE: DNA
<213> ORGANISM: Homo sapiens

<400> SEQUENCE: 876
gacggttttc tgtgaaacac attctgaccc agaaagcctt tcacttggtg atctctccag      60
taaggactga agacagtgcc acttactact gtgcctttag                            100

<210> SEQ ID NO 877
<211> LENGTH: 100
<212> TYPE: DNA
<213> ORGANISM: Homo sapiens

<400> SEQUENCE: 877
tcttccaact tggaagggag aacgaagtca gtcaccaggc tgactgggtc atctgctgaa      60
atcacctgtg atcttcctgg agcaagtacc ttatacatcc                            100

<210> SEQ ID NO 878
<211> LENGTH: 100
<212> TYPE: DNA
<213> ORGANISM: Homo sapiens

<400> SEQUENCE: 878
aaagtatgac actggaagca caaggagcaa ttggaatttg agactgcaaa atctaattaa      60
aaatgattct gggttctatt actgtgccac ctgggacagg                            100

<210> SEQ ID NO 879
<211> LENGTH: 100
<212> TYPE: DNA
<213> ORGANISM: Homo sapiens

<400> SEQUENCE: 879
ttatcaaaag tggagcagtt ccagctatcc atttccacgg aagtcaagaa aagtattgac      60
ataccttgca agatatcgag cacaaggttt gaaacagatg                            100

<210> SEQ ID NO 880
<211> LENGTH: 100
<212> TYPE: DNA
<213> ORGANISM: Homo sapiens

<400> SEQUENCE: 880
aggcaagaaa gaattctcaa actctcactt caatccttac catcaagtcc gtagagaaag      60
aagacatggc cgtttactac tgtgctgcgt ggtgggtggc                            100

<210> SEQ ID NO 881
<211> LENGTH: 100
<212> TYPE: DNA
<213> ORGANISM: Homo sapiens

<400> SEQUENCE: 881
ttatcaaaag tggagcagtt ccagctatcc atttccacgg aagtcaagaa aagtattgac      60
ataccttgca agatatcgag cacaaggttt gaaacagatg                            100

<210> SEQ ID NO 882
<211> LENGTH: 100
<212> TYPE: DNA
<213> ORGANISM: Homo sapiens

<400> SEQUENCE: 882
```

```
tggaggcaag aaagaattct caaactctca cttcaatcct taccatcaag tccgtagaga    60
aagaagacat ggccgtttac tactgtgctg cgtgggatta                        100

<210> SEQ ID NO 883
<211> LENGTH: 100
<212> TYPE: DNA
<213> ORGANISM: Homo sapiens

<400> SEQUENCE: 883
cttgggcagt tggaacaacc tgaaatatct atttccagac cagcaaataa gagtgcccac    60
atatcttgga aggcatccat ccaaggcttt agcagtaaaa                        100

<210> SEQ ID NO 884
<211> LENGTH: 100
<212> TYPE: DNA
<213> ORGANISM: Homo sapiens

<400> SEQUENCE: 884
ggtaagtaaa aatgctcaca cttccacttc cactttgaaa ataagttct tagagaaaga    60 agatgaggtg gtgtaccact gtgcctgctg gattaggcac                        100

<210> SEQ ID NO 885
<211> LENGTH: 100
<212> TYPE: DNA
<213> ORGANISM: Homo sapiens

<400> SEQUENCE: 885
cttgggcagt tggaacaacc tgaaatatct atttccagac cagcaaataa gagtgcccac    60
atatcttgga aggcatccat ccaaggcttt agcagtaaaa                        100

<210> SEQ ID NO 886
<211> LENGTH: 100
<212> TYPE: DNA
<213> ORGANISM: Homo sapiens

<400> SEQUENCE: 886
gataagtaaa aatgctcaca cttccacttc cactttgaaa ataagttct tagagaaaga    60 agatgaggtg gtgtaccact gtgcctgctg gattaggcac                        100

<210> SEQ ID NO 887
<211> LENGTH: 100
<212> TYPE: DNA
<213> ORGANISM: Homo sapiens

<400> SEQUENCE: 887
tcttccaact tggaagggag aacgaagtca gtcatcaggc agactgggtc atctgctgaa    60
atcacttgtg atcttgctga aggaagtaac ggctacatcc                        100

<210> SEQ ID NO 888
<211> LENGTH: 100
<212> TYPE: DNA
<213> ORGANISM: Homo sapiens

<400> SEQUENCE: 888
gtattatact tacgcaagca caaggaacaa cttgagattg atactgcgaa atctaattga    60
aaatgactct ggggtctatt actgtgccac ctgggacggg                        100

<210> SEQ ID NO 889
<211> LENGTH: 100
```

```
<212> TYPE: DNA
<213> ORGANISM: Homo sapiens

<400> SEQUENCE: 889
tcttccaact tggaagggag aacgaagtca gtcatcaggc agactgggtc atctgctgaa      60
atcacttgtg atcttgctga aggaagtaac ggctacatcc                          100

<210> SEQ ID NO 890
<211> LENGTH: 100
<212> TYPE: DNA
<213> ORGANISM: Homo sapiens

<400> SEQUENCE: 890
gaagtattat acttacgcaa gcacaaggaa caacttgaga ttgatactgc aaaatctaat      60
tgaaaatgac tctggggtct attactgtgc cacctgggac                          100

<210> SEQ ID NO 891
<211> LENGTH: 100
<212> TYPE: DNA
<213> ORGANISM: Homo sapiens

<400> SEQUENCE: 891
tcttccaact tggaagggag aacgaagtca gtcaccaggc agactgggtc atctgctgaa      60
atcacttgcg atcttactgt aacaaatacc ttctacatcc                          100

<210> SEQ ID NO 892
<211> LENGTH: 100
<212> TYPE: DNA
<213> ORGANISM: Homo sapiens

<400> SEQUENCE: 892
gtattatact catacaccca ggaggtggag ctggatattg agactgcaaa atctaattga      60
aaatgattct ggggtctatt actgtgccac ctgggacagg                          100

<210> SEQ ID NO 893
<211> LENGTH: 100
<212> TYPE: DNA
<213> ORGANISM: Homo sapiens

<400> SEQUENCE: 893
tcttccaact tggaagggag aacgaagtca gtcaccaggc agactgggtc atctgctgaa      60
atcacttgcg atcttactgt aacaaatacc ttctacatcc                          100

<210> SEQ ID NO 894
<211> LENGTH: 100
<212> TYPE: DNA
<213> ORGANISM: Homo sapiens

<400> SEQUENCE: 894
agtattatac tcatacaccc aggaggtgga gctggatatt gagactgcaa aatctaattg      60
aaaatgattc tggggtctat tactgtgcca cctgggacag                          100

<210> SEQ ID NO 895
<211> LENGTH: 100
<212> TYPE: DNA
<213> ORGANISM: Homo sapiens

<400> SEQUENCE: 895
tcttccaact tggaagggag aacgaagtca gtcatcaggc agactgggtc atctgctgaa      60
```

```
atcacttgtg atcttgctga aggaagtacc ggctacatcc                         100
```

<210> SEQ ID NO 896
<211> LENGTH: 100
<212> TYPE: DNA
<213> ORGANISM: Homo sapiens

<400> SEQUENCE: 896

```
gtatgatact tatggaagca caaggaagaa cttgagaatg atactgcgaa atcttattga    60
aaatgactct ggagtctatt actgtgccac ctgggatggg                         100
```

<210> SEQ ID NO 897
<211> LENGTH: 100
<212> TYPE: DNA
<213> ORGANISM: Homo sapiens

<400> SEQUENCE: 897

```
tcttccaact tggaagggag aacgaagtca gtcatcaggc agactgggtc atctgctgaa    60
atcacttgtg atcttgctga aggaagtacc ggctacatcc                         100
```

<210> SEQ ID NO 898
<211> LENGTH: 100
<212> TYPE: DNA
<213> ORGANISM: Homo sapiens

<400> SEQUENCE: 898

```
gtatgatact tacggaagca caaggaagaa cttgagaatg atactgcgaa atcttattga    60
aaatgactct ggagtctatt actgtgccac ctgggatggg                         100
```

<210> SEQ ID NO 899
<211> LENGTH: 100
<212> TYPE: DNA
<213> ORGANISM: Homo sapiens

<400> SEQUENCE: 899

```
tcttccaact tggaagggggg aacgaagtca gtcacgaggc cgactaggtc atctgctgaa   60
atcacttgtg accttactgt aataaatgcc ttctacatcc                         100
```

<210> SEQ ID NO 900
<211> LENGTH: 100
<212> TYPE: DNA
<213> ORGANISM: Homo sapiens

<400> SEQUENCE: 900

```
gtattatact catacaccca ggaggtggag ctggatattg atactacgaa atctaattga    60
aaatgattct ggggtctatt actgtgccac ctgggacagg                         100
```

<210> SEQ ID NO 901
<211> LENGTH: 100
<212> TYPE: DNA
<213> ORGANISM: Homo sapiens

<400> SEQUENCE: 901

```
tcttccaact tggaagggag aatgaagtca gtcaccaggc cgactgggtc atctgctgaa    60
atcacttgtg accttactgt aataaatgcc gtctacatcc                         100
```

<210> SEQ ID NO 902
<211> LENGTH: 100
<212> TYPE: DNA
<213> ORGANISM: Homo sapiens

<400> SEQUENCE: 902
gtattatact catacaccga ggaggtggag ctggaatttg agactgcaaa atctaattga    60
aaatgattct ggggtctatt actgtgccac ctggggcagg                         100

<210> SEQ ID NO 903
<211> LENGTH: 100
<212> TYPE: DNA
<213> ORGANISM: Homo sapiens

<400> SEQUENCE: 903
tcttccaact tggaagggag aatgaagtca gtcaccaggc cgactgggtc atctgctgaa    60
atcacttgtg accttactgt aataaatgcc gtctacatcc                         100

<210> SEQ ID NO 904
<211> LENGTH: 100
<212> TYPE: DNA
<213> ORGANISM: Homo sapiens

<400> SEQUENCE: 904
gtattatact catacaccga ggaggtggag ctggaatttg agactgcaaa atctaattga    60
aaatgattct ggggtctatt actgtgccac ctggggcagg                         100

<210> SEQ ID NO 905
<211> LENGTH: 100
<212> TYPE: DNA
<213> ORGANISM: Homo sapiens

<400> SEQUENCE: 905
tctactaact tggaagcgaa aataaagtca ggcaccaggc agatggggtc atctgctgta    60
atcacctgtg atcttcctgt agaaaatgcc ttctacatcc                         100

<210> SEQ ID NO 906
<211> LENGTH: 100
<212> TYPE: DNA
<213> ORGANISM: Homo sapiens

<400> SEQUENCE: 906
gcatgatact tatggaagta gaaggataag ctggaaattt atacctccaa aactaaatga    60
aaatgcctct ggggtctatt actgtgccac ctaggacagg                         100

<210> SEQ ID NO 907
<211> LENGTH: 100
<212> TYPE: DNA
<213> ORGANISM: Homo sapiens

<400> SEQUENCE: 907
tctactaact tggaagcgaa aataaagtca ggcaccaggc agatggggtc atctgctgta    60
atcacctgtg atcttcctgt agaaaatgcc ttctacatcc                         100

<210> SEQ ID NO 908
<211> LENGTH: 100
<212> TYPE: DNA
<213> ORGANISM: Homo sapiens

<400> SEQUENCE: 908
gcatgatact tatggaagta gaaggataag ctggaaattt atacctccaa aactaaatga    60
aaatgcctct ggggtctatt actgtgccac ctaggacagg                         100

```
<210> SEQ ID NO 909
<211> LENGTH: 100
<212> TYPE: DNA
<213> ORGANISM: Homo sapiens

<400> SEQUENCE: 909
tcttccaact tgcaagggag aaggaagtca gtcaccaggc cagctgggtc atctgctgta      60
atcacttgtg atcttactgt aataaatacc ttctacatcc                          100

<210> SEQ ID NO 910
<211> LENGTH: 100
<212> TYPE: DNA
<213> ORGANISM: Homo sapiens

<400> SEQUENCE: 910
agtattttac ttatgcaagc atgaggagga gctggaaatt gatactgcaa aatctaattg      60
aaaatgattc tggatctatt actgtgccac ctgggacagg                          100

<210> SEQ ID NO 911
<211> LENGTH: 100
<212> TYPE: DNA
<213> ORGANISM: Homo sapiens

<400> SEQUENCE: 911
tcttccaact tggaagggag aacaaagtca gtcaccaggc caactgggtc atcagctgta      60
atcacttgtg atcttcctgt agaaaatgcc gtctacaccc                          100

<210> SEQ ID NO 912
<211> LENGTH: 100
<212> TYPE: DNA
<213> ORGANISM: Homo sapiens

<400> SEQUENCE: 912
gtatcatact tatgcaagca cagggaagag ccttaaattt atactggaaa atctaattga      60
acgtgactct ggggtctatt actgtgccac ctgggatagg                          100

<210> SEQ ID NO 913
<211> LENGTH: 100
<212> TYPE: DNA
<213> ORGANISM: Homo sapiens

<400> SEQUENCE: 913
gcaggtcacc tagagcaacc tcaaatttcc agtactaaaa cgctgtcaaa acagcccgc      60 ctggaatgtg tggtgtctgg aataacaatt tctgcaacat                          100

<210> SEQ ID NO 914
<211> LENGTH: 100
<212> TYPE: DNA
<213> ORGANISM: Homo sapiens

<400> SEQUENCE: 914
tgaggtggat aggatacctg aaacgtctac atccactctc accattcaca atgtagagaa      60
acaggacata gctacctact actgtgcctt gtgggaggtg                          100

<210> SEQ ID NO 915
<211> LENGTH: 100
<212> TYPE: DNA
<213> ORGANISM: Homo sapiens

<400> SEQUENCE: 915
```

```
gcaggtcacc tagagcaacc tcaaatttcc agtactaaaa cgctgtcaaa aacagcccgc    60
ctggaatgtg tggtgtctgg aataaaaatt tctgcaacat                         100
```

<210> SEQ ID NO 916
<211> LENGTH: 100
<212> TYPE: DNA
<213> ORGANISM: Homo sapiens

<400> SEQUENCE: 916

```
tgaggtggat aggatacctg aaacgtctac atccactctc accattcaca atgtagagaa    60
acaggacata gctacctact actgtgcctt gtgggaggtg                         100
```

<210> SEQ ID NO 917
<211> LENGTH: 100
<212> TYPE: DNA
<213> ORGANISM: Homo sapiens

<400> SEQUENCE: 917

```
ctcatcaggc cggagcagct ggcccatgtc ctggggcact agggaagctt ggtcatcctg    60
cagtgcgtgg tccgcaccag gatcagctac acccactggt                         100
```

<210> SEQ ID NO 918
<211> LENGTH: 100
<212> TYPE: DNA
<213> ORGANISM: Homo sapiens

<400> SEQUENCE: 918

```
agataaaatc atagccaagg atggcagcag ctctatcttg gcagtactga agttggagac    60
aggcatcgag ggcatgaact actgcacaac ctgggccctg                         100
```

<210> SEQ ID NO 919
<211> LENGTH: 100
<212> TYPE: DNA
<213> ORGANISM: Homo sapiens

<400> SEQUENCE: 919

```
tttaaagcaa taaaaatgt caactacatt tttgtcaaca gagcaacaga taaaagtgtc     60
taggtatctt gtgtggtgtc cactgaagac tttgtaaata                         100
```

<210> SEQ ID NO 920
<211> LENGTH: 100
<212> TYPE: DNA
<213> ORGANISM: Homo sapiens

<400> SEQUENCE: 920

```
cttgaggcaa gaacaaattt tcaaatgtct acttcagtct ttaccataaa cttcatagga    60
aaggaagatg aggccattta ctactgcact gcttaggacc                         100
```

<210> SEQ ID NO 921
<211> LENGTH: 100
<212> TYPE: DNA
<213> ORGANISM: Homo sapiens

<400> SEQUENCE: 921

```
aatagagaca cggggcatgg tatgaaagta ttacctccca gttgcaattt ggcaaaggaa    60
ccagagtttc cacttctccc cgtacgtctg cccatgccca                         100
```

<210> SEQ ID NO 922

```
<211> LENGTH: 100
<212> TYPE: DNA
<213> ORGANISM: Homo sapiens

<400> SEQUENCE: 922
gaggcatcaa acactgtgat actcacggga ggaggaaaca aactcacctt tgggacaggc    60
actcagctaa aagtggaact cagtaagtat gagattctat                         100

<210> SEQ ID NO 923
<211> LENGTH: 100
<212> TYPE: DNA
<213> ORGANISM: Homo sapiens

<400> SEQUENCE: 923
tatggggatt tgctatagtg tgaattcagg atacagcacc ctcacctttg ggaaggggac    60
tatgcttcta gtctctccag gtacatgtta accccatccc                         100

<210> SEQ ID NO 924
<211> LENGTH: 100
<212> TYPE: DNA
<213> ORGANISM: Homo sapiens

<400> SEQUENCE: 924
actgactaag aaacactgtg ggatggatag cagctataaa ttgatcttcg ggagtgggac    60
cagactgctg gtcaggcctg gtaagtaagg tgtcagagag                         100

<210> SEQ ID NO 925
<211> LENGTH: 100
<212> TYPE: DNA
<213> ORGANISM: Homo sapiens

<400> SEQUENCE: 925
aaggcaggca ttacagtgtg aattctgggg gttaccagaa agttaccttt ggaattggaa    60
caaagctcca agtcatccca agtgagtcca atttcctatg                         100

<210> SEQ ID NO 926
<211> LENGTH: 100
<212> TYPE: DNA
<213> ORGANISM: Homo sapiens

<400> SEQUENCE: 926
aaaggcaggc attacagtgt gaattctggg ggttaccaga agttaccttt ggaactgga     60 acaaagctcc aagtcatccc aagtgagtcc aatttcctat                         100

<210> SEQ ID NO 927
<211> LENGTH: 100
<212> TYPE: DNA
<213> ORGANISM: Homo sapiens

<400> SEQUENCE: 927
tttgtcaggc agcacagtgc tgtgatttat agcacattca tctttgggag tgggacaaga    60
ttatcagtaa aacctggtaa gtaggcaata tgtcactaaa                         100

<210> SEQ ID NO 928
<211> LENGTH: 100
<212> TYPE: DNA
<213> ORGANISM: Homo sapiens

<400> SEQUENCE: 928
cagggcctca tttcactgtg ccaaccaggc aggaactgct ctgatctttg ggaagggaac    60
```

```
caccttatca gtgagttcca gtaagtacct gataattatt                                    100

<210> SEQ ID NO 929
<211> LENGTH: 100
<212> TYPE: DNA
<213> ORGANISM: Homo sapiens

<400> SEQUENCE: 929
cagggcctca tttcactgtg ccaaccaggc aggaactgct ctgatctttg ggaagggaac              60
ccacctatca gtgagttcca gtaagtacct gataattatt                                   100

<210> SEQ ID NO 930
<211> LENGTH: 100
<212> TYPE: DNA
<213> ORGANISM: Homo sapiens

<400> SEQUENCE: 930
tggtacaata gatcactgtg ggttttcaga tggccagaag ctgctctttg caagggaac              60 catgttaaag gtggatctta gtaagtatta ttactaatga                                   100

<210> SEQ ID NO 931
<211> LENGTH: 100
<212> TYPE: DNA
<213> ORGANISM: Homo sapiens

<400> SEQUENCE: 931
cctgtggttt tgctgggcc ttaaatcatt gtgtgatcaa agctgcaggc aacaagctaa              60
cttttggagg aggaaccagg gtgctagtta aaccaagtga                                   100

<210> SEQ ID NO 932
<211> LENGTH: 100
<212> TYPE: DNA
<213> ORGANISM: Homo sapiens

<400> SEQUENCE: 932
aggggaccag cattgtgccg acagaggctc aaccctgggg aggctatact ttggaagagg              60
aactcagttg actgtctggc ctggtgagtg agtcgctttc                                   100

<210> SEQ ID NO 933
<211> LENGTH: 100
<212> TYPE: DNA
<213> ORGANISM: Homo sapiens

<400> SEQUENCE: 933
ttttgcagag gacagatgtg gctatcaaag attttacaat ttcaccttg gaaagggatc              60 caaacataat gtcactccaa gtaagtgagc agccttttgt                                   100

<210> SEQ ID NO 934
<211> LENGTH: 100
<212> TYPE: DNA
<213> ORGANISM: Homo sapiens

<400> SEQUENCE: 934
tggtgtcacc tacggtatga atactggagg aacaattgat aaactcacat ttgggaaagg              60
gacccatgta ttcattatat ctggtgagtc atcccaggtg                                   100

<210> SEQ ID NO 935
<211> LENGTH: 100
<212> TYPE: DNA
```

<213> ORGANISM: Homo sapiens

<400> SEQUENCE: 935

```
tgtaggcgac ctcgcactgt ggttctaacg actacaagct cagctttgga gccggaacca      60
cagtaactgt aagagcaagt aagtaagaaa gaaaagtcca                           100
```

<210> SEQ ID NO 936
<211> LENGTH: 100
<212> TYPE: DNA
<213> ORGANISM: Homo sapiens

<400> SEQUENCE: 936

```
tgtaatgcca ataaacatgg tgtacaactt caacaaattt tactttggat ctgggaccaa      60
actcaatgta aaccaagta agttatagtt gcctagaaga                            100
```

<210> SEQ ID NO 937
<211> LENGTH: 100
<212> TYPE: DNA
<213> ORGANISM: Homo sapiens

<400> SEQUENCE: 937

```
gttgagcaaa tcatagtgtt tcttctggtt ctgcaaggca actgaccttt ggatctggga      60
cacaattgac tgttttacct ggtaggctgc ctcaattaaa                           100
```

<210> SEQ ID NO 938
<211> LENGTH: 100
<212> TYPE: DNA
<213> ORGANISM: Homo sapiens

<400> SEQUENCE: 938

```
aggatatgta acacagtgtg atttataacc agggaggaaa gcttatcttc ggacagggaa      60
cggagttatc tgtgaaaccc agtaagtata aaattgtatc                           100
```

<210> SEQ ID NO 939
<211> LENGTH: 100
<212> TYPE: DNA
<213> ORGANISM: Homo sapiens

<400> SEQUENCE: 939

```
gactggatgt gttttgaca ggatatgtaa cacagtgtga tttataacca gggaggaaag       60
cttatcttcg gacagggaac ggagctatct gtgaaaccca                           100
```

<210> SEQ ID NO 940
<211> LENGTH: 100
<212> TYPE: DNA
<213> ORGANISM: Homo sapiens

<400> SEQUENCE: 940

```
gaggtgtttg tcacagtgtg acaactgaca gctgggggaa attcgagttt ggagcaggga      60
cccaggttgt ggtcacccca ggtaagccca ttcctggagc                           100
```

<210> SEQ ID NO 941
<211> LENGTH: 100
<212> TYPE: DNA
<213> ORGANISM: Homo sapiens

<400> SEQUENCE: 941

```
gaggtgtttg tcacagtgtg acaactgaca gctgggggaa attgcagttt ggagcaggga      60
cccaggttgt ggtcacccca ggtaagcccc attccctgga                           100
```

<210> SEQ ID NO 942
<211> LENGTH: 100
<212> TYPE: DNA
<213> ORGANISM: Homo sapiens

<400> SEQUENCE: 942
atgctgagat aatcactatg cagaaggaca aggcttctcc tttatctttg ggaagggac    60 aaggctgctt gtcaagccaa gtaagtgaca tataatttat                         100

<210> SEQ ID NO 943
<211> LENGTH: 100
<212> TYPE: DNA
<213> ORGANISM: Homo sapiens

<400> SEQUENCE: 943
ctgagcccag aaacactgtg gggataacta tggtcagaat tttgtctttg gtcccggaac    60
cagattgtcc gtgctgccct gtaagtacag ttaagtggag                         100

<210> SEQ ID NO 944
<211> LENGTH: 100
<212> TYPE: DNA
<213> ORGANISM: Homo sapiens

<400> SEQUENCE: 944
caatagcact aaagactgtg taacaccaat gcaggcaaat caacctttgg ggatgggact    60
acgctcactg tgaagccaag taagttgtgt tcttctttgc                         100

<210> SEQ ID NO 945
<211> LENGTH: 100
<212> TYPE: DNA
<213> ORGANISM: Homo sapiens

<400> SEQUENCE: 945
agaaaggaaa ctctgtgcat actctggggc tgggagttac caactcactt tcgggaaggg    60
gaccaaactc tcggtcatac caagtaagtt cttctttctg                         100

<210> SEQ ID NO 946
<211> LENGTH: 100
<212> TYPE: DNA
<213> ORGANISM: Homo sapiens

<400> SEQUENCE: 946
ttatggagga aatcactgtg ggaattcagg aaacacacct cttgtctttg gaaagggcac    60
aagactttct gtgattgcaa gtaagtgttt ctagccatcc                         100

<210> SEQ ID NO 947
<211> LENGTH: 100
<212> TYPE: DNA
<213> ORGANISM: Homo sapiens

<400> SEQUENCE: 947
aaagacctta cccacagtgg gggtacagca gtgcttccaa gataatcttt ggatcaggga    60
ccagactcag catccggcca agtaagtaga atgaagcagg                         100

<210> SEQ ID NO 948
<211> LENGTH: 100
<212> TYPE: DNA
<213> ORGANISM: Homo sapiens

```
<400> SEQUENCE: 948
gttatggtcc caatcacagt gtgaacagag atgacaagat catctttgga aaagggacac    60
gacttcatat tctccccagt aagtgctgtt tatgtgattt                         100

<210> SEQ ID NO 949
<211> LENGTH: 100
<212> TYPE: DNA
<213> ORGANISM: Homo sapiens

<400> SEQUENCE: 949
agtaaaggca ggaagtgctg tggaataaca atgccagact catgtttgga gatggaactc    60
agctggtggt gaagcccagt aagtggccat gttttattga                        100

<210> SEQ ID NO 950
<211> LENGTH: 100
<212> TYPE: DNA
<213> ORGANISM: Homo sapiens

<400> SEQUENCE: 950
ggctctgaag gactgtgtga attatggcgg tgctacaaac aagctcatct ttggaactgg    60
cactctgctt gctgtccagc caagtacgta agtagtggca                        100

<210> SEQ ID NO 951
<211> LENGTH: 100
<212> TYPE: DNA
<213> ORGANISM: Homo sapiens

<400> SEQUENCE: 951
gtgattcagc cacctacctc tgtgccgatg gtggtgctac aaacaagctc atctttggaa    60
ctggcactct gcttgctgtc cagccaaata tccagaaccc                        100

<210> SEQ ID NO 952
<211> LENGTH: 100
<212> TYPE: DNA
<213> ORGANISM: Homo sapiens

<400> SEQUENCE: 952
gttaaggttt ttgtgtctgt gtggatagca actatcagtt aatctggggc gctgggacca    60
agctaattat aaagccaggt aagtctcaga gatgtgactg                        100

<210> SEQ ID NO 953
<211> LENGTH: 89
<212> TYPE: DNA
<213> ORGANISM: Homo sapiens

<400> SEQUENCE: 953 aggttttgt agatctcagt atcactgtgt cttataacac cgacaagctc atctttggga    60
ctgggaccag attacaagtc tttccaagt                                     89

<210> SEQ ID NO 954
<211> LENGTH: 100
<212> TYPE: DNA
<213> ORGANISM: Homo sapiens

<400> SEQUENCE: 954
taaaagaatg agccattgtg gataggcttt gggaatgtgc tgcattgcgg gtccggcact    60
caagtgattg ttttaccacg taagtatatc ttttctcatt                        100
```

```
<210> SEQ ID NO 955
<211> LENGTH: 100
<212> TYPE: DNA
<213> ORGANISM: Homo sapiens

<400> SEQUENCE: 955
tactgggcag aaacactgtg tcaaactggg gcaaacaacc tcttctttgg gactggaacg    60
agactcaccg ttattccctg taagtcctta cctcttgaca                         100

<210> SEQ ID NO 956
<211> LENGTH: 100
<212> TYPE: DNA
<213> ORGANISM: Homo sapiens

<400> SEQUENCE: 956
aaagtacagc attagagtgt ggctctggca acacaggcaa actaatcttt gggcaaggga    60
caactttaca agtaaaacca ggtaggtctg gatgtttcca                         100

<210> SEQ ID NO 957
<211> LENGTH: 100
<212> TYPE: DNA
<213> ORGANISM: Homo sapiens

<400> SEQUENCE: 957
ctcagcggtg tacttctgtg ctcttcatgg ctctagcaac acaggcaaac taatctttgg    60
gcaagggaca actttacaag taaaaccaga tatccagaac                         100

<210> SEQ ID NO 958
<211> LENGTH: 100
<212> TYPE: DNA
<213> ORGANISM: Homo sapiens

<400> SEQUENCE: 958
aaagctttct atgactgtgt aatgctggca acaaccgtaa gctgatttgg ggattgggaa    60
caagcctggc agtaaatccg agtgagtctt cgtgttaact                         100

<210> SEQ ID NO 959
<211> LENGTH: 100
<212> TYPE: DNA
<213> ORGANISM: Homo sapiens

<400> SEQUENCE: 959
cagccgaaga tcactgtgtg aataataatg caggcaacat gctcaccttt ggaggggggaa   60 caaggttaat ggtcaaaccc cgtgagtatc tctgctgaat                         100

<210> SEQ ID NO 960
<211> LENGTH: 100
<212> TYPE: DNA
<213> ORGANISM: Homo sapiens

<400> SEQUENCE: 960
aagcaccatc tgattgtgtg ttttctggtg gctacaataa gctgattttt ggagcaggga    60
ccaggctggc tgtacaccca tgtgagtatg accctgcaag                         100

<210> SEQ ID NO 961
<211> LENGTH: 97
<212> TYPE: DNA
<213> ORGANISM: Homo sapiens

<400> SEQUENCE: 961
```

```
tatgttggtt tatgtagaga cacataacac tgtgactacc tcaggaacct acaaatacat    60
ctttggaaca ggcaccaggc tgaaggtttt agcaagt                            97

<210> SEQ ID NO 962
<211> LENGTH: 100
<212> TYPE: DNA
<213> ORGANISM: Homo sapiens

<400> SEQUENCE: 962
ttagggagaa cgcactgtgg aactcaaatt ccgggtatgc actcaacttc ggcaaaggca    60
cctcgctgtt ggtcacaccc cgtgagtttt tgtggtttac                         100

<210> SEQ ID NO 963
<211> LENGTH: 100
<212> TYPE: DNA
<213> ORGANISM: Homo sapiens

<400> SEQUENCE: 963
agccccatag gactgtgtga attatggagg aagccaagga atctcatct ttggaaaagg     60 cactaaactc tctgttaaac caagtaagtg ttggggattc                         100

<210> SEQ ID NO 964
<211> LENGTH: 100
<212> TYPE: DNA
<213> ORGANISM: Homo sapiens

<400> SEQUENCE: 964
ttgttagagc atgtattact gtgacaataa caatgacatg cgctttggag cagggaccag    60
actgacagta aaccaagta agttggggga atgggtcaat                          100

<210> SEQ ID NO 965
<211> LENGTH: 94
<212> TYPE: DNA
<213> ORGANISM: Homo sapiens

<400> SEQUENCE: 965
aggtttctgt tatgaagcat ctcacagtgt aaataccggc actgccagta aactcacctt    60
tgggactgga acaagacttc aggtcacgct cggt                               94

<210> SEQ ID NO 966
<211> LENGTH: 100
<212> TYPE: DNA
<213> ORGANISM: Homo sapiens

<400> SEQUENCE: 966
agggttggcc cagagtgtgt attcaggagg aggtgctgac ggactcacct ttggcaaagg    60
gactcatcta atcatccagc cctgtaagtg cttttgcctg                         100

<210> SEQ ID NO 967
<211> LENGTH: 100
<212> TYPE: DNA
<213> ORGANISM: Homo sapiens

<400> SEQUENCE: 967
aagctgctga cagccgtgag aagaaaagca gcggagacaa gctgactttt gggaccggga    60
ctcgtttagc agttaggccc agtaagtctg agcagaaagt                         100

<210> SEQ ID NO 968
<211> LENGTH: 100
```

<212> TYPE: DNA
<213> ORGANISM: Homo sapiens

<400> SEQUENCE: 968
gtagaggagt ttgacgctgt gtggaatatg gaaacaaact ggtctttggc gcaggaacca    60
ttctgagagt caagtcctgt gagtatamaa cacactcaag                          100

<210> SEQ ID NO 969
<211> LENGTH: 100
<212> TYPE: DNA
<213> ORGANISM: Homo sapiens

<400> SEQUENCE: 969
gtgtactatt gcatctcggc cctggaatat ggaaacaagc tggtctttgg cgcaggaacc    60
attctgagag tcaagtccta tatccagaac cctgaccctg                          100

<210> SEQ ID NO 970
<211> LENGTH: 100
<212> TYPE: DNA
<213> ORGANISM: Homo sapiens

<400> SEQUENCE: 970
atgacttaga acactgtgta tctaactttg gaaatgagaa attaaccttt gggactggaa    60
caagactcac catcataccc agtaagttct tcatccttgg                          100

<210> SEQ ID NO 971
<211> LENGTH: 100
<212> TYPE: DNA
<213> ORGANISM: Homo sapiens

<400> SEQUENCE: 971
tgttgagctt cctatcacag tggaacaccg gtaaccagtt ctattttggg acagggacaa    60
gtttgacggt cattccaagt aagtcaaaga aaattttcca                          100

<210> SEQ ID NO 972
<211> LENGTH: 100
<212> TYPE: DNA
<213> ORGANISM: Homo sapiens

<400> SEQUENCE: 972
tactgtgatg taccagggtg tggacacggg caggagagca cttacttttg ggagtggaac    60
aagactccaa gtgcaaccaa gtaagtaccc aaacttaggc                          100

<210> SEQ ID NO 973
<211> LENGTH: 100
<212> TYPE: DNA
<213> ORGANISM: Homo sapiens

<400> SEQUENCE: 973
taaaggtttg gatggctgtg tgaaaacctc ctacgacaag gtgatatttg ggccagggac    60
aagcttatca gtcattccaa gtaagtgtcc ctggggtgct                          100

<210> SEQ ID NO 974
<211> LENGTH: 100
<212> TYPE: DNA
<213> ORGANISM: Homo sapiens

<400> SEQUENCE: 974
aaactccctg aagcagggag atgcgtgaca gctatgagaa gctgatattt ggaaaggaga    60

| | |
|---|---|
| catgactaac tgtgaagcca agcaagctgg aaagacctaa | 100 |

<210> SEQ ID NO 975
<211> LENGTH: 100
<212> TYPE: DNA
<213> ORGANISM: Homo sapiens

<400> SEQUENCE: 975

| | |
|---|---|
| gcctccagtg cagtgctaat gctggtggta ctagctatgg aaagctgaca tttggacaag | 60 |
| ggaccatctt gactgtccat ccaagtaagt gtaacaagac | 100 |

<210> SEQ ID NO 976
<211> LENGTH: 100
<212> TYPE: DNA
<213> ORGANISM: Homo sapiens

<400> SEQUENCE: 976

| | |
|---|---|
| agccttctgt ggctgtgaga atagtggagg tagcaactat aaactgacat ttggaaaagg | 60 |
| aactctctta accgtgaatc caagtaagtt tgaagggagt | 100 |

<210> SEQ ID NO 977
<211> LENGTH: 100
<212> TYPE: DNA
<213> ORGANISM: Homo sapiens

<400> SEQUENCE: 977

| | |
|---|---|
| taaagcctcg tgctgtggtg taattcaggg agcccagaag ctggtatttg gccaaggaac | 60 |
| caggctgact atcaacccaa gtaagtatga cagggtgaag | 100 |

<210> SEQ ID NO 978
<211> LENGTH: 100
<212> TYPE: DNA
<213> ORGANISM: Homo sapiens

<400> SEQUENCE: 978

| | |
|---|---|
| gaggatggat ccctgttagt gacaagtgct ggtaatgctc ctgttgggga aaggggatga | 60 |
| gtacaaaaat aaatccaagt aagtgtggag ggacaagaag | 100 |

<210> SEQ ID NO 979
<211> LENGTH: 100
<212> TYPE: DNA
<213> ORGANISM: Homo sapiens

<400> SEQUENCE: 979

| | |
|---|---|
| agatcctcgt gtcattgtgt tatactggag ccaatagtaa gctgacattt ggaaaaggaa | 60 |
| taactctgag tgttagacca ggtatgtttt aatgaatgtt | 100 |

<210> SEQ ID NO 980
<211> LENGTH: 100
<212> TYPE: DNA
<213> ORGANISM: Homo sapiens

<400> SEQUENCE: 980

| | |
|---|---|
| aagcagtctg tgggggtgta actcaggcg gatctgaaaa gctggtcttt ggaaagggaa | 60 |
| cgaaactgac agtaaaccca tgtaagtctg aataatgctt | 100 |

<210> SEQ ID NO 981
<211> LENGTH: 100
<212> TYPE: DNA
<213> ORGANISM: Homo sapiens

<400> SEQUENCE: 981
aagcccctca gcacagtgtt taagaaacca gtggctctag gttgaccttt ggggaaggaa        60
cacagctcac agtgaatcct ggtaagtgga ggggagcatt                              100

<210> SEQ ID NO 982
<211> LENGTH: 100
<212> TYPE: DNA
<213> ORGANISM: Homo sapiens

<400> SEQUENCE: 982
atgtaaaggc agcagctcct gtgggaagga aggaaacagg aaatttacat ttggaatggg        60
gacgcaagtg agagtgaagc tatctttaaa ccaaaggtgt                              100

<210> SEQ ID NO 983
<211> LENGTH: 98
<212> TYPE: DNA
<213> ORGANISM: Homo sapiens

<400> SEQUENCE: 983
caggttttat caaaggctgt cctcactgtg tgcatcagga ggaagctaca tacctacatt        60
tggaagagga accagcctta ttgttcatcc gtgtaagt                                98

<210> SEQ ID NO 984
<211> LENGTH: 100
<212> TYPE: DNA
<213> ORGANISM: Homo sapiens

<400> SEQUENCE: 984
gtaaagggcc tgggcactat gtgaagatca cctagatgct caactttggg aaggggactg        60
agttaattgt gagcctgggt gagtacctca actccagagg                              100

<210> SEQ ID NO 985
<211> LENGTH: 100
<212> TYPE: DNA
<213> ORGANISM: Homo sapiens

<400> SEQUENCE: 985
taaaggtgcc cactcctgtg ggtaccgggt taataggaaa ctgacatttg gagccaacac        60
tagaggaatc atgaaactca gcaagtaata tttggcagaa                              100

<210> SEQ ID NO 986
<211> LENGTH: 100
<212> TYPE: DNA
<213> ORGANISM: Homo sapiens

<400> SEQUENCE: 986
tgtaatacac ttacacagtg tgactatggg aacaacagac tcgcttttgg gaaggggaac        60
caagtggtgg tcataccaag taagtgagct gggatcctcc                              100

<210> SEQ ID NO 987
<211> LENGTH: 100
<212> TYPE: DNA
<213> ORGANISM: Homo sapiens

<400> SEQUENCE: 987
tacagagtta tgtcagagtg tgaacacagg ctttcagaaa cttgtatttg gaactggcac        60
ccgacttctg gtcagtccaa gtaagtcaaa tctgcagaaa                              100

<210> SEQ ID NO 988
<211> LENGTH: 100
<212> TYPE: DNA
<213> ORGANISM: Homo sapiens

<400> SEQUENCE: 988
cgcagtgcaa atcactgtgg gaaatactgg aggcttcaaa actatctttg gagcaggaac    60
aagactattt gttaaagcaa gtaagttcca tgaaataacc                         100

<210> SEQ ID NO 989
<211> LENGTH: 100
<212> TYPE: DNA
<213> ORGANISM: Homo sapiens

<400> SEQUENCE: 989
ttttcacctt gacccctgtc actgtgtgaa cactgaagct ttctttggac aaggcaccag    60
actcacagtt gtaggtaaga catttttcag gttcttttgc                         100

<210> SEQ ID NO 990
<211> LENGTH: 100
<212> TYPE: DNA
<213> ORGANISM: Homo sapiens

<400> SEQUENCE: 990
ttttagagtg gctatattct tatgtgctaa ctatggctac accttcggtt cggggaccag    60
gttaaccgtt gtaggtaagg ctgggggtct ctaggagggg                         100

<210> SEQ ID NO 991
<211> LENGTH: 100
<212> TYPE: DNA
<213> ORGANISM: Homo sapiens

<400> SEQUENCE: 991
tttgaagtgg ccctgggagg ctgtgctctg gaaacaccat atattttgga gagggaagtt    60
ggctcactgt tgtaggtgag taagtcaagg ctggacagct                         100

<210> SEQ ID NO 992
<211> LENGTH: 100
<212> TYPE: DNA
<213> ORGANISM: Homo sapiens

<400> SEQUENCE: 992
ttccttccag tctttaatgt tgtgcaacta atgaaaaact gttttttggc agtggaaccc    60
agctctctgt cttgggtatg taaaagactt ctttcgggat                         100

<210> SEQ ID NO 993
<211> LENGTH: 100
<212> TYPE: DNA
<213> ORGANISM: Homo sapiens

<400> SEQUENCE: 993
tttgccacac tcatgatgca ctgtgtagca atcagcccca gcattttggt gatgggactc    60
gactctccat cctaggtaag ttggcagaat cagggtggta                         100

<210> SEQ ID NO 994
<211> LENGTH: 100
<212> TYPE: DNA
<213> ORGANISM: Homo sapiens

<400> SEQUENCE: 994

```
ttatctaagc ctctgcagct gtgctcctat aattcacccc tccactttgg gaatgggacc      60
aggctcactg tgacaggtat gggggctcca ctcttgactc                           100

<210> SEQ ID NO 995
<211> LENGTH: 100
<212> TYPE: DNA
<213> ORGANISM: Homo sapiens

<400> SEQUENCE: 995
ttatctaagc ctctgcagct gtgctcctat aattcacccc tccactttgg gaacgggacc      60
aggctcactg tgacaggtat gggggctcca ctcttgactc                           100

<210> SEQ ID NO 996
<211> LENGTH: 100
<212> TYPE: DNA
<213> ORGANISM: Homo sapiens

<400> SEQUENCE: 996
ttctgggcag ccccttccca ctgtgctcct acaatgagca gttcttcggg ccagggacac      60
ggctcaccgt gctaggtaag aagggggctc caggtgggag                           100

<210> SEQ ID NO 997
<211> LENGTH: 100
<212> TYPE: DNA
<213> ORGANISM: Homo sapiens

<400> SEQUENCE: 997
tgcgccaggg tccccagggc tgtgcgaaca ccggggagct gttttttgga gaaggctcta      60
ggctgaccgt actgggtaag gaggcggctg gggctccgga                           100

<210> SEQ ID NO 998
<211> LENGTH: 100
<212> TYPE: DNA
<213> ORGANISM: Homo sapiens

<400> SEQUENCE: 998
agctgcccca ctctgagagg ggctgtgctg agaggcgctg ctgggcgtct gggcggagga      60
ctcctggttc tgggtgctgg gagagcgatg gggctctcag                           100

<210> SEQ ID NO 999
<211> LENGTH: 100
<212> TYPE: DNA
<213> ORGANISM: Homo sapiens

<400> SEQUENCE: 999
ttttgtcctg ggcctccagg ctgtgagcac agatacgcag tattttggcc caggcacccg      60
gctgacagtg ctcggtaagc gggggctccc gctgaagccc                           100

<210> SEQ ID NO 1000
<211> LENGTH: 100
<212> TYPE: DNA
<213> ORGANISM: Homo sapiens

<400> SEQUENCE: 1000
ttctgtgccg cgtctcgggg ctgtgagcca aaaacattca gtacttcggc gccgggaccc      60
ggctctcagt gctgggtaag ctggggccgc cgggggaccg                           100

<210> SEQ ID NO 1001
```

```
<211> LENGTH: 100
<212> TYPE: DNA
<213> ORGANISM: Homo sapiens

<400> SEQUENCE: 1001
tttttgtgcg gggctcgggg gccgtgacca agagacccag tacttcgggc caggcacgcg    60
gctcctggtg ctcggtgagc gcgggctgct ggggcgcggg                          100

<210> SEQ ID NO 1002
<211> LENGTH: 100
<212> TYPE: DNA
<213> ORGANISM: Homo sapiens

<400> SEQUENCE: 1002
ttgcggggag tccccgggct gtgctctggg gccaacgtcc tgactttcgg ggccggcagc    60
aggctgaccg tgctgggtga gttttcgcgg gaccacccgg                          100

<210> SEQ ID NO 1003
<211> LENGTH: 100
<212> TYPE: DNA
<213> ORGANISM: Homo sapiens

<400> SEQUENCE: 1003
tttgcatgcg ggggtgcacc tccgtgctcc tacgagcagt acttcgggcc gggcaccagg    60
ctcacggtca caggtgagat tcgggcgtct ccccaccttc                          100

<210> SEQ ID NO 1004
<211> LENGTH: 100
<212> TYPE: DNA
<213> ORGANISM: Homo sapiens

<400> SEQUENCE: 1004
tttgcatgcg gggatgcacc tccgtgctcc tacgagcagt acgtcgggcc gggcaccagg    60
ctcacggtca caggtgagat tcgggcgtct ccccaccttc                          100

<210> SEQ ID NO 1005
<211> LENGTH: 100
<212> TYPE: DNA
<213> ORGANISM: Homo sapiens

<400> SEQUENCE: 1005
ttttggaacg tcctcaagtg ctgtgacacc gataaactca tctttggaaa aggaacccgt    60
gtgactgtgg aaccaagtaa gtaactcatt atttatctga                          100

<210> SEQ ID NO 1006
<211> LENGTH: 100
<212> TYPE: DNA
<213> ORGANISM: Homo sapiens

<400> SEQUENCE: 1006
tttttcgtaa tgacgcctgt ggtagtgctt tgacagcaca actcttcttt ggaaagggaa    60
cacaactcat cgtggaacca ggtaagttat gcattttact                          100

<210> SEQ ID NO 1007
<211> LENGTH: 100
<212> TYPE: DNA
<213> ORGANISM: Homo sapiens

<400> SEQUENCE: 1007
tgaggcactg tcataatgtg ctcctgggac acccgacaga tgttttttcgg aactggcatc    60
```

```
aaactcttcg tggagccccg tgagttgatc ttttttcctat                   100
```

<210> SEQ ID NO 1008
<211> LENGTH: 76
<212> TYPE: DNA
<213> ORGANISM: Homo sapiens

<400> SEQUENCE: 1008

```
atgagacata caaaaaggta atgccgcccc agacccctga tctttggcaa aggaacctat    60
ctggaggtac aacaac                                                    76
```

<210> SEQ ID NO 1009
<211> LENGTH: 100
<212> TYPE: DNA
<213> ORGANISM: Homo sapiens

<400> SEQUENCE: 1009

```
ttttgatatg gactgaatca ctgtggaatt attataagaa actctttggc agtggaacaa    60
cactggttgt cacaggtaag tatcggaaga atacaacatt                         100
```

<210> SEQ ID NO 1010
<211> LENGTH: 71
<212> TYPE: DNA
<213> ORGANISM: Homo sapiens

<400> SEQUENCE: 1010

```
tactgtgcct tgtgggaggt gcttattata agaaactctt tggcagtgga acaacacttg    60
ttgtcacagg t                                                         71
```

<210> SEQ ID NO 1011
<211> LENGTH: 100
<212> TYPE: DNA
<213> ORGANISM: Homo sapiens

<400> SEQUENCE: 1011

```
ttttgatatg gactgaatca ctgtggaatt attataagaa actctttggc agtggaacaa    60
cacttgttgt cacaggtaag tatcggaaga atacaacatt                         100
```

<210> SEQ ID NO 1012
<211> LENGTH: 100
<212> TYPE: DNA
<213> ORGANISM: Homo sapiens

<400> SEQUENCE: 1012

```
ataaaggctt ctcaggtggt gggcaagagt tgggcaaaaa aatcaaggta tttggtcccg    60
gaacaaagct tatcattaca ggtaagtttt ctttaaattt                         100
```

<210> SEQ ID NO 1013
<211> LENGTH: 94
<212> TYPE: DNA
<213> ORGANISM: Homo sapiens

<400> SEQUENCE: 1013

```
gattttcta gaagcttaga ccggtgtgat accactggtt ggttcaagat atttgctgaa     60
gggactaagc tcatagtaac ttcacctggt aagt                                94
```

<210> SEQ ID NO 1014
<211> LENGTH: 94
<212> TYPE: DNA

<213> ORGANISM: Homo sapiens

<400> SEQUENCE: 1014

```
gatttttgta aagcttaga ccagtgtgat agtagtgatt ggatcaagac gtttgcaaaa    60
gggactaggc tcatagtaac ttcgcctggt aagt                              94
```

<210> SEQ ID NO 1015
<211> LENGTH: 100
<212> TYPE: DNA
<213> ORGANISM: Homo sapiens

<400> SEQUENCE: 1015

```
caggtcgttt ttcttcattc cttagtcgct ctgatagtta tggttacctc cttctacagg    60
agctccagat gaaagactct gcctcttact tctgcgctgt                          100
```

<210> SEQ ID NO 1016
<211> LENGTH: 100
<212> TYPE: DNA
<213> ORGANISM: Homo sapiens

<400> SEQUENCE: 1016

```
catctgggtt caacgggctg ttctggtacc agcaacatgc tggcgaagca cccacatttc    60
tgtcttacaa tgttctggat ggtctggagg agaaaggtcg                          100
```

<210> SEQ ID NO 1017
<211> LENGTH: 100
<212> TYPE: DNA
<213> ORGANISM: Homo sapiens

<400> SEQUENCE: 1017

```
acagcacacg tcaatagagc cagccagtat atttccctgc tcatcagaga ctccaagctc    60
agtgattcag ccacctacct ctgtgtggtg aacattcgcc                          100
```

<210> SEQ ID NO 1018
<211> LENGTH: 100
<212> TYPE: DNA
<213> ORGANISM: Homo sapiens

<400> SEQUENCE: 1018

```
gtttacagca cagctcaata aagccagcca gtatgtttct ctgctcatca gagactccca    60
gcccagtgat tcagccacct acctctgtgc cgtgtaccac                          100
```

<210> SEQ ID NO 1019
<211> LENGTH: 100
<212> TYPE: DNA
<213> ORGANISM: Homo sapiens

<400> SEQUENCE: 1019

```
aaggtttaca gcacagctca ataaagccag ccagtatgtt tctctgctca tcagagactc    60
ccagcccagt gattcagcca cctacctctg tgccgtgaac                          100
```

<210> SEQ ID NO 1020
<211> LENGTH: 100
<212> TYPE: DNA
<213> ORGANISM: Homo sapiens

<400> SEQUENCE: 1020

```
aggtttacag cacaggtcga taaatccagc aagtatatct ccttgttcat cagagactca    60
cagcccagtg attcagccac ctacctctgt gcaatgagcg                          100
```

<210> SEQ ID NO 1021
<211> LENGTH: 100
<212> TYPE: DNA
<213> ORGANISM: Homo sapiens

<400> SEQUENCE: 1021
tgttacattg aacaagacag ccaaacattt ctccctgcac atcacagaga cccaacctga      60
agactcggct gtctacttct gtgcagcaag taggaaggac                          100

<210> SEQ ID NO 1022
<211> LENGTH: 100
<212> TYPE: DNA
<213> ORGANISM: Homo sapiens

<400> SEQUENCE: 1022
gcttattata gacattcgtt caaatgtggg cgaaaagaaa gaccaacgaa ttgctgttac      60
attgaacaag acagccaaac atttctccct gcagatcaca                          100

<210> SEQ ID NO 1023
<211> LENGTH: 100
<212> TYPE: DNA
<213> ORGANISM: Homo sapiens

<400> SEQUENCE: 1023
caaagagtca ccgtttttatt gaataagaca gtgaaacatc tctctctgca aattgcagct     60
actcaacctg gagactcagc tgtctacttt tgtgcagaga                          100

<210> SEQ ID NO 1024
<211> LENGTH: 100
<212> TYPE: DNA
<213> ORGANISM: Homo sapiens

<400> SEQUENCE: 1024
aggtcgctac tcattgaatt tccagaaggc aagaaaatcc gccaaccttg tcatctccgc      60
ttcacaactg ggggactcag caatgtattt ctgtgcaatg                          100

<210> SEQ ID NO 1025
<211> LENGTH: 100
<212> TYPE: DNA
<213> ORGANISM: Homo sapiens

<400> SEQUENCE: 1025
gcaacagaag gtcgctactc attgaatttc cagaaggcaa gaaaatccgc caaccttgtc      60
atctccgctt cacaactggg ggactcagca atgtacttct                          100

<210> SEQ ID NO 1026
<211> LENGTH: 100
<212> TYPE: DNA
<213> ORGANISM: Homo sapiens

<400> SEQUENCE: 1026
gggacgatac aacatgacct atgaacggtt ctcttcatcg ctgctcatcc tccaggtgcg      60
ggaggcagat gctgctgttt actactgtgc tgtggcctgg                          100

<210> SEQ ID NO 1027
<211> LENGTH: 100
<212> TYPE: DNA
<213> ORGANISM: Homo sapiens

<400> SEQUENCE: 1027
aaaggagaaa gaaaggctaa aagccacatt aacaaagaag gaaagctttc tgcacatcac    60
agcccctaaa cctgaagact cagccactta tctctgtgct                          100

<210> SEQ ID NO 1028
<211> LENGTH: 100
<212> TYPE: DNA
<213> ORGANISM: Homo sapiens

<400> SEQUENCE: 1028
agaaaaggag aaagaaaggc taaaagccac attaacaaag aaggaaagct ttctgcacat    60
cacagcccct aaacctgaag actcagccac ttatctctgt                          100

<210> SEQ ID NO 1029
<211> LENGTH: 100
<212> TYPE: DNA
<213> ORGANISM: Homo sapiens

<400> SEQUENCE: 1029
aaaggagaaa gaaaggctaa aagccacatt aacaaagaag gaaagctttc tgcacatcac    60
agcccctaaa cctgaagact cagccactta tctctgtgct                          100

<210> SEQ ID NO 1030
<211> LENGTH: 100
<212> TYPE: DNA
<213> ORGANISM: Homo sapiens

<400> SEQUENCE: 1030
aagtggaaga cttaatgcct cgctggataa atcatcagga cgtagtactt tatacattgc    60
agcttctcag cctggtgact cagccaccta cctctgtgct                          100

<210> SEQ ID NO 1031
<211> LENGTH: 100
<212> TYPE: DNA
<213> ORGANISM: Homo sapiens

<400> SEQUENCE: 1031
agattcacaa tctccttcaa taaaagtgcc aagcagttct cattgcatat catggattcc    60
cagcctggag actcagccac ctacttctgt gcagcaagcg                          100

<210> SEQ ID NO 1032
<211> LENGTH: 100
<212> TYPE: DNA
<213> ORGANISM: Homo sapiens

<400> SEQUENCE: 1032
agattcacaa tctccttcaa taaaagtgcc aagcagttct cattgcatat catggattcc    60
cagcctggag actcagccac ctacttctgt gcagcaagca                          100

<210> SEQ ID NO 1033
<211> LENGTH: 100
<212> TYPE: DNA
<213> ORGANISM: Homo sapiens

<400> SEQUENCE: 1033
gaaagaagga agattcacaa tctccttcaa taaaagtgcc aagcagttct cattgcatat    60
catggattcc cagcctggag actcagccac ctacttctgt                          100

```
<210> SEQ ID NO 1034
<211> LENGTH: 100
<212> TYPE: DNA
<213> ORGANISM: Homo sapiens

<400> SEQUENCE: 1034
ggacgaataa gtgccactct aataccaag gagggttaca gctatttgta catcaaagga      60
tcccagcctg aagattcagc cacataccct tgtgccttta                          100

<210> SEQ ID NO 1035
<211> LENGTH: 100
<212> TYPE: DNA
<213> ORGANISM: Homo sapiens

<400> SEQUENCE: 1035
ctctgatcat cacagaagac agaaagtcca gcaccttgat cctgcccac gctacgctga      60 gagacactgc tgtgtactat tgcatcgtca gagattgggt                          100

<210> SEQ ID NO 1036
<211> LENGTH: 100
<212> TYPE: DNA
<213> ORGANISM: Homo sapiens

<400> SEQUENCE: 1036
caatgaaatg gcctctctga tcatcacaga agacagaaag tccagcacct tgatcctgcc      60
ccacgctacg ctgagagaca ctgctgtgta ctattgcatc                          100

<210> SEQ ID NO 1037
<211> LENGTH: 100
<212> TYPE: DNA
<213> ORGANISM: Homo sapiens

<400> SEQUENCE: 1037
ccctcccagg gtccagagta cgtgattcat ggtcttacaa gcaatgtgaa caacagaatg      60
gcctgtgtgg caatcgctga agacagaaag tccagtacct                          100

<210> SEQ ID NO 1038
<211> LENGTH: 100
<212> TYPE: DNA
<213> ORGANISM: Homo sapiens

<400> SEQUENCE: 1038
tgaagagact aacctttcag tttggtgatg caagaaagga cagttctctc cacatcactg      60
cggcccagcc tggtgataca ggccactacc tctgtgcagg                          100

<210> SEQ ID NO 1039
<211> LENGTH: 100
<212> TYPE: DNA
<213> ORGANISM: Homo sapiens

<400> SEQUENCE: 1039
gctgaagaga ctaacctttc agtttggtga tgcaagaaag gacagttctc tccacatcac      60
tgcagcccag actggtgata caggcctcta cctctgtgca                          100

<210> SEQ ID NO 1040
<211> LENGTH: 100
<212> TYPE: DNA
<213> ORGANISM: Homo sapiens

<400> SEQUENCE: 1040
```

```
aagattcact gttttcttaa acaaaagtgc caagcacctc tctctcgaca ttgtgccctc    60
ccagcctgga gactctgcag tgtacttctg tgcagcaagc                         100

<210> SEQ ID NO 1041
<211> LENGTH: 100
<212> TYPE: DNA
<213> ORGANISM: Homo sapiens

<400> SEQUENCE: 1041
agattcactg ttttcttaaa caaaagtgcc aagcacctct ctctgcacat tgtgccctcc    60
cagcctggag actctgcagt gtacttctgt gcagcaagcg                         100

<210> SEQ ID NO 1042
<211> LENGTH: 100
<212> TYPE: DNA
<213> ORGANISM: Homo sapiens

<400> SEQUENCE: 1042
ctttgaagct gaatttaaca agagccaaac ctccttccac ctgaagaaac catctgccct    60
tgtgagcgac tccgctttgt acttctgtgc tgtgagaccc                         100

<210> SEQ ID NO 1043
<211> LENGTH: 100
<212> TYPE: DNA
<213> ORGANISM: Homo sapiens

<400> SEQUENCE: 1043
tcgtgaaaaa atatctgctt catttaatga aaaaaagcag caaagctccc tgtaccttac    60
ggcctcccag ctcagttact caggaaccta cttctgcggg                         100

<210> SEQ ID NO 1044
<211> LENGTH: 100
<212> TYPE: DNA
<213> ORGANISM: Homo sapiens

<400> SEQUENCE: 1044
tcatgaaaaa atatctgctt catttaatga aaaaaagcgg caaagctccc tgtaccttac    60
ggcctcccag ctcagttact caggaaccta cttctgcggc                         100

<210> SEQ ID NO 1045
<211> LENGTH: 100
<212> TYPE: DNA
<213> ORGANISM: Homo sapiens

<400> SEQUENCE: 1045
tcctgatgat attactgaag ggtggagaac agaagcgtca tgaaaaaata tctgcttcat    60
ttaatgaaaa aaagcagcaa agctccctgt accttacggc                         100

<210> SEQ ID NO 1046
<211> LENGTH: 100
<212> TYPE: DNA
<213> ORGANISM: Homo sapiens

<400> SEQUENCE: 1046
aaatggaaga ctgactgctc agtttggtat aaccagaaag gacagcttcc tgaatatctc    60
agcatccata cctagtgatg taggcatcta cttctgtgct                         100

<210> SEQ ID NO 1047
<211> LENGTH: 100
```

```
<212> TYPE: DNA
<213> ORGANISM: Homo sapiens

<400> SEQUENCE: 1047
ggaagactaa gtagcatatt agataagaaa gaacttttca gcatcctgaa catcacagcc      60
acccagaccg gagactcggc cgtctacctc tgtgctgtgg                           100

<210> SEQ ID NO 1048
<211> LENGTH: 100
<212> TYPE: DNA
<213> ORGANISM: Homo sapiens

<400> SEQUENCE: 1048
gtcaggaaga ctaagtagca tattagataa gaaagaactt ttcagcatcc tgaacatcac      60
agccacccag accggagact cggccgtcta cctctgtgct                          100

<210> SEQ ID NO 1049
<211> LENGTH: 100
<212> TYPE: DNA
<213> ORGANISM: Homo sapiens

<400> SEQUENCE: 1049
tcaggaagac taagtagcat attagataag aaagaacttt tcagcatcct gaacatcaca      60
gccacccaga ccggagactc ggccgtctac ctctgtgctg                          100

<210> SEQ ID NO 1050
<211> LENGTH: 100
<212> TYPE: DNA
<213> ORGANISM: Homo sapiens

<400> SEQUENCE: 1050
gagaatcgtt tctctgtgaa cttccagaaa gcagccaaat ccttcagtct caagatctca      60
gactcacagc tgggggacac tgcgatgtat ttctgtgctt                          100

<210> SEQ ID NO 1051
<211> LENGTH: 100
<212> TYPE: DNA
<213> ORGANISM: Homo sapiens

<400> SEQUENCE: 1051
aatcgtttct ctgtgaactt ccagaaagca gccaaatcct tcagtctcaa gatctcagac      60
tcacagctgg gggacactgc gatgtatttc tgtgctttca                          100

<210> SEQ ID NO 1052
<211> LENGTH: 100
<212> TYPE: DNA
<213> ORGANISM: Homo sapiens

<400> SEQUENCE: 1052
ggagaatcgt ttctctgtga acttccagaa agcagccaaa tccttcagtc tcaagatctc      60
agactcacag ctgggggaca ctgcgatgta tttctgtgca                          100

<210> SEQ ID NO 1053
<211> LENGTH: 100
<212> TYPE: DNA
<213> ORGANISM: Homo sapiens

<400> SEQUENCE: 1053
gaaagaaaga ctgaaggtca cctttgatac caccccttaaa cagagtttgt ttcatatcac      60
```
agcctcccag cctgcagact cagctaccta cctctgtgct 100

<210> SEQ ID NO 1054
<211> LENGTH: 100
<212> TYPE: DNA
<213> ORGANISM: Homo sapiens

<400> SEQUENCE: 1054
gaaagaaaga ctgaaggtca cctttgatac caccccttaaa cagagtttgt ttcatatcac 60
agcctcccag cctgcagact cagctaccta cctctgtgct 100

<210> SEQ ID NO 1055
<211> LENGTH: 100
<212> TYPE: DNA
<213> ORGANISM: Homo sapiens

<400> SEQUENCE: 1055
gaaagaaaga ctgaaggtca cctttgatac caccccttaaa cagagtttgt ttcatgtcac 60
agcctcccag cctgcagact cagctaccta cctctgtgct 100

<210> SEQ ID NO 1056
<211> LENGTH: 100
<212> TYPE: DNA
<213> ORGANISM: Homo sapiens

<400> SEQUENCE: 1056
gaaagaaaga ctgaaggtca cctttgatac caccccttaaa cagagtttgt ttcatatcac 60
agcctcccag cctgcagact cagctaccta cctctgtgct 100

<210> SEQ ID NO 1057
<211> LENGTH: 100
<212> TYPE: DNA
<213> ORGANISM: Homo sapiens

<400> SEQUENCE: 1057
ccaggaagag gccctgtttt cttgctactc atacgtgaaa atgagaaaga aaaaaggaaa 60
gaaagactga aggtcacctt tgataccacc cttaaccaga 100

<210> SEQ ID NO 1058
<211> LENGTH: 100
<212> TYPE: DNA
<213> ORGANISM: Homo sapiens

<400> SEQUENCE: 1058
ttttcagggg atccactggt taaaggcatc aagggcgttg aggctgaatt tataaagagt 60
aaattctcct ttaatctgag gaaaccctct gtgcagtgga 100

<210> SEQ ID NO 1059
<211> LENGTH: 100
<212> TYPE: DNA
<213> ORGANISM: Homo sapiens

<400> SEQUENCE: 1059
tttaagaaga gtgaaacctc cttccacctg acgaaaccct cagcccatat gagcgacgcg 60
gctgagtact tctgtgttgt gacccgtcac gagctttcag 100

<210> SEQ ID NO 1060
<211> LENGTH: 100
<212> TYPE: DNA
<213> ORGANISM: Homo sapiens

<400> SEQUENCE: 1060
aggctttgag gctgaattta agaggagtca atcttccttc aacctgagga aaccctctgt    60
gcattggagt gatgctgctg agtacttctg tgctgtggtt                          100

<210> SEQ ID NO 1061
<211> LENGTH: 100
<212> TYPE: DNA
<213> ORGANISM: Homo sapiens

<400> SEQUENCE: 1061
tattaaaggc tttgaggctg aatttaagag gagtcaatct tccttcaatc tgaggaaacc    60
ctctgtgcat tggagtgatg cgtctgagta cttctgtgct                          100

<210> SEQ ID NO 1062
<211> LENGTH: 100
<212> TYPE: DNA
<213> ORGANISM: Homo sapiens

<400> SEQUENCE: 1062
gaatttaaga agagtgaaac ctccttccac ctgacaaaac cctcagccca tatgagcgac    60
gcggctgagt acttctgtgc tgtgagtgat ctcgaaccga                          100

<210> SEQ ID NO 1063
<211> LENGTH: 100
<212> TYPE: DNA
<213> ORGANISM: Homo sapiens

<400> SEQUENCE: 1063
catcaacggt tttgaggctg aatttaagaa gagtgaaacc tccttccacc tgacgaaacc    60
ctcagcccat atgagcgacg cggctgagta cttctgtgct                          100

<210> SEQ ID NO 1064
<211> LENGTH: 100
<212> TYPE: DNA
<213> ORGANISM: Homo sapiens

<400> SEQUENCE: 1064
aggcatcaac ggttttgagg ctgaatttaa gaagagtgaa acctccttcc acctgacgaa    60
accctcagcc catatgagcg acgcggctga gtacttctgt                          100

<210> SEQ ID NO 1065
<211> LENGTH: 100
<212> TYPE: DNA
<213> ORGANISM: Homo sapiens

<400> SEQUENCE: 1065
ggctgaattt aagaagagtg aaacctcctt ccacctgacg aaaccctcag cccatatgag    60
cgacgcggct gagtacttct gtgctgtgag tgagtctcca                          100

<210> SEQ ID NO 1066
<211> LENGTH: 100
<212> TYPE: DNA
<213> ORGANISM: Homo sapiens

<400> SEQUENCE: 1066
gaatttaaga agagtgaaac ctccttccac ctgacgaaac ccgcagccca tatgagcgac    60
gcggctgagt acttctgtgc tgtgagtgat ctcgaaccga                          100

<210> SEQ ID NO 1067
<211> LENGTH: 100
<212> TYPE: DNA
<213> ORGANISM: Homo sapiens

<400> SEQUENCE: 1067
acggttttga ggctgaattt aaaaagagtg aaacctcctt ccacctgacg aaaccctcag    60
cccatatgac cgacccggct gagtacttct gtgctgtgag                         100

<210> SEQ ID NO 1068
<211> LENGTH: 100
<212> TYPE: DNA
<213> ORGANISM: Homo sapiens

<400> SEQUENCE: 1068
caacaaaggt tttgaagcca cataccgtaa agaaaccact tctttccact tggagaaagg    60
ctcagttcaa gtgtcagact cagcggtgta cttctgtgct                         100

<210> SEQ ID NO 1069
<211> LENGTH: 100
<212> TYPE: DNA
<213> ORGANISM: Homo sapiens

<400> SEQUENCE: 1069
caacaaaggt tttgaagcca cataccgtaa ggaaaccact tctttccact tggagaaagg    60
ctcagttcaa gtgtcagact cagcggtgta cttctgtgct                         100

<210> SEQ ID NO 1070
<211> LENGTH: 100
<212> TYPE: DNA
<213> ORGANISM: Homo sapiens

<400> SEQUENCE: 1070
caacaaaggt tttgaagcca cataccgtaa ggaaaccact tctttccact tggagaaagg    60
ctcagttcaa gtgtcagact cagcggtgta cttctgtgct                         100

<210> SEQ ID NO 1071
<211> LENGTH: 100
<212> TYPE: DNA
<213> ORGANISM: Homo sapiens

<400> SEQUENCE: 1071
ctaacaaagg agaagtctca gatggctaca gtgtctctag atcaaacaca gaggacctcc    60
ccctcactct gtagtctgct gcctcctccc agacatctgt                         100

<210> SEQ ID NO 1072
<211> LENGTH: 100
<212> TYPE: DNA
<213> ORGANISM: Homo sapiens

<400> SEQUENCE: 1072
agataaagga gaagtccccg atggctacgt tgtctccaga tccaagacag agaatttccc    60
cctcactctg gagtcagcta cccgctccca gacatctgtg                         100

<210> SEQ ID NO 1073
<211> LENGTH: 100
<212> TYPE: DNA
<213> ORGANISM: Homo sapiens

<400> SEQUENCE: 1073

```
agaagtctca gatggctata gtgtctctag atcaaagaca gaggatttcc tcctcactct    60
ggagtccgct accagctccc agacatctgt gtacttctgt                         100

<210> SEQ ID NO 1074
<211> LENGTH: 100
<212> TYPE: DNA
<213> ORGANISM: Homo sapiens

<400> SEQUENCE: 1074
agaagtctca gatggctata gtgtctctag atcaaagaca gaggatttcc tcctcactct    60
ggagtccgct accagctccc agacatctgt gtacttctgt                         100

<210> SEQ ID NO 1075
<211> LENGTH: 100
<212> TYPE: DNA
<213> ORGANISM: Homo sapiens

<400> SEQUENCE: 1075
ggatcgattt tctgcagaga ggctcaaagg agtagactcc actctcaaga tccagcctgc    60
aaagcttgag aactcggccg tgtatctctg tgccagcagt                         100

<210> SEQ ID NO 1076
<211> LENGTH: 100
<212> TYPE: DNA
<213> ORGANISM: Homo sapiens

<400> SEQUENCE: 1076
ggatcgattt tctgcagaga ggctcaaagg agtagactcc actctcaaga tccaacctgc    60
aaagcttgag gactcggccg tgtatctctg tgccagcagc                         100

<210> SEQ ID NO 1077
<211> LENGTH: 100
<212> TYPE: DNA
<213> ORGANISM: Homo sapiens

<400> SEQUENCE: 1077
ggatcgattt tctgcagaga ggctcaaagg agtagactcc actctcaaga tccagcctgc    60
agagcttggg gactcggccg tgtatctctg tgccagcagc                         100

<210> SEQ ID NO 1078
<211> LENGTH: 100
<212> TYPE: DNA
<213> ORGANISM: Homo sapiens

<400> SEQUENCE: 1078
ggatcgattt tctgcagaga ggctcaaagg agtagactcc actctcaaga tccagccagc    60
agagcttggg gactcggcca tgtatctctg tgccagcagc                         100

<210> SEQ ID NO 1079
<211> LENGTH: 100
<212> TYPE: DNA
<213> ORGANISM: Homo sapiens

<400> SEQUENCE: 1079
tcgattctca gctaagatgc ctaatgcatc attctccact ctgaggatcc agccctcaga    60
acccagggac tcagctgtgt acttctgtgc cagcagttta                         100

<210> SEQ ID NO 1080
```

```
<211> LENGTH: 100
<212> TYPE: DNA
<213> ORGANISM: Homo sapiens

<400> SEQUENCE: 1080
tgatcgattc tcagctcaac agttcagtga ctatcattct gaactgaaca tgagctcctt      60
ggagctgggg gactcagccc tgtacttctg tgccagcagc                            100

<210> SEQ ID NO 1081
<211> LENGTH: 100
<212> TYPE: DNA
<213> ORGANISM: Homo sapiens

<400> SEQUENCE: 1081
caatcgattc ttagctgaaa ggactggagg gacgtattct actctgaagg tgcagcctgc      60
agaactggag gattctggag tttatttctg tgccagcagc                            100

<210> SEQ ID NO 1082
<211> LENGTH: 100
<212> TYPE: DNA
<213> ORGANISM: Homo sapiens

<400> SEQUENCE: 1082
tgataacttc caatccagga ggccgaacac ttctttctgc tttcttgaca tccgctcacc      60
aggcctgggg gacgcagcca tgtacctgtg tgccaccagc                            100

<210> SEQ ID NO 1083
<211> LENGTH: 100
<212> TYPE: DNA
<213> ORGANISM: Homo sapiens

<400> SEQUENCE: 1083
tgataacttc caatccagga ggccgaacac ttctttctgc tttctagaca tccgctcacc      60
aggcctgggg gacgcagcca tgtaccagtg tgccaccagc                            100

<210> SEQ ID NO 1084
<211> LENGTH: 100
<212> TYPE: DNA
<213> ORGANISM: Homo sapiens

<400> SEQUENCE: 1084
ggaaagattt tcagctaagt gcctcccaaa ttcaccctgt agccttgaga tccaggctac      60
gaagcttgag gattcagcag tgtatttttg tgccagcagc                            100

<210> SEQ ID NO 1085
<211> LENGTH: 100
<212> TYPE: DNA
<213> ORGANISM: Homo sapiens

<400> SEQUENCE: 1085
tgaagggtac agcgtctctc gggagaagaa ggaatccttt cctctcactg tgacatcggc      60
ccaaaagaac ccgacagctt tctatctctg tgccagtagc                            100

<210> SEQ ID NO 1086
<211> LENGTH: 100
<212> TYPE: DNA
<213> ORGANISM: Homo sapiens

<400> SEQUENCE: 1086
tgatcaattc tcagttgaaa ggcctgatgg atcaaatttc actctgaaga tccggtccac      60
```
aaagctggag gactcagcca tgtacttctg tgccagcagt              100

<210> SEQ ID NO 1087
<211> LENGTH: 100
<212> TYPE: DNA
<213> ORGANISM: Homo sapiens

<400> SEQUENCE: 1087
tcaattctca gttgagaggc ctgatggatc aaatttcact ctgaagatcc ggtccacaaa    60
gctggaggac tcagccatgt acttctgtgc cagcagtgaa                          100

<210> SEQ ID NO 1088
<211> LENGTH: 100
<212> TYPE: DNA
<213> ORGANISM: Homo sapiens

<400> SEQUENCE: 1088
gaaggacaag tttctcatca accatgcaag cctgaccttg tccactctga cagtgaccag    60
tgcccatcct gaagacagca gcttctacat ctgcagtgct                          100

<210> SEQ ID NO 1089
<211> LENGTH: 100
<212> TYPE: DNA
<213> ORGANISM: Homo sapiens

<400> SEQUENCE: 1089
ggacaagttt ctcatcaacc atgcaagcct gaccttgtcc actctgacag tgaccagtgc    60
ccatcctgaa gacagcagct ctacatctg cagtgctagt                           100

<210> SEQ ID NO 1090
<211> LENGTH: 100
<212> TYPE: DNA
<213> ORGANISM: Homo sapiens

<400> SEQUENCE: 1090
ggacaagttt ctcatcaacc atgcaagcct gaccttgtcc actctgacag tgaccagtgc    60
ccatcctgaa gacagcagct ctacatctg cagtgctaga                           100

<210> SEQ ID NO 1091
<211> LENGTH: 100
<212> TYPE: DNA
<213> ORGANISM: Homo sapiens

<400> SEQUENCE: 1091
gaaggacaag tttctcatca accatgcaag cctgaccttg tccactctga cagtgaccag    60
tgcccatcct gaagacagca gcttctacat ctgcagtgct                          100

<210> SEQ ID NO 1092
<211> LENGTH: 100
<212> TYPE: DNA
<213> ORGANISM: Homo sapiens

<400> SEQUENCE: 1092
ggacaagttt ctcatcaacc atgcaagcct gaccttgtcc actctgacag tgaccagtgc    60
ccatcctgaa gacagcagct ctacatctg cagtgctaga                           100

<210> SEQ ID NO 1093
<211> LENGTH: 100
<212> TYPE: DNA

<213> ORGANISM: Homo sapiens

<400> SEQUENCE: 1093
gaaggacaag tttcccatca accatccaaa cctgaccttc tccgctctga cagtgacctg    60
tgcccatcct gaagacagca gcttctacat ctgcagtgct                          100

<210> SEQ ID NO 1094
<211> LENGTH: 100
<212> TYPE: DNA
<213> ORGANISM: Homo sapiens

<400> SEQUENCE: 1094
gtttttgatt tcctttcaga atgaacaagt tcttcaagaa atggagatgc acaagaagcg    60
attctcatct caatgcccca agaacgcacc ctgcagcctg                          100

<210> SEQ ID NO 1095
<211> LENGTH: 100
<212> TYPE: DNA
<213> ORGANISM: Homo sapiens

<400> SEQUENCE: 1095
cagttgatct attgctcctt tgatgtcaaa atatataaac aaaagagaga tctctgatgg    60
atacagtgtc tcttgacagg aacaggctaa attctccctg                          100

<210> SEQ ID NO 1096
<211> LENGTH: 100
<212> TYPE: DNA
<213> ORGANISM: Homo sapiens

<400> SEQUENCE: 1096
gagttaattc cacagagaag ggagatcttt gctctgagtc aacagtctcc agaataagga    60
tagagcgttt tccctgacc ctggagtctg ccagcccctc                           100

<210> SEQ ID NO 1097
<211> LENGTH: 100
<212> TYPE: DNA
<213> ORGANISM: Homo sapiens

<400> SEQUENCE: 1097
tgacaagttt cccatcagcc gcccaaacct aacattctca agtctgactg tgagcaacat    60
gagccctgaa gacagcagca tatatctctg cagcgttgaa                          100

<210> SEQ ID NO 1098
<211> LENGTH: 100
<212> TYPE: DNA
<213> ORGANISM: Homo sapiens

<400> SEQUENCE: 1098
tgacaagttt cccatcagcc gcccaaacct aacattctca actctgactg tgagcaacat    60
gagccctgaa gacagcagca tatatctctg cagcgcgggc                          100

<210> SEQ ID NO 1099
<211> LENGTH: 100
<212> TYPE: DNA
<213> ORGANISM: Homo sapiens

<400> SEQUENCE: 1099
tccaaatcga ttctcaccta aatctccaga caaagctaaa ttaaatcttc acatcaattc    60
cctggagctt ggtgactctg ctgtgtattt ctgtgccagc                          100

<210> SEQ ID NO 1100
<211> LENGTH: 100
<212> TYPE: DNA
<213> ORGANISM: Homo sapiens

<400> SEQUENCE: 1100
tcgcttctca cctgactctc cagacaaagt tcatttaaat cttcacatca attccctgga    60
gcttggtgac tctgctgtgt atttctgtgc cagcagccaa                         100

<210> SEQ ID NO 1101
<211> LENGTH: 100
<212> TYPE: DNA
<213> ORGANISM: Homo sapiens

<400> SEQUENCE: 1101
agaatctctc agcctccaga ccccaggacc ggcagttcat cctgagttct aagaagctcc    60
tcctcagtga ctctggcttc tatctctgtg cctggagtgt                         100

<210> SEQ ID NO 1102
<211> LENGTH: 100
<212> TYPE: DNA
<213> ORGANISM: Homo sapiens

<400> SEQUENCE: 1102
ccagaatctc tcagcctcca gaccccagga ccggcagttc attctgagtt ctaagaagct    60
cctcctcagt gactctggct tctatctctg tgcctggagt                         100

<210> SEQ ID NO 1103
<211> LENGTH: 100
<212> TYPE: DNA
<213> ORGANISM: Homo sapiens

<400> SEQUENCE: 1103
ccagaatctc tcagcctcca gaccccagga ccggcagttc atcctgagtt ctaagaagct    60
ccttctcagt gactctggct tctatctctg tgcctgggga                         100

<210> SEQ ID NO 1104
<211> LENGTH: 100
<212> TYPE: DNA
<213> ORGANISM: Homo sapiens

<400> SEQUENCE: 1104
tcgcttctca cctgaatgcc ccaacagctc tctcttaaac cttcacctac acgccctgca    60
gccagaagac tcagccctgt atctctgcgc cagcagccaa                         100

<210> SEQ ID NO 1105
<211> LENGTH: 100
<212> TYPE: DNA
<213> ORGANISM: Homo sapiens

<400> SEQUENCE: 1105
aagtcgcttc tcacctgaat gccccaacag ctctcactta tgccttcacc tacacaccct    60
gcagccagaa gactcggccc tgtatctctg tgccagcacc                         100

<210> SEQ ID NO 1106
<211> LENGTH: 100
<212> TYPE: DNA
<213> ORGANISM: Homo sapiens

<400> SEQUENCE: 1106
aagtcgcttc tcacctgaat gccccaacag ctctcactta tcccttcacc tacacaccct    60
gcagccagaa gactcggccc tgtatctctg cgccagcagc    100

<210> SEQ ID NO 1107
<211> LENGTH: 100
<212> TYPE: DNA
<213> ORGANISM: Homo sapiens

<400> SEQUENCE: 1107
aagtcgcttc tcacctgaat gccccaacag ctctcactta ttccttcacc tacacaccct    60
gcagccagaa gactcggccc tgtatctctg cgccagcagc    100

<210> SEQ ID NO 1108
<211> LENGTH: 100
<212> TYPE: DNA
<213> ORGANISM: Homo sapiens

<400> SEQUENCE: 1108
aagtcgcttc tcacctgaat gccccaacag ctctcactta ttccttcacc tacacaccct    60
gcagccagaa gactcggccc tgtatctctg cgccagcagc    100

<210> SEQ ID NO 1109
<211> LENGTH: 100
<212> TYPE: DNA
<213> ORGANISM: Homo sapiens

<400> SEQUENCE: 1109
tcgattctca gggcgccagt tctctaactc tcgctctgag atgaatgtga gcaccttgga    60 gctggggac tcggcccttt atctttgcgc cagcgcttgc    100

<210> SEQ ID NO 1110
<211> LENGTH: 100
<212> TYPE: DNA
<213> ORGANISM: Homo sapiens

<400> SEQUENCE: 1110
tcctagattc tcaggtctcc agttccctaa ttataactct gagctgaatg tgaacgcctt    60
ggagctggac gactcggccc tgtatctctg tgccagcagc    100

<210> SEQ ID NO 1111
<211> LENGTH: 100
<212> TYPE: DNA
<213> ORGANISM: Homo sapiens

<400> SEQUENCE: 1111
tcctagattc tcaggtctcc agttccctaa ttatagctct gagctgaatg tgaacgcctt    60
ggagctggac gactcggccc tgtatctctg tgccagcagc    100

<210> SEQ ID NO 1112
<211> LENGTH: 100
<212> TYPE: DNA
<213> ORGANISM: Homo sapiens

<400> SEQUENCE: 1112
tcctagattc tcaggtctcc agttccctaa ttatagctct gagctgaatg tgaacgcctt    60
ggagctggac gactcggccc tgtatctctg tgccagcagc    100

```
<210> SEQ ID NO 1113
<211> LENGTH: 100
<212> TYPE: DNA
<213> ORGANISM: Homo sapiens

<400> SEQUENCE: 1113
tgatcgattc tcagctcgcc agttccctaa ctatagctct gagctgaatg tgaacgcctt      60
gttgctgggg gactcggccc tgtatctctg tgccagcagc                           100

<210> SEQ ID NO 1114
<211> LENGTH: 100
<212> TYPE: DNA
<213> ORGANISM: Homo sapiens

<400> SEQUENCE: 1114
tgatcgattc tcagctcgcc agttccctaa ctatagctct gagctgaatg tgaacgcctt      60
gttgctgggg gactcggccc tgtatctctg tgccagcagc                           100

<210> SEQ ID NO 1115
<211> LENGTH: 100
<212> TYPE: DNA
<213> ORGANISM: Homo sapiens

<400> SEQUENCE: 1115
tcctagattt tcaggtcgcc agttccctaa ttatagctct gagctgaatg tgaacgcctt      60
ggagctggag gactcggccc tgtatctctg tgccagcagc                           100

<210> SEQ ID NO 1116
<211> LENGTH: 100
<212> TYPE: DNA
<213> ORGANISM: Homo sapiens

<400> SEQUENCE: 1116
tggctacaat gtctccagat taaaaaaaca gaatttcctg ctggggttgg agtcggctgc      60
tccctcccaa acatctgtgt acttctgtgc cagcagccct                           100

<210> SEQ ID NO 1117
<211> LENGTH: 100
<212> TYPE: DNA
<213> ORGANISM: Homo sapiens

<400> SEQUENCE: 1117
gaatggctac aacgtctcca gatcaaccac agaggatttc ccgctcaggc tggagttggc      60
tgctccctcc cagacatctg tgtacttctg tgccagcagt                           100

<210> SEQ ID NO 1118
<211> LENGTH: 100
<212> TYPE: DNA
<213> ORGANISM: Homo sapiens

<400> SEQUENCE: 1118
tggctacaat gtctccagat caaccacaga ggatttcccg ctcaggctgg agttggctgc      60
tccctcccag acatctgtgt acttctgtgc cagcagtcga                           100

<210> SEQ ID NO 1119
<211> LENGTH: 100
<212> TYPE: DNA
<213> ORGANISM: Homo sapiens

<400> SEQUENCE: 1119
```

```
gaatggctac aacgtctcca gatcaaccac agaggatttc ccgctcaggc tggagttggc    60
tgctgcctcc cagacatctg tgtacttctg tgccagcagc                         100

<210> SEQ ID NO 1120
<211> LENGTH: 100
<212> TYPE: DNA
<213> ORGANISM: Homo sapiens

<400> SEQUENCE: 1120
gcttctctgc agagaggact ggggaatccg tctccactct gacgatccag cgcacacagc    60
aggaggactc ggccgtgtat ctctgtacca gcagcttagc                         100

<210> SEQ ID NO 1121
<211> LENGTH: 100
<212> TYPE: DNA
<213> ORGANISM: Homo sapiens

<400> SEQUENCE: 1121
tcgcttctct gcagagagga ctgggggatc cgtctccact ctgacgatcc agcgcacaca    60
gcaggaggac tcggccgtgt atctctgtgc cagcagctta                         100

<210> SEQ ID NO 1122
<211> LENGTH: 100
<212> TYPE: DNA
<213> ORGANISM: Homo sapiens

<400> SEQUENCE: 1122
cgatcggttc tttgcagtca ggcctgaggg atccgtctct actctgaaga tccagcgcac    60
agagcggggg gactctgccg tgtatctctg tgccagcagc                         100

<210> SEQ ID NO 1123
<211> LENGTH: 100
<212> TYPE: DNA
<213> ORGANISM: Homo sapiens

<400> SEQUENCE: 1123
cgatcggttc tttgcagtca ggcctgaggg atccgtctct actctgaaga tccagcgcac    60
agagcggggg gactcagccg tgtatctctg tgccagcagc                         100

<210> SEQ ID NO 1124
<211> LENGTH: 100
<212> TYPE: DNA
<213> ORGANISM: Homo sapiens

<400> SEQUENCE: 1124
aacgagacaa atcagggcgg cccagtggtc ggttctctgc agagaggcct gagagatcgt    60
ctccactccg aagatccagc gcacagagca ggggactca                         100

<210> SEQ ID NO 1125
<211> LENGTH: 100
<212> TYPE: DNA
<213> ORGANISM: Homo sapiens

<400> SEQUENCE: 1125
tgatcggttc tctgcagaga ggcctgaggg atccatctcc actctgacga tccagcgcac    60
agagcagcgg gactcggcca tgtatcgctg tgccagcagc                         100

<210> SEQ ID NO 1126
<211> LENGTH: 100
```

<212> TYPE: DNA
<213> ORGANISM: Homo sapiens

<400> SEQUENCE: 1126
tgatcggttc tctgcagaga ggcctgaggg atccatctcc actctgacga ttcagcgcac      60
agagcagcgg gactcagcca tgtatcgctg tgccagcagc                            100

<210> SEQ ID NO 1127
<211> LENGTH: 100
<212> TYPE: DNA
<213> ORGANISM: Homo sapiens

<400> SEQUENCE: 1127
tcgcttcttt gcagaaaggc ctgagggatc cgtctccact ctgaagatcc agcgcacaca      60
gcaggaggac tccgccgtgt atctctgtgc cagcagccga                            100

<210> SEQ ID NO 1128
<211> LENGTH: 100
<212> TYPE: DNA
<213> ORGANISM: Homo sapiens

<400> SEQUENCE: 1128
tcggttctct gcagagaggc ctaagggatc tttctccacc ttggagatcc agcgcacaga      60 gcaggggac tcggccatgt atctctgtgc cagcagctta                             100

<210> SEQ ID NO 1129
<211> LENGTH: 100
<212> TYPE: DNA
<213> ORGANISM: Homo sapiens

<400> SEQUENCE: 1129
tcggatctct gcagagaggc ctaagggatc tttctccacc ttggagatcc agcgcacaga      60 gcaggggac tcggccatgt atctctgtgc cagcagctct                             100

<210> SEQ ID NO 1130
<211> LENGTH: 100
<212> TYPE: DNA
<213> ORGANISM: Homo sapiens

<400> SEQUENCE: 1130
tcggttctct gcagagaggc ctaagggatc tctctccacc ttggagatcc agcgcacaga      60 gcaggggac tcggccatgt atctctgtgc cagcaccaaa                             100

<210> SEQ ID NO 1131
<211> LENGTH: 100
<212> TYPE: DNA
<213> ORGANISM: Homo sapiens

<400> SEQUENCE: 1131
tcggttctct gcagagaggc ctaagggatc tctttccacc ttggagatcc agcgcacaga      60 gcaggggac tcggccatgt atctctgtgc cagcacgttg                             100

<210> SEQ ID NO 1132
<211> LENGTH: 100
<212> TYPE: DNA
<213> ORGANISM: Homo sapiens

<400> SEQUENCE: 1132
gttctctgca gagaggccta agggatcttt ctccaccttg gagatccagc gcacagagga      60

```
ggggactcg gccatgtatc tctgtgccag cagcagcagt                          100
```

<210> SEQ ID NO 1133
<211> LENGTH: 100
<212> TYPE: DNA
<213> ORGANISM: Homo sapiens

<400> SEQUENCE: 1133

```
tgaacgattc tccgcacaac agttccctga cttgcactct gaactaaacc tgagctctct    60
ggagctgggg gactcagctt tgtatttctg tgccagcagc                         100
```

<210> SEQ ID NO 1134
<211> LENGTH: 100
<212> TYPE: DNA
<213> ORGANISM: Homo sapiens

<400> SEQUENCE: 1134

```
gaagtattat acttacgcaa gcacaaggaa caacttgaga ttgatactgc aaaatctaat    60
tgaaaatgac tctggggtct attactgtgc cacctgggac                         100
```

<210> SEQ ID NO 1135
<211> LENGTH: 100
<212> TYPE: DNA
<213> ORGANISM: Homo sapiens

<400> SEQUENCE: 1135

```
gaaggacaag tttctcatca accatgcaag cctgaccttg tccactctga cagtgaccag    60
tgcccatcct gaagacagca gcttctacat ctgcagtgct                         100
```

<210> SEQ ID NO 1136
<211> LENGTH: 100
<212> TYPE: DNA
<213> ORGANISM: Homo sapiens

<400> SEQUENCE: 1136

```
gcatgatact tatggaagta gaaggataag ctggaaattt atacctccaa aactaaatga    60
aaatgcctct ggggtctatt actgtgccac ctaggacagg                         100
```

<210> SEQ ID NO 1137
<211> LENGTH: 100
<212> TYPE: DNA
<213> ORGANISM: Homo sapiens

<400> SEQUENCE: 1137

```
gtatgatact tacggaagca caaggaagaa cttgagaatg atactgcgaa atcttattga    60
aaatgactct ggagtctatt actgtgccac ctgggatggg                         100
```

<210> SEQ ID NO 1138
<211> LENGTH: 100
<212> TYPE: DNA
<213> ORGANISM: Homo sapiens

<400> SEQUENCE: 1138

```
gtattatact catacaccga ggaggtggag ctggaatttg agactgcaaa atctaattga    60
aaatgattct ggggtctatt actgtgccac ctggggcagg                         100
```

<210> SEQ ID NO 1139
<211> LENGTH: 100
<212> TYPE: DNA
<213> ORGANISM: Homo sapiens

```
<400> SEQUENCE: 1139
gctatagtgt ctctagatca aagacagagg atttcctcct cactctggag tccgctacca    60
gctcccagac atctgtgtac ttctgtgcca tcagtgagtc                         100

<210> SEQ ID NO 1140
<211> LENGTH: 100
<212> TYPE: DNA
<213> ORGANISM: Homo sapiens

<400> SEQUENCE: 1140
atacagtgtc tctcgacagg cacaggctaa attctccctg tccctagagt ctgccatccc    60
caaccagaca gctctttact tctgtgccac cagtgatttg                         100

<210> SEQ ID NO 1141
<211> LENGTH: 100
<212> TYPE: DNA
<213> ORGANISM: Homo sapiens

<400> SEQUENCE: 1141
acaagtttcc catcaaccat ccaaacctga ccttctccgc tctgacagtg accagtgccc    60
atcctgaaga cagcagcttc tacatctgca gtgctagaga                         100

<210> SEQ ID NO 1142
<211> LENGTH: 100
<212> TYPE: DNA
<213> ORGANISM: Homo sapiens

<400> SEQUENCE: 1142
ggtaagtaaa aatgctcaca cttccacttc cactttgaaa ataaagttct tagagaaaga    60
agatgaggtg gtgtaccact gtgcctgctg gattaggcac                         100

<210> SEQ ID NO 1143
<211> LENGTH: 100
<212> TYPE: DNA
<213> ORGANISM: Homo sapiens

<400> SEQUENCE: 1143
gcttctttgc agaaaggcct gagggatccg tctccactct gaagatccag cgcacacaga    60
aggaggactc cgccgtgtat ctctgtgcca gcagcttagc                         100

<210> SEQ ID NO 1144
<211> LENGTH: 100
<212> TYPE: DNA
<213> ORGANISM: Homo sapiens

<400> SEQUENCE: 1144
ggttctttgc agtcaggcct gagggatccg tctctactct gaagatccag cgcacagagc    60 aggggactc agccgtgtat ctccgtgcca gcagcttaac                          100

<210> SEQ ID NO 1145
<211> LENGTH: 100
<212> TYPE: DNA
<213> ORGANISM: Homo sapiens

<400> SEQUENCE: 1145
aggcaagaaa gaattctcaa actctcactt caatccttac catcaagtcc gtagagaaag    60
aagacatggc cgtttactac tgtgctgcgt ggtgggtggc                         100
```

<210> SEQ ID NO 1146
<211> LENGTH: 100
<212> TYPE: DNA
<213> ORGANISM: Homo sapiens

<400> SEQUENCE: 1146
tgaggtggat aggatacctg aaacgtctac atccactctc accattcaca atgtagagaa    60
acaggacata gctacctact actgtgcctt gtgggaggtg                         100

<210> SEQ ID NO 1147
<211> LENGTH: 100
<212> TYPE: DNA
<213> ORGANISM: Homo sapiens

<400> SEQUENCE: 1147
gacggttttc tgtgaaacac attctgaccc agaaagcctt tcacttggtg atctctccag    60
taaggactga agacagtgcc acttactact gtgcctttag                         100

<210> SEQ ID NO 1148
<211> LENGTH: 100
<212> TYPE: DNA
<213> ORGANISM: Homo sapiens

<400> SEQUENCE: 1148
aatttccaag gtgacattga tattgcaaag aacctggctg tacttaagat acttgcacca    60
tcagagagag atgaagggtc ttactactgt gcctgtgaca                         100

<210> SEQ ID NO 1149
<211> LENGTH: 100
<212> TYPE: DNA
<213> ORGANISM: Homo sapiens

<400> SEQUENCE: 1149
agtattatac tcatacaccc aggaggtgga gctggatatt gagactgcaa aatctaattg    60
aaaatgattc tggggtctat tactgtgcca cctgggacag                         100

<210> SEQ ID NO 1150
<211> LENGTH: 100
<212> TYPE: DNA
<213> ORGANISM: Homo sapiens

<400> SEQUENCE: 1150
tttccaaggt gacattgata ttgcaaagaa cctggctgta cttaagatac ttgcaccatc    60
agagagagat gaagggtctt actactgtgc ctgtgacacc                         100

<210> SEQ ID NO 1151
<211> LENGTH: 100
<212> TYPE: DNA
<213> ORGANISM: Homo sapiens

<400> SEQUENCE: 1151
ggtacagcgt ctctcgggag aagaaggaat cctttcctct cactgtgaca tcggcccaaa    60
agaacccgac agctttctat ctctgtgcca gtagtataga                         100

<210> SEQ ID NO 1152
<211> LENGTH: 100
<212> TYPE: DNA
<213> ORGANISM: Homo sapiens

<400> SEQUENCE: 1152

```
actcattgaa tttccagaag gcaagaaaat ccgccaacct tgtcatctcc gcttcacaac    60
tgggggactc agcaatgtac ttctgtgcaa tgagagaggg                         100
```

<210> SEQ ID NO 1153
<211> LENGTH: 100
<212> TYPE: DNA
<213> ORGANISM: Homo sapiens

<400> SEQUENCE: 1153

```
gcttctcacc tgactctcca gacaaagttc atttaaatct tcacatcaat tccctggagc    60
ttggtgactc tgctgtgtat ttctgtgcca gcagccaaga                         100
```

<210> SEQ ID NO 1154
<211> LENGTH: 100
<212> TYPE: DNA
<213> ORGANISM: Homo sapiens

<400> SEQUENCE: 1154

```
tggaggcaag aaagaattct caaactctca cttcaatcct taccatcaag tccgtagaga    60
aagaagacat ggccgtttac tactgtgctg cgtgggatta                         100
```

<210> SEQ ID NO 1155
<211> LENGTH: 100
<212> TYPE: DNA
<213> ORGANISM: Homo sapiens

<400> SEQUENCE: 1155

```
caaatatttt aagaactgc ttggaaaaga aaattttat agtgtttgga atatcgcagc     60
ctctcatctg ggagattcag ccacctactt ctgtgctttg                         100
```

<210> SEQ ID NO 1156
<211> LENGTH: 100
<212> TYPE: DNA
<213> ORGANISM: Homo sapiens

<400> SEQUENCE: 1156

```
aacttgccta attgattctc agctcaccac gtccataact attactgagt caaacacgga    60
gctaggggac tcagccctgt atctctgtgc cagcaacttg                         100
```

<210> SEQ ID NO 1157
<211> LENGTH: 100
<212> TYPE: DNA
<213> ORGANISM: Homo sapiens

<400> SEQUENCE: 1157

```
ggaagggtac aatgtctctg gaaacaagct caagcatttt ccctcaaccc tggagtctac    60
tagcaccagc cagacctctg tacctctgtg gcagtgcatc                         100
```

<210> SEQ ID NO 1158
<211> LENGTH: 100
<212> TYPE: DNA
<213> ORGANISM: Homo sapiens

<400> SEQUENCE: 1158

```
tctctgtgaa cttccagaaa gcagccaaat ccttcagtct caagatctca gactcacagc    60
tgggggacac tgcgatgtat ttctgtgctt tcatgaagca                         100
```

<210> SEQ ID NO 1159

```
<211> LENGTH: 100
<212> TYPE: DNA
<213> ORGANISM: Homo sapiens

<400> SEQUENCE: 1159
aggctacgtg tctgccaaga ggagaagggg ctatttcttc tcagggtgaa gttggcccac    60
accagccaaa cagctttgta cttctgtcct gggagcgcac                          100

<210> SEQ ID NO 1160
<211> LENGTH: 100
<212> TYPE: DNA
<213> ORGANISM: Homo sapiens

<400> SEQUENCE: 1160
gattttcagc taagtgcctc ccaaattcac cctgtagcct tgagatccag gctacgaagc    60
ttgaggattc agcagtgtat ttttgtgcca gcagccaatc                          100

<210> SEQ ID NO 1161
<211> LENGTH: 100
<212> TYPE: DNA
<213> ORGANISM: Homo sapiens

<400> SEQUENCE: 1161
agaatctctc agcctccaga ccccaggacc ggcagttcat cctgagttct aagaagctcc    60
ttctcagtga ctctggcttc tatctctgtg cctggagtgt                          100

<210> SEQ ID NO 1162
<211> LENGTH: 100
<212> TYPE: DNA
<213> ORGANISM: Homo sapiens

<400> SEQUENCE: 1162
tttgaagctg aatttaacaa gagccaaacc tccttccacc tgaagaaacc atctgccctt    60
gtgagcgact ccgctttgta cttctgtgct gtgagagaca                          100

<210> SEQ ID NO 1163
<211> LENGTH: 100
<212> TYPE: DNA
<213> ORGANISM: Homo sapiens

<400> SEQUENCE: 1163
gcctctctga tcatcacaga agacagaaag tccagcacct tgatcctgcc ccacgctacg    60
ctgagagaca ctgctgtgta ctattgcatc gtcagagtcg                          100

<210> SEQ ID NO 1164
<211> LENGTH: 100
<212> TYPE: DNA
<213> ORGANISM: Homo sapiens

<400> SEQUENCE: 1164
aggctcactg tactgttgaa taaaaatgct aaacatgtct ccctgcatat tacagccacc    60
caaccaggag actcattcct gtacttctgt gcagtgagaa                          100

<210> SEQ ID NO 1165
<211> LENGTH: 100
<212> TYPE: DNA
<213> ORGANISM: Homo sapiens

<400> SEQUENCE: 1165
gcaaagcctg tgaactttga aaaaaagaaa aagttcatca acctcaccat caattcctta    60
```

```
aaactgactc agccaagtac ttctgtgctc tcaggaatcc                         100
```

<210> SEQ ID NO 1166
<211> LENGTH: 100
<212> TYPE: DNA
<213> ORGANISM: Homo sapiens

<400> SEQUENCE: 1166

```
gattctcagc tcaacagttc agtgactatc attctgaact gaacatgagc tccttggagc    60
tgggggactc agccctgtac ttctgtgcca gcagcttagg                         100
```

<210> SEQ ID NO 1167
<211> LENGTH: 100
<212> TYPE: DNA
<213> ORGANISM: Homo sapiens

<400> SEQUENCE: 1167

```
acttccaatc caggaggccg aacacttctt tctgctttct tgacatccgc tcaccaggcc    60 tggggacac agccatgtac ctgtgtgcca ccagcagaga                          100
```

<210> SEQ ID NO 1168
<211> LENGTH: 100
<212> TYPE: DNA
<213> ORGANISM: Homo sapiens

<400> SEQUENCE: 1168

```
agggacgata caacatgacc tatgaacggt tctcttcatc gctgctcatc ctccaggtgc    60
gggaggcaga tgctgctgtt tactactgtg ctgtggagga                         100
```

<210> SEQ ID NO 1169
<211> LENGTH: 100
<212> TYPE: DNA
<213> ORGANISM: Homo sapiens

<400> SEQUENCE: 1169

```
ggttctctgc acagaggtct gagggatcca tctccactct gaagttccag cgcacacagc    60 aggggggactt ggctgtgtat ctctgtgcca gcagctcagc                        100
```

<210> SEQ ID NO 1170
<211> LENGTH: 100
<212> TYPE: DNA
<213> ORGANISM: Homo sapiens

<400> SEQUENCE: 1170

```
gattctcatc tcaatgcccc aagaacgcac cctgcagcct ggcaatcctg tcctcagaac    60
cgggagacac ggcactgtat ctctgcgcca gcagtcaatc                         100
```

<210> SEQ ID NO 1171
<211> LENGTH: 100
<212> TYPE: DNA
<213> ORGANISM: Homo sapiens

<400> SEQUENCE: 1171

```
gatgcacaag aagcgattct catctcaatg ccccaagaac ccaccctgca gcctggcaat    60
cctgtcctcg gaaccgggag acaccgcact gtatctctgt                         100
```

<210> SEQ ID NO 1172
<211> LENGTH: 100
<212> TYPE: DNA

-continued

<213> ORGANISM: Homo sapiens

<400> SEQUENCE: 1172

```
tccctattga aaatatttcc tggcaaaaaa tagaagttct ctttggctct gaaatctgca    60
actccctttc aggtgtccct gtgtccttgt accgtcactc                        100
```

<210> SEQ ID NO 1173
<211> LENGTH: 100
<212> TYPE: DNA
<213> ORGANISM: Homo sapiens

<400> SEQUENCE: 1173

```
tccctgttga aaatatttcc cggcaaaaaa cagaagttcc ctttggctct gaaatctgca    60
aagcccttcc agatgtccct gtgtccttgt gccgtcactc                        100
```

<210> SEQ ID NO 1174
<211> LENGTH: 100
<212> TYPE: DNA
<213> ORGANISM: Homo sapiens

<400> SEQUENCE: 1174

```
gattctcagc acagatgcct gatgtatcat tctccactct gaggatccag cccatggaac    60
ccagggactt gggcctatat ttctgtgcca gcagctttgc                        100
```

<210> SEQ ID NO 1175
<211> LENGTH: 100
<212> TYPE: DNA
<213> ORGANISM: Homo sapiens

<400> SEQUENCE: 1175

```
ggtatcatgt ttcttgaaat actatagcat cttttctcct gaccctgaag tctgctagca    60
ccaaccagac atgtgtgtat ctctgcgcca gcagttcatc                        100
```

<210> SEQ ID NO 1176
<211> LENGTH: 100
<212> TYPE: DNA
<213> ORGANISM: Homo sapiens

<400> SEQUENCE: 1176

```
tgaggtggat aggatacctg aaacgtctac atccactctc accattcaca atgtagagaa    60
acaggacata gctacctact actgtgcctt gtgggaggtg                        100
```

<210> SEQ ID NO 1177
<211> LENGTH: 100
<212> TYPE: DNA
<213> ORGANISM: Homo sapiens

<400> SEQUENCE: 1177

```
cttgaggcaa gaacaaattt tcaaatgtct acttcagtct ttaccataaa cttcatagga    60
aaggaagatg aggccattta ctactgcact gcttaggacc                        100
```

<210> SEQ ID NO 1178
<211> LENGTH: 100
<212> TYPE: DNA
<213> ORGANISM: Homo sapiens

<400> SEQUENCE: 1178

```
ggttctttgc agtcaggcct gagggatccg tctctactct gaagatccag cgcacagagc    60
gggggggactc agccgtgtat ctctgtgcca gcagcttaac                       100
```

<210> SEQ ID NO 1179
<211> LENGTH: 100
<212> TYPE: DNA
<213> ORGANISM: Homo sapiens

<400> SEQUENCE: 1179
ggttctctgc agagaggcct aagggatctt tctccacctt ggagatccag cgcacagagc    60 aggggactc ggccatgtat ctctgtgcca gcagcttagc                          100

<210> SEQ ID NO 1180
<211> LENGTH: 100
<212> TYPE: DNA
<213> ORGANISM: Homo sapiens

<400> SEQUENCE: 1180
gcttctctgc agagaggact gggggatccg tctccactct gacgatccag cgcacacagc    60
aggaggactc ggccgtgtat ctctgtgcca gcagcttagc                         100

<210> SEQ ID NO 1181
<211> LENGTH: 100
<212> TYPE: DNA
<213> ORGANISM: Homo sapiens

<400> SEQUENCE: 1181
gcttctctgc agagaggact ggggaatccg tctccactct gacgatccag cgcacacagc    60
aggaggactc ggccgtgtat ctctgtgcca gcagcttagc                         100

<210> SEQ ID NO 1182
<211> LENGTH: 100
<212> TYPE: DNA
<213> ORGANISM: Homo sapiens

<400> SEQUENCE: 1182
ggttctctgc agagaggcct gagggatcca tctccactct gacgattcag cgcacagagc    60
agcgggactc agccatgtat cgctgtgcca gcagcttagc                         100

<210> SEQ ID NO 1183
<211> LENGTH: 100
<212> TYPE: DNA
<213> ORGANISM: Homo sapiens

<400> SEQUENCE: 1183
gcttctttgc agaaaggcct gagggatccg tctccactct gaagatccag cgcacacagc    60
aggaggactc cgccgtgtat ctctgtgcca gcagcttagc                         100

<210> SEQ ID NO 1184
<211> LENGTH: 100
<212> TYPE: DNA
<213> ORGANISM: Homo sapiens

<400> SEQUENCE: 1184
aacgattcac agctgaaaga cctaacggaa cgtcttccac gctgaagatc catcccgcag    60
agccgaggga ctcagccgtg tatctctaca gtagcggtgg                         100

<210> SEQ ID NO 1185
<211> LENGTH: 100
<212> TYPE: DNA
<213> ORGANISM: Homo sapiens

```
<400> SEQUENCE: 1185
agattttcag gtcgccagtt ccctaattat agctctgagc tgaatgtgaa cgccttggag      60
ctggaggact cggccctgta tctctgtgcc agcagcttgg                          100

<210> SEQ ID NO 1186
<211> LENGTH: 100
<212> TYPE: DNA
<213> ORGANISM: Homo sapiens

<400> SEQUENCE: 1186
caattctcag gtcaccagtt ccctaactat agctctgagc tgaatgtgaa cgccttgttg      60
ctaggggact cggccctcta tctctgtgcc agcagcttgg                          100

<210> SEQ ID NO 1187
<211> LENGTH: 100
<212> TYPE: DNA
<213> ORGANISM: Homo sapiens

<400> SEQUENCE: 1187
cgattctcag gtcaccagtt ccctaactat agctctgagc tgaatgtgaa cgccttgttg      60
ctgggggact cggccctcta tctctgtgcc agcagcttgg                          100

<210> SEQ ID NO 1188
<211> LENGTH: 100
<212> TYPE: DNA
<213> ORGANISM: Homo sapiens

<400> SEQUENCE: 1188
cgattctcag ctcgccagtt ccctaactat agctctgagc tgaatgtgaa cgccttgttg      60
ctgggggact cggccctgta tctctgtgcc agcagcttgg                          100

<210> SEQ ID NO 1189
<211> LENGTH: 100
<212> TYPE: DNA
<213> ORGANISM: Homo sapiens

<400> SEQUENCE: 1189
agattctcag gtctccagtt ccctaattat agctctgagc tgaatgtgaa cgccttggag      60
ctggacgact cggccctgta tctctgtgcc agcagcttgg                          100

<210> SEQ ID NO 1190
<211> LENGTH: 100
<212> TYPE: DNA
<213> ORGANISM: Homo sapiens

<400> SEQUENCE: 1190
cgattctcag ggcgccagtt ctctaactct cgctctgaga tgaatgtgag caccttggag      60
ctgggggact cggcccttta tctttgcgcc agcagcttgg                          100

<210> SEQ ID NO 1191
<211> LENGTH: 100
<212> TYPE: DNA
<213> ORGANISM: Homo sapiens

<400> SEQUENCE: 1191
gcttctcacc taaatctcca gacaaagctc acttaaatct tcacatcaat tccctggagc      60
ttggtgactc tgctgtgtat ttctgtgcca gcagccaaga                          100
```

```
<210> SEQ ID NO 1192
<211> LENGTH: 100
<212> TYPE: DNA
<213> ORGANISM: Homo sapiens

<400> SEQUENCE: 1192
acttcacacc tgaatgccct gacagctctc gcttatacct tcatgtggtc gcactgcagc    60
aagaagactc agctgcgtat ctctgcacca gcagccaaga                         100

<210> SEQ ID NO 1193
<211> LENGTH: 100
<212> TYPE: DNA
<213> ORGANISM: Homo sapiens

<400> SEQUENCE: 1193
cgattctcag ggcgccagtt ccatgactgt tgctctgaga tgaatgtgag tgccttggag    60
ctgggggact cggccctgta tctctgtgcc agaagcttgg                         100

<210> SEQ ID NO 1194
<211> LENGTH: 100
<212> TYPE: DNA
<213> ORGANISM: Homo sapiens

<400> SEQUENCE: 1194
cgattctcag ggcgccagtt ccatgactat tgctctgaga tgaatgtgag tgccttggag    60
ctgggggact cggccctgta tctctgtgcc agaagcttgg                         100

<210> SEQ ID NO 1195
<211> LENGTH: 100
<212> TYPE: DNA
<213> ORGANISM: Homo sapiens

<400> SEQUENCE: 1195
cgattctccg cacaacagtt ccctgacttg cactctgaac taaacctgag ctctctggag    60
ctgggggact cagctttgta tttctgtgcc agcagcgtag                         100

<210> SEQ ID NO 1196
<211> LENGTH: 100
<212> TYPE: DNA
<213> ORGANISM: Homo sapiens

<400> SEQUENCE: 1196
gcttctcacc tgactctcca gacaaagctc atttaaatct tcacatcaat tccctggagc    60
ttggtgactc tgctgtgtat ttctgtgcca gcagccaaga                         100

<210> SEQ ID NO 1197
<211> LENGTH: 100
<212> TYPE: DNA
<213> ORGANISM: Homo sapiens

<400> SEQUENCE: 1197
aattctcagt tgaaaggcct gatggatcaa atttcactct gaagatccgg tccacaaagc    60
tggaggactc agccatgtac ttctgtgcca gcagtgaagc                         100

<210> SEQ ID NO 1198
<211> LENGTH: 100
<212> TYPE: DNA
<213> ORGANISM: Homo sapiens

<400> SEQUENCE: 1198
```

```
gcttctcacc tgaatgcccc aacagctctc acttattcct tcacctacac accctgcagc    60
cagaagactc ggccctgtat ctctgcgcca gcagccaaga                         100
```

<210> SEQ ID NO 1199
<211> LENGTH: 100
<212> TYPE: DNA
<213> ORGANISM: Homo sapiens

<400> SEQUENCE: 1199

```
gcttctcacc tgaatgcccc aacagctctc tcttaaacct tcacctacac gccctgcagc    60
cagaagactc agccctgtat ctctgcgcca gcagccaaga                         100
```

<210> SEQ ID NO 1200
<211> LENGTH: 100
<212> TYPE: DNA
<213> ORGANISM: Homo sapiens

<400> SEQUENCE: 1200

```
gcttctcacc tgaatgcccc aacagctctc acttattcct tcacctacac accctgcagc    60
cagaagactc ggccctgtat ctctgtgcca gcagccaaga                         100
```

<210> SEQ ID NO 1201
<211> LENGTH: 100
<212> TYPE: DNA
<213> ORGANISM: Homo sapiens

<400> SEQUENCE: 1201

```
aagataactg ccaagttgga tgagaaaaag cagcaaagtt ccctgcatat cacagcctcc    60
cagcccagcc atgcaggcat ctacctctgt ggagcagaca                         100
```

<210> SEQ ID NO 1202
<211> LENGTH: 100
<212> TYPE: DNA
<213> ORGANISM: Homo sapiens

<400> SEQUENCE: 1202

```
ggtacagtgt ctctagagag aagaaggagc gcttctccct gattctggag tccgccagca    60
ccaaccagac atctatgtac ctctgtgcca gcagtttatg                         100
```

<210> SEQ ID NO 1203
<211> LENGTH: 100
<212> TYPE: DNA
<213> ORGANISM: Homo sapiens

<400> SEQUENCE: 1203

```
acaagtttct catcaaccat gcaagcctga ccttgtccac tctgacagtg accagtgccc    60
atcctgaaga cagcagcttc tacatctgca gtgctagaga                         100
```

<210> SEQ ID NO 1204
<211> LENGTH: 100
<212> TYPE: DNA
<213> ORGANISM: Homo sapiens

<400> SEQUENCE: 1204

```
acaagtttcc catcaaccat ccaaacctga ccttctccgc tctgacagtg accagtgccc    60
atcctgaaga cagcagcttc tacatctgca gtgctagaga                         100
```

<210> SEQ ID NO 1205
<211> LENGTH: 100

```
<212> TYPE: DNA
<213> ORGANISM: Homo sapiens

<400> SEQUENCE: 1205
gaatggctac aacgtctcca gatcaaccac agaggatttc ccgctcaggc tggagttggc    60
tgctccctcc cagacatctg tgtacttctg tgccagcagt                          100

<210> SEQ ID NO 1206
<211> LENGTH: 100
<212> TYPE: DNA
<213> ORGANISM: Homo sapiens

<400> SEQUENCE: 1206
gctacaacgt ctccagatca accacagagg atttcccgct caggctggag ttggctgctc    60
cctcccagac atctgtgtac ttctgtgcca gcagttactc                          100

<210> SEQ ID NO 1207
<211> LENGTH: 100
<212> TYPE: DNA
<213> ORGANISM: Homo sapiens

<400> SEQUENCE: 1207
gctacaatgt ctccagatca accacagagg atttcccgct caggctgctg tcggctgctc    60
cctcccagac atctgtgtac ttctgtgcca gcagttactc                          100

<210> SEQ ID NO 1208
<211> LENGTH: 100
<212> TYPE: DNA
<213> ORGANISM: Homo sapiens

<400> SEQUENCE: 1208
gctacaatgt ctctagatta aacacagagg atttcccact caggctggtg tcggctgctc    60
cctcccagac atctgtgtac ttgtgtgcca gcagttactc                          100

<210> SEQ ID NO 1209
<211> LENGTH: 100
<212> TYPE: DNA
<213> ORGANISM: Homo sapiens

<400> SEQUENCE: 1209
gctacaatgt atccagatca aacacagagg atttcccgct caggctggag tcagctgctc    60
cctcccagac atctgtatac ttctgtgcca gcagttattc                          100

<210> SEQ ID NO 1210
<211> LENGTH: 100
<212> TYPE: DNA
<213> ORGANISM: Homo sapiens

<400> SEQUENCE: 1210
gctacaatgt ctccagatca aacacagagg atttccccct caagctggag tcagctgctc    60
cctctcagac ttctgtttac ttctgtgcca gcagttactc                          100

<210> SEQ ID NO 1211
<211> LENGTH: 100
<212> TYPE: DNA
<213> ORGANISM: Homo sapiens

<400> SEQUENCE: 1211
gattctcagc taagatgcct aatgcatcat tctccactct gaagatccag ccctcagaac    60
```
ccagggactc agctgtgtac ttctgtgcca gcagtttagc    100

<210> SEQ ID NO 1212
<211> LENGTH: 100
<212> TYPE: DNA
<213> ORGANISM: Homo sapiens

<400> SEQUENCE: 1212
gattctcagc taagatgcct aatgcatcat tctccactct gaagatccag ccctcagaac    60
ccagggactc agctgtgtac ttctgtgcca gcagtttagc    100

<210> SEQ ID NO 1213
<211> LENGTH: 100
<212> TYPE: DNA
<213> ORGANISM: Homo sapiens

<400> SEQUENCE: 1213
gattctcagc agagatgcct gatgcaactt tagccactct gaagatccag ccctcagaac    60
ccagggactc agctgtgtat ttttgtgcta gtggtttggt    100

<210> SEQ ID NO 1214
<211> LENGTH: 100
<212> TYPE: DNA
<213> ORGANISM: Homo sapiens

<400> SEQUENCE: 1214
gattctcagc tgagaggcct gatggatcat tctctactct gaagatccag cctgcagagc    60 aggggactc ggccgtgtat gtctgtgcaa gtcgcttagc    100

<210> SEQ ID NO 1215
<211> LENGTH: 100
<212> TYPE: DNA
<213> ORGANISM: Homo sapiens

<400> SEQUENCE: 1215
gctacaatgt ctccagatta aacaaacggg agttctcgct caggctggag tcggctgctc    60
cctcccagac atctgtgtac ttctgtgcca gcagtgaagc    100

<210> SEQ ID NO 1216
<211> LENGTH: 100
<212> TYPE: DNA
<213> ORGANISM: Homo sapiens

<400> SEQUENCE: 1216
ggttctctgc agagaggcct gagagatccg tctccactct gaagatccag cgcacagagc    60 aggggactc agctgtgtat ctctgtgcca gcagcttagc    100

<210> SEQ ID NO 1217
<211> LENGTH: 100
<212> TYPE: DNA
<213> ORGANISM: Homo sapiens

<400> SEQUENCE: 1217
tcaattctcc acagagaggt ctgaggatct ttctccacct gaagatccag cgcacagagc    60
aagggcgact cggctgtgta tctctgtgcc agaagcttag    100

<210> SEQ ID NO 1218
<211> LENGTH: 100
<212> TYPE: DNA
<213> ORGANISM: Homo sapiens

<400> SEQUENCE: 1218
aaagaaaggc taaaagccac attaacaaag aaggaaagct ttctgcacat cacagcccct    60
aaacctgaag actcagccac ttatctctgt gctgtgcagg    100

<210> SEQ ID NO 1219
<211> LENGTH: 100
<212> TYPE: DNA
<213> ORGANISM: Homo sapiens

<400> SEQUENCE: 1219
gattttctgc agagaggctc aaaggagtag actccactct caagatccag cctgcagagc    60
ttggggactc ggccatgtat ctctgtgcca gcagcttagc    100

<210> SEQ ID NO 1220
<211> LENGTH: 100
<212> TYPE: DNA
<213> ORGANISM: Homo sapiens

<400> SEQUENCE: 1220
acattttaaa gaagcgcttg gaaaagagaa gtttttatagt gttttgaata tgctggtctc    60
tcatcctgga gattcaggca cctacttctg tgctttgagg    100

<210> SEQ ID NO 1221
<211> LENGTH: 100
<212> TYPE: DNA
<213> ORGANISM: Homo sapiens

<400> SEQUENCE: 1221
aaaggaagac taaatgctac attactgaag aatggaagca gcttgtacat tacagccgtg    60
cagcctgaag attcagccac ctatttctgt gctgtagatg    100

<210> SEQ ID NO 1222
<211> LENGTH: 100
<212> TYPE: DNA
<213> ORGANISM: Homo sapiens

<400> SEQUENCE: 1222
gcttcactgc tgaccttaac aaaggcgaga catctttcca cctgaagaaa ccatttgctc    60
aagaggaaga ctcagccatg tattactgtg ctctaagtgg    100

<210> SEQ ID NO 1223
<211> LENGTH: 100
<212> TYPE: DNA
<213> ORGANISM: Homo sapiens

<400> SEQUENCE: 1223
agactgaagg tcacctttga taccaccctt aaacagagtt tgtttcatat cacagcctcc    60
cagcctgcag actcagctac ctacctctgt gctctagaca    100

<210> SEQ ID NO 1224
<211> LENGTH: 100
<212> TYPE: DNA
<213> ORGANISM: Homo sapiens

<400> SEQUENCE: 1224
ggtacagcgt ctctcgggag aagaaggaat cctttcctct cactgtgaca tcggcccaaa    60
agaacccgac agctttctat ctctgtgcca gtagtataga    100

<210> SEQ ID NO 1225
<211> LENGTH: 100
<212> TYPE: DNA
<213> ORGANISM: Homo sapiens

<400> SEQUENCE: 1225
actcattgaa tttccagaag gcaagaaaat ccgccaacct tgtcatctcc gcttcacaac    60
tgggggactc agcaatgtat ttctgtgcaa tgagagaggg                          100

<210> SEQ ID NO 1226
<211> LENGTH: 100
<212> TYPE: DNA
<213> ORGANISM: Homo sapiens

<400> SEQUENCE: 1226
gttttgaagc catgtaccgt aaagaaacca cttctttcca cttggagaaa gactcagttc    60
aagagtcaga ctccgctgtg tacttctgtg ctctgagtga                          100

<210> SEQ ID NO 1227
<211> LENGTH: 100
<212> TYPE: DNA
<213> ORGANISM: Homo sapiens

<400> SEQUENCE: 1227
gttttgaagc cacataccgt aaagaaacca cttctttcca cttggagaaa ggctcagttc    60
aagtgtcaga ctcagcggtg tacttctgtg ctctgagtga                          100

<210> SEQ ID NO 1228
<211> LENGTH: 100
<212> TYPE: DNA
<213> ORGANISM: Homo sapiens

<400> SEQUENCE: 1228 gttttcttc attccttagt cgctctgata gttatggtta cctccttcta caggagctcc     60
agatgaaaga ctctgcctct tacttctgcg ctgtgagaga                          100

<210> SEQ ID NO 1229
<211> LENGTH: 100
<212> TYPE: DNA
<213> ORGANISM: Homo sapiens

<400> SEQUENCE: 1229
ttctctgtga acttccagaa agcagccaaa tccttcagtc tcaagatctc agactcacag    60
ctgggggatg ccgcgatgta tttctgtgct tataggagcg                          100

<210> SEQ ID NO 1230
<211> LENGTH: 100
<212> TYPE: DNA
<213> ORGANISM: Homo sapiens

<400> SEQUENCE: 1230
attcttggaa cttccagaaa tccaccagtt ccttcaactt caccatcaca gcctcacaag    60
tcgtggactc agcagtatac ttctgtgctc tgagtgaggc                          100

<210> SEQ ID NO 1231
<211> LENGTH: 100
<212> TYPE: DNA
<213> ORGANISM: Homo sapiens

<400> SEQUENCE: 1231

```
aaaatatctg cttcatttaa tgaaaaaaag cagcaaagct ccctgtacct tacggcctcc    60
cagctcagtt actcaggaac ctacttctgc ggcacagaga                         100
```

<210> SEQ ID NO 1232
<211> LENGTH: 100
<212> TYPE: DNA
<213> ORGANISM: Homo sapiens

<400> SEQUENCE: 1232

```
agtatttac ttatgcaagc atgaggagga gctggaaatt gatactgcaa aatctaattg    60
aaaatgattc tggatctatt actgtgccac ctgggacagg                         100
```

<210> SEQ ID NO 1233
<211> LENGTH: 100
<212> TYPE: DNA
<213> ORGANISM: Homo sapiens

<400> SEQUENCE: 1233

```
aaagtatgac actggaagca caaggagcaa ttggaatttg agactgcaaa atctaattaa    60
aaatgattct gggttctatt actgtgccac ctgggacagg                         100
```

<210> SEQ ID NO 1234
<211> LENGTH: 100
<212> TYPE: DNA
<213> ORGANISM: Homo sapiens

<400> SEQUENCE: 1234

```
gtattatact catacaccca ggaggtggag ctggatattg agactgcaaa atctaattga    60
aaatgattct ggggtctatt actgtgccac ctgggacagg                         100
```

<210> SEQ ID NO 1235
<211> LENGTH: 100
<212> TYPE: DNA
<213> ORGANISM: Homo sapiens

<400> SEQUENCE: 1235

```
gtattatact catacaccca ggaggtggag ctggatattg atactacgaa atctaattga    60
aaatgattct ggggtctatt actgtgccac ctgggacagg                         100
```

<210> SEQ ID NO 1236
<211> LENGTH: 100
<212> TYPE: DNA
<213> ORGANISM: Homo sapiens

<400> SEQUENCE: 1236

```
gtatcatact tatgcaagca cagggaagag ccttaaattt atactggaaa atctaattga    60
acgtgactct ggggtctatt actgtgccac ctgggatagg                         100
```

<210> SEQ ID NO 1237
<211> LENGTH: 100
<212> TYPE: DNA
<213> ORGANISM: Homo sapiens

<400> SEQUENCE: 1237

```
gtatgatact tatggaagca caaggaagaa cttgagaatg atactgcgaa atcttattga    60
aaatgactct ggagtctatt actgtgccac ctgggatggg                         100
```

<210> SEQ ID NO 1238

```
<211> LENGTH: 100
<212> TYPE: DNA
<213> ORGANISM: Homo sapiens

<400> SEQUENCE: 1238
gtattatact tacgcaagca caaggaacaa cttgagattg atactgcgaa atctaattga      60
aaatgactct ggggtctatt actgtgccac ctgggacggg                          100

<210> SEQ ID NO 1239
<211> LENGTH: 100
<212> TYPE: DNA
<213> ORGANISM: Homo sapiens

<400> SEQUENCE: 1239
gtattatact catacaccga ggaggtggag ctggaatttg agactgcaaa atctaattga      60
aaatgattct ggggtctatt actgtgccac ctggggcagg                          100

<210> SEQ ID NO 1240
<211> LENGTH: 100
<212> TYPE: DNA
<213> ORGANISM: Homo sapiens

<400> SEQUENCE: 1240
aagacttaat gcctcgctgg ataaatcatc aggacgtagt actttataca ttgcagcttc      60
tcagcctggt gactcagcca cctacctctg tgctgtgagg                          100

<210> SEQ ID NO 1241
<211> LENGTH: 100
<212> TYPE: DNA
<213> ORGANISM: Homo sapiens

<400> SEQUENCE: 1241
acaagtttcc catcagccgc ccaaacctaa cattctcaac tctgactgtg agcaacagga      60
gacctgaaga cagcagcata tacctctgca gcgttgaaga                          100

<210> SEQ ID NO 1242
<211> LENGTH: 100
<212> TYPE: DNA
<213> ORGANISM: Homo sapiens

<400> SEQUENCE: 1242
agattcacag ccaggcttaa aaaggagac cagcacattt ccctgcacat acaggattcc       60
cagctccatg actcaaccac attcttctgc gcagcaagca                          100

<210> SEQ ID NO 1243
<211> LENGTH: 100
<212> TYPE: DNA
<213> ORGANISM: Homo sapiens

<400> SEQUENCE: 1243
gattttcagc ccaatgcccc caaaactcac cctgtacctt ggagatccag tccacggagt      60
caggagacac agcacggtat ttctgtgcca acagcaaagc                          100

<210> SEQ ID NO 1244
<211> LENGTH: 100
<212> TYPE: DNA
<213> ORGANISM: Homo sapiens

<400> SEQUENCE: 1244
gatttttagc ccaatgctcc aaaaactcat cctgtacctt ggagatccag tccacggagt      60
``` cagggggacac agcactgtat ttctgtgcca gcagcaaagc         100

<210> SEQ ID NO 1245
<211> LENGTH: 100
<212> TYPE: DNA
<213> ORGANISM: Homo sapiens

<400> SEQUENCE: 1245
gttttgaggc tgaatttaac aagagtcaaa cttccttcca cttgaggaaa ccctcagtcc    60
atataagcga cacggctgag tacttctgtg ctgtgagtga                         100

<210> SEQ ID NO 1246
<211> LENGTH: 100
<212> TYPE: DNA
<213> ORGANISM: Homo sapiens

<400> SEQUENCE: 1246
gctttgaggc tgaatttaag aggagtcaat cttccttcaa tctgaggaaa ccctctgtgc    60
attggagtga tgctgctgag tacttctgtg ctgtgggtgc                         100

<210> SEQ ID NO 1247
<211> LENGTH: 100
<212> TYPE: DNA
<213> ORGANISM: Homo sapiens

<400> SEQUENCE: 1247
acaagtttcc catcagccgc ccaaacctaa cattctcaac tctgactgtg agcaacatga    60
gccctgaaga cagcagcata tatctctgca gcgttgaaga                         100

<210> SEQ ID NO 1248
<211> LENGTH: 100
<212> TYPE: DNA
<213> ORGANISM: Homo sapiens

<400> SEQUENCE: 1248
agtcaacagt ctccagaata aggatagagc gttttcccct gaccctggag tctgccagcc    60
cctcacatac ctctcagtac ctctgtgcca gcagtgaata                         100

<210> SEQ ID NO 1249
<211> LENGTH: 100
<212> TYPE: DNA
<213> ORGANISM: Homo sapiens

<400> SEQUENCE: 1249
agtcaacagt ctccagaata aggacggagc attttcccct gaccctggag tctgccaggc    60
cctcacatac ctctcagtac ctctgtgcca gcagtgaata                         100

<210> SEQ ID NO 1250
<211> LENGTH: 100
<212> TYPE: DNA
<213> ORGANISM: Homo sapiens

<400> SEQUENCE: 1250
aagactgact gctcagtttg gtataaccag aaaggacagc ttcctgaata tctcagcatc    60
catacctagt gatgtaggca tctacttctg tgctgggcag                         100

<210> SEQ ID NO 1251
<211> LENGTH: 100
<212> TYPE: DNA

```
<213> ORGANISM: Homo sapiens

<400> SEQUENCE: 1251
gaaaagactg acatttcagt ttggagaagc aaaaaagaac agctccctgc acatcacagc      60
cacccagact acagatgtag gaacctactt ctgtgcaggg                           100

<210> SEQ ID NO 1252
<211> LENGTH: 100
<212> TYPE: DNA
<213> ORGANISM: Homo sapiens

<400> SEQUENCE: 1252
aggtttacag cacagctcaa taaagccagc cagtatgttt ctctgctcat cagagactcc      60
cagcccagtg attcagccac ctacctctgt gccgtgaaca                           100

<210> SEQ ID NO 1253
<211> LENGTH: 100
<212> TYPE: DNA
<213> ORGANISM: Homo sapiens

<400> SEQUENCE: 1253
aggtttacag cacagctcaa tagagccagc cagtatattt ccctgctcat cagagactcc      60
aagctcagtg attcagccac ctacctctgt gtggtgaaca                           100

<210> SEQ ID NO 1254
<211> LENGTH: 100
<212> TYPE: DNA
<213> ORGANISM: Homo sapiens

<400> SEQUENCE: 1254
aggtttacag cacaggtcga taaatccagc aagtatatct ccttgttcat cagagactca      60
cagcccagtg attcagccac ctacctctgt gcaatgagcg                           100

<210> SEQ ID NO 1255
<211> LENGTH: 100
<212> TYPE: DNA
<213> ORGANISM: Homo sapiens

<400> SEQUENCE: 1255
agattcacaa tctccttcaa taaaagtgcc aagcagttct cattgcatat catggattcc      60
cagcctggag actcagccac ctacttctgt gcagcaagca                           100

<210> SEQ ID NO 1256
<211> LENGTH: 100
<212> TYPE: DNA
<213> ORGANISM: Homo sapiens

<400> SEQUENCE: 1256
agattaagcg ccacgactgt cgctacggaa cgctacagct tattgtacat ttcctcttcc      60
cagaccacag actcaggcgt ttatttctgt gctgtggagc                           100

<210> SEQ ID NO 1257
<211> LENGTH: 100
<212> TYPE: DNA
<213> ORGANISM: Homo sapiens

<400> SEQUENCE: 1257
aagattaatt gccacaataa acatacagga aaagcacagc tccctgcaca tcacagcctc      60
ccatcccaga gactctgccg tctacatctg tgctgtcaga                           100
```

<210> SEQ ID NO 1258
<211> LENGTH: 100
<212> TYPE: DNA
<213> ORGANISM: Homo sapiens

<400> SEQUENCE: 1258
cgattaatgg cctcacttga taccaaagcc cgtctcagca ccctccacat cacagctgcc    60
gtgcatgacc tctctgccac ctacttctgt gccgtggaca                         100

<210> SEQ ID NO 1259
<211> LENGTH: 100
<212> TYPE: DNA
<213> ORGANISM: Homo sapiens

<400> SEQUENCE: 1259
agactaagta gcatattaga taagaaagaa ctttccagca tcctgaacat cacagccacc    60
cagaccggag actcggccat ctacctctgt gctgtggagg                         100

<210> SEQ ID NO 1260
<211> LENGTH: 100
<212> TYPE: DNA
<213> ORGANISM: Homo sapiens

<400> SEQUENCE: 1260
agattcactg tcttcttaaa caaaagtgcc aagcacctct ctctgcacat tgtgccctcc    60
cagcctggag actctgcagt gtacttctgt gcagcaagcg                         100

<210> SEQ ID NO 1261
<211> LENGTH: 100
<212> TYPE: DNA
<213> ORGANISM: Homo sapiens

<400> SEQUENCE: 1261
aagagactaa cctttcagtt tggtgatgca agaaaggaca gttctctcca catcactgca    60
gcccagcctg gtgatacagg cctctacctc tgtgcaggag                         100

<210> SEQ ID NO 1262
<211> LENGTH: 100
<212> TYPE: DNA
<213> ORGANISM: Homo sapiens

<400> SEQUENCE: 1262
gttatagtgt ctccagagca aacacagatg atttccccct cacgttggcg tctgctgtac    60
cctctcagac atctgtgtac ttctgtgcca gcagtgactc                         100

<210> SEQ ID NO 1263
<211> LENGTH: 100
<212> TYPE: DNA
<213> ORGANISM: Homo sapiens

<400> SEQUENCE: 1263
gctacagtgt ctctagatca aacacagagg acctcccccct cactctggag tctgctgcct    60
cctcccagac atctgtatat ttctgcgcca gcagtgagtc                         100

<210> SEQ ID NO 1264
<211> LENGTH: 100
<212> TYPE: DNA
<213> ORGANISM: Homo sapiens

<400> SEQUENCE: 1264
gctatgttgt ctccagatcc aagacagaga atttcccct cactctggag tcagctaccc      60
gctcccagac atctgtgtat ttctgcgcca gcagtgagtc                          100

<210> SEQ ID NO 1265
<211> LENGTH: 100
<212> TYPE: DNA
<213> ORGANISM: Homo sapiens

<400> SEQUENCE: 1265
gctacaatgt ctccagatta aaaaaacaga atttcctgct ggggttggag tcggctgctc      60
cctcccaaac atctgtgtac ttctgtgcca gcagttactc                          100

<210> SEQ ID NO 1266
<211> LENGTH: 100
<212> TYPE: DNA
<213> ORGANISM: Homo sapiens

<400> SEQUENCE: 1266
gctatagtgt ctctagatca aagacagagg atttcctcct cactctggag tccgctacca      60
gctcccagac atctgtgtac ttctgtgcca tcagtgagtc                          100

<210> SEQ ID NO 1267
<211> LENGTH: 100
<212> TYPE: DNA
<213> ORGANISM: Homo sapiens

<400> SEQUENCE: 1267
ggacgaataa gtgccactct taataccaag gagggttaca gctatttgta catcaaagga      60
tcccagcctg aagactcagc cacatacctc tgtgccttta                          100

<210> SEQ ID NO 1268
<211> LENGTH: 100
<212> TYPE: DNA
<213> ORGANISM: Homo sapiens

<400> SEQUENCE: 1268
gattcttagc tgaaaggact ggagggacgt attctactct gaaggtgcag cctgcagaac      60
tggaggattc tggagtttat ttctgtgcca gcagccaaga                          100

<210> SEQ ID NO 1269
<211> LENGTH: 100
<212> TYPE: DNA
<213> ORGANISM: Homo sapiens

<400> SEQUENCE: 1269
atacagtgtc tctcgacagg cacaggctaa attctccctg tccctagagt ctgccatccc      60
caaccagaca gctctttact tctgtgccac cagtgatttg                          100

<210> SEQ ID NO 1270
<211> LENGTH: 100
<212> TYPE: DNA
<213> ORGANISM: Homo sapiens

<400> SEQUENCE: 1270
agtgtctctt gacaggaaca ggctaaattc tccctgtccc tagagcctgc cacccccaac      60
cagacagctt ctaggttact tcagtgccac cagtgatttc                          100

```
<210> SEQ ID NO 1271
<211> LENGTH: 100
<212> TYPE: DNA
<213> ORGANISM: Homo sapiens

<400> SEQUENCE: 1271
gttttgaggc tgaatttaag aagagtgaaa cctccttcca cctgacgaaa ccctcagccc      60
atatgagcga cgcggctgag tacttctgtg ttgtgagtga                          100

<210> SEQ ID NO 1272
<211> LENGTH: 100
<212> TYPE: DNA
<213> ORGANISM: Homo sapiens

<400> SEQUENCE: 1272
gttttgaggc tgaatttaag aagagtgaaa cctccttcca cctgacgaaa ccctcagccc      60
atatgagcga cgcggctgag tacttctgtg ctgtgagtga                          100

<210> SEQ ID NO 1273
<211> LENGTH: 100
<212> TYPE: DNA
<213> ORGANISM: Homo sapiens

<400> SEQUENCE: 1273
ggctacggtg tctcccgaga ggagaagggg ctgtttcttc tcatggtgaa gctggcccac      60
accagccaaa cagctctgta cttctgtcct gggagtgcac                          100

<210> SEQ ID NO 1274
<211> LENGTH: 100
<212> TYPE: DNA
<213> ORGANISM: Homo sapiens

<400> SEQUENCE: 1274
ggcctctctg gcaatcgctg aagacagaaa gtccagtacc ttgatcctgc accgtgctac      60
cttgagagat gctgctgtgt actactgcat cctgagagac                          100

<210> SEQ ID NO 1275
<211> LENGTH: 100
<212> TYPE: DNA
<213> ORGANISM: Homo sapiens

<400> SEQUENCE: 1275
gattttctgc agagaggctc aaaggagtag actccactct caagatccag cctgcaaagc      60
ttgaggactc ggccgtgtat ctctgtgcca gcagcttaga                          100

<210> SEQ ID NO 1276
<211> LENGTH: 100
<212> TYPE: DNA
<213> ORGANISM: Homo sapiens

<400> SEQUENCE: 1276
gattttctgc agagaggctc aaaggagtag actccactct caagatccag cctgcagagc      60
ttggggactc ggccgtgtat ctctgtgcca gcagcttaga                          100

<210> SEQ ID NO 1277
<211> LENGTH: 100
<212> TYPE: DNA
<213> ORGANISM: Homo sapiens

<400> SEQUENCE: 1277
```

```
gctttgaggc tgaatttata aagagtaaat tctcctttaa tctgaggaaa ccctctgtgc    60
agtggagtga cacagctgag tacttctgtg ccgtgaatgc                         100
```

<210> SEQ ID NO 1278
<211> LENGTH: 100
<212> TYPE: DNA
<213> ORGANISM: Homo sapiens

<400> SEQUENCE: 1278

```
caattctcca cagagaggtc tgaggatctt tctccacctg aagatccagc gcacagagca    60
agggcgactc ggctgtgtat ctctgtgtca gaagcttagc                          100
```

<210> SEQ ID NO 1279
<211> LENGTH: 100
<212> TYPE: DNA
<213> ORGANISM: Homo sapiens

<400> SEQUENCE: 1279

```
ggttctctgc agagaggcct gagggatcca tctccactct gacgatccag cgcacagagc    60
agcgggactc ggccatgtat cgctgtgcca gcagcttagc                          100
```

<210> SEQ ID NO 1280
<211> LENGTH: 100
<212> TYPE: DNA
<213> ORGANISM: Homo sapiens

<400> SEQUENCE: 1280

```
gataagtaaa aatgctcaca cttccacttc cactttgaaa ataaagttct tagagaaaga    60
agatgaggtg gtgtaccact gtgcctgctg gattaggcac                          100
```

<210> SEQ ID NO 1281
<211> LENGTH: 100
<212> TYPE: DNA
<213> ORGANISM: Homo sapiens

<400> SEQUENCE: 1281

```
agattaagag tcacgcttga cacttccaag aaaagcagtt ccttgttgat cacggcttcc    60
cgggcagcag acactgcttc ttacttctgt gctacggacg                          100
```

<210> SEQ ID NO 1282
<211> LENGTH: 100
<212> TYPE: DNA
<213> ORGANISM: Homo sapiens

<400> SEQUENCE: 1282

```
ggtacaaagt ctctcgaaaa gagaagagga atttccccct gatcctggag tcgcccagcc    60
ccaaccagac ctctctgtac ttctgtgcca gcagtttatc                          100
```

<210> SEQ ID NO 1283
<211> LENGTH: 100
<212> TYPE: DNA
<213> ORGANISM: Homo sapiens

<400> SEQUENCE: 1283

```
attctgtcaa cttcaagaaa gcagcgaaat ccgtcgcctt aaccatttca gccttacagc    60
tagaagattc agcaaagtac ttttgtgctc ttggggaact                          100
```

<210> SEQ ID NO 1284
<211> LENGTH: 100

```
<212> TYPE: DNA
<213> ORGANISM: Homo sapiens

<400> SEQUENCE: 1284
gattttctgc tgaatttccc aaagagggcc ccagcatcct gaggatccag caggtagtgc    60
gaggagattc ggcagcttat ttctgtgcca gctcaccacc                         100

<210> SEQ ID NO 1285
<211> LENGTH: 100
<212> TYPE: DNA
<213> ORGANISM: Homo sapiens

<400> SEQUENCE: 1285
agactcactg ttctattgaa taaaaaggat aaacatctgt ctctgcgcat tgcagacacc    60
cagactgggg actcagctat ctacttctgt gcagagagta                         100

<210> SEQ ID NO 1286
<211> LENGTH: 100
<212> TYPE: DNA
<213> ORGANISM: Homo sapiens

<400> SEQUENCE: 1286
agagtcaccg ttttattgaa taagacagtg aaacatctct ctctgcaaat tgcagctact    60
caacctggag actcagctgt ctacttttgt gcagagaata                         100

<210> SEQ ID NO 1287
<211> LENGTH: 100
<212> TYPE: DNA
<213> ORGANISM: Homo sapiens

<400> SEQUENCE: 1287
tttccaaggt gacattgata ttgcaaagaa cctggctgta cttaagatac ttgcaccatc    60
agagagagat gaagggtctt actactgtgc ctgtgacacc                         100

<210> SEQ ID NO 1288
<211> LENGTH: 100
<212> TYPE: DNA
<213> ORGANISM: Homo sapiens

<400> SEQUENCE: 1288
gtttttcttc attccttagt cggtctaaag ggtacagtta cctccttttg aaggagctcc    60
agatgaaaga ctctgcctct tacctctgtg ctgtgagaga                         100

<210> SEQ ID NO 1289
<211> LENGTH: 100
<212> TYPE: DNA
<213> ORGANISM: Homo sapiens

<400> SEQUENCE: 1289
gacggttttc tgtgaaacac attctgaccc agaaagcctt tcacttggtg atctctccag    60
taaggactga agacagtgcc acttactact gtgcctttag                         100

<210> SEQ ID NO 1290
<211> LENGTH: 100
<212> TYPE: DNA
<213> ORGANISM: Homo sapiens

<400> SEQUENCE: 1290
tattctgtga gcttccagaa aacaactaaa actattcagc ttatcatatc atcatcacag    60
```

```
ccagaagacc tgcaacatat ttctgttgtc tcaaagagcc                          100
```

<210> SEQ ID NO 1291
<211> LENGTH: 100
<212> TYPE: DNA
<213> ORGANISM: Homo sapiens

<400> SEQUENCE: 1291

```
agatatacag caactctgga tgcagacaca aagcaaagct ctctgcacat cacagcctcc    60
cagctcagcg attcagcctc ctacatctgt gtggtgagcg                          100
```

<210> SEQ ID NO 1292
<211> LENGTH: 100
<212> TYPE: DNA
<213> ORGANISM: Homo sapiens

<400> SEQUENCE: 1292

```
gaagactaaa atccgcagtc aaagctgagg aactttatgg ccacctatac atcagattcc    60
cagcctgagg actcagctat ttacttctgt gctgtgggga                          100
```

<210> SEQ ID NO 1293
<211> LENGTH: 100
<212> TYPE: DNA
<213> ORGANISM: Homo sapiens

<400> SEQUENCE: 1293

```
aaaacttcgg aggcggaaat attaaagaca aaaactcccc cattgtgaaa tattcagtcc    60
aggtatcaga ctcagccgtg tactactgtc ttctgggaga                          100
```

<210> SEQ ID NO 1294
<211> LENGTH: 100
<212> TYPE: DNA
<213> ORGANISM: Homo sapiens

<400> SEQUENCE: 1294

```
gcatgatact tatggaagta gaaggataag ctggaaattt atacctccaa aactaaatga    60
aaatgcctct ggggtctatt actgtgccac ctaggacagg                          100
```

<210> SEQ ID NO 1295
<211> LENGTH: 100
<212> TYPE: DNA
<213> ORGANISM: Homo sapiens

<400> SEQUENCE: 1295

```
gttttcaggc cagtcctatc aagagtgaca gttccttcca cctggagaag ccctcggtgc    60
agctgtcgga ctctgccgtg tactactgcg ctctgagaga                          100
```

<210> SEQ ID NO 1296
<211> LENGTH: 100
<212> TYPE: DNA
<213> ORGANISM: Homo sapiens

<400> SEQUENCE: 1296

```
ggtatcatgt ttcttgaaat actatagcat cttttcccct gaccctgaag tctgccagca    60
ccaaccagac atctgtgtat ctctatgcca gcagttcatc                          100
```

<210> SEQ ID NO 1297
<211> LENGTH: 100
<212> TYPE: DNA
<213> ORGANISM: Homo sapiens

<400> SEQUENCE: 1297 agagggtac tgtgtttctt gaaacaagct tgagcatttc cccaatcctg gcatccacca    60
gcaccagcca gacctatctg taccactgtg gcagcacatc    100

<210> SEQ ID NO 1298
<211> LENGTH: 100
<212> TYPE: DNA
<213> ORGANISM: Homo sapiens

<400> SEQUENCE: 1298
agataaaatc atagccaagg atggcagcag ctctatcttg gcagtactga agttggagac    60
aggcatcgag ggcatgaact actgcacaac ctgggccctg    100

<210> SEQ ID NO 1299
<211> LENGTH: 100
<212> TYPE: DNA
<213> ORGANISM: Homo sapiens

<400> SEQUENCE: 1299
gcctccctgt ttatccctgc cgacagaaag tccagcactc tgagcctgcc ccgggtttcc    60
ctgagcgaca ctgctgtgta ctactgcctc gtgggtgaca    100

<210> SEQ ID NO 1300
<211> LENGTH: 100
<212> TYPE: DNA
<213> ORGANISM: Homo sapiens

<400> SEQUENCE: 1300
aggctgaatt taagaagagc gaaacctcct tctacctgag gaaaccatca acccatgtga    60
gtgatgctgc tgagtacttc tgtgctgtgg gtgacaggag    100

<210> SEQ ID NO 1301
<211> LENGTH: 100
<212> TYPE: DNA
<213> ORGANISM: Homo sapiens

<400> SEQUENCE: 1301
cgaattgctg ttacattgaa caagacagcc aaacatttct ccctgcacat cacagagacc    60
caacctgaag actcggctgt ctacttctgt gcagcaagta    100

<210> SEQ ID NO 1302
<211> LENGTH: 100
<212> TYPE: DNA
<213> ORGANISM: Homo sapiens

<400> SEQUENCE: 1302
gactctgaga ccctctgcag cagcagccta tcagtgcagc cacatcctct ctgagcggat    60
atgacaaacc ccagggttga agcgacctaa cctatgagcc    100

<210> SEQ ID NO 1303
<211> LENGTH: 100
<212> TYPE: DNA
<213> ORGANISM: Homo sapiens

<400> SEQUENCE: 1303
tggacactta tcacttcccc aatcaatacc cctgtgattt cctatgcctg tctttacttt    60
aatctcttaa tcctgtcagc tgaggaggat gtatgtcacc    100

<210> SEQ ID NO 1304
<211> LENGTH: 100
<212> TYPE: DNA
<213> ORGANISM: Homo sapiens

<400> SEQUENCE: 1304

```
gattttcagc taagtgcctc ccaaattcac cctgtagcct tgagatccag gctacgaagc    60
ttgaggattc agcagtgtat ttttgtgcca gcagccaatc                         100
```

<210> SEQ ID NO 1305
<211> LENGTH: 100
<212> TYPE: DNA
<213> ORGANISM: Homo sapiens

<400> SEQUENCE: 1305

```
ggtatcatgt ttcttgaaat actatagcat ctttttctcct gaccctgaag tctgctagca   60
ccaaccagac atgtgtgtat ctctgcgcca gcagttcatc                         100
```

<210> SEQ ID NO 1306
<211> LENGTH: 100
<212> TYPE: DNA
<213> ORGANISM: Homo sapiens

<400> SEQUENCE: 1306

```
ggttctttgc agtcaggcct gagggatccg tctctactct gaagatccag cgcacagagc    60
aggggactc agccgcgtat ctccgtgcca gcagcttaac                          100
```

<210> SEQ ID NO 1307
<211> LENGTH: 100
<212> TYPE: DNA
<213> ORGANISM: Homo sapiens

<400> SEQUENCE: 1307

```
tgatcggttc tctgcagaga ggcctaaggg atctttctcc accttggaga tccagcgcac    60
agagcagggg gactcggcca tgtatctctg tgccagcagc                         100
```

<210> SEQ ID NO 1308
<211> LENGTH: 100
<212> TYPE: DNA
<213> ORGANISM: Homo sapiens

<400> SEQUENCE: 1308

```
cgattctccg cacaacagtt ccctgacttg cactctgaac taaacctgag ctctctggag    60
ctgggggact cagctttgta tttctgtgcc agcagcgtag                         100
```

<210> SEQ ID NO 1309
<211> LENGTH: 100
<212> TYPE: DNA
<213> ORGANISM: Homo sapiens

<400> SEQUENCE: 1309

```
acaagttttcc catcagccgc ccaaacctaa cattctcaac tctgactgtg agcaacagga   60
gacctgaaga cagcagcata tacctctgca gcgttgaaga                         100
```

<210> SEQ ID NO 1310
<211> LENGTH: 100
<212> TYPE: DNA
<213> ORGANISM: Homo sapiens

<400> SEQUENCE: 1310

```
gttttgaggc tgaatttaac aagagtcaaa cttccttcca cttgaggaaa ccctcagtcc    60
atataagcga cacggctgag tacttctgtg ctgtgagtga                         100

<210> SEQ ID NO 1311
<211> LENGTH: 100
<212> TYPE: DNA
<213> ORGANISM: Homo sapiens

<400> SEQUENCE: 1311
gttatagtgt ctccagagca aacacagatg atttccccct cacgttggcg tctgctgtac    60
cctctcagac atctgtgtac ttctgtgcca gcagtgactc                         100

<210> SEQ ID NO 1312
<211> LENGTH: 100
<212> TYPE: DNA
<213> ORGANISM: Homo sapiens

<400> SEQUENCE: 1312
agatggctac agtgtctcta gatcaaacac agaggacctc cccctcactc tggagtctgc    60
tgcctcctcc cagacatctg tatatttctg cgccagcagt                         100

<210> SEQ ID NO 1313
<211> LENGTH: 100
<212> TYPE: DNA
<213> ORGANISM: Homo sapiens

<400> SEQUENCE: 1313
gctacaatgt ctccagatta aaaaaacaga atttcctgct ggggttggag tcggctgctc    60
cctcccaaac atctgtgtac ttctgtgcca gcagttactc                         100

<210> SEQ ID NO 1314
<211> LENGTH: 100
<212> TYPE: DNA
<213> ORGANISM: Homo sapiens

<400> SEQUENCE: 1314
aatagagaca cggggcatgg tatgaaagta ttacctccca gttgcaattt ggcaaaggaa    60
ccagagtttc cacttctccc cgtacgtctg cccatgccca                         100

<210> SEQ ID NO 1315
<211> LENGTH: 100
<212> TYPE: DNA
<213> ORGANISM: Homo sapiens

<400> SEQUENCE: 1315
gaggcatcaa acactgtgat actcacggga ggaggaaaca aactcacctt tgggacaggc    60
actcagctaa aagtggaact cagtaagtat gagattctat                         100

<210> SEQ ID NO 1316
<211> LENGTH: 100
<212> TYPE: DNA
<213> ORGANISM: Homo sapiens

<400> SEQUENCE: 1316
tatggggatt tgctatagtg tgaattcagg atacagcacc ctcacctttg ggaaggggac    60
tatgcttcta gtctctccag gtacatgttg accccatccc                         100

<210> SEQ ID NO 1317
```

```
<211> LENGTH: 100
<212> TYPE: DNA
<213> ORGANISM: Homo sapiens

<400> SEQUENCE: 1317
actgactaag aaacactgtg ggatggatag cagctataaa ttgatcttcg ggagtgggac    60
cagactgctg gtcaggcctg gtaagtaagg tgtcagagag                         100

<210> SEQ ID NO 1318
<211> LENGTH: 100
<212> TYPE: DNA
<213> ORGANISM: Homo sapiens

<400> SEQUENCE: 1318
aaggcaggca ttacagtgtg aattctgggg gttaccagaa agttaccttt ggaattggaa    60
caaagctcca agtcatccca agtgagtcca atttcctatg                         100

<210> SEQ ID NO 1319
<211> LENGTH: 100
<212> TYPE: DNA
<213> ORGANISM: Homo sapiens

<400> SEQUENCE: 1319
aaaggcaggc attacagtgt gaattctggg ggttaccaga aagttacctt tggaactgga    60
acaaagctcc aagtcatccc aagtgagtcc aatttcctat                         100

<210> SEQ ID NO 1320
<211> LENGTH: 100
<212> TYPE: DNA
<213> ORGANISM: Homo sapiens

<400> SEQUENCE: 1320
tttgtcaggc agcacagtgc tgtgatttat agcacattca tctttgggag tgggacaaga    60
ttatcagtaa aacctggtaa gtaggcaata tgtcactaaa                         100

<210> SEQ ID NO 1321
<211> LENGTH: 100
<212> TYPE: DNA
<213> ORGANISM: Homo sapiens

<400> SEQUENCE: 1321
cagggcctca tttcactgtg ccaaccaggc aggaactgct ctgatctttg ggaagggaac    60
caccttatca gtgagttcca gtaagtacct gataattatt                         100

<210> SEQ ID NO 1322
<211> LENGTH: 100
<212> TYPE: DNA
<213> ORGANISM: Homo sapiens

<400> SEQUENCE: 1322
cagggcctca tttcactgtg ccaaccaggc aggaactgct ctgatctttg ggaagggaac    60 ccaccctatca gtgagttcca gtaagtacct gataattatt                        100

<210> SEQ ID NO 1323
<211> LENGTH: 100
<212> TYPE: DNA
<213> ORGANISM: Homo sapiens

<400> SEQUENCE: 1323
tggtacaata gatcactgtg ggttttcaga tggccagaag ctgctctttg caaggggaac    60
```

```
catgttaaag gtggatctta gtaagtatta ttactaatga                          100
```

<210> SEQ ID NO 1324
<211> LENGTH: 100
<212> TYPE: DNA
<213> ORGANISM: Homo sapiens

<400> SEQUENCE: 1324

```
cctgtggttt ttgctgggcc ttaaatcatt gtgtgatcaa agctgcaggc aacaagctaa    60
cttttggagg aggaaccagg gtgctagtta aaccaagtga                          100
```

<210> SEQ ID NO 1325
<211> LENGTH: 100
<212> TYPE: DNA
<213> ORGANISM: Homo sapiens

<400> SEQUENCE: 1325

```
aggggaccag cattgtgccg acagaggctc aaccctgggg aggctatact ttggaagagg    60
aactcagttg actgtctggc ctggtgagtg agtcgctttc                          100
```

<210> SEQ ID NO 1326
<211> LENGTH: 100
<212> TYPE: DNA
<213> ORGANISM: Homo sapiens

<400> SEQUENCE: 1326

```
ttttgcagag gacagatgtg gctatcaaag attttacaat ttcacctttg gaaagggatc    60
caaacataat gtcactccaa gtaagtgagc agccttttgt                          100
```

<210> SEQ ID NO 1327
<211> LENGTH: 100
<212> TYPE: DNA
<213> ORGANISM: Homo sapiens

<400> SEQUENCE: 1327

```
tggtgtcacc tacggtatga atactggagg aacaattgat aaactcacat ttgggaaagg    60
gacccatgta ttcattatat ctggtgagtc atcccaggtg                          100
```

<210> SEQ ID NO 1328
<211> LENGTH: 100
<212> TYPE: DNA
<213> ORGANISM: Homo sapiens

<400> SEQUENCE: 1328

```
tgtaggcgac ctcgcactgt ggttctaacg actacaagct cagctttgga gccggaacca    60
cagtaactgt aagagcaagt aagtaagaaa gaaaagtcca                          100
```

<210> SEQ ID NO 1329
<211> LENGTH: 100
<212> TYPE: DNA
<213> ORGANISM: Homo sapiens

<400> SEQUENCE: 1329

```
tgtaatgcca ataaacatgg tgtacaactt caacaaattt tactttggat ctgggaccaa    60
actcaatgta aaaccaagta agttatagtt gcctagaaga                          100
```

<210> SEQ ID NO 1330
<211> LENGTH: 100
<212> TYPE: DNA

<213> ORGANISM: Homo sapiens

<400> SEQUENCE: 1330

```
gttgagcaaa tcatagtgtt tcttctggtt ctgcaaggca actgaccttt ggatctggga    60
cacaattgac tgttttacct ggtaggctgc ctcaattaaa                         100
```

<210> SEQ ID NO 1331
<211> LENGTH: 100
<212> TYPE: DNA
<213> ORGANISM: Homo sapiens

<400> SEQUENCE: 1331

```
aggatatgta acacagtgtg atttataacc agggaggaaa gcttatcttc ggacagggaa    60
cggagttatc tgtgaaaccc agtaagtata aaattgtatc                         100
```

<210> SEQ ID NO 1332
<211> LENGTH: 100
<212> TYPE: DNA
<213> ORGANISM: Homo sapiens

<400> SEQUENCE: 1332

```
gactggatgt gtttttgaca ggatatgtaa cacagtgtga tttataacca gggaggaaag    60
cttatcttcg gacagggaac ggagctatct gtgaaaccca                         100
```

<210> SEQ ID NO 1333
<211> LENGTH: 100
<212> TYPE: DNA
<213> ORGANISM: Homo sapiens

<400> SEQUENCE: 1333

```
gaggtgtttg tcacagtgtg acaactgaca gctgggggaa attcgagttt ggagcaggga    60
cccaggttgt ggtcacccca ggtaagccca ttcctggagc                         100
```

<210> SEQ ID NO 1334
<211> LENGTH: 100
<212> TYPE: DNA
<213> ORGANISM: Homo sapiens

<400> SEQUENCE: 1334

```
gaggtgtttg tcacagtgtg acaactgaca gctgggggaa attgcagttt ggagcaggga    60
cccaggttgt ggtcacccca ggtaagcccc attccctgga                         100
```

<210> SEQ ID NO 1335
<211> LENGTH: 100
<212> TYPE: DNA
<213> ORGANISM: Homo sapiens

<400> SEQUENCE: 1335

```
atgctgagat aatcactatg cagaaggaca aggcttctcc tttatctttg ggaaggggac    60
aaggctgctt gtcaagccaa gtaagtgaca tataatttat                         100
```

<210> SEQ ID NO 1336
<211> LENGTH: 100
<212> TYPE: DNA
<213> ORGANISM: Homo sapiens

<400> SEQUENCE: 1336

```
ctgagcccag aaacactgtg gggataacta tggtcagaat tttgtctttg gtcccggaac    60
cagattgtcc gtgctgccct gtaagtacag ttaagtggag                         100
```

<210> SEQ ID NO 1337
<211> LENGTH: 100
<212> TYPE: DNA
<213> ORGANISM: Homo sapiens

<400> SEQUENCE: 1337
caatagcact aaagactgtg taacaccaat gcaggcaaat caacctttgg ggatgggact    60
acgctcactg tgaagccaag taagttgtgt tcttctttgc                         100

<210> SEQ ID NO 1338
<211> LENGTH: 100
<212> TYPE: DNA
<213> ORGANISM: Homo sapiens

<400> SEQUENCE: 1338
agaaaggaaa ctctgtgcat actctggggc tgggagttac caactcactt tcgggaaggg    60
gaccaaactc tcggtcatac caagtaagtt cttctttctg                         100

<210> SEQ ID NO 1339
<211> LENGTH: 100
<212> TYPE: DNA
<213> ORGANISM: Homo sapiens

<400> SEQUENCE: 1339
ttatggagga aatcactgtg ggaattcagg aaacacacct cttgtctttg gaaagggcac    60
aagactttct gtgattgcaa gtaagtgttt ctagccatcc                         100

<210> SEQ ID NO 1340
<211> LENGTH: 100
<212> TYPE: DNA
<213> ORGANISM: Homo sapiens

<400> SEQUENCE: 1340
aaagacctta cccacagtgg gggtacagca gtgcttccaa gataatcttt ggatcaggga    60
ccagactcag catccggcca agtaagtaga atgaagcagg                         100

<210> SEQ ID NO 1341
<211> LENGTH: 100
<212> TYPE: DNA
<213> ORGANISM: Homo sapiens

<400> SEQUENCE: 1341
gttatggtcc caatcacagt gtgaacagag atgacaagat catctttgga aaagggacac    60
gacttcatat tctccccagt aagtgctgtt tatgtgattt                         100

<210> SEQ ID NO 1342
<211> LENGTH: 100
<212> TYPE: DNA
<213> ORGANISM: Homo sapiens

<400> SEQUENCE: 1342
agtaaaggca ggaagtgctg tggaataaca atgccagact catgtttgga gatggaactc    60
agctggtggt gaagcccagt aagtggccat gttttattga                         100

<210> SEQ ID NO 1343
<211> LENGTH: 100
<212> TYPE: DNA
<213> ORGANISM: Homo sapiens

<400> SEQUENCE: 1343
ggctctgaag gactgtgtga attatggcgg tgctacaaac aagctcatct ttggaactgg    60
cactctgctt gctgtccagc caagtacgta agtagtggca                         100

<210> SEQ ID NO 1344
<211> LENGTH: 100
<212> TYPE: DNA
<213> ORGANISM: Homo sapiens

<400> SEQUENCE: 1344
gtgattcagc cacctacctc tgtgccgatg gtggtgctac aaacaagctc atctttggaa    60
ctggcactct gcttgctgtc cagccaaata tccagaaccc                         100

<210> SEQ ID NO 1345
<211> LENGTH: 100
<212> TYPE: DNA
<213> ORGANISM: Homo sapiens

<400> SEQUENCE: 1345
gttaaggttt ttgtgtctgt gtggatagca actatcagtt aatctggggc gctgggacca    60
agctaattat aaagccaggt aagtctcaga gatgtgactg                         100

<210> SEQ ID NO 1346
<211> LENGTH: 89
<212> TYPE: DNA
<213> ORGANISM: Homo sapiens

<400> SEQUENCE: 1346 aggttttgt agatctcagt atcactgtgt cttataacac cgacaagctc atctttggga    60
ctgggaccag attacaagtc tttccaagt                                      89

<210> SEQ ID NO 1347
<211> LENGTH: 100
<212> TYPE: DNA
<213> ORGANISM: Homo sapiens

<400> SEQUENCE: 1347
taaaagaatg agccattgtg ataggctttt gggaatgtgc tgcattgcgg gtccggcact    60
caagtgattg ttttaccacg taagtatatc ttttctcatt                         100

<210> SEQ ID NO 1348
<211> LENGTH: 100
<212> TYPE: DNA
<213> ORGANISM: Homo sapiens

<400> SEQUENCE: 1348
tactgggcag aaacactgtg tcaaactggg gcaaacaacc tcttctttgg gactggaacg    60
agactcaccg ttattccctg taagtcctta cctcttgaca                         100

<210> SEQ ID NO 1349
<211> LENGTH: 100
<212> TYPE: DNA
<213> ORGANISM: Homo sapiens

<400> SEQUENCE: 1349
aaagtacagc attagagtgt ggctctggca acacaggcaa actaatcttt gggcaaggga    60
caactttaca agtaaaacca ggtaggtctg gatgtttcca                         100

<210> SEQ ID NO 1350
<211> LENGTH: 100
<212> TYPE: DNA
<213> ORGANISM: Homo sapiens

<400> SEQUENCE: 1350
ctcagcggtg tacttctgtg ctcttcatgg ctctagcaac acaggcaaac taatctttgg    60
gcaagggaca actttacaag taaaaccaga tatccagaac                         100

<210> SEQ ID NO 1351
<211> LENGTH: 100
<212> TYPE: DNA
<213> ORGANISM: Homo sapiens

<400> SEQUENCE: 1351
aaagctttct atgactgtgt aatgctggca acaaccgtaa gctgatttgg ggattgggaa    60
caagcctggc agtaaatccg agtgagtctt cgtgttaact                         100

<210> SEQ ID NO 1352
<211> LENGTH: 100
<212> TYPE: DNA
<213> ORGANISM: Homo sapiens

<400> SEQUENCE: 1352
cagccgaaga tcactgtgtg aataataatg caggcaacat gctcaccttt ggaggggaa     60 caaggttaat ggtcaaaccc cgtgagtatc tctgctgaat                         100

<210> SEQ ID NO 1353
<211> LENGTH: 100
<212> TYPE: DNA
<213> ORGANISM: Homo sapiens

<400> SEQUENCE: 1353
aagcaccatc tgattgtgtg ttttctggtg gctacaataa gctgattttt ggagcaggga    60
ccaggctggc tgtacaccca tgtgagtatg accctgcaag                         100

<210> SEQ ID NO 1354
<211> LENGTH: 97
<212> TYPE: DNA
<213> ORGANISM: Homo sapiens

<400> SEQUENCE: 1354
tatgttggtt tatgtagaga cacataacac tgtgactacc tcaggaacct acaaatacat    60
ctttggaaca ggcaccaggc tgaaggtttt agcaagt                            97

<210> SEQ ID NO 1355
<211> LENGTH: 100
<212> TYPE: DNA
<213> ORGANISM: Homo sapiens

<400> SEQUENCE: 1355
ttagggagaa cgcactgtgg aactcaaatt ccgggtatgc actcaacttc ggcaaaggca    60
cctcgctgtt ggtcacaccc cgtgagtttt tgtggtttac                         100

<210> SEQ ID NO 1356
<211> LENGTH: 100
<212> TYPE: DNA
<213> ORGANISM: Homo sapiens

<400> SEQUENCE: 1356

```
agccccatag gactgtgtga attatggagg aagccaagga aatctcatct ttggaaaagg      60
cactaaactc tctgttaaac caagtaagtg ttggggattc                          100

<210> SEQ ID NO 1357
<211> LENGTH: 100
<212> TYPE: DNA
<213> ORGANISM: Homo sapiens

<400> SEQUENCE: 1357
ttgttagagc atgtattact gtgacaataa caatgacatg cgctttggag cagggaccag      60
actgacagta aaaccaagta agttggggga atgggtcaat                          100

<210> SEQ ID NO 1358
<211> LENGTH: 94
<212> TYPE: DNA
<213> ORGANISM: Homo sapiens

<400> SEQUENCE: 1358
aggtttctgt tatgaagcat ctcacagtgt aaataccggc actgccagta aactcacctt      60
tgggactgga acaagacttc aggtcacgct cggt                                 94

<210> SEQ ID NO 1359
<211> LENGTH: 100
<212> TYPE: DNA
<213> ORGANISM: Homo sapiens

<400> SEQUENCE: 1359
agggttggcc cagagtgtgt attcaggagg aggtgctgac ggactcacct ttggcaaagg      60
gactcatcta atcatccagc cctgtaagtg cttttgcctg                          100

<210> SEQ ID NO 1360
<211> LENGTH: 100
<212> TYPE: DNA
<213> ORGANISM: Homo sapiens

<400> SEQUENCE: 1360
aagctgctga cagccgtgag aagaaaagca gcggagacaa gctgactttt gggaccggga      60
ctcgtttagc agttaggccc agtaagtctg agcagaaagt                          100

<210> SEQ ID NO 1361
<211> LENGTH: 100
<212> TYPE: DNA
<213> ORGANISM: Homo sapiens

<400> SEQUENCE: 1361
gtagaggagt ttgacgctgt gtggaatatg gaaacaaact ggtctttggc gcaggaacca      60
ttctgagagt caagtcctgt gagtatataaaa cacactcaag                        100

<210> SEQ ID NO 1362
<211> LENGTH: 100
<212> TYPE: DNA
<213> ORGANISM: Homo sapiens

<400> SEQUENCE: 1362
gtgtactatt gcatctcggc cctggaatat ggaaacaagc tggtctttgg cgcaggaacc      60
attctgagag tcaagtccta tatccagaac cctgaccctg                          100

<210> SEQ ID NO 1363
<211> LENGTH: 100
```

<212> TYPE: DNA
<213> ORGANISM: Homo sapiens

<400> SEQUENCE: 1363

```
atgacttaga acactgtgta tctaactttg gaaatgagaa attaaccttt gggactggaa      60
caagactcac catcataccc agtaagttct tcatccttgg                           100
```

<210> SEQ ID NO 1364
<211> LENGTH: 100
<212> TYPE: DNA
<213> ORGANISM: Homo sapiens

<400> SEQUENCE: 1364

```
tgttgagctt cctatcacag tggaacaccg gtaaccagtt ctattttggg acagggacaa      60
gtttgacggt cattccaagt aagtcaaaga aaattttcca                           100
```

<210> SEQ ID NO 1365
<211> LENGTH: 100
<212> TYPE: DNA
<213> ORGANISM: Homo sapiens

<400> SEQUENCE: 1365

```
tactgtgatg taccagggtg tggacacggg caggagagca cttacttttg ggagtggaac      60
aagactccaa gtgcaaccaa gtaagtaccc aaacttaggc                           100
```

<210> SEQ ID NO 1366
<211> LENGTH: 100
<212> TYPE: DNA
<213> ORGANISM: Homo sapiens

<400> SEQUENCE: 1366

```
taaaggtttg gatggctgtg tgaaaacctc ctacgacaag gtgatatttg ggccagggac      60
aagcttatca gtcattccaa gtaagtgtcc ctggggtgct                           100
```

<210> SEQ ID NO 1367
<211> LENGTH: 100
<212> TYPE: DNA
<213> ORGANISM: Homo sapiens

<400> SEQUENCE: 1367

```
aaactccctg aagcagggag atgcgtgaca gctatgagaa gctgatattt ggaaaggaga      60
catgactaac tgtgaagcca agcaagctgg aaagacctaa                           100
```

<210> SEQ ID NO 1368
<211> LENGTH: 100
<212> TYPE: DNA
<213> ORGANISM: Homo sapiens

<400> SEQUENCE: 1368

```
gcctccagtg cagtgctaat gctggtggta ctagctatgg aaagctgaca tttggacaag      60
ggaccatctt gactgtccat ccaagtaagt gtaacaagac                           100
```

<210> SEQ ID NO 1369
<211> LENGTH: 100
<212> TYPE: DNA
<213> ORGANISM: Homo sapiens

<400> SEQUENCE: 1369

```
agccttctgt ggctgtgaga atagtggagg tagcaactat aaactgacat ttggaaaagg      60
```

```
aactctctta accgtgaatc caagtaagtt tgaagggagt                                100
```

<210> SEQ ID NO 1370
<211> LENGTH: 100
<212> TYPE: DNA
<213> ORGANISM: Homo sapiens

<400> SEQUENCE: 1370

```
taaagcctcg tgctgtggtg taattcaggg agcccagaag ctggtatttg gccaaggaac         60
caggctgact atcaacccaa gtaagtatga cagggtgaag                              100
```

<210> SEQ ID NO 1371
<211> LENGTH: 100
<212> TYPE: DNA
<213> ORGANISM: Homo sapiens

<400> SEQUENCE: 1371

```
gaggatggat ccctgttagt gacaagtgct ggtaatgctc ctgttgggga aagggatga          60
gtacaaaaat aaatccaagt aagtgtggag ggacaagaag                              100
```

<210> SEQ ID NO 1372
<211> LENGTH: 100
<212> TYPE: DNA
<213> ORGANISM: Homo sapiens

<400> SEQUENCE: 1372

```
agatcctcgt gtcattgtgt tatactggag ccaatagtaa gctgacattt ggaaaaggaa         60
taactctgag tgttagacca ggtatgtttt aatgaatgtt                              100
```

<210> SEQ ID NO 1373
<211> LENGTH: 100
<212> TYPE: DNA
<213> ORGANISM: Homo sapiens

<400> SEQUENCE: 1373

```
aagcagtctg tggggtgta actcagggcg atctgaaaa gctggtcttt ggaaagggaa           60
cgaaactgac agtaaaccca tgtaagtctg aataatgctt                              100
```

<210> SEQ ID NO 1374
<211> LENGTH: 100
<212> TYPE: DNA
<213> ORGANISM: Homo sapiens

<400> SEQUENCE: 1374

```
aagcccctca gcacagtgtt taagaaacca gtggctctag gttgaccttt ggggaaggaa         60
cacagctcac agtgaatcct ggtaagtgga ggggagcatt                              100
```

<210> SEQ ID NO 1375
<211> LENGTH: 100
<212> TYPE: DNA
<213> ORGANISM: Homo sapiens

<400> SEQUENCE: 1375

```
atgtaaaggc agcagctcct gtgggaagga aggaaacagg aaatttacat ttggaatggg         60
gacgcaagtg agagtgaagc tatctttaaa ccaaaggtgt                              100
```

<210> SEQ ID NO 1376
<211> LENGTH: 98
<212> TYPE: DNA
<213> ORGANISM: Homo sapiens

```
<400> SEQUENCE: 1376
caggttttat caaaggctgt cctcactgtg tgcatcagga ggaagctaca tacctacatt    60
tggaagagga accagcctta ttgttcatcc gtgtaagt                            98

<210> SEQ ID NO 1377
<211> LENGTH: 100
<212> TYPE: DNA
<213> ORGANISM: Homo sapiens

<400> SEQUENCE: 1377
gtaaagggcc tgggcactat gtgaagatca cctagatgct caactttggg aaggggactg    60
agttaattgt gagcctgggt gagtacctca actccagagg                         100

<210> SEQ ID NO 1378
<211> LENGTH: 100
<212> TYPE: DNA
<213> ORGANISM: Homo sapiens

<400> SEQUENCE: 1378
taaaggtgcc cactcctgtg ggtaccgggt taataggaaa ctgacatttg gagccaacac    60
tagaggaatc atgaaactca gcaagtaata tttggcagaa                         100

<210> SEQ ID NO 1379
<211> LENGTH: 100
<212> TYPE: DNA
<213> ORGANISM: Homo sapiens

<400> SEQUENCE: 1379
tgtaatacac ttacacagtg tgactatggg aacaacagac tcgcttttgg gaaggggaac    60
caagtggtgg tcataccaag taagtgagct gggatcctcc                         100

<210> SEQ ID NO 1380
<211> LENGTH: 100
<212> TYPE: DNA
<213> ORGANISM: Homo sapiens

<400> SEQUENCE: 1380
tacagagtta tgtcagagtg tgaacacagg ctttcagaaa cttgtatttg gaactggcac    60
ccgacttctg gtcagtccaa gtaagtcaaa tctgcagaaa                         100

<210> SEQ ID NO 1381
<211> LENGTH: 100
<212> TYPE: DNA
<213> ORGANISM: Homo sapiens

<400> SEQUENCE: 1381
cgcagtgcaa atcactgtgg gaaatactgg aggcttcaaa actatctttg gagcaggaac    60
aagactattt gttaaagcaa gtaagttcca tgaaataacc                         100

<210> SEQ ID NO 1382
<211> LENGTH: 100
<212> TYPE: DNA
<213> ORGANISM: Homo sapiens

<400> SEQUENCE: 1382
ttttcacctt gaccectgtc actgtgtgaa cactgaagct ttctttggac aaggcaccag    60
actcacagtt gtaggtaaga cattttttcag gttcttttgc                        100
```

<210> SEQ ID NO 1383
<211> LENGTH: 100
<212> TYPE: DNA
<213> ORGANISM: Homo sapiens

<400> SEQUENCE: 1383
ttttagagtg gctatattct tatgtgctaa ctatggctac accttcggtt cggggaccag    60
gttaaccgtt gtaggtaagg ctgggggtct ctaggagggg                         100

<210> SEQ ID NO 1384
<211> LENGTH: 100
<212> TYPE: DNA
<213> ORGANISM: Homo sapiens

<400> SEQUENCE: 1384
tttgaagtgg ccctgggagg ctgtgctctg gaaacaccat atattttgga gagggaagtt    60
ggctcactgt tgtaggtgag taagtcaagg ctggacagct                         100

<210> SEQ ID NO 1385
<211> LENGTH: 100
<212> TYPE: DNA
<213> ORGANISM: Homo sapiens

<400> SEQUENCE: 1385
ttccttccag tctttaatgt tgtgcaacta atgaaaaact gttttttggc agtggaaccc    60
agctctctgt cttgggtatg taaaagactt ctttcgggat                         100

<210> SEQ ID NO 1386
<211> LENGTH: 100
<212> TYPE: DNA
<213> ORGANISM: Homo sapiens

<400> SEQUENCE: 1386
tttgccacac tcatgatgca ctgtgtagca atcagcccca gcattttggt gatgggactc    60
gactctccat cctaggtaag ttggcagaat cagggtggta                         100

<210> SEQ ID NO 1387
<211> LENGTH: 100
<212> TYPE: DNA
<213> ORGANISM: Homo sapiens

<400> SEQUENCE: 1387
ttatctaagc ctctgcagct gtgctcctat aattcacccc tccactttgg gaatgggacc    60
aggctcactg tgacaggtat gggggctcca ctcttgactc                         100

<210> SEQ ID NO 1388
<211> LENGTH: 100
<212> TYPE: DNA
<213> ORGANISM: Homo sapiens

<400> SEQUENCE: 1388
ttatctaagc ctctgcagct gtgctcctat aattcacccc tccactttgg gaacgggacc    60
aggctcactg tgacaggtat gggggctcca ctcttgactc                         100

<210> SEQ ID NO 1389
<211> LENGTH: 100
<212> TYPE: DNA
<213> ORGANISM: Homo sapiens

<400> SEQUENCE: 1389

```
ttctgggcag cccctteeca ctgtgctcct acaatgagca gttcttcggg ccagggacac    60
ggctcaccgt gctaggtaag aagggggctc caggtgggag                         100
```

<210> SEQ ID NO 1390
<211> LENGTH: 100
<212> TYPE: DNA
<213> ORGANISM: Homo sapiens

<400> SEQUENCE: 1390

```
tgcgccaggg tccccagggc tgtgcgaaca ccggggagct gttttttgga gaaggctcta    60
ggctgaccgt actgggtaag gaggcggctg gggctccgga                         100
```

<210> SEQ ID NO 1391
<211> LENGTH: 100
<212> TYPE: DNA
<213> ORGANISM: Homo sapiens

<400> SEQUENCE: 1391

```
agctgcccca ctctgagagg ggctgtgctg agaggcgctg ctgggcgtct gggcggagga    60
ctcctggttc tgggtgctgg gagagcgatg gggctctcag                         100
```

<210> SEQ ID NO 1392
<211> LENGTH: 100
<212> TYPE: DNA
<213> ORGANISM: Homo sapiens

<400> SEQUENCE: 1392

```
ttttgtcctg ggcctccagg ctgtgagcac agatacgcag tattttggcc caggcacccg    60
gctgacagtg ctcggtaagc gggggctccc gctgaagccc                         100
```

<210> SEQ ID NO 1393
<211> LENGTH: 100
<212> TYPE: DNA
<213> ORGANISM: Homo sapiens

<400> SEQUENCE: 1393

```
ttctgtgccg cgtctcgggg ctgtgagcca aaaacattca gtacttcggc gccgggaccc    60
ggctctcagt gctgggtaag ctggggccgc cgggggaccg                         100
```

<210> SEQ ID NO 1394
<211> LENGTH: 100
<212> TYPE: DNA
<213> ORGANISM: Homo sapiens

<400> SEQUENCE: 1394

```
tttttgtgcg gggctcgggg gccgtgacca agagacccag tacttcgggc caggcacgcg    60
gctcctggtg ctcggtgagc gcgggctgct ggggcgcggg                         100
```

<210> SEQ ID NO 1395
<211> LENGTH: 100
<212> TYPE: DNA
<213> ORGANISM: Homo sapiens

<400> SEQUENCE: 1395

```
ttgcggggag tccccgggct gtgctctggg gccaacgtcc tgactttcgg ggccggcagc    60
aggctgaccg tgctgggtga gttttcgcgg gaccacccgg                         100
```

<210> SEQ ID NO 1396

```
<211> LENGTH: 100
<212> TYPE: DNA
<213> ORGANISM: Homo sapiens

<400> SEQUENCE: 1396
tttgcatgcg ggggtgcacc tccgtgctcc tacgagcagt acttcgggcc gggcaccagg    60
ctcacggtca caggtgagat cgggcgtct ccccaccttc                           100

<210> SEQ ID NO 1397
<211> LENGTH: 100
<212> TYPE: DNA
<213> ORGANISM: Homo sapiens

<400> SEQUENCE: 1397
tttgcatgcg gggatgcacc tccgtgctcc tacgagcagt acgtcgggcc gggcaccagg    60
ctcacggtca caggtgagat cgggcgtct ccccaccttc                           100

<210> SEQ ID NO 1398
<211> LENGTH: 100
<212> TYPE: DNA
<213> ORGANISM: Homo sapiens

<400> SEQUENCE: 1398
ttttggaacg tcctcaagtg ctgtgacacc gataaactca tctttggaaa aggaacccgt    60
gtgactgtgg aaccaagtaa gtaactcatt atttatctga                          100

<210> SEQ ID NO 1399
<211> LENGTH: 100
<212> TYPE: DNA
<213> ORGANISM: Homo sapiens

<400> SEQUENCE: 1399
tttttcgtaa tgacgcctgt ggtagtgctt tgacagcaca actcttcttt ggaaagggaa    60
cacaactcat cgtggaacca ggtaagttat gcattttact                          100

<210> SEQ ID NO 1400
<211> LENGTH: 100
<212> TYPE: DNA
<213> ORGANISM: Homo sapiens

<400> SEQUENCE: 1400
tgaggcactg tcataatgtg ctcctgggac acccgacaga tgttttttcgg aactggcatc   60 aaactcttcg tggagccccg tgagttgatc ttttttcctat                         100

<210> SEQ ID NO 1401
<211> LENGTH: 76
<212> TYPE: DNA
<213> ORGANISM: Homo sapiens

<400> SEQUENCE: 1401
atgagacata caaaaaggta atgccgcccc agacccctga tctttggcaa aggaacctat    60
ctggaggtac aacaac                                                    76

<210> SEQ ID NO 1402
<211> LENGTH: 100
<212> TYPE: DNA
<213> ORGANISM: Homo sapiens

<400> SEQUENCE: 1402
ttttgatatg gactgaatca ctgtggaatt attataagaa actctttggc agtggaacaa    60
```

```
cactggttgt cacaggtaag tatcggaaga atacaacatt                    100

<210> SEQ ID NO 1403
<211> LENGTH: 71
<212> TYPE: DNA
<213> ORGANISM: Homo sapiens

<400> SEQUENCE: 1403
tactgtgcct tgtgggaggt gcttattata agaaactctt tggcagtgga acaacacttg    60
ttgtcacagg t                                                          71

<210> SEQ ID NO 1404
<211> LENGTH: 100
<212> TYPE: DNA
<213> ORGANISM: Homo sapiens

<400> SEQUENCE: 1404
ttttgatatg gactgaatca ctgtggaatt attataagaa actctttggc agtggaacaa    60
cacttgttgt cacaggtaag tatcggaaga atacaacatt                         100

<210> SEQ ID NO 1405
<211> LENGTH: 100
<212> TYPE: DNA
<213> ORGANISM: Homo sapiens

<400> SEQUENCE: 1405
ataaaggctt ctcaggtggt gggcaagagt tgggcaaaaa aatcaaggta tttggtcccg    60
gaacaaagct tatcattaca ggtaagtttt ctttaaattt                         100

<210> SEQ ID NO 1406
<211> LENGTH: 94
<212> TYPE: DNA
<213> ORGANISM: Homo sapiens

<400> SEQUENCE: 1406
gatttttcta gaagcttaga ccggtgtgat accactggtt ggttcaagat atttgctgaa    60
gggactaagc tcatagtaac ttcacctggt aagt                                94

<210> SEQ ID NO 1407
<211> LENGTH: 94
<212> TYPE: DNA
<213> ORGANISM: Homo sapiens

<400> SEQUENCE: 1407
gatttttgta gaagcttaga ccagtgtgat agtagtgatt ggatcaagac gtttgcaaaa    60
gggactaggc tcatagtaac ttcgcctggt aagt                                94
```

HYBRID-CAPTURE SEQUENCING FOR DETERMINING IMMUNE CELL CLONALITY

CROSS-REFERENCE TO RELATED APPLICATIONS

This application is a national phase application under 35 U.S.C. § 371 of International Application No. PCT/CA2017/000084 filed 13 Apr. 2017, which claims priority to U.S. Provisional Application No. 62/322,999 filed 15 Apr. 2016. The entire contents of each of the above-referenced disclosures is specifically incorporated by reference herein without disclaimer.

FIELD OF THE INVENTION

The invention relates to methods of capturing and sequencing immune-associated nucleotide sequences, and more particularly to methods of determining clonality of immune cells.

BACKGROUND OF THE INVENTION

The maturation of lymphocytes is a fascinating process that is marked not only by immunophenotypic changes, but also by discrete and regulated molecular events[1-3]. As T-cells mature, an important part of the associated molecular "maturation" involves the somatic alteration of the germline configuration of the T-cell receptor (TR) genes to a semi-unique configuration in order to permit the development of a clone of T-cells with an extracellular receptor specific to a given antigen[1-3]. B-cells undergo a similar maturation process involving different loci that encode the antibody-containing B-cell receptor (BC). These clones, when considered together as a population, produce a repertoire of antigen sensitivity orders of magnitude larger than would be possible by way of inherited immunological diversity alone[3]. Indeed, the somatic rearrangement of the TR and BR genes is one of the key ontological events permitting the adaptive immune response[3].

When molecular carcinogenesis occurs in a lymphoid cell lineage, the result is the selective growth and expansion of the tumoural lymphocytes relative to their normal counterparts[2]. The so-called precursor (historically termed "lymphoblastic") lesions are believed to reflect molecular carcinogenesis in lymphoid cells at a relatively immature stage of maturation[2]. In contrast, if molecular carcinogenesis occurs at a point during or after the process of T-cell receptor gene re-arrangement (TRGR), the result is a "mature" (often also termed "peripheral") T-cell lymphoma in which the tumour contains a massively expanded population of malignant T-cells with an immunophenotype reminiscent of mature lymphocytes, most if not all bearing an identical TR gene configuration[4]. It is this molecular "homogeneity" of the TR configuration within a T-cell neoplasm that defines the concept of clonality in T-cell neoplasia[1,2,4].

The T-cell receptor is a heteroduplex molecule anchored to the external surface of T lymphocytes[5,21]; there the TR, in cooperation with numerous additional signalling and structural proteins, functions to recognize an antigen with a high degree of specificity. This specificity, and indeed the vast array of potential antigenic epitopes that may be recognized by the population of T-cells on the whole, is afforded by (1) the number of TR encoding regions of a given T-cell receptor's genes as present in the germline; and (2) the intrinsic capacity of the TR gene loci to undergo somatic re-arrangement[3]. There are four TR gene loci, whose protein products combine selectively to form functional TRs: T-cell receptor alpha (TRA) and T-cell receptor beta (TRB) encode the α and β chains, respectively, whose protein products pair to form a functional α/β TR; T-cell receptor gamma (TRG) and T-cell receptor delta (TRD) encode the γ and δ chains, respectively, whose protein products pair to form a functional γ/δ TR. The vast majority (>95%) of circulating T-cells are of the α/β type[21,22]; for reasons as yet not fully understood, γ/δ T-cells tend to home mainly to epithelial tissues (e.g. skin and mucosae) and appear to have a different function than the more common α/β type T-cells.

The TRA locus is found on the long arm of chromosome 14 in band 14811.2 and spans a total of 1000 kilobases (kb)[23]; interestingly, sandwiched between the TRA V and J domains, is the TRD locus (14q11.2), itself spanning only 60 kb[24]. The TRB locus is found on the long arm of chromosome 7 in band 7q35 and spans a total of 620 kb[25]. The TRG locus is found on the short arm of chromosome 7 in region 7p15-p14 and spans 160 kb[26].

Within each TR gene locus are a variable number of variable (V) and join (J) segments[23-26]; additional diversity (D) segments are present within the TRB and TRD loci[24, 26]. These V, D and J segments are grouped into respective V, D and J regions (see FIG. 1-1). In the germline configuration, a full complement of V (numbering from 4-6 in TRG to 45-47 in TRA), D (2 in TRB and 3 in TRD) and J (numbering as few as 4 in TRD to as many as 61 in TRA) segments can be detected, varying based on inheritance[23-26]. In this configuration, the specificity of any resulting coding sequence would be uniformly based on inherited variation. During maturation, however, somatic mutation (i.e. rearrangement) occurs such that there is semi-random recombination of variable numbers of the V, D and J segments to produce a lineage of cells with a "re-arranged" configuration of TR gene segments. This gene re-arrangement, when later subject to gene transcription and translation, produces a TR unique to the given T-lymphocyte (and its potential daughter cells). This process is represented pictorially in FIG. 1-2. Although the specific details of this re-arrangement process are far beyond the scope of this work, the process is at least partly mediated by enzymes of similar function to those used to perform splicing[21,22].

BIOMED-2[29] is a product of several years of collaborative expert study, resulting in a thoroughly studied consensus T-cell clonality assay. The BIOMED-2 assay includes multiplexed primer sets for both Immunoglobulin (IG) and TR clonality assessment and can be implemented with commercially available electrophoresis systems (e.g. Applied Biosystems fluorescence electrophoresis platforms)[29]. These commercially available primer sets have the advantage of standardization and ease of implementation. In addition, by virtue of the extensive study performed by the BIOMED consortium, the BIOMED-2 assay has the well-documented advantage of capturing the mono-clonality of the vast majority of control lymphomas bearing productive T-cell receptors (i.e. flow-sorted positive for either α/β or γ/δ T-cell receptors) using the specified TRB and TRG primer sets[29]. Of note, having been in use for over a decade, the BIOMED-2 has been globally accepted as the diagnostic assay primer set of choice.

The current approach to TRGR testing is subject to a number of technical and practical caveats that dilute the applicability of TRGR testing to the full breadth of real-world contexts.

Because the PCR-based techniques that are employed in TRGR assays are subject to amplicon size restrictions[29,34], the sheer size of the TRA locus prevents a complete assay of the TRA gene in clinical settings. Indeed, although of smaller size, the TRB locus as a whole is also prohibitively large to sequence in its germline configuration. It is therefore of no surprise that much of the published data pertaining to the utility and validity of TRGR assays has stemmed from assays specific to only subparts of TRB as well as TRG, a locus of size much more amenable to a single-assay. In addition, since the TRD locus is often deleted after TR gene rearrangement (since it is contained within the TRA locus and excised whenever the TRA locus is rearranged), assays for TRD have also not been as rigorously studied. For this reason, any BIOMED-2-based T-cell clonality assay aimed at directing immunotherapy, requiring a complete sequence-based understanding of the TR genes involved, would be insufficient.

The BIOMED-2 assay is subject to additional technical challenges. As part of the standard TRGR assay, most laboratories rely on the demonstration of electrophoretic migration patterns for the determination of TR clonality. Interpretation of the assay depends on the demonstration (or lack thereof) of a dominant amplicon of specific (albeit not pre-defined) molecular weight, rather than the normal Gaussian distribution of amplicons of variable size. This approach, as has been described previously[35-37], is subject to interpretative error and other technical problems. Also, given the large amounts of DNA required for the multitude of multiplex tubes making up the assay, the overall assay can very quickly deplete DNA supplies, especially when obtained from limited sample sources.

Finally, and arguably of greatest import, is the issue of diagnostic bias used in the study of TRGR assay performance. More precisely, when laboratories seek to validate a TRGR assay, the requirement of "standard" samples will typically require that the laboratory utilize previously established clonal samples or samples previously diagnosed and accepted to represent clonal entities (e.g. previously diagnosed cases of lymphoma); these samples are in turn compared to "normal" controls. In contrast, the demographics of subsequent "real-life" test samples are unlikely to be so decidedly parsed into "normal" and "abnormal" subsets.

Current T-Cell Receptor (TCR) rearrangement profiling assays rely on targeted PCR amplification of rearranged TCR genomic loci. The simplest method for assessing clonality of T-cells involves qualitative assessment through multiplexed amplification of the individual loci using defined primer sets and interpretation of fragment size distributions according to the BIOMED2 protocol[41,2]. Next-generation sequencing can be used as a read-out to provide quantitative assessment of the TCR repertoire including detection of low abundance rearrangements from bulk immune cells, or even pairing of the heterodimeric chain sequences with single cell preparation methods[43,4]. Hybrid-capture based library subsetting is an alternative method to PCR-based amplification that can improve coverage uniformity and library complexity when sample is not limiting and allows for targeted enrichment of genetic loci of interest from individual genes to entire exomes[45]. In hybrid-capture methods, the formation of probe-library fragment DNA duplexes are used to recover regions of interest[46 7,8].

Similar to T-cells, B-cells involved in adaptive immunity also undergo somatic rearrangement of germline DNA to encode a functional B-cell receptor (BR). Like TRs, these sequences comprise by discrete V, D, J segments that are rearranged and potentially altered during B-cell maturation to encode a diversity of unique immunoglobulin proteins. The clonal diversity of B-cell populations may have clinical utility and, similar to T-cell lymphomas, several cancers are characterized by clonal expansion of specific BR/Ig sequences.

SUMMARY OF THE INVENTION

There is described herein, the development of a novel NGS-based T-cell clonality assay, incorporating all four TR loci. The assay was both analytically and clinically validated. For the former, a series of idealized specimens was used, with combined PCR/Electrophoresis and Sanger Sequencing to confirm NGS-data. The latter validation compared NGS results to the current gold standard for clinical T-cell clonality testing (i.e. the BIOMED-2 primer PCR method) on an appropriately-sized minimally-biased sample of hematopathology specimens. In the latter dataset also, the patterns of T-cell clonality were also correlated with clinical, pathologic, and outcome data.

In an aspect, there is provided, a method of capturing a population of T-Cell receptor and/or immunoglobulin sequences with variable regions within a patient sample, said method comprising: extracting/preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene segment within the T cell receptor and/or immunoglobulin genomic loci.

In an aspect, there is provided, a method of immunologically classifying a population of T-Cell receptor and/or immunoglobulin sequences, the method comprising:

(a) identifying all sequences containing a V gene segment from the sequences of the DNA fragments by aligning the sequences of the DNA fragments to a library of known V gene segment sequences;

(b) trimming the identified sequences in (a) to remove any sequences corresponding to V gene segments to produce a collection of V-trimmed nucleotide sequences;

(c) identifying all sequences containing a J gene segment in the population of V-trimmed nucleotide sequences by aligning the V-trimmed nucleotide sequences to a library of known J gene segment sequences;

(d) trimming the V-trimmed nucleotide sequences identified in (c) to remove any sequences corresponding to J gene segments to produce VJ-trimmed nucleotide sequences;

(e) identifying any D gene segment comprised in the VJ-trimmed nucleotide sequences identified in (d) by aligning the VJ-trimmed nucleotide sequences to a library of known D gene segment sequences;

(f) for each VJ-trimmed nucleotides sequence identified in (d), assembling a nucleotide sequence comprising the V gene segment, any D gene segment, and the J gene segment identified in steps (a), (e) and (c) respectively;

(g) selecting from the nucleotide sequence assembled in step (f) a junction nucleotide sequence comprising at least the junction between the V gene segment and the J gene segment, including any D gene segment, the junction nucleotide sequence comprising between 18 bp and 140 bp, preferably 40-100 bp, further preferably about 80 bp;

and optionally (h) and (i):

(h) translating each reading frame of the junction nucleotide sequence and its complementary strand to produce 6 translated sequences; and (i) comparing the 6 translated sequences to a library of known CDR3 regions of T-Cell receptor and/or immunoglobulin sequences to identify the CDR3 region in the DNA fragments.

In an aspect, there is provided, a method of identifying CDR3 regions in T-Cell receptor and/or immunoglobulin sequences, the method comprising:

(a) identifying a V gene segment comprised in the immunoglobulin sequence by aligning the immunoglobulin sequence to a library of known V gene segment sequences;

(b) identifying a J gene segment comprised in the immunoglobulin sequence by aligning the immunoglobulin sequence to a library of known J gene segment sequences;

(c) if V and J gene segments are identified, then comparing the immunoglobulin sequence to a library of known CDR3 regions of T-Cell receptor and/or immunoglobulin sequences to identify any CDR3 region in the immunoglobulin sequence.

BRIEF DESCRIPTION OF FIGURES

The patent or application file contains at least one drawing executed in color. Copies of this patent or patent application publication with color drawing(s) will be provided by the Office upon request and payment of the necessary fee.

These and other features of the preferred embodiments of the invention will become more apparent in the following detailed description in which reference is made to the appended drawings wherein.

DETAILED DESCRIPTION

Figure 1:
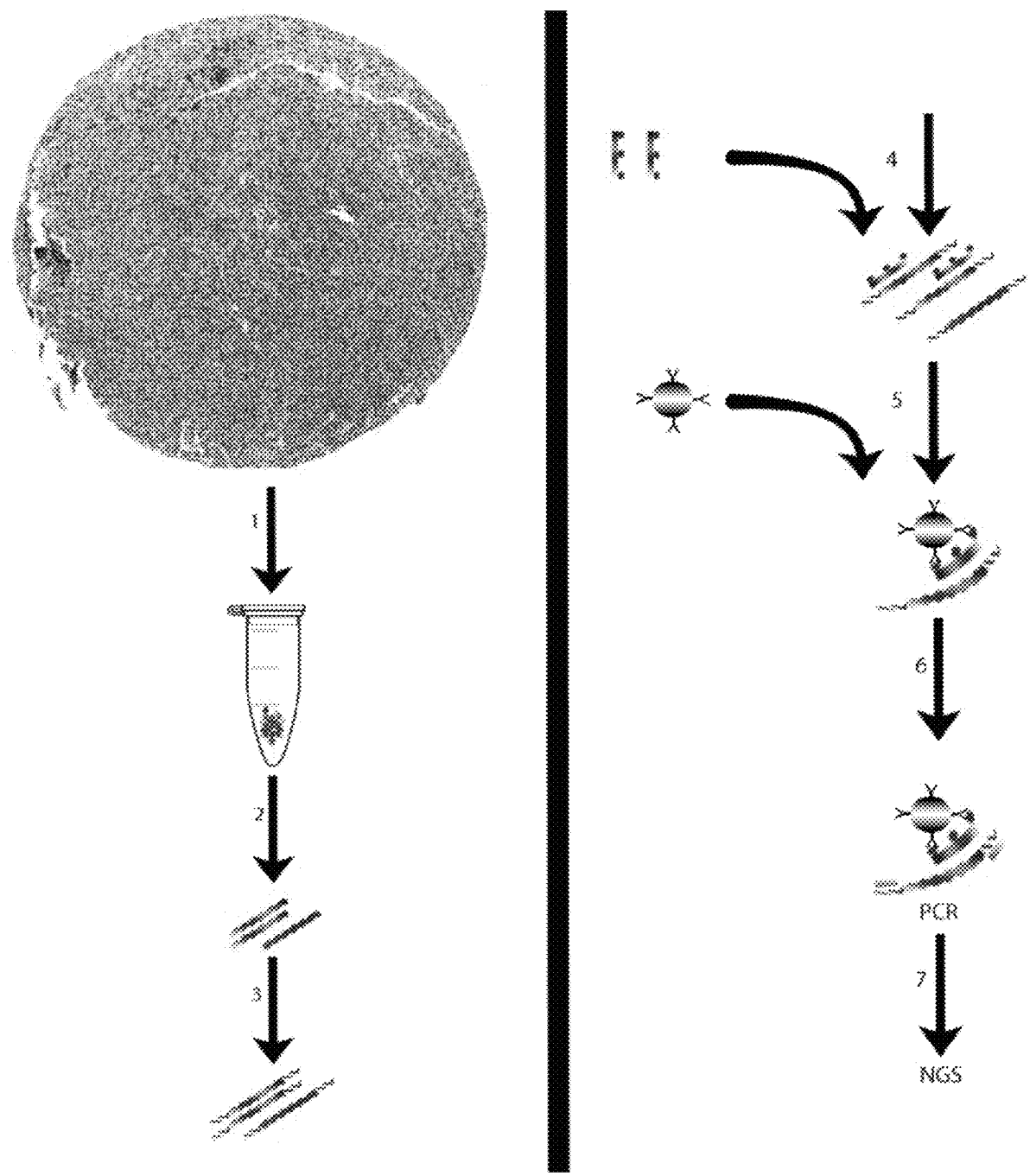
FIG. 1: TRGR Assay Wet-Bench Work-Flow Schematic. 1, DNA isolation; 2, Shearing (~200 bp); 3, Library Production; 4, Hybridization with Biotinylated DNA Probes; 5, Enrichment with Streptavidin-Bound Paramagnetic Beads; 6, PCR; 7, Illumina sequencing.
Figure 2:
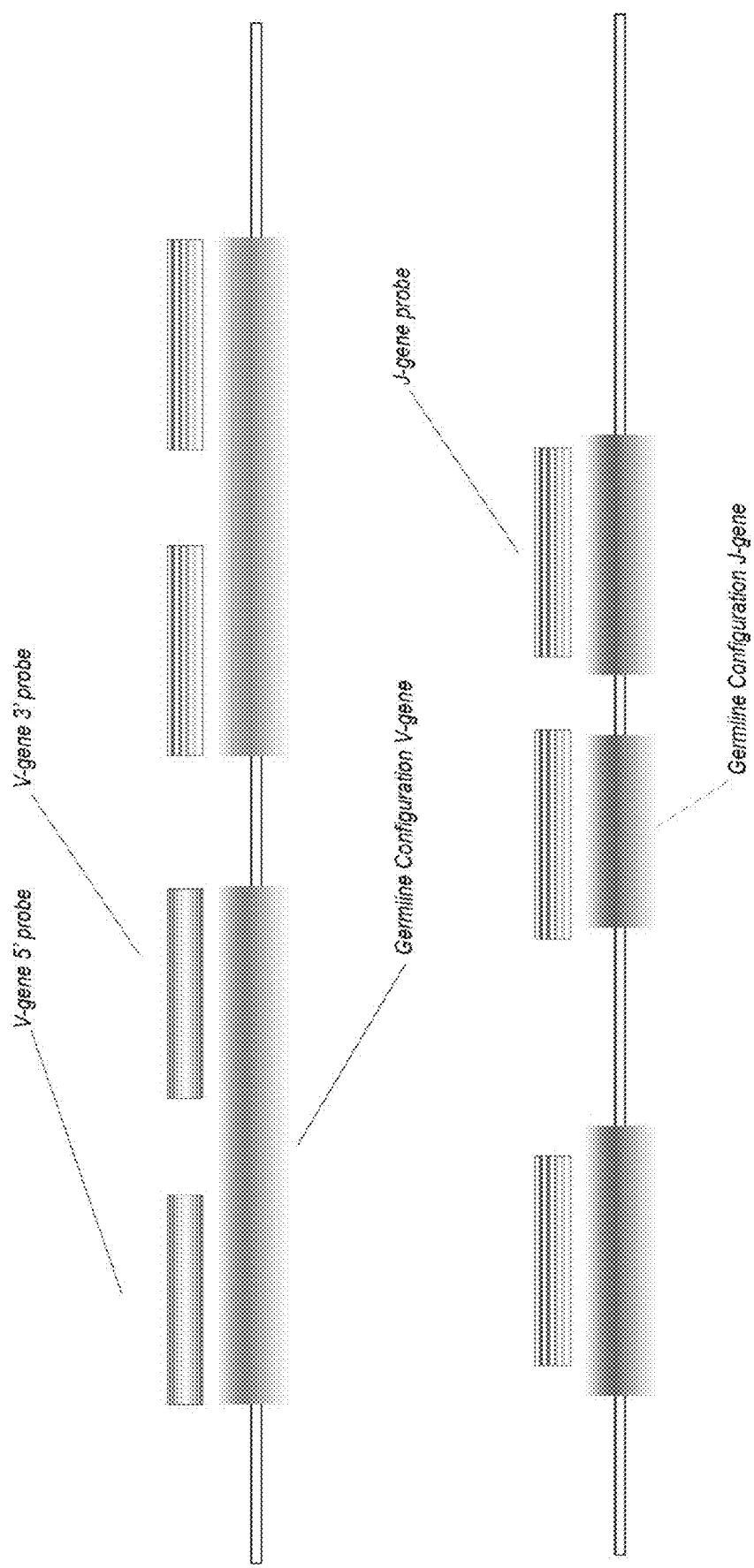
FIG. 2: Schematic Representation of V and J Gene Probe Placement Relative to the Germline. The germline V-genes are highlighted in solid red, with 100 bp probe placement shown above; probes are oriented inward and abut the 5' & 3' ends of the germline V-gene configuration. The germline J-genes are highlighted in solid blue, with 100 bp probe placement shown above; J-gene probes cover the entire J-gene, and on occasion some flanking extragenic sequence.

In the following description, numerous specific details are set forth to provide a thorough understanding of the invention. However, it is understood that the invention may be practiced without these specific details.

The advantages of high-throughput DNA sequencing technologies could potentially be applied to T-cell clonality testing. The nature of T-cell gene diversity, requiring the consideration of potential variability arising from four distinct gene loci, makes obvious the benefit of multiplexing; what has traditionally required multiple separate tests could be combined in a single reaction. The capacity of modern DNA sequencing technologies to query longer contiguous segments of DNA in greater quantities relative to traditional techniques also provides an opportunity to explore the potential meaning of TRA and TRB sequence rearrangements. Sequence-level data might afford a greater ease of assay result interpretation. Indeed, the generation of sequence-level data in a TRGR assay would likely be much more informative than gross estimates of DNA electrophoretic migration patterns when disease trends are being studied; the high-level analysis of such data might help the identification of heretofore hidden patterns of TR rearrangement in specific T-cell lymphoma subtypes. The issue of replicate numbers for establishing test sensitivity/specificity can be easily overcome by exploiting the high-throughput capacity of modern DNA sequencing platforms; for a comparable investment of time (and possibly cost), sequencing-based approach to TRGR could perform a greater number of individual tests, thereby potentially allowing a more statistically robust estimate of test performance.

Traditional sequencing uses PCR-based techniques to markedly amplify input template DNA, thus improving the sensitivity of detection during the sequencing step. Indeed, many sequencing-based technologies still perform directed library preparation using PCR-based techniques to isolate and sequence regions of interest[38]. By this approach, one might employ specific primer sets to enrich for regions of interest in the library preparation step. In the context of TRGR, however, a primer-based approach to library preparation would be challenging: in order to provide the sufficient breadth of coverage required to interrogate the status of the vast number of TR genes (especially in the TRA locus), a massive array of primers would be required. Although it is theoretically possible to prime multiple regions in tandem, previous data suggest that such an approach might open the door to the possibility of technical error (for a more thorough review of the details of these errors and the studies that have supported this evidence, see[38]). In the context of TRGR, furthermore, a primer-based approach to library preparation introduces the possibility of allele dropout when the assay attempts to prime a rearranged gene based on the known germline configuration (an easily digestible review to this effect may be found here[39]).

A paradigm shift away from PCR primer-directed amplification of genomic areas of interest was required for sequencing experiments aimed at large numbers of genes. Indeed most sequencing-based technologies rather employ the upfront production of vast libraries of template oligonucleotides followed by a series of template enrichment steps[38]. These latter steps may simply involve the extraction of DNA of specific lengths or quality, or rather the focus may be to enrich DNA containing specific sequences of interest. In the latter scenario, when specific sequence motifs are enriched for during library preparation, the resulting sequencing data will be enriched for the sequences of interest. Additionally, using the above stepwise approach, library preparation may be generalized to permit the enrichment of specific sequences out of a mix of "all" sequences produced from the primary non-specific amplification step; it is easy to see how this approach may be used to permit multiple separate assays using different enrichment approaches applied to a single input library[40].

Hybrid capture is a form of library enrichment in which a library is probed for known sequences of interest using tagged nucleic acid probes followed by a subsequent "pull-down" of the tagged hybrids[38]; for example, DNA probes tagged with biotin can be efficiently enriched when hybridization is followed by a streptavidin enrichment step[38,40-43]. The biotin/streptavidin enrichment procedure is schematized in FIG. 1. In reference to the assessment of TRGR, this approach has the advantage of enriching TR genes based on the available well-defined germline TR gene sequences, which can be performed in a massively parallel fashion using several hundred probes. Notably, this approach also allows for enrichment of rearranged sequences as the hybrid-capture probes can also hybridize to (and therefore enrich for) subsequences of the rearrangement product. This latter "pull-down" of rearranged TR genes would be difficult using a primer-only approach to library preparation.

Rather than restricting the assessment of test performance of the above DNA sequencing approaches to a pre-set (and potentially biased) sample of "malignant" and "benign" T-cell lymphoproliferative disorders, a more prudent sampling rubric might use a "real-world" series of consecutive samples taken from a population as similar to the "test population" as possible. In the context of TRGR validation, such a sample might consist of a series of consecutive tissue samples from patients being worked-up by a hematologist and submitted for molecular (i.e. T-cell clonality) assessment. The overall sample size could be established based on an estimate of the historical incidence of T-cell lymphomas in such a population, such that the total size of the sample is adequately large to include a sufficient "expected" number of clonal T-cell lymphoproliferative disorders.

In many validation studies, the final pathology diagnosis is used as the gold standard against which the novel test is measured[44]. While not unreasonable, there are arguments against employing such an approach. Of foremost concern is the potential for diagnostic or interpretative error, by which "true positivity" of disease could be misappropriated[44]. In the realm of T-cell lymphomas, given at least partly due to their rarity, the frequent lack of pathologist experience might make this problem more likely. Furthermore, evidence indicates that even when diagnoses are based on consensus or panel based interpretation, the possibility of diagnostic bias by dominant opinion should be considered[45].

When a single clearly-defined outcome measure does not exist (or is limited by bias), a composite gold-standard might be more appropriate[46]. Composite gold-standards might include a number of individual test results or clinical observations logically combined to produce "positive" or "negative" composites[46]; of key import is that (1) well-defined rules of composition be set out a priori and (2) the number of samples or subjects with each of the composite test results should be well-described[46]. Ideally, all samples or subjects should be evaluated using each of the composite tests[46].

In order to best study a novel test of TLPDs, rather than limiting the reference test to the gold-standard BIOMED-2 T-cell clonality assay or to pathology diagnoses, a series of both individual and composite references might be considered. From the perspective of analytical validity, one might consider validating an sequencing-based TRGR assay using standard PCR techniques followed by Sanger sequence verification. Since the sequences of each of the TR V and J genes are known, forward and reverse primer sets for each V and J genes, respectively, identified by the capture and sequencing assay could be used to verify that the detected result is valid; this could be followed by Sanger sequencing to validate the result of the DNA sequencing result (with deference specifically to the CDR3 variability-defining region).

In another experiment, one might consider comparing a sequencing-based TRGR result to the BIOMED-2 result (with each test applied to all specimens under study). The primary limitation of this approach would be that the BIOMED-2 assay, as explained above, does not test for any TRA rearrangements; thus this comparison alone would be insufficient. Additional comparisons might involve assessment of the sensitivity and specificity of each of the BIOMED-2 and sequencing-based TRGR assays at identifying benign or malignant TLPDs. For this, a composite gold-standard including histologic features (i.e. pathology diagnosis), immunophenotypic features, additional molecular features (as available, e.g. cytogenetic changes), clinical observations (e.g. presence or absence of features of malignancy), and outcome results (e.g. significant deviation in individual patient survival from the median) might be considered. The clinical validity of the sequencing results could thus be assessed against the current diagnostic standard by means of a much more thorough evaluation.

T-cell lymphomas are cancers of immune cell development that result in clonal expansion of malignant clones that dominate the T-cell repertoire of affected patients. Therefore, clonality assessment of these cell populations is essential for the identification and monitoring of T-cell lymphomas. We have developed a hybrid-capture method that recovers rearranged sequences of T-cell receptor (TCR) chains from all four classes (alpha, beta, gamma, and delta loci) in a single reaction from an Illumina sequencing library. We use this method to describe the TCR V(D)J repertoire of monoclonal cancer cell lines, tumor-derived lymphocyte cultures, and peripheral blood mononuclear cells from a healthy donor, as well as a set of 63 clinical isolates sent for clinical clonality testing for suspected T-cell lymphoma. PCR amplification and Sanger sequencing confirmed cell line and tumor predominant rearrangements, individual beta locus V and J allele prevalence was well correlated with results from a commercial PCR-based DNA sequencing assay with an $r^2$ value of 0.94, and BIOMED2 PCR fragment size beta and gamma locus clonotyping of clinical isolates showed 73% and 77% agreement respectively. Our method allows for rapid, high-throughput and low cost characterization of TCR repertoires that will enhance sensitivity of tumor surveillance as well as facilitate serial analysis of patient samples with a quantitative read-out during clinical immunotherapy interventions.

In an aspect, there is provided, a method of capturing a population of T-Cell receptor and/or immunoglobulin sequences with variable regions within a patient sample, said method comprising: extracting/preparing DNA fragments from the patient sample; ligating a nucleic acid adapter to the DNA fragments, the nucleic acid adapter suitable for recognition by a pre-selected nucleic acid probe; capturing DNA fragments existing in the patient sample using a collection of nucleic acid hybrid capture probes, wherein each capture probe is designed to hybridize to a known V gene segment and/or a J gene segment within the T cell receptor and/or immunoglobulin genomic loci.

As used herein, "T-Cell Receptor" or "TCR" means a molecule found on the surface of T lymphocytes (or T cells), preferably human, that is responsible for recognizing fragments of antigen as peptides bound to major histocompatibility complex (MHC) molecules. The TCR is a disulfide-linked membrane-anchored heterodimeric protein normally consisting of the highly variable alpha (α) and beta (δ) chains expressed as part of a complex with the invariant CD3 chain molecules. T cells expressing this receptor are referred to as α:β (or αβ) T cells, though a minority of T cells express an alternate receptor, formed by variable gamma (γ) and delta (δ) chains, referred as γδ T cells. Each chain is composed of two extracellular domains: Variable (V) region and a Constant (C) region. The variable domain of both the TCR α-chain and β-chain each have three hypervariable or complementarity determining regions (CDRs). CDR3 is the main CDR responsible for recognizing processed antigen.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known. The "light chains" of mammalian antibodies are assigned to one of two clearly distinct types: kappa (κ) and lambda (λ), based on the amino acid sequences of their constant domains and some amino acids in the framework regions of their variable domains. The variable domains comprise the complementarity determining regions (CDRs). The methods described herein may be applied to immunoglobulin sequences, including B-cell immunoglobulin sequences.

"V gene segments", "J gene segments" and "D gene segments" as used herein, refer to the variable (V), joining (J), and diversity (D) gene segments involved in V(D)J recombination, less commonly known as somatic recombination. V(D)J recombination is the mechanism of genetic recombination that occurs in developing lymphocytes during the early stages of T and B cell maturation. The process results in the highly diverse immune repertoire of antibodies/immunoglobulins (Igs) and T cell receptors (TCRs) found on B cells and T cells, respectively.

The term "nucleic acid" includes DNA and RNA and can be either double stranded or single stranded.

The term "probe" as used herein refers to a nucleic acid sequence that will hybridize to a nucleic acid target sequence. In one example, the probe hybridizes to the RNA biomarker or a nucleic acid sequence complementary thereof. The length of probe depends on the hybridization conditions and the sequences of the probe and nucleic acid target sequence. In one embodiment, the probe is at least 8, 10, 15, 20, 25, 50, 75, 100, 150, 200, 250, 400, 500 or more nucleotides in length.

The term "adapter" as used herein refers a moiety capable of conjugation to a nucleic acid sequence for a particular purpose. For example, the adapter may be used to identify or barcode the nucleic acid. Alternatively, the adapter may be a primer which can be used to amplify the nucleic acid sequence.

The term "hybridize" or "hybridizable" refers to the sequence specific non-covalent binding interaction with a complementary nucleic acid. In a preferred embodiment, the hybridization is under stringent conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0× sodium chloride/ sodium citrate (SSC) at about 45° C., followed by a wash of 2.0×SSC at 50° C. may be employed.

In some embodiments, the method further comprises sequencing the captured DNA fragments, wherein the sequencing can be used to determine clonotypes within the patient sample. Various sequencing techniques are known to the person skilled in the art, such as polymerase chain reaction (PCR) followed by Sanger sequencing. Also available are next-generation sequencing (NGS) techniques, also known as high-throughput sequencing, which includes various sequencing technologies including: Illumina (Solexa) sequencing, Roche 454 sequencing, Ion torrent: Proton/PGM sequencing, SOLiD sequencing. NGS allow for the sequencing of DNA and RNA much more quickly and cheaply than the previously used Sanger sequencing. In some embodiments, said sequencing is optimized for short read sequencing.

In some embodiments, the method further comprises amplifying the population of sequences using nucleic acid amplification probes/oligonucleotides that recognize the adapter prior to said sequencing.

In some embodiments, the method further comprises fragmenting DNA extracted from the patient sample to generate the DNA fragments.

In some embodiments, the ligating step is performed before the capturing step.

In some embodiments, the capturing step is performed before the ligating step.

The term "patient" as used herein refers to any member of the animal kingdom, preferably a human being and most preferably a human being that has AML or that is suspected of having AML.

The term "sample" as used herein refers to any fluid, cell or tissue sample from a subject which can be assayed for nucleic acid sequences. In some embodiments, the patient sample comprises tissue, urine, cerebral spinal fluid, saliva, feces, ascities, pleural effusion, blood or blood plasma.

In some embodiments, the patient sample comprises cell-free nucleic acids in blood plasma.

In some embodiments, the clonality analyses described herein may be use to track clonality across samples types.

In some embodiments, the hybrid capture probes are at least 30 bp in length. In a further embodiment, the hybrid capture probes are between 60 bp and 150 bp in length. In a further embodiment, the hybrid capture probes are between 80 bp and 120 bp in length. In a further embodiment, the hybrid capture probes are about 100 bp in length.

In some embodiments, the hybrid capture probes hybridize to at least 30 bp, preferably 50 bp, more preferably 100 bp of the V gene segment and/or J gene segment.

In some embodiments, the hybrid capture probes hybridize to at least a portion of the V gene segment and/or J gene segment at either the 3' end or the 5' end of the V gene segment and/or J gene segment respectively.

In some embodiments, the screening probes hybridize to at least a portion of the V gene segment.

In some embodiments, the screening probes hybridize to at least a portion of the V gene segment at the 3' end.

In some embodiments, hybridizing comprises hybridizing under stringent conditions, preferably very stringent conditions.

In some embodiments, the collection of nucleic acid hybrid capture probes comprise at least 2, 5, 10, 20, 30, 80, 100, 300, 400, 500, 600, 700, 800 or 900 unique hybrid capture probes.

In some embodiments, the collection of nucleic acid hybrid capture probes is sufficient to capture at least 50%, 60%, 70%, 80%, 90% or 99% of known T-Cell receptor and/or immunoglobulin loci clonotypes.

In some embodiments, the hybrid capture probes are immobilized on an array.

In some embodiments, the hybrid capture probes comprise a label. In a further embodiment, the label is used to distinguish between sequences bound to the screening probes and unbound double stranded fragments, and preferably the capture is performed in solution.

In some embodiments, preparing the DNA fragments comprises extracting RNA from the patient sample and preparing corresponding cDNA.

In some embodiments, the method further comprises a depletion step, comprising depleting the DNA fragments of non-rearranged sequences using probes that recognize nucleic acid sequences adjacent to V and/or J gene segments in the genome. In some embodiments, the capturing of DNA fragments using V gene segment and J gene segment hybrid capture probes is performed in separate steps, and in any order with the depletion step, preferably in the following order: J gene capture, depletion, then V gene capture.

In an aspect, there is provided, a method of immunologically classifying a population of T-Cell receptor and/or immunoglobulin sequences, the method comprising:
(a) identifying all sequences containing a V gene segment from the sequences of the DNA fragments by aligning the sequences of the DNA fragments to a library of known V gene segment sequences;
(b) trimming the identified sequences in (a) to remove any sequences corresponding to V gene segments to produce a collection of V-trimmed nucleotide sequences;
(c) identifying all sequences containing a J gene segment in the population of V-trimmed nucleotide sequences by aligning the V-trimmed nucleotide sequences to a library of known J gene segment sequences;
(d) trimming the V-trimmed nucleotide sequences identified in (c) to remove any sequences corresponding to J gene segments to produce VJ-trimmed nucleotide sequences;
(e) identifying any D gene segment comprised in the VJ-trimmed nucleotide sequences identified in (d) by aligning the VJ-trimmed nucleotide sequences to a library of known D gene segment sequences;
(f) for each VJ-trimmed nucleotides sequence identified in (d), assembling a nucleotide sequence comprising the V gene segment, any D gene segment, and the J gene segment identified in steps (a), (e) and (c) respectively;
(g) selecting from the nucleotide sequence assembled in step (f) a junction nucleotide sequence comprising at least the junction between the V gene segment and the J gene segment, including any D gene segment, the junction nucleotide sequence comprising between 18 bp and 140 bp, preferably 40-100 bp, further preferably about 80 bp;
and optionally (h) and (i):
(h) translating each reading frame of the junction nucleotide sequence and its complementary strand to produce 6 translated sequences; and
(i) comparing the 6 translated sequences to a library of known CDR3 regions of T-Cell receptor and/or immunoglobulin sequences to identify the CDR3 region in the DNA fragments.

Alternatively, step (h) may be searching the 6 translated sequences for flanking invariable anchor sequences to define the intervening T-Cell receptor and/or B-cell receptor CDR3 sequences encoded by the DNA fragments.

In some embodiments, the method further comprises, prior to step (a), aligning left and right reads of overlapping initial DNA fragments to produce the DNA fragments on which step (a) is performed.

In some embodiments, steps (a), (c), (e) are performed with BLASTn and step (i) is performed using expression pattern matching to known sequences and IMGT annotated data.

In an aspect, there is provided, a method of identifying CDR3 regions in T-Cell receptor and/or immunoglobulin sequences, the method comprising:
  (a) identifying a V gene segment comprised in the immunoglobulin sequence by aligning the immunoglobulin sequence to a library of known V gene segment sequences;
  (b) identifying a J gene segment comprised in the immunoglobulin sequence by aligning the immunoglobulin sequence to a library of known J gene segment sequences;
  (c) if V and J gene segments are identified, then comparing the immunoglobulin sequence to a library of known CDR3 regions of T-Cell receptor and/or immunoglobulin sequences to identify any CDR3 region in the immunoglobulin sequence.

Alternatively, step (c) may be if V and J gene segments are identified, then searching the immunoglobulin sequence for flanking invariable anchor sequences to define the intervening T-Cell receptor and/or immunoglobulin CDR3 sequences.

In some embodiments, wherein steps (a) and (b) are performed using the Burrows-Wheeler Alignment or other sequence alignment algorithm.

In some embodiments, wherein if a CDR3 region is identified in step (c), then the method further comprises determining whether the identified V and J gene segments could be rearranged in the same locus using a heuristic approach.

In some embodiments, wherein if a CDR3 region is not identified in step (c), then the method further comprises determining if a combination of V(D)J gene segments is present based on Smith Waterman Alignment scores.

In an aspect, there is provided, a method for characterizing the immune repertoire of a subject, the immune repertoire comprising the subject's T-Cell population, the method comprising any of the hybrid capture methods described herein, any of the algorithmic methods described herein, or any combination thereof.

Any of the methods described herein may be used to capture a population of T-Cell receptor sequences, for immunologically classifying a population of T-Cell receptor sequences or for identifying CDR3 regions in T-Cell receptor.

In an aspect, the methods described herein are for characterizing T-cell clonality for a disease in the subject.

In some embodiments, the T-Cell receptor sequences are from tumour infiltrating lymphocytes.

In an aspect, the methods described herein are for identifying therapeutic tumour infiltrating lymphocytes for the purposes of expansion and reinfusion into a patient and/or adoptive cell transfer immunotherapy.

In an aspect, the methods described herein are for monitoring T-cell populations/turnover in a subject, preferably a subject with cancer during cancer therapy, preferably immunotherapy.

In an aspect, the methods described herein are for characterizing the immune repertoire of a subject, the immune repertoire comprising the subject's B-Cell population.

In an aspect, the methods described herein are for capturing a population of B-Cell receptor sequences with variable regions within a patient sample, for immunologically classifying a population of B-Cell receptor sequences, or for identifying CDR3 regions in B-Cell receptor sequences.

In an aspect, the methods described herein are for characterizing B-cell clonality as a feature of a disease in the subject.

The present methods may be used in subjects who have cancer. Cancers include adrenal cancer, anal cancer, bile duct cancer, bladder cancer, bone cancer, brain/cns tumors, breast cancer, castleman disease, cervical cancer, colon/rectum cancer, endometrial cancer, esophagus cancer, ewing family of tumors, eye cancer, gallbladder cancer, gastrointestinal carcinoid tumors, gastrointestinal stromal tumor (gist), gestational trophoblastic disease, hodgkin disease, kaposi sarcoma, kidney cancer, laryngeal and hypopharyngeal cancer, leukemia (acute lymphocytic, acute myeloid, chronic lymphocytic, chronic myeloid, chronic myelomonocytic), liver cancer, lung cancer (non-small cell, small cell, lung carcinoid tumor), lymphoma, lymphoma of the skin, malignant mesothelioma, multiple myeloma, myelodysplastic syndrome, nasal cavity and paranasal sinus cancer, nasopharyngeal cancer, neuroblastoma, non-hodgkin lymphoma, oral cavity and oropharyngeal cancer, osteosarcoma, ovarian cancer, pancreatic cancer, penile cancer, pituitary tumors, prostate cancer, retinoblastoma, rhabdomyosarcoma, salivary gland cancer, sarcoma—adult soft tissue cancer, skin cancer (basal and squamous cell, melanoma, merkel cell), small intestine cancer, stomach cancer, testicular cancer, thymus cancer, thyroid cancer, uterine sarcoma, vaginal cancer, vulvar cancer, waldenstrom macroglobulinemia, and wilms tumor.

In embodiments relating to T-cells, the subject may have a T-cell related disease, such as a T-cell lymphoma.

T-cell lymphomas are types of lymphoma affecting T cells, and can include peripheral T-cell lymphoma not otherwise specified, extranodal T cell lymphoma, cutaneous T cell lymphoma, including Sezary syndrome and Mycosis fungoides, anaplastic large cell lymphoma, angioimmunoblastic T cell lymphoma, adult T-cell Leukemia/Lymphoma (ATLL), blastic NK-cell Lymphoma, enteropathy-type T-cell lymphoma, hematosplenic gamma-delta T-cell Lymphoma, lymphoblastic Lymphoma, nasal NK/T-cell Lymphoma, treatment-related T-cell lymphomas.

In other embodiments relating to B-cells, the subject may have a B-cell related disease, plasma cell disorder, preferably a B-cell lymphoma.

B-cell are types of lymphoma affecting B cells and can include, diffuse large B-cell lymphoma (DLBCL), follicular lymphoma, marginal zone B-cell lymphoma (MZL) or mucosa-associated lymphatic tissue lymphoma (MALT), small lymphocytic lymphoma (also known as chronic lymphocytic leukemia, CLL), mantle cell lymphoma (MCL), DLBCL variants or sub-types of primary mediastinal (thymic) large B cell lymphoma, T cell/histiocyte-rich large B-cell lymphoma, primary cutaneous diffuse large B-cell lymphoma, leg type (Primary cutaneous DLBCL, leg type), EBV positive diffuse large B-cell lymphoma of the elderly, diffuse large B-cell lymphoma associated with inflammation, Burkitt's lymphoma, lymphoplasmacytic lymphoma, which may manifest as Waldenström's macroglobulinemia, nodal marginal zone B cell lymphoma (NMZL), splenic marginal zone lymphoma (SMZL), intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHV8-associated multicentric Castleman's disease, B-cell lymphoma, unclassifiable with features intermediate between diffuse large B-cell lymphoma and Burkitt lymphoma, B-cell lymphoma, unclassifiable with features intermediate between diffuse large B-cell lymphoma and classical Hodgkin lymphoma, AIDS-related lymphoma, classic Hodgkin's lymphoma and nodular lymphocyte predominant Hodgkin's lymphoma.

In an aspect, the methods described herein are for identifying therapeutic B-cells for the purposes of expansion and reinfusion into a patient.

In an aspect, the methods described herein are for monitoring B-cell populations/turnover in a subject, preferably a subject with cancer during cancer therapy, preferably immunotherapy.

In an aspect, the methods described herein are for detecting minimal residual disease, whereby TCR or immunoglobulin rearrangements may be used as a marker of disease.

In an aspect, there is provided a library of probes comprising the depletion probes in Table D or at least one of the V-gene and J-gene probes set forth in any of Tables 2.1, 4, B1, or B2.

In some embodiments, the clonality analyses described herein may be performed serially.

In some embodiments, the clonality analyses described herein may be used to distinguish between samples.

The advantages of the present invention are further illustrated by the following examples. The examples and their particular details set forth herein are presented for illustration only and should not be construed as a limitation on the claims of the present invention.

Example 1

Methods and Materials
Assay Development

Several important theoretical considerations were entertained during the design phase of our novel sequecing-based TRGR assay (heretofore referred to as the NTRA).

Unlike the current BIOMED approach, we wished to avoid a gene-specific primer-based approach to signal amplification. To accomplish this, we chose a "hybrid capture" target enrichment approach by which input genomic DNA containing the TR genes might be enriched (or "captured") relative to other segments of the genome. Several methodological approaches to target enrichment already exist, with multiple commercially available and rigorously optimized kits capable of enriching nearly any well-defined gene target(s)[47,48].

The NTRA needed to be robust enough to accommodate sample types of variable DNA quality; this requirement reflects the clinical need to apply TRGR assays to a wide variety of specimens in a wide variety of contexts. Knowing that Formalin-fixed paraffin-embedded (FFPE) specimens typically contain degraded and often poor quality DNA (as such representing the "lowest common denominator" of specimen quality)[49], it was deemed necessary to specifically evaluate NTRA performance on FFPE specimens. Furthermore, the use of hybrid capture is also amenable to highly fragmented DNA specimens such as those from circulating cell-free DNA.

Likewise, the most useful NTRA should allow users to both accurately assess the "clonality" of an input sample (as can be done using BIOMED-2 based assays) but also fully characterize the clonotypes of constituent TRGR configurations. Thus it was essential that the NTRA not simply produce a binary "clonal" vs. "polyclonal" result but also provide a much more robust and quantitative data output, including the genes and CDR3 regions present within identified TRGR configurations.

We recognized that much of the utility of the NTRA would depend on the design of a robust bioinformatic analysis pipeline. Of note, at the time at which this project was undertaken, only a single widely-used pipeline existed (the International standard source for ImMunoGeneTics sequences & metadata (IMGT) V-QUEST system), mainly designed around 5'RACE PCR followed by Roche 454 sequencing[51]. As outlined below, several methodological and logistic motivations demanded a novel pipeline of our own design.

Current sequencing-based applications generally require that resultant sequence data (i.e. reads) be mapped to a reference (typically the genome of the organism of interest) using some form of alignment algorithm. Once this alignment is complete, secondary and tertiary tools are used to search for and catalogue sequence deviation from the reference. For our purposes, however, using the entire human genome as a reference map would be unnecessarily cumbersome, especially since the presence of closely juxtaposed V(D)J sequence within a single short (i.e. <500 basepairs (bp)) fragment of DNA is tantamount to evidence of TRGR. Furthermore, aligning to a single reference genome raises the informatics challenge of detecting gene rearrangements from a single alignment step. As such, a strategy of mapping sequence reads to only the reference genes in a parallel fashion (i.e. one mapping procedure to the V genes, and one separate mapping procedure to the J genes) was selected, along with an integrated TRGR detection algorithm This strategy required the theoretical consideration that short sequence read input might result in excessive false negatives (i.e. artificially low TRGR detection rates). This problem might be mitigated, in theory at least, by ensuring that input DNA fragment lengths (and the resulting sequencing read lengths) are carefully set to within a reasonable range of sensitivity for the detection of TRGR in a given sequence. Since all possible TRGRs are combinatorially vast, this process could only be simulated using, for our purposes, an artificial test set of simply-concatenated sequences of all catalogued V, D, and J genes (a test set numbering 197400). By evaluating k-mer subsequences over a range of lengths (k), centred (without loss of generality) about the median of each artificial junction, an estimate of the sensitivity of TRGR detection for variable sequencing windows can be produced. This sequencing window can then be used as an "evidence-based" DNA insert length.

Insert Length Simulation

Appendix 2.0 outlines a MATLAB script designed to estimate the optimal DNA insert length (a value also generalizable to optimal shearing length and minimal Paired-end rEAd mergeR (PEAR)-assembled sequencing length) for the purposes of the NTRA. This optimum is subject to an important restriction: for our purposes, using the Illumina NEXTSEQ platform, read lengths are limited to paired-ended reads of 150 bp each—this translates to <300 bp read lengths when paired-ends are joined by overlapping sequence (using, in our case, the PEAR algorithm[52]). Briefly, the code produces a simulation read set of all possible combinations of V-D-J sequences by way of simple concatenation (with the caveat that a much larger diversity of sequence is found in nature stemming from alterations of junctional sequence by way of splicing inconsistencies); next, the algorithm selects a k-mer (of length from k=32 to 302, in intervals of 30 bp) from within each simulation sequence; the resulting k-mer (centred, without loss of generality, at the junction median) is then subject to Burrows-Wheeler Alignment algorithm (BWA) alignment against the known reference V and J genes (as in the TRSeq pipeline) to evaluate how well the k-mers of each of the artificial reads can be mapped to both V and J genes (representing bioinformatic identification of TRGR within the sequence in question). A histogram of percent detection vs. read length was then produced; analysis of those artificial V-D-J read combinations that could be reliably detected was also performed.

DNA Probe Design

We began by reviewing the sequence and metadata of all reference TR genes obtained by way of a (FASTA-formatted) data download from the IMGT database. All sequences were subjected to a series of Clustal W[53] alignment analyses to verify that sequence alignment was limited to known reference motifs (i.e. the J-gene F/W-G-X-G motif and V-gene conserved Cysteine[54]) and to allele-to-allele overlap.

DNA probe design was then performed using the IMGT reference sequences (including all annotated V and J gene functional, pseudogene and open reading frame sequences) using the XGEN LOCKDOWN probe technology. Briefly, this technology is a hybrid-capture-based technology by which biotin-tagged DNA probes (complementary to known sequences/genomic regions set at a 1× depth of coverage) are allowed to hybridize with sample DNA, followed by a streptavidin elution procedure performed to enrich the target sequences[40-43].

In line with previous studies employing XGEN LOCKDOWN probes[40-43], each DNA probe was designed to a length as close to 100 bp as possible. Using the IMGT database, germline-configuration sequences were extracted for all alleles of all J-genes, with additional leading and trailing IMGT nucleotides added (as necessary) to obtain 100 bp probe lengths; for those instances in which the IMGT data was insufficient to prepare 100 bp probes, additional random nucleotides were added to the leading and trailing ends of the available sequences. Again using the IMGT database, germline-configuration sequences were extracted for all alleles of all V-genes, with additional leading and trailing IMGT nucleotides added to ensure that the 5' and 3' ends of the germline-configuration genes were covered by a given probe (this design, it was theorized, would be able to account for gene re-arrangement at either end of a V-gene, regardless of strandedness, while still covering the vast majority of the sequence of each gene/allele). With careful placement of the probes as outlined above, we hoped that this design would also limit any specific stoichiometric bias among the V-genes represented in the target pool.

Table 2.1 outlines the complete list of XGEN LOCKDOWN probe design sequences (with relevant associated metadata).

NTRA Work-Flow

The NTRA work-flow is summarized in FIGS. 1 and 3. Briefly, the process begins with DNA isolation, performed for the purposes of this study according to the protocol of Appendix 2.1. Isolated DNA was retrieved from frozen archives and quantified using the QUBIT assay, per Appendix 2.2. Input DNA was shorn using a Covaris sonicator (Appendix 2.3) set to a desired mean DNA length of 200 base pairs; adequate shearing was confirmed using TAPESTATION assessment. Sequence libraries for each specimen were prepared using the protocol outlined in Appendix 2.4; multiplexing was accommodated using either TRUSEQ or NEXTFLEX-96 indices (the latter employed in the final validation run to permit large-scale multiplexing). Library preparation results were validated relative to input short DNA using TAPESTATION assessment. Subsequently, hybrid-capture with the above described XGEN LOCKDOWN probes was performed; captures were performed in pools of 9-13 input libraries, based on a pre-calculated balance of input DNA. The captured library fragments were then repeat-amplified, followed by final QUBIT and TAPESTATION QC-steps. Finally, paired-end 150-bp sequencing was performed on the Illumina NEXTSEQ platform using either a mid- or high-output kit (depending on sample throughput), according to the manufacturer's instructions (Appendix 2.5). The resulting read-pair zipped FASTQ-formatted data files were de-compressed and merged using the publically available PEAR alignment algorithm using a minimum of 25 bp overlap; this allowed the 150-bp sequencing maximum to be expanded to at least 200 bp, as suggest by the results of Section 2.1.2. Non-paired results were also tallied as a means of quality assurance. Subsequent analyses were performed using the custom-designed TRSeq analysis pipeline, as described below.

NTRA Data Analysis: The TRSeq Pipeline

The NTRA TRSeq pipeline was designed around three main algorithmic steps. The first performs local alignment indexed to the TR V and J genes implemented using the Burrows-Wheeler-Alignment (BWA) algorithm[55]. From this algorithm, two important results are obtained: the first is a "reads-on-target" estimate (since the genes enriched for (i.e. the TR V and J genes) are those genes used as the index reference gene set); second, by way of the resulting Sequence Alignment Map (SAM) file output, the original input reads are filtered to exclude those unlikely to contain any of the TR V or J genes. This latter step reduces the informatic burden of input to the (relatively computationally slow) second algorithm step (using either heuristics or the Smith-Waterman Alignment (SWA)). Of note, the BWA algorithm could be implemented on a UNIX-based platform only[55].

The second algorithm step is designed to extract CDR3 sequences wherever present. This algorithm was implemented in MATLAB, guided by previous publications[56], and using a regular-expression (regexp) based search algorithm.

The third step combined the above alignment and CDR3 data (where present), to decide whether a given read contains a TRGR. To do this, one of two decision approaches is used: if a CDR3 is identified in a read, a heuristic approach is employed to decide if the BWA-alignment reference genes could be rearranged within the same locus; the second, in the event that a CDR3 is not detected, relies on the SWA-determined alignment scores to determine if a given combination of V(D)J genes is present.

Bioinformatic Target Enrichment (Burrows-Wheeler-Alignment Algorithm)

Much like the technical aspects of the NTRA function to enrich TR genes at the DNA level, so too can an informatics target-enrichment approach be employed. Using the BWA algorithm[55], a series of FASTQ-formatted reads are first mapped relative to a reference index of IMGT TR V and J genes. Any reads containing sequence mapping to any of the reference genes are flagged as such in the SAM-formatted output file as mapped, whereas those not containing any TR V or J gene mapped sequence are assigned the SAM Flag 4. In this context, unmapped reads are unlikely to contain any detectable TR V(D)J gene rearrangements; this predicate is logical inasmuch as sufficient residual germline sequence of a TR V and/or J gene are required in a read to permit TRGR detection.

Reads-on-target and gene-coverage estimates are also derived using the BWA algorithm, since NTRA input probes consist only of TR V and J genes; this measure is calculated as a percentage of the number of unique reads mapped to the IMGT reference TR V and J gene indices relative to the total number of reads in the input FASTQ-formatted file.

CDR3 Sequence Extraction and SWA Alignment

This part of the TRSeq algorithm was implemented in MATLAB using strategies similar to those employed by the IMGT[66-68]. The IMGT/V-QUEST system utilizes a CDR3 sequence extraction algorithm[57,59] and an SWA[60] algorithm performed against the IMGT reference sequences; the IMGT algorithms are all implemented in JAVA and processing is performed on IMGT servers.

As highlighted previously, we were unable to rely solely on the IMGT system for informatics results for several reasons: (1) the export of patient sequence data to an external non-secured network can be risky if insufficiently censored identifying metadata are also included; (2) the IMGT/High V-Quest system has a 500,000 sequence input limit (which may be substantially less than the number of sequence reads that need to be analyzed in the run of even a single high-throughput sequencing run); and (3) the queueing used by the IMGT can be lengthy, requiring a wait of possibly several days for sequence interpretation to begin.

A MATLAB implementation was chosen for convenience, programming familiarity, and because of easy vectorization, parallel computation and object-oriented programming capabilities. In addition, the MATLAB programming and command-line environments are able to easily incorporate UNIX and PERL-based scripts, including the BWA[Li, 2009] and CIRCOS software[61] suites, respectively.

The full coding of the analysis algorithm is presented in Appendix 2.6.2. The MATLAB code was written to accommodate FASTQ-formatted data, align each read using BWA to the reference TR V and J gene germline sequences, index the resultant data, test each indexed read for (and extract if present) a CDR3 sequence (using the uniformly present C-X(5 . . . 21)-F/W-G-X-G amino acid motif, per the IMGT canonical sequence motif[62,63]), and perform either an heuristic or SWA alignment-based validation of the reads mapped by BWA as evidence of a rearrangement within the read in question.

The SWA algorithm produces an optimal local alignment[60,64] of two co-input sequences (in this case, a query sequence relative to an IMGT reference sequence), and provides an alignment score (a unit-less measure of the degree to which the alignment perfectly matches an input sequence to its co-input sequence). For the purpose of this instance of the algorithm, for any case in which multiple possible alignments were produced, the alphabetical highest-scoring alignment was selected as the "correct" alignment, provided that this score was at least greater than the minimum cut-off score.

The minimum SWA alignment cut-off score was empirically determined for each of the three V, D, and J-gene gene groups using a large set of confirmed-negative sequences evaluated using the IMGT/HighV-QUEST system[66,67]. The MATLAB code required for implementation of this algorithm is outlined in Appendix 2.6.1. A "practice" set obtained from the IMGT database[66,66] was also employed to test the pipeline, consisting of IMGT PCR-confirmed TRGR sequences with known V-D-J combinations and CDR3 sequences (see Section 3.1.3 for results of this practice set analysis).

Analytical Validation

A selection of 10 "First-Run" samples formed the basis of the analytical validation. These samples included 6 de-identified actual patient samples, obtained from flow-sorted peripheral blood specimens, tumour-infiltrating lymphocyte populations or in vitro cultures of lymphocytes. These samples were each subjected to flow-cytometric evaluation and cell-counting for basic immunophenotyping and cell-input consistency. In addition, four cell lines with known and well-described TR gene rearrangements (based on references cited by the IMGT database[67]) were also included (i.e. Jurkat (Deutsche Sammlung von Mikroorganismen and Zellkulturen (DSMZ) ACC-282), SUPT1 (American Type Culture Collection (ATCC) CRL-1942), CEM (ATCC CCL-119) and MOLT4 (ATCC CRL-1582)).

A three-part analytical validation approach was employed. First, the results obtainable by analysis of the sequencing data using the IMGT/High V-Quest pipeline were directly compared with the results of the TRSeq pipeline. Next, a PCR & Gel Electrophoresis experiment was designed to confirm the presence of the upper $90^{th}$ centile of rearrangement configurations. Finally, the predominant rearrangements with accompanying TRSeq-identified CDR3 sequences were further Sanger-sequenced to validate this latter component of the NTRA analysis.

Comparison with IMGT Results

Given the limited input size capacity of the IMGT/High V-Quest system, a read-by-read comparison of a 10% random subset of the NTRA sequencing data was performed. From the IMGT analysis, a read was assumed to contain evidence of a rearrangement when the IMGT pipeline Junction analysis yielded an in-frame result. In addition, a read-by-read comparison of the alignment results (by gene name, for all V, D and J genes) was also performed.

PCR & Gel Electrophoresis Validation

A PCR-based experiment was deemed a reasonable orthogonal validation approach, given the gold standard BIOMED-2 assay methodology. Knowing that the number of possible rearrangements detected by the NTRA might be substantially large, the PCR validation was arbitrarily limited to those TRSeq-detected rearrangements in the upper 90th centile (i.e. percent rearrangement of greater than 10% of total rearrangements). Given this restriction, however, to ensure an adequate denominator of reactions for comparative purposes, all PCR validation experiments were uniformly performed across all 10 first-run samples.

PCR validation primer sets were constructed modeling the standard V-D-J orientation of rearranged TR genes; specifically, the PCR forward primer was set in the V gene and the reverse primer set in the anti-sense strand of the J gene. For each TRSeq-identified rearrangement above 10% of total rearrangements, the V and J genes were identified and the IMGT primer set database searched for gene (not allele) specific primers. While the IMGT primer database did contain a number of suggested primers, many of the TR genes did not have an available appertaining primer. As a result, where necessary, the anticipated rearrangement sequence (containing the V gene sequence artificially positioned before the J gene) was used to derive custom primers using the NCBI Primer-Blast tool[68]. Careful attention was paid to ensure that each resulting theoretical PCR product length was at least 100 bp (the lower limit of fragment size reliably detectable by standard gel electrophoresis) and that a sufficient amount of the anticipated CDR3 region sequence would be preserved in the PCR product. In addition, the theoretical product length was recorded as an approximate size reference for analysis of the resulting electrophoresis migration patterns.

All putative primer pairs were then re-submitted to Primer-Blast[68] to assess for the possibility of non-specific products; the final set of putative primers pairs was also evaluated using the UCSC in silico PCR algorithm[69] to confirm that no germline configuration products of less than 4 kb might be produced. Primer set physicochemical characteristics were evaluated using the IDT OligoAnalyzer Tool (v 3.1); Clustal W[53] alignments were used to identify significant primer sequence overlaps (Clustal W alignments note significant overlap of the TRGJ1 and TRGJ2 primers. This overlap was considered acceptable in order to define which of the TRGJ1 and TRGJ2 genes were present (given the presence of 5' end non-homology). Since the PCR/electrophoresis results suggested the presence of both TRGJ1 and TRGJ2 positive products, the dominant TRGJ1 primer was selected for subsequent analyses and the TRGJ2 results excluded). The final primer-set sequences are listed in Table 2.2.

Custom primer set production was performed commercially by IDT and the forward and reverse primers were then mixed according to the design outlined in Appendix 2.7.2. PCR was performed in a 384-well plate on an Applied Biosystems VERITI thermal cycler using the Thermo Scientific 2× REDDYMIX PCR Master Mix kit according to the manufacturer's instructions; several control reactions were included, as highlighted in Appendix 2.7.2. Gel electrophoresis was performed in a 96-well Bio-Rad SUB-CELL Agarose Gel Electrophoresis System (necessitating 4 separate runs); electrophoretic migration was referenced against an Invitrogen TRACKIT 1 kb DNA ladder and visualized using ethidium bromide fluorescence, photographed in a ALPHAIMAGER Gel Imaging System. Electropherograms were digitally rendered, adjusted and composited using ADOBE PHOTOSHOP CC 2014. The resulting electrophoretic results were used in Receiver-Operating Characteristic (ROC) curve analyses relative to the corresponding TRSeq normalized read counts.

Sanger Sequencing Validation

Based on the results of the above PCR & Gel Electrophoresis experiment, rearrangement-positive PCR products were purified using a QIAQUICK Spin PCR purification kit (100 bp to 1 kb range) according to the manufacturer's instructions (Appendix 2.7.3). Purified PCR products were then quantified by QUBIT and 20 ng equivalent aliquots were taken (with an additional volume reduction step using a SPEEDVAC, as required, for large volumes). The corresponding primer of the original primer pair with the lowest melting point was then selected for the purposes of single-direction Sanger Sequencing (performed at the TCGA Sick Kids Hospital Sequencing Facility).

The resulting sequencing results were analyzed using the FinchTV v 1.4 software suite, with corrections to sequencing error and reverse-complement sequence corrections performed manually as required. The originating TRSeq CDR3 sequences were then compared to the "reference" Sanger Sequence result. This comparison was performed in two ways: first, a basic multi-alignment comparison was performed (using the multialign algorithm of the MATLAB Bioinformatics Toolbox); second, a k-mer based PHRED-quality adjusted comparison was performed.

For the k-mer based approach, for a given V and J gene configuration, the most frequently detected TRSeq CDR3 sequences were aligned to the corresponding Sanger Sequencing result. In this context the Sanger Sequencing results were taken to represent a "consensus" of sequence data produced over all possible V and J configuration CDR3 sequences for that V-J gene configuration (reflecting the possibility of variable TRGR subclones). As such, in order to adjust the Sanger sequencing results to account for the potential alignment of a non-dominant subclone, a quality-based alignment algorithm was employed, based on the methods of[70]. Each input TRSeq CDR3 sequence was aligned along a progressive series of k-mers of the Sanger sequence using a custom quality-based alignment algorithm (code outlined in Appendix 2.8). For each alignment result, if the optimal alignment score occurred within the expected sequencing region (thereby representing an optimal alignment within a region of Sanger sequence expected to contain the actual CDR3 based on flanking primer sets), as outlined in Table 3.1A, the CDR3 sequence was classified as correct (and vice-versa). This classification was then used to perform ROC analysis to determine what number of TRSeq CDR3 sequence read counts might be considered a validated cut-off.

Coverage Analysis

In addition to the above validation results, more detailed assessment of NTRA technical performance was also performed. Specifically, given that the NTRA relies on target enrichment, an assessment of the gene coverage of the NTRA was required. In addition, given that much of the utility of the NTRA might relate to identifying clonal cell populations, it was necessary to assess the dynamic sensitivity of the NTRA to decreasing numbers of cells bearing specific TR gene rearrangement configurations and, conversely, assess how standardized read counts might correlate with approximate input cell numbers.

Coverage Dynamics by Specimen Clonality

Given the nature of TRGR, by which genomic components are excised upon rearrangement, we evaluated the coverage dynamics across the first-run specimens. This analysis served not only as a mean of qualitatively comparing how V and J gene coverage might be expected to vary in specific types of specimens, but also to evaluate which coverage metrics might be most predictive of specimen type (i.e. clonal vs not) and what specific cut-off criteria might be used to this effect. To do this, ROC-based analyses of mean overall and locus-specific coverage data for V and J genes was performed, as well as percent genes at least 100× for each of V and J gene types.

Negative Control Coverage Assessment

For the purposes of this project, a fully germline TR gene configuration was approximated using a cell lines of embryonic origin and a cell line that has been fully sequenced without any known/reported TR gene derangements. The former scenario was approximated using the HEK293 cell line (an embryonic kidney cell line; ATCC CRL-1573) and the latter using a Coriell cell line (whose genome has been well-characterized and is not known to contain TR rearrangements). Use of the latter cell line was incorporated given that, in our hands, this cell line had been previously and purposefully degraded by FFPE treatment, representing a scenario of TR gene coverage assessment in the context of degraded DNA.

Total genomic DNA was extracted from previously cultured HEK293 cells and FFPE treated Coriell cell cultures and subsequently subjected to the NTRA, as outlined in Appendices 2.1 to 2.5. Standard TRSeq analyses were performed for each sample, with special deference paid to the coverage results.

Dilution Series

A rigorous dilution series experiment, in the context of this project, might involve a flow-sort spike of cells with a known TR gene configuration into a population previously determined to be "polyclonal"; this might be approximated, for example, using a well-characterized cell line spiked into a population of lymphocytes obtained from normal blood. Rather than undertaking this more complex and expensive approach, an approximation of this dilution experiment was undertaken with DNA obtained from the Jurkat cell line spiked into a known-polyclonal lymphocyte population DNA isolate (the A037 sample; see Results section 3.2). Specifically, Jurkat DNA was spiked in at log-decrements (as outlined in Table 2.3) based on a lymphocyte total DNA complement assumed to be 0.7 pg, given the results of previous publications[71-73]. The total DNA of each sample in the dilution series was verified (and compared to expected values) using a QUBIT assay; the samples were then subjected to the NTRA, as outlined in Appendices 2.1 to 2.5. Standard TRSeq analyses were performed, with special deference to changes in the raw read counts of Jurkat-specific TRGR configurations across the dilution series.

Alternative Method and Algorithm

Hybrid-Capture Protocol

For T cell receptor (TCR) diversity and clonality analyses we investigated genomic DNA isolated from flow sorted T cells isolated by affinity magnetic bead isolation, peripheral blood mononuclear cells (PBMC) isolated from blood by density gradient separation, cell-free plasma DNA extracted from blood, or scraped and pelleted immortalized cell lines.

Isolated DNA is sheared to ~275 bp fragments by sonication in 130 uL volumes (Covaris). DNA libraries are generated for illumina platform sequencing from 100-1000 ng of sheared DNA by ligation of sequencing library adaptors (NEXTFLEX) using the KAPA library preparation kit with standard conditions. Libraries are visually assessed (Agilent TAPESTATION) and quantified (QUBIT) for quality.

Hybridization with probes specifically targeting the V and J genes is performed under standard SEQCAP (Roche) conditions with XGEN blocking oligos (IDT) and human cot-1 blocking DNA (Invitrogen). Hybridization is performed either at 65 C overnight. The target capture panel consists of 598 probes (IDT) targeting the 3' and 5' 100 bp of all TCR V gene regions, and 95 probes targeting the 5' 100 bp of all TCR J gene regions as annotated by IMGT (four loci, 1.8 Mb, total targeted 36 kb). Hybridization and capture can be performed as a single step with a combined V/J panel, as a single step with only the V panel, or as a three step process when non-rearranged fragment depletion is desired consisting of a V capture, then depletion, then J capture.

For depletion of non-rearranged fragments 500 ng-1000 ng of library is depleted by hybridization with a panel of 137 probes (IDT) targeting the 5' 120 bp of selected TCR V gene region 3' untranslated regions as annotated by IMGT (four loci, 1.8 Mb, total targeted 16.5 kb) and 131 probes (IDT) targeting the 5' 120 bp of selected Ig V gene region 3' untranslated regions as annotated by IMGT (three loci, 3.1 Mb, total targeted 15.7 kb). A modified and truncated SEQCAP protocol is employed wherein following incubation with M-270 streptavidin linked magnetic beads (Invitrogen), the hybridization reaction is diluted with wash buffer I, beads are discarded and the supernatant is cleaned up by standard Agencourt AMPURE XP SPRI bead purification (Beckman).

Algorithm

A custom Bash/Python/R pipeline is employed for analysis of paired read sequencing data generated by Illumina NEXTSEQ 2500 instrument from the hybrid-capture products. Referring to FIG. 3, this pipeline consists of four major steps: (1) Merging of the paired reads; (2) Identification of specific V, J, and D genes within the fragment sequence; (3) identification of the V/J junction position as well as the antigen specificity determining Complementarity Determining Region 3 (CDR3) sequence at this site; (4) Calculation and visualization of capture efficiency and clone frequency within and across individual samples.

(1) 150 bp paired-end reads are merged using PEAR 0.9.6 with a 25 bp overlap parameter. This results in an approximate 275 bp sequence for each fragment and enhances the sensitivity of V,J,D gene detection using the subsequent search strategies.

(2) Individual BLAST databases are created using all annotated V, D, J gene segments from IMGT. These full-length gene sequences are the targets of the hybrid-capture probe panel. Individual merged reads are iteratively aligned using BLASTn with an e value cut-off of 1 to the V database, J database then D database with word size of 5 for D segment queries. Trimming of identified V or J segments in the query sequence is performed prior to subsequent alignment to reduce false positives and increase specificity, particularly for the D gene query.

(3) In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TCR class as determined by sequence alignments of polyclonal hybrid-captured data from a healthy patient as well as TCR polypeptides annotated by IMGT.

(4) Calculation of capture efficiency (on-target/off-target capture ratio) is performed by aligning all recovered, merged reads to the human genome (BWA) and dividing the number of reads aligning to the TCR loci by the total number of reads. The total number of unique TCR clones is determined by finding the unique minimum set of V/J combinations and the number of occurrences of each is tabulated. This data is visualized using R as stacked bar charts to generate figures that can be quickly visually assessed on a sample-by-sample basis for monoclonal or polyclonal signatures or clinically relevant enrichment of particular clones.

Application of the Algorithm to Existing Sequencing Data

The custom pipeline is not dependent on our hybrid-capture protocol and can be performed on non-target captured whole genome or RNA-seq data. In this situation, an in silico capture is performed by extracting reads aligning to the four TCR loci (7:38250000-38450000, 7:141950000-142550000, 14:22000000-23100000) or Ig loci (chr2:89,100,000-90,350,000, chr14:106,400,000-107,300,000, chr22:22,350,000-23,300,000) from DNA (BWA) or RNA (STAR) sequence data (SamTools), followed by paired-end nucleotide sequencing data extraction (PicardTools). These reads are then inserted in to the previously described computational pipeline.

Results and Discussion

Informatics

Insert Length Simulation

The DNA Insert Length Simulation results were generated (data not shown). The analysis suggested a plateau of sensitivity of greater than 99.1% reached after 182 bp. For convenience, an adequately "evidence-based" insert length and informatics read length goal of 200 bp was chosen for the NTRA.

After further analysis excluded extra-locus V-D-J gene combinations (i.e. combinations not likely to result from rearrangements within the same TR locus), the number of missed combinations was reduced from 1752 to 80.

From among the above 80 intra-locus combinations, missed rearrangements originated only from among the TRB and TRG loci, with particular enrichment of TRBV6-2"01 and TRBV6-3×01 within the former (65 of 80) and enrichment of the TRGJ1*02 within the latter (15 of 80).

Analysis by phylogenetic sequence alignment (using the SWA alignment algorithm) within the TRBV6 group showed significant cophenetic linkage between the TRBV6-2*01 and TRBV6-3*01 genes (data not shown). Similarly, analysis by phylogenetic sequence alignment within the TRGJ gene group suggested significant cophenetic linkage between TRGJ1*02 and TRGJ2*01 (data not shown). These results suggest that combinations within the artificial read set involving either of these TRBV genes were likely misaligned to another TRBV gene (likely the next closest cophenetic "cousin," TRBV6-2*02) and that the TRGJ1*02 gene was likely misaligned to the TRGJ1*01 gene. Of note, the observation of closer cophenetic linkage between TRBV6-2*01 and TRBV6-3*01 rather than between TRBV6-2*01 and TRBV6-2*02 (as would be expected for two alleles of the same TR gene) and of closer cophenetic linkage between TRGJ1*02 and TRGJ2*01 rather than between TRGJ1*01 and TRGJ1*02, suggests error on the part of the IMGT classification.

MATLAB SWA Score Cut-Off Determination

The results of the empirical V, D and J-gene MATLAB alignment score cut-off score experiment were generated (data not shown). This experiment employed the code presented in Appendix 2.6.1 run on a test set of 91375 Illumina sequencing reads obtained from anonymized myeloid leukemia samples enriched for sequences outside of the IG/TR loci. These sequences were "confirmed" negative for V, D, and J gene sequences using the IMGT/High V-QUEST system (Brochet et al., 2008; Giudicelli et al., 2011). Given an experimental number of sequencing reads of at least 1 million, a 6-sigma cut-off score for MATLAB TRSeq analysis suggests 53.23 for the V genes; 19.02 for the D genes; and 34.43 for the J genes. It is easily observed that the cut-off values increase respectively from D, to J, to V genes; this observation parallels the mean length of the reference sequences from D to J to V genes.

TRSeq Analysis of IMGT-Produced TRGR Sample Sequence Reads

A sample of 268 short read sequences was downloaded from the IMGT website. These sequences consist of a variety of previously characterized TR and IG gene rearrangements available for download in FASTA format. After re-formatting into FASTQ format (using arbitrary quality scores), the dataset was analyzed using the TRSeq pipeline. Of the 268 short read sequences, 55 were identified by the IMGT as containing TR genes (either V or J genes); to these reads, there was perfect (100%) TRSeq alignment concordance, both in relation to gene name and allele. The TRSeq algorithm identified 50 of the 55 reads as containing evidence of TRGR; the 5 remaining reads were identified by the IMGT as containing rearrangements within the TRD locus, each with a TRSeq CDR3 region correctly identified. These results suggest that the 5 TRSeq "false-negatives" were informatically rejected by the TRSeq algorithm based on insufficient TRD D-gene SWA alignment score values; this form of error is not alarming given the more stringent means by which the TRSeq SWA alignment score cut-off values were determined relative to the IMGT/High V-QUEST pipeline[56,58].

First-Run Results Summary

Table 2.5 outlines the flow-cytometric features of the 6 patient lymphocyte samples. These immunophenotypic features were in keeping with the lymphocyte sample sources of origin (also documented in Table 2.5), varying from normal patient peripheral blood mononuclear cells to highly immuno-sensitized lymphocyte cultures from tumour infiltrating lymphocyte specimens. Notably, the A037 sample served as a model of a "polyclonal" lymphocyte population whereas, for the purposes of qualitative assessment at least, the L2D8 sample could be immunophenotypically interpreted as highly "clonal" in nature.

In addition, model "clonal" samples were included, consisting of the Jurkat, CEM, SUPT1 and MOLT4 cell lines. Table 2.6 lists the previously documented rearrangements, as cited in the IMGT database[67].

Prior to target enrichment and sequencing, adequate quality control was assured, as documented by pre and post-library preparation TAPESTATION tracings (data not shown). Post-target enrichment quality control was assured in the same manner.

Illumina NEXTSEQ sequencing was then performed on TAPESTATION-normalized pooled input target-enriched DNA. The appertaining read-pair FASTQ-formatted zipped files were decompressed and the PEAR paired-end merging algorithm was run with a minimum strand sequence overlap of 25 bp. A breakdown of the PEAR results were generated (data not shown). The resulting PEAR-merged FASTQ-formatted read files were input to the TRSeq pipeline.

TRSeq metadata for the first-run sample series were generated (data not shown), including input reads, reads-on-target, summary coverage statistics, and a histogram of read counts for the proportion of each locus contributing to identified TRGR's, respectively.

One important highlight is the variation in coverage seen across the 10 specimens relating to the D locus. As described in the introduction, since the D locus genes are sandwiched within the larger A locus, the D locus genes are often deleted upon A locus rearrangement. The coverage profiles of the D locus therefore paralleled this phenomenon with lower D locus coverage identified in the clearly clonal or oligoclonal samples relative to the polyclonal samples (e.g. L2D8 and cell line samples vs. A037 peripheral blood sample).

Composites of the circos plots obtained from the 10 first-run samples were generated (data not shown). Much as the coverage profiles differed across the samples (data not shown), the resulting circos plots demonstrated a clear aesthetic difference from polyclonal to clonal/oligoclonal samples, with emphasis on the number and relative width of the composite circos links (i.e. fewer and broader in width in the more clonal cases and vice versa). Also of note, the color distributions were distinctly different with the more polyclonal cases, containing a larger number of smaller-quantity "subclones" involving a more disparate number of TR genes.

Analytical Validation

IMGT/High V-Quest Comparison

Comparison of the IMGT/High V-Quest pipeline analysis to the TRSeq results were generated (data not shown). The degree of concordance of read-to-read interpretation with respect to identifiable rearrangements (as present or not identified) is excellent (99%), as is the degree of concordance of named D genes (99%). A lower degree of concordance is noted for named V and J genes (68% and 84%, respectively). These results may relate to different initial alignment algorithms employed, as well as different gene-identity cut-off values employed in the SWA algorithms of the IMGT/High V-Quest and TRSeq pipelines. In light of the results seen in Section 3.1.1, the possibility of V and J gene phylogenetic sequence misclassification in the publically-available IMGT sequence databases should also be considered as a possible contributing factor.

The high D-gene concordance relative to the V and J-gene values may relate to both the shorter reference sequences of the D-genes relative to the V and J genes, as well as the lower number of reference D-genes available for rearrangement. It is important to point out the possibility of a theoretical bias against D-gene identification in input reads, given that TRGR reads containing D-genes require 3 rather than 2 composite genes, which could be more difficult to detect in the context of restricted average read lengths. This consideration was brought to bear during the NTRA assay design phase (as described in Section 3.1.1), with the conclusion that adequate flanking 5' and 3' sequence would be available on average in the scenario of read input length of 200 bp or more to reliably identify reads containing V-D-J rearrangements.

PCR & Gel Electrophoresis

PCR primers were mixed and the results by Agarose gel electrophoresis were generated (data not shown). Note that results obtained from PCR reactions using the TRGJ2 reverse primer are excluded, as noted in Section 2.2.2. Two classification approaches may then be entertained, one based on dark-staining PCR bands only, and the other based on any staining (assuming bands to be of appropriate molecular weights, as set out in Table 3.1A). When these classifiers are compared with the read-count-normalized results of the TRSeq algorithm (as set out in Table 3.1A), the ROC curves are obtained, respectively (data not shown). In the former scenario, the ROC Area-Under-the-Curve (AUC)=0.91 and p-value <0.001, with a TRSeq normalized read count of 6.7 or more. Based on the results, a less stringent classification results in a reduced AUC=0.71 and p-value <0.001, with a TRSeq normalized read count of 1.7 or more.

Sanger Sequencing Results

PCR reactions that were post-PCR purified were submitted for Sanger Sequencing. Alignment of each corresponding TRSeq CDR3 sequence (and associated raw read count) in relation to the manually-verified/corrected Sanger Sequencing Result were generated (data not shown); only those Sanger Sequencing specimens containing TRSeq-identified CDR3 regions, those of sufficient quality for interpretation, and those not rejected based on use of the TRGJ2 reverse primer were further considered.

There appears to be a trend for each distinct primer configuration inasmuch as TRSeq-identified CDR3 sequence configurations having sufficient associated read counts (data not shown), as suggested from Section 3.3.2, show the best contiguous alignments to the corresponding "reference" Sanger Sequences.

To better quantify this relationship, we utilized a k-mer based quality-score adjusted alignment analysis. For each relevant primer configuration, the corresponding CDR3 was aligned using PHRED-based quality-score adjustment across the length of the Sanger "reference" sequence. If the optimal alignment from this process was present within the sequence window in which a CDR3 was theoretically predicted to exist, the CDR3 read configuration was classified as "compatible." The resulting classification analysis is represented by the ROC curve (AUC=0.832, p-value=0.006) (data not shown). Based on this analysis, the optimal TRSeq normalized read count cut-off is 4.9.

Coverage Analysis

Coverage Dynamics by Specimen Clonality

Using the qualitative data of Table 2.5, specimens were classified as either "clonal" or "polyclonal." The resulting ROC curves for the various coverage metrics were prepared (data not shown). Of note, a mean V-gene coverage assessment of the gamma locus appeared to suggest the highest non-unity AUC. Further, the ROC analysis suggested that a mean V-gene coverage of greater than/equal to 4366.4 showed optimal sensitivity and specificity (86% and 67%, respectively) for predicting whether a specimen was unlikely to be clonal. Care should be taken not to use these cut-off points without additional validation, however, given the low number of data points constituting the analysis. Rather, these data stand to suggest a need for further evaluation of the potential predictability of "clonal" status derived from coverage analysis within the gamma locus.

Negative Control Coverage Assessment

The NTRA was tested on samples of previously cultured HEK293 and Coriell cell lines; these analyses aimed mainly at estimating coverage ceilings for the NTRA, but also served as added negative control specimens (i.e. specimens known or expected not to contain any TRGRs).

Applying the PEAR algorithm[52] (with a minimum 25 bp forward-reverse read overlap) resulted in pairing of 83% of input reads in the HEK293 sample and 90% of input reads in the Coriell sample.

In both instances, the number of subsequently identified TRGR configurations did not meet the TRSeq cut-off criteria (TRGRs were identified in 0 of 5,729,205 total input reads in the HEK293 cell line and only 7 of 2,761,466 total input reads in the Coriell cell line). This was in keeping with the anticipated fully-germline configuration of each of these non-lymphoid origin cell types.

For the HEK293 cell line, the percent V and J genes at or above 100× coverage was 100%; the overall TR V gene coverage averaged 29960×; and the overall TR J gene coverage averaged 8789×.

For the Coriell cell line, the percent V and J genes at or above 100× coverage was 100%; the overall TR V gene coverage averaged 13379×; and the overall TR J gene coverage averaged 3925×.

Dilution Series

A dilution experiment was performed at log-reduction intervals, set up according to the design of Table 2.3, and adjusted according to Table 3.2 to account for Jurkat DNA concentration discrepancies. Three Jurkat cell line unique TRGR configurations were selected for inter-dilution comparison, namely the TRAV8-4-TRAJ3, TRGV11-TRGJ1 and TRGV8-TRGJ2 rearrangements identified & confirmed in Section 3.3. The above configurations were confirmed absent in the polyclonal (A037) sample. In addition, each of these configurations showed a specific dominant CDR3 sequence.

The mean of the raw read-counts (i.e. not normalized) across the three tracked V-J configurations (with error bars for standard deviation) vs. expected approximate Jurkat cell numbers (with adjustments for significant digits) from Table 3.2 were generated (data not shown). An exponential trend line could be applied, with R-squared=0.9996.

Of note, when the extremum of the first dilution is excluded, the dilution curve is remarkably linear (data not shown), but with a positive slope. This suggests a linear direct correspondence between read count and number of cells bearing a given V-J configuration at low levels.

In contrast to the reliable low-level detection by way of V-J configuration, detection narrowed to absolute clonotype (by including the CDR3 sequence) was limited to only the first three dilution specimens (i.e. sensitivity down to an approximated 1 in 125 cells; data not shown).

This limited sensitivity speaks to the sensitivity of the TRSeq junction finder to sequencing error. Indeed, if even a single base is changed relative to the canonical regular expression required for detection of a CDR3 sequence, the junction finder will not identify the sequence correctly; likewise, any non-triplicate base insertion will not be detected as an in-frame CDR3 sequence. In contrast, since the TRSeq V and J gene enumeration scheme uses alignment-based algorithms, the TRSeq results relating to V and J gene enumeration are much more forgiving of higher the higher likelihood of sequencing error in clonotypes with low read counts, thus substantially improving the assay sensitivity for characteristically unique V-J gene configurations.

Support for these suppositions is echoed in part by previous work pertaining to core clonotype analyses[27]. Indeed, when the proposed criteria of Bolotin, et. al.[27] for gathering low-level reads of similar but error-prone sequence into common core clonotypes are applied to the dilution experiment (implemented in Appendix 3), it is possible to identify reads comparable to the clonotypes described above in even the most dilute samples.

For example, running the code of Appendix 3 with the input core clonotype of the TRGV8-TRGJ2 configuration, and allowing for a maximum of 3 sequence mismatches, 3 or more reads of satisfactory clonotype can be identified in dilutions 2-5. If the number of sequence mismatches is increased to 4, reads of satisfactory clonotype can be identified in all dilutions (i.e. down to an estimated sensitivity of 1 in 185646 cells).

The importance of these results stems from the applicability of this form of core clonotype analysis to a more accurate identification of minimal-residual disease, for example, at very low levels with remarkable sensitivity, even in the absence of traditional primer-directed sequence enrichment[7].

NTRA—BIOMED-2 Comparison

In keeping with the general approach used to assess BIOMED-2 results, the NTRA TRB and TRG clonotype tables were analyzed to compare the ratio of the dominant clonotype read count relative to the "background" read count. The largest read count not satisfying the normalized TRSeq read count according to the results of Section 3.3 was taken as the background read count value; alternatively, in the case where the dominant clonotype did not satisfy the normalized TRSeq read count cut-off of Section 3.3, the next largest clonotype read count was taken as "background". From among each of the TRB and TRG loci, the largest dominant clonotype-to-background ratios were compared to the overall BIOMED-2 results using a ROC analysis.

The ROC analysis result could be classified as "good"[78] with AUC=0.82, p-value <0.001 (data not shown). Of note, this AUC value appears comparable to those observed in Section 3.3. Of even more impressive note is that the ROC-suggested dominant clonotype-to-background cut-off value was also comparable to that outlined in the current BIOMED-2 TRGR assay interpretation guidelines[79]; indeed, the ROC analysis-suggested value of 3.4, which is effectively the median value of the "indeterminate" range of dominant peak-to-background ratios recommended for BIOMED-2 result interpretation[79].

Interestingly, when the above process was broken down into two separate comparisons of the TRB and TRG loci, the TRG locus was found to be the significant driver: the TRG locus comparison alone yielded a ROC AUC=0.81 (p-value <0.001) whereas the TRB locus comparison alone yielded a ROC AUC=0.60 (p-value=0.17).

NTRA Coverage Metrics—BIOMED-2 Comparison

As in Section 3.4, an analysis of coverage variation in relating to clonal status was undertaken. In contrast to the results of Section 3.4, a far less significant series of areas-under-the-curve were observed from this analysis. The greatest AUC was noted by analysis of mean V-gene coverage (i.e. mean V-gene coverage over all four loci) with AUC=0.59, p-value=0.213.

Furthermore, the data from Section 3.4 suggested that analysis of coverage from the Gamma locus might be predictive of clonal status. Unfortunately, these hypotheses were not substantiated by way of the clinical validation set, from which the AUC for the TRG locus V-gene analysis and TRG locus J-gene analysis were 0.59 and 0.57, respectively.

The clear discordance between these results and those of Section 3.4 likely relates to several factors. First, the sample size in Section 3.4 is one-sixth that of the clinical validation set, making the results of Section 3.4 much more vulnerable to the effects of outliers. Second, the overall coverage in the analytical validation set was lower, owing to base-output restrictions using the mid-output NEXTSEQ kit; as such, coverage correlations made in Section 3.4 might not necessarily be applicable to experiments performed using the high-output NEXTSEQ kit. Thirdly, the clinical validation experiment was not subject to bias of assumption as to the clonality of each input specimen; rather clonality was specifically assayed using an orthogonal method.

SUMMARY

Described above is the first hybrid-capture-based T-cell clonality assay designed to assess clonality and provide clonotype data over all four T-cell gene loci. For this purpose, a custom MATLAB-based analysis pipeline was implemented using optimized object-oriented programming integrating the ultra-fast BWA alignment system and the aesthetically-pleasing circos-based genomic data visualization suite. The latter visualization was designed with current methods in mind, in which electropherographic plots serve as the primary means by which clonotypes are visualized.

Advantages of NTRA Over Traditional T-Cell Clonality Testing Assays

Not only can the NTRA identify clonotypes from all four loci, the use of hybrid capture makes the process platform-agnostic. The laboratory work-flow can be integrated into any standard library preparation work-flow with the addition of a single hybridization step, capable of enriching for sequences containing T-cell genes of a several specimens at a time. In addition, as part of laboratory work-flows already using a hybrid-capture approach for other purposes, the probes used as part of the NTRA are amenable to "spike-in" combined hybridization reactions, provided that there is no significant probe-set sequence overlap or complementarity.

In comparison to the current BIOMED-2 based clonality assays, the NTRA adds a dearth of extra data, especially as pertaining to clonotype data from the gene-rich alpha-locus. This locus has traditionally been too diffusely distributed within the genome to be amenable to primer-based amplification, a challenge easily overcome using a hybrid-capture approach. Akin to the requirements of the IMGT, the NTRA outputs a clonotype table containing data specific to the best aligned allele. In contrast, however, visualized data is restricted to gene-level only, thereby providing a means of visualization comparable to electropherographic output. In addition, included with the latter, is the in-frame CDR3 sequence (where detected), data currently not available using either standard PCR-based techniques or the mainstream sequencing-based solutions (e.g. Invivoscribe).

In addition to validating the wet-bench and informatics using a number of orthogonal approaches, the NTRA was also shown to be theoretically sensitive to low-level clonotypes. This latter observation is an important boon to the hybrid-capture approach, suggesting that carefully performed hybrid-capture methods can provide signal amplification comparable to flow-cytometric[81] and molecular approaches[32][82][83].

Assay Cost & Efficiency Considerations

As highlighted in Section 3.8, the assay may be considered cost effective, depending on the specific scenario of interest. In addition, the use of a hybrid-capture approach allows for spike-ins of additional probes for other genomic regions of interest. This allows the possibility of running multiple assays from a single library preparation step, requiring only bioinformatic separation of the resulting enriched sequences.

Applications

Assessment of lymphocyte clonality is integral to the diagnosis of diseases and cancer affecting the immune system. In addition, sequencing of the T-cell repertoire of a patient has gained clinical value with the recent understanding of T-cell mediated recognition and destruction of neoplasms. Further, the development of adoptive cell therapy and recombinatorial engineering of T-cell receptors requires high-throughput molecular characterization of in vitro T-cell populations before transplant. PCR-based methods such as BIOMED-2 and Immunoseq are currently in use for TCR characterization however their costs and complexity remain barriers for clinical deployment requiring high-throughput multi-patient, multi-sample work-flows at low cost. We have therefore developed a hybrid-capture-based method that recovers rearranged TCR sequences of heavy and light TCR chains from all four classes in one tube per sample at low cost. TCR clonality and CDR3 prevalence can be rapidly assessed in a three-day turn-around time with an automated pipeline generating summary figures that can be rapidly assessed by clinicians.

Adaptive T-cell immunotherapy has become a field of great interest in the treatment of multiple solid-tumor cancer types. Non-childhood cancers, particularly those linked to chronic exposure of known carcinogens, are driven by the accumulation of mutations. Some of these mutations drive pro-tumorigenic changes, while others result in non-tumorigenic changes to proteins expressed by the carrier cell. During normal protein turnover these modified proteins are broken down in to short polypeptides and make their way to the surface of the cell in association with molecular surveillance molecules (MHC I). In this context these modified polypeptides are recognized as foreign neo-antigens by the host immune system, and in the context of other signals, lead to the activation of T-cells that direct the destruction of cells expressing these modified proteins.

It is now understood that many solid-tumours exist in a state where their presence recruits neo-antigen specific T-cell lymphocytes to the margins however further advance and effective destruction of the tumor is prevented by expression of checkpoint inhibition molecules on the tumor cell surfaces. Therefore immunotherapy has become a major area of advance in cancer therapy wherein such checkpoint inhibition molecules are masked through transfusion of antibodies. This allows recognition of tumor and its destruction by neo-antigen specific T cells. In order to further enhance such anti-tumor activity, tumor infiltrating lymphocytes (TIL) can be isolated from tumor biopsies and expanded in vitro, followed by subsequent transfusion in great numbers back in to the patient following immunodepletion to enhance transplant colonization thereby driving a durable antitumor response.

T-cell lymphocytes are fundamental to this process, however due to their exquisite specificity, only neo-antigen specific T-cells are capable of driving anti-tumor activity. As a result there is a need for molecular characterization of circulating T-cells in the patient before and after treatment, infiltrating T-cells in the tumor before and after treatment, and screening of expanded populations in vitro for safety and efficacy. Our method provides a high-throughput, low cost and rapid turn-around method for T-cell receptor characterization in order to facilitate clinical deployment and uptake of adoptive cell transfer immunotherapy.

This method is not only of use in immunotherapy applications, as any disease involving expansion of T-cell clones would benefit from its use. The symptoms of autoimmune diseases are driven largely by T-cell mediated cytotoxicity of "self" tissue and therefore the identification and expansion of specific T-cell clones can be monitored using this method. This method would also be useful to follow immune challenges such as infection or immunization in the development of anti-infectives or vaccines.

Example 2

There is also described herein a laboratory and bioinformatic workflow for targeted hybrid-capture enrichment of T-cell receptor loci followed by Illumina sequencing to assess the clonality of a range of specimens with variable T-cell clonal complexity as well as a set of 63 T-cell isolates referred for clinical testing at our institution.

Methods and Materials

Probe design—All annotated V, D, J gene segments were retrieved from the IMGT/LIGM-DB website (www.imgt.org[9]). The 100 bp of annotated 3' V gene coding regions and up to 100 bp, when available, of annotated 5' J gene coding regions were selected as baits. Probes with duplicate sequences were not included.

DNA isolation—CD3+ T cells were isolated by flow assisted cell sorting of PBMC populations separated from whole blood. Peripheral blood mononuclear cells (PBMC) were isolated from whole blood by centrifugation followed by DNA isolation with a GENTRA PUREGENE kit (Qiagen) according to manufacturer protocol. In the case of fresh/frozen tissues, a QIAGEN ALLPREP (Qiagen) kit was employed, according to the manufacturer's instructions. In contrast, for FFPE samples a previously optimized in-house approach was used. First, sample FFPE tissue blocks were cored with a sterilized TISSUE-TEK QUICK-RAY punch (Sakura) in a pre-selected area of representative tissue; alternatively, under sterile conditions, 10×10 µm DNA curls/unstained slides were obtained for each submitted block of FFPE tissue. In a fumehood, 400-1000 µL xylene was aliquot into each tube (volume increased for larger FFPE fragments), followed by vigorous vortexing for 10 sec, incubation in a 65° C. water bath for 5 min, and centrifugation at 13200 rpm for 2 min. The supernatant was then discarded and step an additional xylene treatment step was performed. Subsequently, addition of 400-1000 µL ethanol (volume adjusted for larger input tissue volumes) was performed, followed by vigorous vortexing for 10 sec, and centrifugation at 13200 rpm for 2 min. The supernatant was then discarded and the ethanol treatment step repeated. The resulting pellet was then dried using a SPEEDVAC (Thermo Scientific) for 5 min, after which 150 µL of QIAAMP buffer ATL (Qiagen) was added, followed by 48-hour incubation at 65° C. with 50-150 µL of proteinase K (volume increased for higher input volumes). A final ethanol clean-up step was performed, as above, to produce a purified DNA product. Resuspension in TE buffer (Qiagen) was then performed.

Hybrid capture—Isolated genomic DNA was diluted in TE buffer to 130 uL volumes. Shearing to ~275 bp was then performed on either a Covaris M220 Focused-ultrasonicator or E220 Focused-ultrasonicator, depending on sample throughput, with the following settings: for a sample volume of 130 µL and desired peak length of 200 bp, Peak Incident Power was set to 175 W; duty factor was set to 10%; cycles per burst was set to 200; treatment time was set to 180 s. In addition, temperature and water levels were carefully held to manufacturer's recommendations given the instrument in use.

Illumina DNA libraries were generated from 100-1000 ng of fragmented DNA using the KAPA HYPERPREP Kit (Sigma) library preparation kit following manufacturer's protocol version 5.16 employing NETFLEX sequencing library adapters (B100 Scientific). Library fragment size distribution was determined using the Agilent TAPESTATION D1000 kit and quantified by fluorometry using the Invitrogen QUBIT.

Hybridization with probes specifically targeting V and J loci (Supplemental Table 3) was performed under standard SEQCAP (Roche) conditions with XGEN blocking oligos (IDT) and human Cot-1 blocking DNA (Invitrogen). Hybridization is performed either at 65 C overnight. The target capture panel consists of 598 probes (IDT) targeting the 3' and 5' 100 bp of all TR V gene regions, and 95 probes targeting the 5' 100 bp of all TR J gene regions as annotated by IMGT (four loci, 1.8 Mb, total targeted 36 kb).

Capture Analysis—A custom Bash/Python/R pipeline was employed for analysis of paired read sequencing data generated by Illumina NEXTSEQ 2500 instrument from the hybrid-capture products. First, 150 bp paired reads were merged using PEAR 0.9.6 with a 25 bp overlap parameter[418]. This results in a single 275 bp sequence for each sequenced fragment. Next, specific V, J, and D genes within the fragment sequence were identified by aligning regions against a reference sequence database. Specifically, individual BLAST databases were created using all annotated V, D, J gene segments retrieved from the IMGT/LIGM-DB website (www.imgt.org[49]), as these full-length gene sequences were the source of probes used to design the hybrid-capture probe panel. Individual merged reads are iteratively aligned using BLASTn with an e value cut-off of 1 to the V database, J database then D database with word size of 5 for D segment queries[419]. Trimming of identified V or J segments in the query sequence is performed prior to subsequent alignment. From reads containing V and J sequences, we identified V/J junction position and the antigen specificity determining Complementarity Determining Region 3 (CDR3) sequences. In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TR class as determined by sequence alignments of polyclonal hybrid-captured data from rearranged TR polypeptides annotated by IMGT[9]

Results and Discussion

Figure 3A:
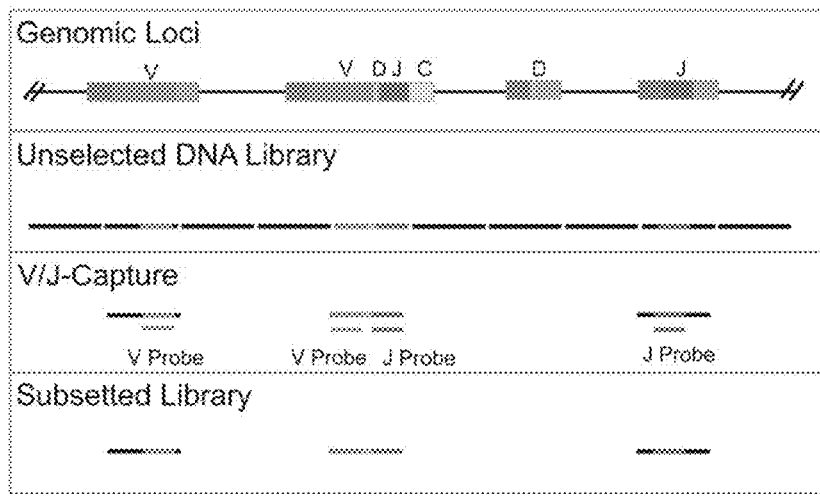
FIG. 3: An overview of the CapTCR-Seq hybrid-capture method. (A) Hybrid-capture method experimental flow diagram. Fragments are colored based on whether they contain V-region targets (blue), J-region targets (red), D-regions (green), constant regions (yellow) or non-TCR coding regions (black). (B) V(D)J rearrangement and CDR3 sequence detection algorithm flow diagram. (C) Number of unique VJ pairs recovered relative to library DNA input amount for one-step V capture of A037 PBMC derived libraries. (D) A037 polyclonal human beta locus VJ rearrangements determined by CapTCR-seq. (E) A037 polyclonal human beta locus VJ rearrangements determined by a PCR-based profiling service. (F) Subtractive comparison between CapTCR-seq and PCR-based profiling service. Red indicates relative enrichment of indicated pair by CapTCR-seq while blue indicates relative enrichment of indicated pair by PCR-based profiling.

The CapTCR-seq method employs hybrid capture biotinylated probe sets designed based on all unique Variable (V) gene and Joining (J) gene annotations retrieved from the IMGT database version 1.1, LIGMDB_V12[9]. These probe sets specifically target the 3' regions of V gene coding regions and the 5' regions of J gene coding regions that together flank the short Diversity (D) gene fragment in heavy chain encoding loci and which together form the antigen specificity conferring CDR3 (FIG. 3A). D regions (absent in alpha and gamma rearrangements) were not probed due to their short lengths, high potential junctional diversity introduced by the recombination process, and to permit a single universal probe set for both light and heavy chain loci. These biotinylated probes are hybridized with a fragmented DNA sequencing library, and probe-target hybrid duplexes are subsequently recovered by way of streptavidin-linked magnetic beads. The subsetted library is PCR amplified from the bead-purified hybrid-duplex population using a single set of adapter-specific amplification primers and the resulting library is subjected to paired read 150 bp sequencing on an Illumina NEXTSEQ 500 instrument. A 250 bp fragment size was selected as mid-range between the maximum length of a merged fragment from 150 bp paired-end read sequencing (275 bp) and a lower limit of 182 bp based on alignments of simulated reads centered at the VJ junction with variable insert sizes that had successful V and J alignment sensitivity of >99%.

Figure 3B:
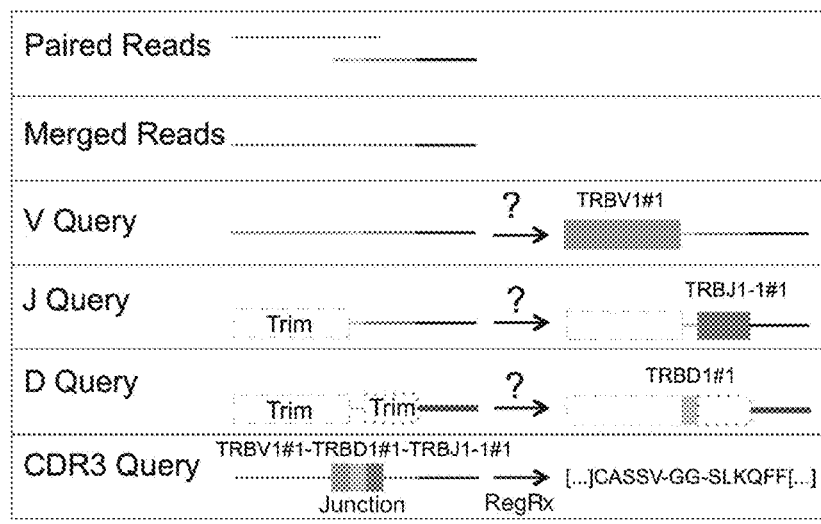

To identify V(D)J rearrangements from the pool of captured V and J sequences, we used a computational method that performed: (1) Read merging to collapse paired reads in to a single long-read sequence to enhance V(D)J and CDR3 identification, (2) progressive BLASTn-based V, J and D detection utilizing iterative end trimming and (3) CDR3 scoring using regular expression pattern matching (FIG. 3B). This BLAST-based sequence alignment approach was employed due to its tolerance for nucleotide mismatches that could arise from junctional diversity or the presence of allelic variants not present in the reference database. We acknowledge that numerous alternative V(D)J and CDR3 calling algorithms are available[410-16] and these may be used in addition or in lieu of our pipeline to analyze V(D)J fragments captured by our laboratory approach. A head-to-head comparison of these methods is beyond the scope of this proof-of-principle report.

Figure 3C:
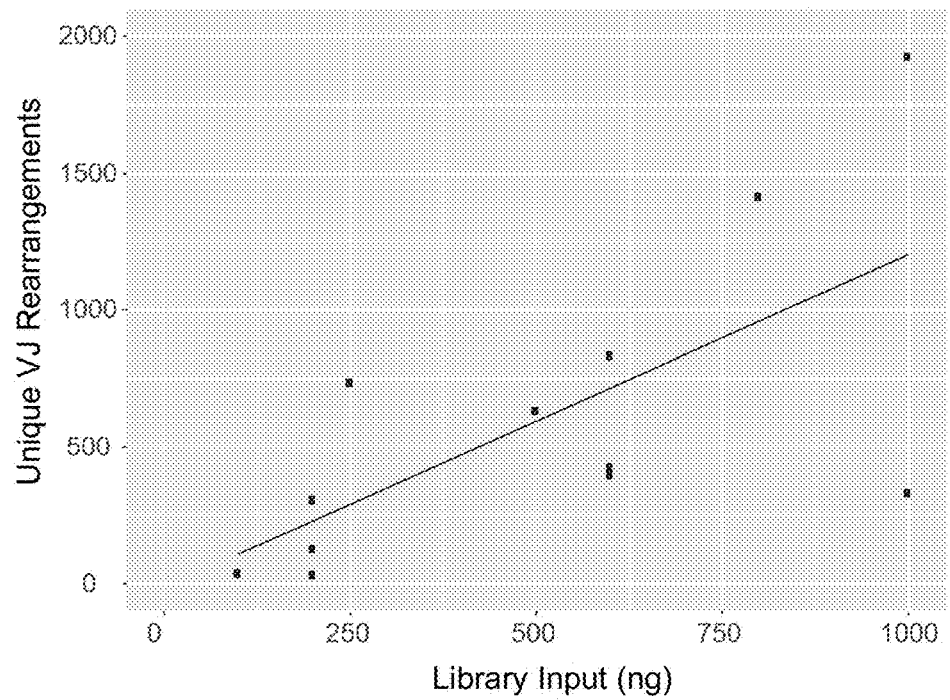

We employed this method to identify V(D)J rearrangements and CDR3 sequences in PBMCs isolated from a healthy human. With a single step hybridization and capture reaction employing the probe panel targeting TCR V genes, the number of detected unique VJ rearrangements increased with increasing amount of sample genomic DNA used to generate the initial library, with 52 times more rearrangements detected with an input of 1,000 ng compared with 100 ng (1925 vs 37) (FIG. 3C). The number of unique VJ rearrangements is dependent on the number of T cells in the original sample with an approximate fourfold increase for CD3+ sorted cells over PBMCs (2475 vs 759) (Supplemental Table 1). Addition of the J probe panel to form a single-step capture using a pooled V and J panel improved recovery of unique CDR3 sequences per 1 ng of library input by 5 fold (single-step V capture mean: 1.7, single-step VJ capture mean: 8.56) (Supplemental Table 1). This modification also increased the ratio of on-target reads, effectively decreasing the amount of sequencing needed to obtain the same number of rearranged fragments (single-step V capture mean: 14.4%, single-step VJ capture mean: 42.9%). Overall, we saw a diverse representation of alleles for all four classes with 2895 alpha, 1100 beta, 59 gamma, 9 delta unique VJ rearrangements observed from 16 independent captures of independent libraries (data not shown). This corresponded to 6257 alpha, 4950 beta, 1802 gamma, 109 delta unique CDR3 sequences. We also submitted a portion of these samples for parallel characterization by a commercial PCR-based TCR profiling service and found similar V/J gene usage and representation with no more than 2% variation (FIG. 3D-F) and correlation with an $r^2$ value of 0.94 (data not shown).

Figure 4:
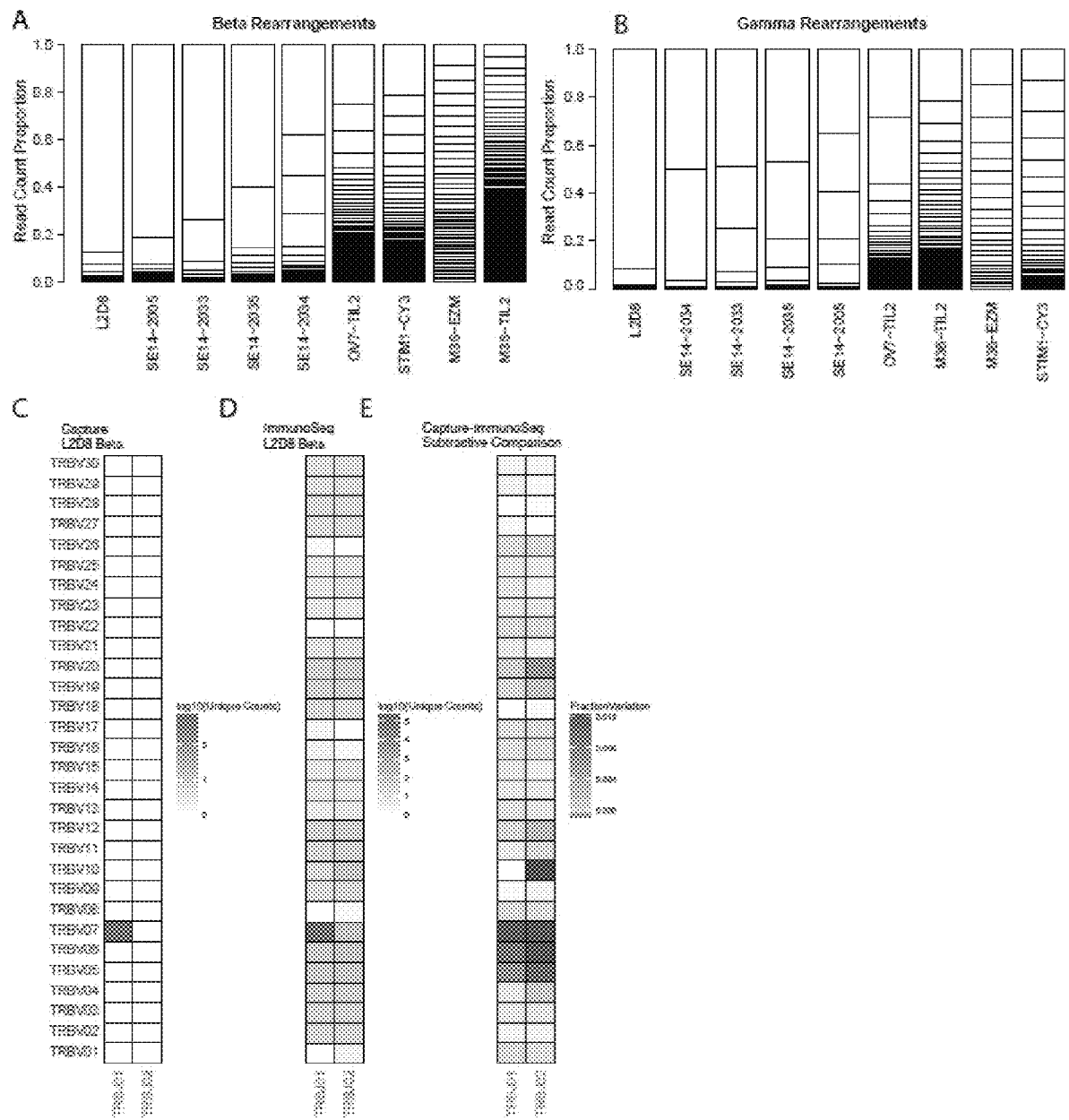
FIG. 4: Cell line and tumor isolate T-cell clonality. Boxes represent individual unique VJ pairs and box size reflects abundance in sample. Samples ordered by decreasing clonality. (A) Beta chain VJ rearrangements. (B) Gamma chain VJ rearrangements. (C) L2D8 Gp100 antigen specific beta locus VJ rearrangements determined by CapTCR-seq. (D) L2D8 Gp100 antigen specific beta locus VJ rearrangements determined by a PCR-based profiling service. (E) Subtractive comparison between CapTCR-seq and PCR-based profiling service. Red indicates relative enrichment of indicated pair by CapTCR-seq while blue indicates relative enrichment of indicated pair by PCR-based profiling.

To test the ability of CapTCR-seq to assess TCR clonality of samples with a range of clonal signatures, we analyzed libraries derived from CD3+ flow-sorted Tumor Infiltrating Lymphocytes (TIL) expanded cultures (oligoclonal) and lymphoblast cell lines (clonal) (FIG. 4A-B; and data not shown). As expected, the cell-lines and antigen-specific cell-sorted samples were more clonal (12-22 unique VJ rearrangements) than the TIL cultures (123-446 unique VJ rearrangements). The predominant alpha rearrangement represented 40-80% of the recovered reads in clonal samples compared to 2.5-17.5% for the latter TIL cultures. Specifically, we detected 12 unique VJ rearrangements in L2D8, a GP100 antigen-specific tumor-infiltrating lymphocyte clone. In OV7, a mixed ovarian tumor-infiltrating lymphocyte population expanded with IL-2 treatment, we found 311 unique VJ rearrangements. We profiled two populations isolated from the same tumor: M36_EZM, a cell suspension of melanoma tumor with brisk CD3 infiltration harbored 123 unique VJ rearrangements, while M36_TIL2, tumor-infiltrating lymphocytes from this tumor expanded in IL-2 harbored 446 unique VJ rearrangements, reflecting a likely expansion of low prevalence T cells. STIM1 is MART1-specific cell line made from peptide stimulation of healthy donor PBMCs, FACS sorting and expansion of tetramer+ cells from which we found 195 unique VJ rearrangements. The cell lines were found to encode previously reported gene rearrangements at the TCR beta and gamma loci, and additional rearrangements not previously reported (Supplemental Table 2)[A17]. Targeted PCR amplification of V/J rearrangement pairs, including the most frequently observed for each sample, was performed on these samples. We observed expected product for all prevalent rearrangements with some amplification failures for low prevalence rearrangements (Sample: Observed bands/expected bands; A037: 9/11; L2D8: 4/5; EZM: 3/4; TIL2: 8/9; OV7: 5/9; STIM1: 7/9; SE14 2005: 4/4; SE14 2033: 3/4; SE14 2034: 4/4; SE14 2035: 4/4) (data not shown). We also submitted the GP100 antigen specific L2D8 sample for beta locus profiling by a PCR-based commercial service and found VJ repertoire usage to be highly congruent (FIG. 4C-E), however the commercial service identified extensive low level VJ gene usage not present in the capture data (FIG. 4D). This signal may represent low-level alternative VJ pair antigen specific clones, or sample contamination with non-antigen specific clones.

To demonstrate the potential clinical utility of our approach, we generated DNA sequencing libraries from an unselected cohort of 63 samples submitted for clinical T-cell receptor rearrangement testing and subjected these to capture, sequencing and analysis (Supplemental Table 1). Samples were found to have varying degrees of clonality, with the predominant CDR3 sequence representing up to 40% of the most clonal sample (average 12.2%; median 6.3%%, range 0.8-100%, data not shown). When a clonal population was defined as having the most abundant to third most abundant rearrangements observed at two or more times the level of the next most abundant rearrangement, we observed three groups of samples: 11 with clonal enrichment of both beta and gamma rearrangements, 12 with clonal enrichment of beta or gamma rearrangements, and 41 that were polyclonal for both beta and gamma. When 61 of these samples were assessed by BIOMED2 assay we observed 73% agreement for beta (44/60) and 77% for gamma (46/60), 60% of samples were in agreement for both beta and gamma clonality measures (36/60). For the beta locus, 13 samples that were scored as clonal by BIOMED2 were scored as polyclonal based on relative prevalence when assessed by hybrid capture profiling. Six had low top clone prevalence (predominant rearrangement relative proportion of 1.3%, 1.8%, 2.6%, 3.1%, 3.4%, 3.8%) with a median unique VJ rearrangement count of 185. Seven had higher top clone prevalence (predominant rearrangement relative proportion of 7.6%, 8.4%, 8.5%, 8.8%, 11.9%, 12.1%, 16.9%) with a considerably lower median unique VJ rearrangement count of 44. These 13 samples had variable diversity but no predominant rearrangement was more than twofold enriched relative to the next most common rearrangement. Conversely, three samples that were scored as polyclonal by BIOMED2 at the beta locus were scored as clonal based on relative prevalence (predominant rearrangement relative proportion of 25.9%, 18.6%, 6.5%) with a median unique VJ rearrangement count of 191. These discrepancies could be resolved with deeper sequencing of these libraries to determine whether insufficient depth was distorting the interpretation or whether these represent incorrect interpretations by the BIOMED2 protocol. Improvements in the BIOMED2 primer sets have led to reduced false positives compared to previous generations, and can be further diminished through the use of higher resolution gel separation and additional analyses[42], however if available, sequencing-based methods provide a more quantitative assessment and relative comparison between all rearrangements. To determine whether there was unexpected enrichment in the A037 or lymphoma data sets we compared their gene usages (data not shown). A037 and the lymphoma collection had similar VJ usage profiles with few individual unique VJ rearrangement proportion enriched in A037 of up to 1% and more enrichments amongst the lymphoma set of up to 3% as expected given the clonal enrichment of select rearrangements in T-cell lymphomas.

In summary, CapTR-Seq allows for rapid, inexpensive and high-throughput profiling of all four loci from multiple samples of diverse types from a given DNA sequencing library with fragment size of 250 bp and sequencing length of 150 bp. This method will permit intensive monitoring of TR repertoires of patients with T-cell malignancies as well as monitoring of tumor-infiltrating lymphocytes in tumors from patients undergoing immune checkpoint blockade, adoptive cell transfer and other immunotherapies.

Example 3

Adoptive Cell Transfer (ACT) of in-vitro expanded Tumour-Infiltrating Lymphocytes (TIL) has emerged as an effective treatment for numerous types of solid tumours, often resulting in a durable response and in some cases a complete remission by the patient[B1]. This intervention effectively replaces nearly the entire heterogenous T-cell repertoire of the patient with tumour antigen and patient-specific effector T cells. Effector T-cells are integral for the adaptive immune response due to their roles in cellular cytotoxicity and cytokine production, with specificity conferred by the TCR-MHC interaction[B2]. The CD8+ effector T-cell repertoire consists of alpha/beta and gamma/delta subtypes, both polyclonal and skewing in the incidence of an antigen-specific response or malignancy[B3]. In high mutation load neoplasms, the MHC molecule often presents tumour-associated neo-antigens generated as a result of mutation that lead to clonal expansion and infiltration of tumour-infiltrating lymphocytes (TILs)[B4]. These TILs are largely clonal and distinct from the circulating repertoire in multiple types of neoplasia[B5]. While these TILs are capable of driving an effective anti-tumour response in vitro, they are often exhausted within the tumour microenvironment as a result of expression of immunosuppressive cell-surface proteins by the tumour but their activities can be restored with immune checkpoint blockade therapy[B6]. The combined effect of immunotherapy intervention: immunodepletion, TIL ACT and checkpoint blockade together present an effective treatment for many patients but have a disruptive effect on the endogenous immune repertoire and therefore proper patient care would benefit from longitudinal monitoring of the T-cell repertoire during the course of disease and treatment.

During ACT immunotherapy, both the requisite immunodepletion and T-cell transfer radically disrupt the abundance and diversity of the endogenous T-cell population and therefore molecular profiling methods are required for monitoring of the patient during the course of immunotherapy[B7]. The TCR repertoire consists of cell-specific heterodimeric receptors uniquely rearranged and expressed from either the alpha/beta or gamma/delta genomic loci[B8]. The TCR has unique specificity for an antigen presented in the context of the an MHC molecule as defined by the combined interactions of the amino acid residues encoded at the V-(D)-J junction known as the complementarity determining region 3 (CDR3), and by the CDR1 and CDR2 regions in the upstream V gene fragment.

Methods and Materials

Probe design—All annotated V (V-panel), D, J (J panel) gene segments and V 3'-UTR (depletion panel) sequences were retrieved from the IMGT/LIGM-DB website (www.imgt.org). The 100 bp of annotated 3' V gene coding regions, up to 100 bp, when available, of annotated 5' J gene coding regions, and 120 bp of V 3'-UTR sequences were selected as baits. Probes with duplicate sequences were not included. The V-panel consists of 299 probes (IDT) targeting the 3' and 5' 100 bp of all TR V gene regions, and the J-panel consists of 95 probes targeting the 5' 100 bp of all TR J gene regions as annotated by IMGT (four loci, 1.8 Mb, total targeted 36 kb). The depletion-panel consists of 131 probes targeting the 5' 120 bp of 3'-UTR Immunoglobulin V regions, and 107 probes tareting the 5' 120 bp of 3'-UTR TCR V regions.

DNA isolation—CD3+ T cells were isolated by flow assisted cell sorting of PBMC populations separated from whole blood. Peripheral blood mononuclear cells (PBMC) were isolated from whole blood by centrifugation followed by DNA isolation with a GENTRA PUREGENE kit (Qiagen) according to manufacturer protocol. In the case of fresh/frozen tissues, a QIAGEN ALLPREP kit (Qiagen) was employed to extract DNA and RNA, according to the manufacturer's instructions. The whole blood plasma fraction was then treated with red blood cell lysis buffer and circulating DNA (cfDNA) was extracted using the QIAGEN NUCLEIC ACID kit (Qiagen) according to manufacturer protocol.

cDNA synthesis—mRNA was separated from isolated total RNA using the NEBNEXT Poly(A) mRNA Magnetic Isolation Module (NEB) according to manufacturer's instructions. To generate cDNA, first NEBNEXT RNA First Strand Synthesis Module (NEB) was used followed by NEBNEXT RNA Second Strand Synthesis Module (NEB) according to manufacturer's instructions.

Library preparation—Isolated genomic DNA or synthesized cDNA was diluted in TE buffer to 130 uL volumes. Shearing to ~275 bp was then performed on either a Covaris M220 Focused-ultrasonicator or E220 Focused-ultrasonicator, depending on sample throughput, with the following settings: for a sample volume of 130 μL and desired peak length of 200 bp, Peak Incident Power was set to 175 W; duty factor was set to 10%; cycles per burst was set to 200; treatment time was set to 180 s. In addition, temperature and water levels were carefully held to manufacturer's recommendations given the instrument in use.

Illumina DNA libraries were generated from 100-1000 ng of fragmented DNA using the KAPA HYPERPREP Kit (Sigma) library preparation kit following manufacturer's protocol version 5.16 employing NEXTFLEX sequencing library adapters (B100 Scientific). Library fragment size distribution was determined using the Agilent TAPESTATION D1000 kit and quantified by fluorometry using the Invitrogen QUBIT.

Hybrid capture—For cDNA derived libraries, hybridization was performed with a pooled panel of probes targeting V and J loci in equimolar concentrations. For genomic DNA derived libraries, hybridization and capture was performed iteratively with probes specifically targeting V loci, 3'-UTR sequences, or J loci under standard SEQCAP (Roche) conditions with XGEN blocking oligos (IDT) and human Cot-1 blocking DNA (Invitrogen). Hybridization is performed at 50 C overnight. The Capture process consisting of bead incubations and washes are performed at 50 C.

For the iterative hybridization and capture process, the first J hybridization and capture is performed in completion with terminal PCR amplification with 4 steps. Following clean-up by Agencourt AMPURE XP SPRI bead purification (Beckman) this product is used as input for a subsequent depletion step. For depletion, a modified and truncated SEQCAP protocol is employed wherein following incubation of the hybridization mixture with M-270 streptavidin linked magnetic beads (Invitrogen), the 15 uL hybridization reaction is separated on a magnetic rack, the supernatant is recovered and diluted to 100 uL with TE buffer, followed by clean up by standard Agencourt AMPURE XP SPRI bead purification (Beckman). The depletion-probe-target-beads are discarded. The purified supernatant is then used as input for a subsequent V-panel capture and hybridization as described above, but with terminal PCR amplification with 16 or amplifications steps to achieve sufficient library for sequencing.

Capture Analysis—A custom Bash/Python/R pipeline was employed for analysis of paired read sequencing data generated by Illumina NEXTSEQ 2500 instrument from the hybrid-capture products. First, 150 bp paired reads were merged using PEAR 0.9.6 with a 25 bp overlap parameter. This results in a single 275 bp sequence for each sequenced fragment. Next, specific V, J, and D genes within the fragment sequence were identified by aligning regions against a reference sequence database. Specifically, individual BLAST databases were created using all annotated V, D, J gene segments retrieved from the IMGT/LIGM-DB website (www.imgt.org), as these full-length gene sequences were the source of probes used to design the hybrid-capture probe panel. Individual merged reads are iteratively aligned using BLASTn with an e value cut-off of 1 to the V database, J database then D database with word size of 5 for D segment queries. Trimming of identified V or J segments in the query sequence is performed prior to subsequent alignment. From reads containing V and J sequences, we identified V/J junction position and the antigen specificity determining Complementarity Determining Region 3 (CDR3) sequences. In order to identify CDR3 sequences, the V/J junction position is extracted from the previous search data for those fragments containing both a V and J search result. 80 bp of DNA sequence flanking this junction is translated to amino acid sequence in all six open reading frames and sequences lacking stop codons are searched for invariable anchor residues using regular expressions specific for each TR class as determined by sequence alignments of polyclonal hybrid-captured data from rearranged TR polypeptides annotated by IMGT.

Results and Discussion

Methods Improvement

Figure 5:
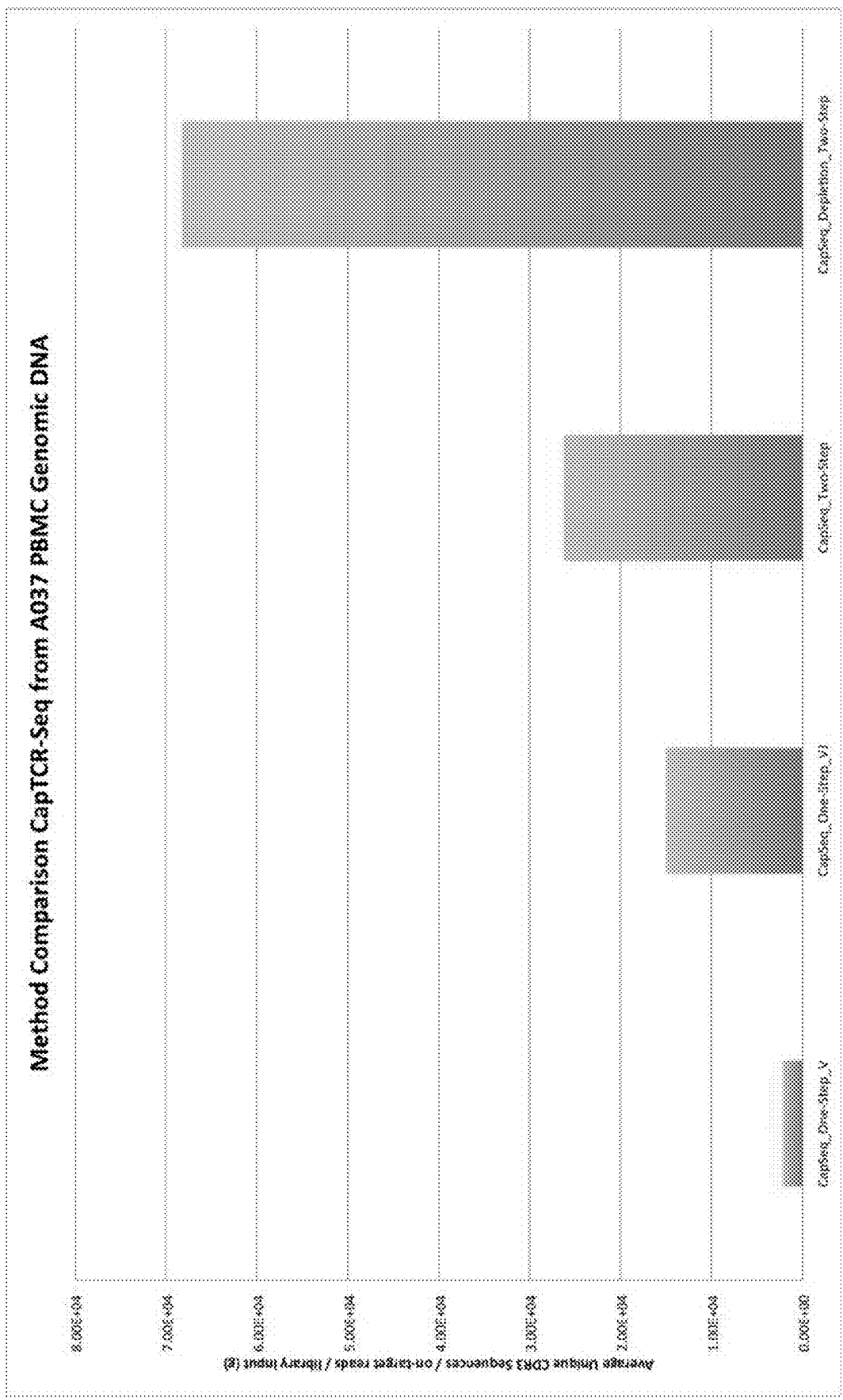
FIG. 5: Comparison of different method variants in terms of yielded average unique CDR3 sequences (normalized to reads and library input).

We experimented with alternate capture methods, using an iterative three-step hybridization and capture, first with a J panel then molecular depletion of unrearranged V-gene sequences, then subsequently with a V panel (data not shown). The depletion probes (V-gene and J-gene) are shown in Table D. These altered protocols improved recovery of unique CDR3 sequences when normalized to reads. When compared to a one-step V-panel capture, the one-step combined VJ-panel capture increased signal by 6.84×, the two-step J and V iterative capture increased signal by 12× (no significant difference was observed for J-V or V-J iterative order), and the three-step J-depletion-V iterative capture increased signal by 31.2× (FIG. 5).

Figure 6:
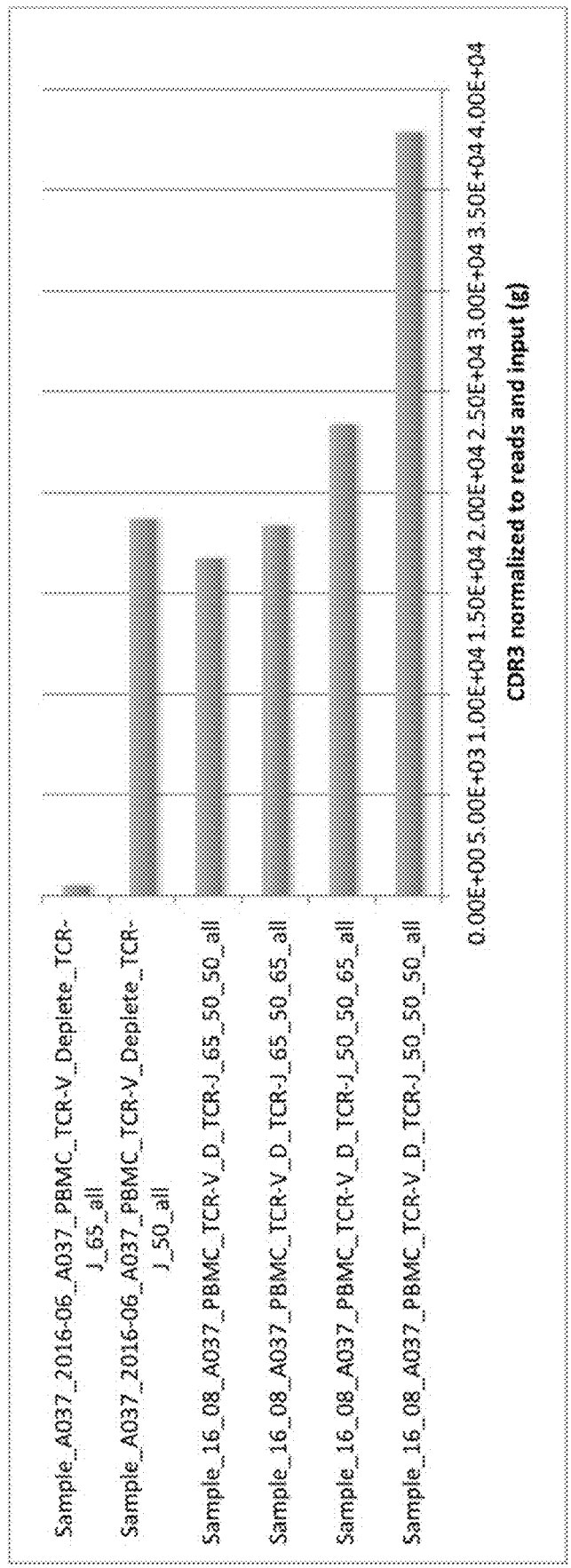
FIG. 6: Comparison of different hybridization and capture temperatures in terms of yielded average unique CDR3 sequences (normalized to reads and library input).

We experimented with reducing hybridization and wash temperatures to improve recovery (FIG. 6). When 50 C to 65 C in 5 C increments were tested at each step of the hybridization and capture, 50 C yielded the highest signal and diversity.

Figure 7:
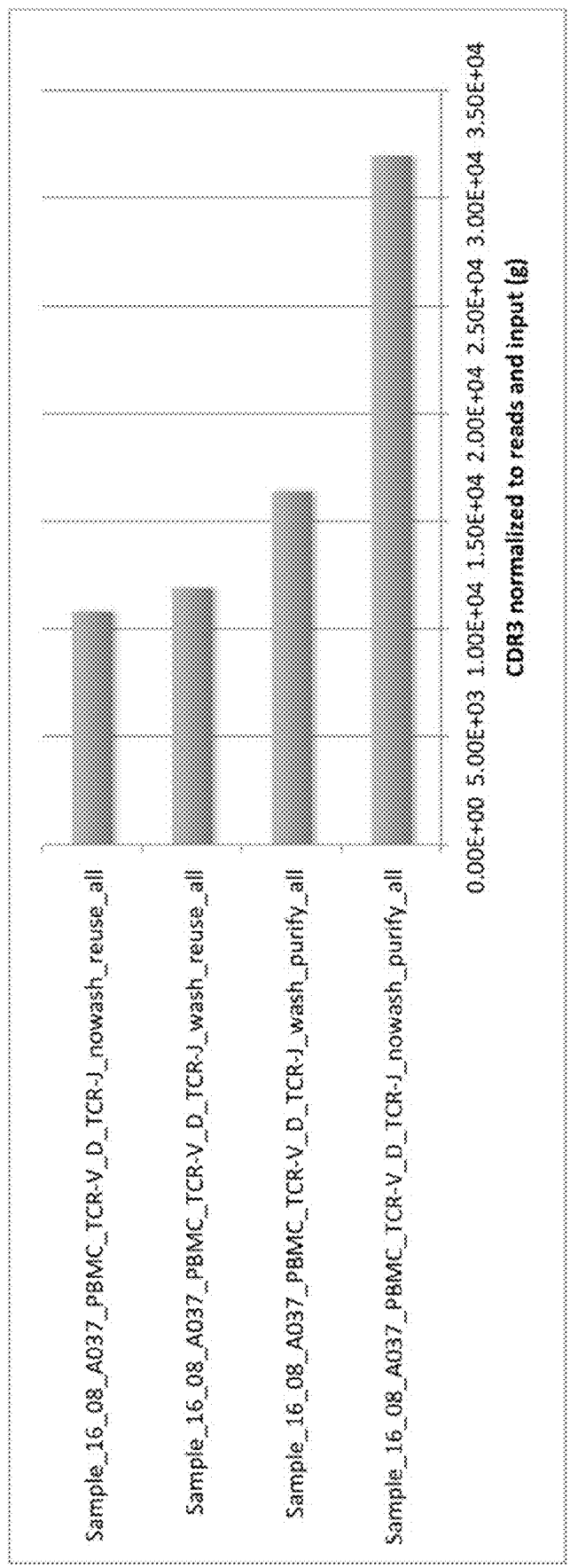
FIG. 7: Comparison of different depletion clean-up steps in terms of yielded average unique CDR3 sequences (normalized to reads and library input).

We determined the best method for depletion (FIG. 7). We found that direct reuse of the hybridization mixture following bead-probe-target separation yielded reduced signal than setting up a new reaction following Agencourt XP bead purification of the supernatant. We also found that direct separation rather than separation of the hybridization following addition of wash buffer yielded increased signal.

Figure 8:
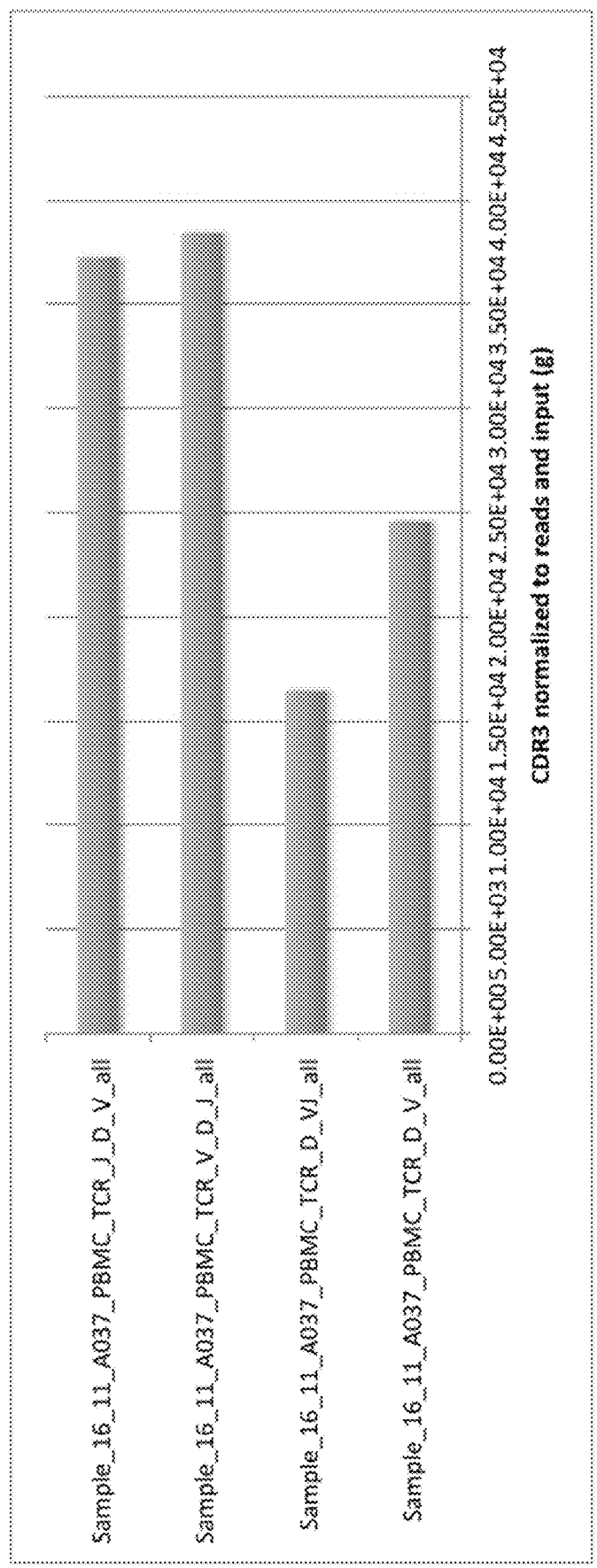
FIG. 8: Comparison of different permutations of iterative captures in terms of yielded average unique CDR3 sequences (normalized to reads and library input).

We tested whether depletion should be preceded by a V or J capture (FIG. 8). We found that direct depletion of the library, followed by V or J capture yielded reduced signal compared to either V-Depletion-J or J-Depletion-V, both of which had increased, yet similar yields.

Input Source Material Comparisons

Figure 9:
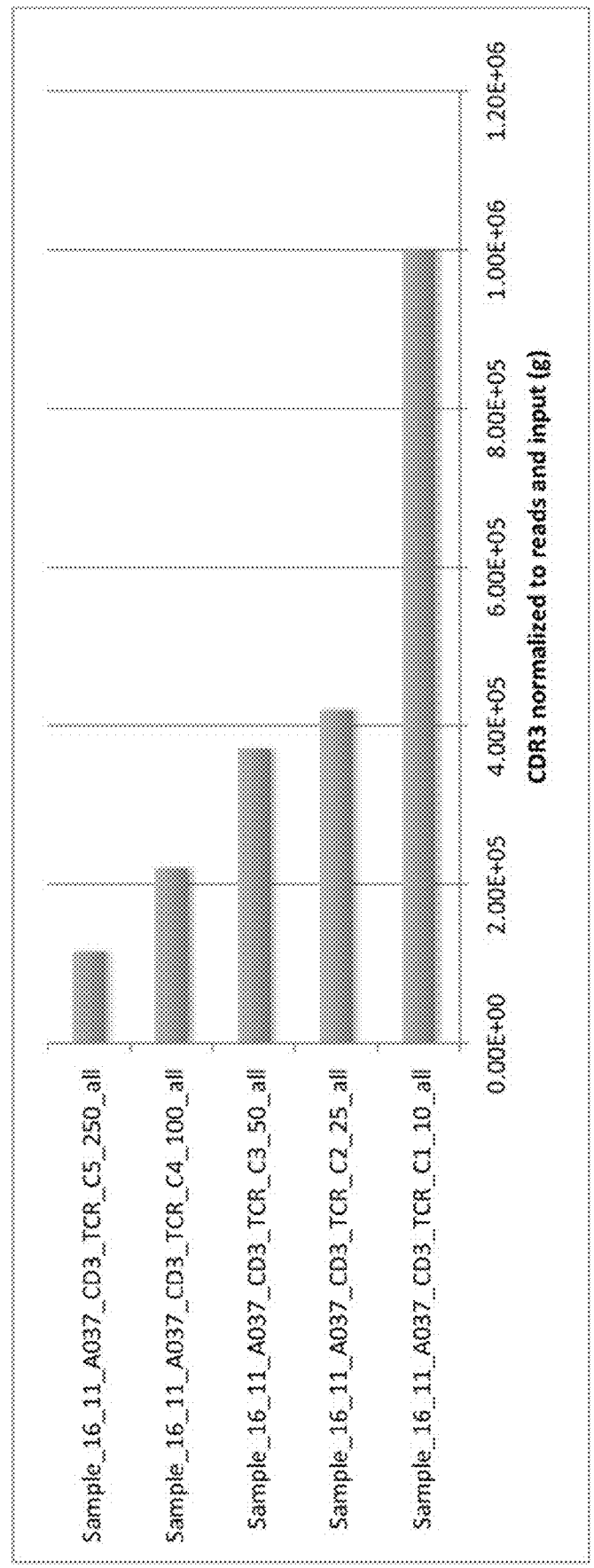
FIG. 9: CD3+ T cell fraction dilution curve. Comparison of average unique CDR3 sequences (normalized to reads and library input) for samples with varying amounts of source material added to generate the library (10 ng-250 ng).
Figure 10:
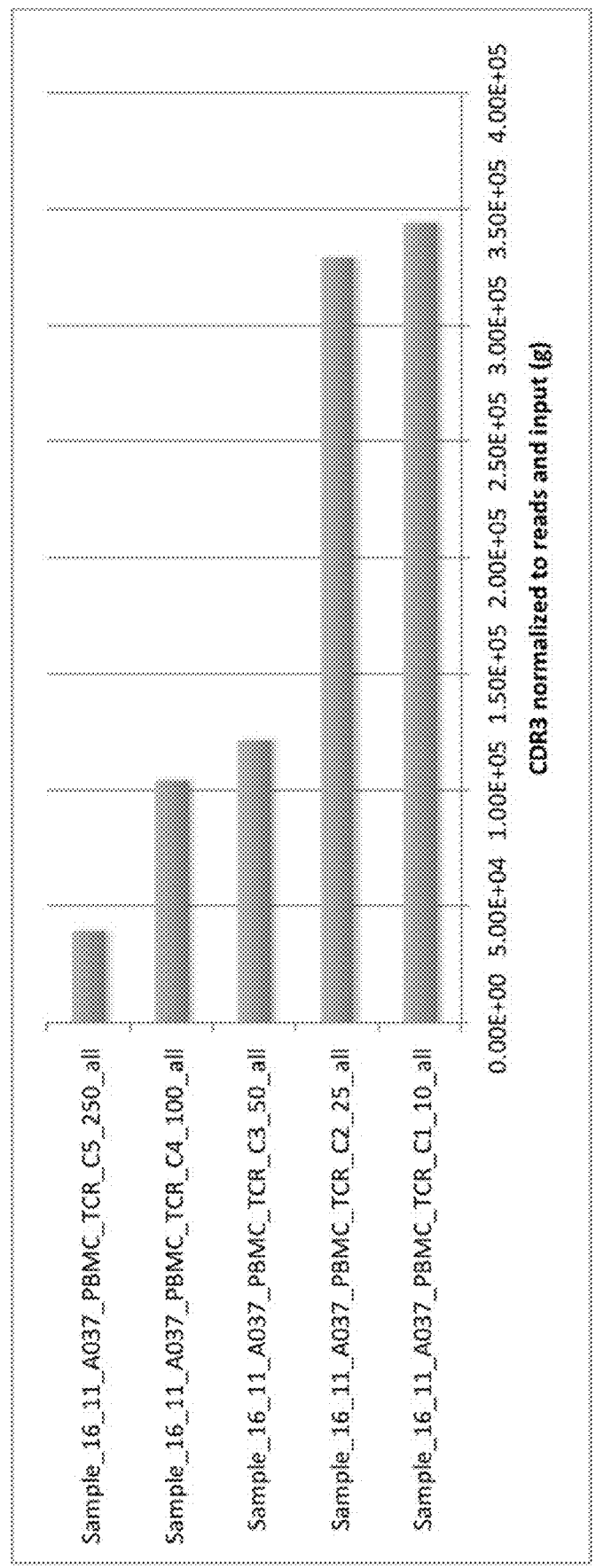
FIG. 10: PBMC fraction dilution curve. Comparison of average unique CDR3 sequences (normalized to reads and library input) for samples with varying amounts of source material added to generate the library (10 ng-250 ng).
Figure 11:
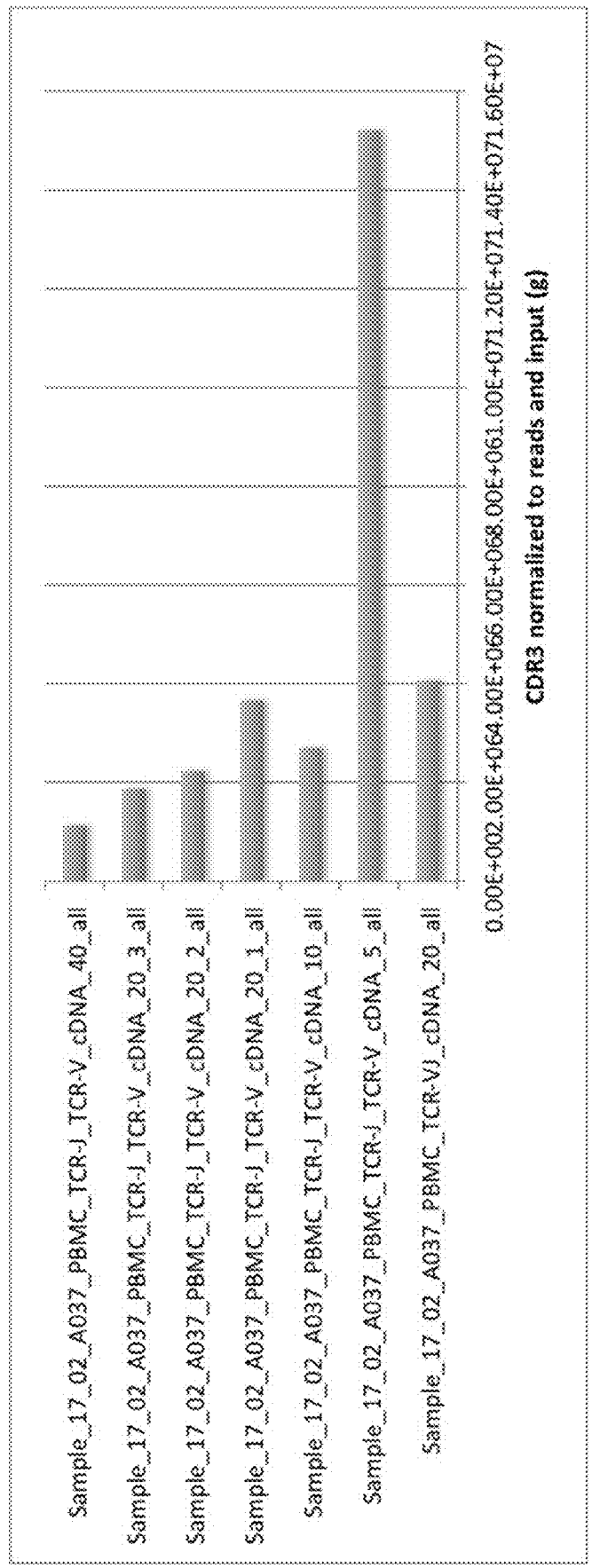
FIG. 11: PBMC fraction cDNA dilution curve. Comparison of average unique CDR3 sequences (normalized to reads and library input) for samples with varying amounts of source material added to generate the library (5 ng-40 ng).

To determine whether we could characterize the TCR repertoire from both low and high signal samples, we performed a series of dilution curves for CD3+ genomic DNA (FIG. 9), PBMC genomic DNA (FIG. 10), and PBMC derived cDNA (FIG. 11). Less input actually yielded a higher amount of diversity when normalized for input and reads suggesting that high input libraries are being under-sequenced or that probes are being saturated and leaving behind less preferable, but still on-target, targets. Additionally, we observed yields for the cDNA samples to be ~100× that of genomic DNA reflecting enrichment of the TCR signal as a consequence of the high level of transcript expression of the rearranged TCR gene relative to other genes. In contrast, signal from genomic DNA is a related to the fraction of the complete genome of the target sequence and capture efficiency.

Since each sequenced sample represents only a snapshot of the TCR repertoire with the extent dependent on the amount of input material and the complexity of the source repertoire, we were interested in whether the method could assay complete VJ or CDR3 saturation of a patient. We looked at unique VJ pair recovery across multiple samples derived from a single patient blood draw (data not shown). Beta locus VJ saturation was achieved with fewer than ten runs. With sufficient input and sequencing depth, VJ saturation could be achieved in a single run. We also looked at CDR3 saturation across these same samples and were able to achieve approximately 50% beta locus saturation (data not shown). This level could be achieved with fewer samples by using cDNA libraries as input with deeper sequencing.

Figure 12:
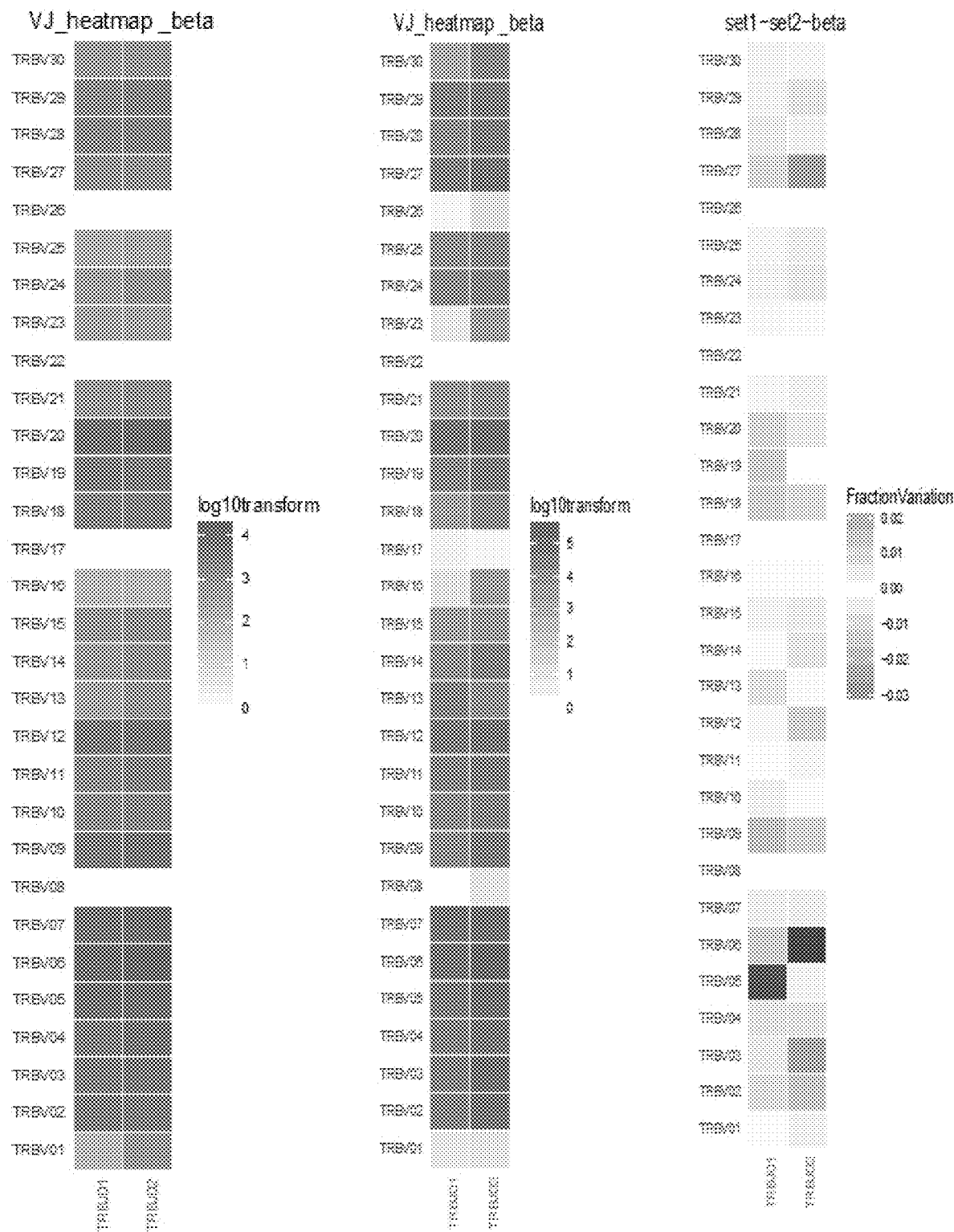
FIG. 12: Comparison of VJ beta locus repertoire for A037 sample derived from genomic DNA (panel 1) and from cDNA (panel 2). A subtractive heatmap is shown in panel 3 that shows differences in overall repertoire between the two samples. Red indicates deviation for genomic, while blue indicates deviation for cDNA.

We looked at whether the genomic DNA and cDNA samples were recapitulating the same VJ combinations at the beta locus (FIG. 12). This was largely the case with only two discordant VJ pairs showing greater (<3% overall) change.

Figure 13:
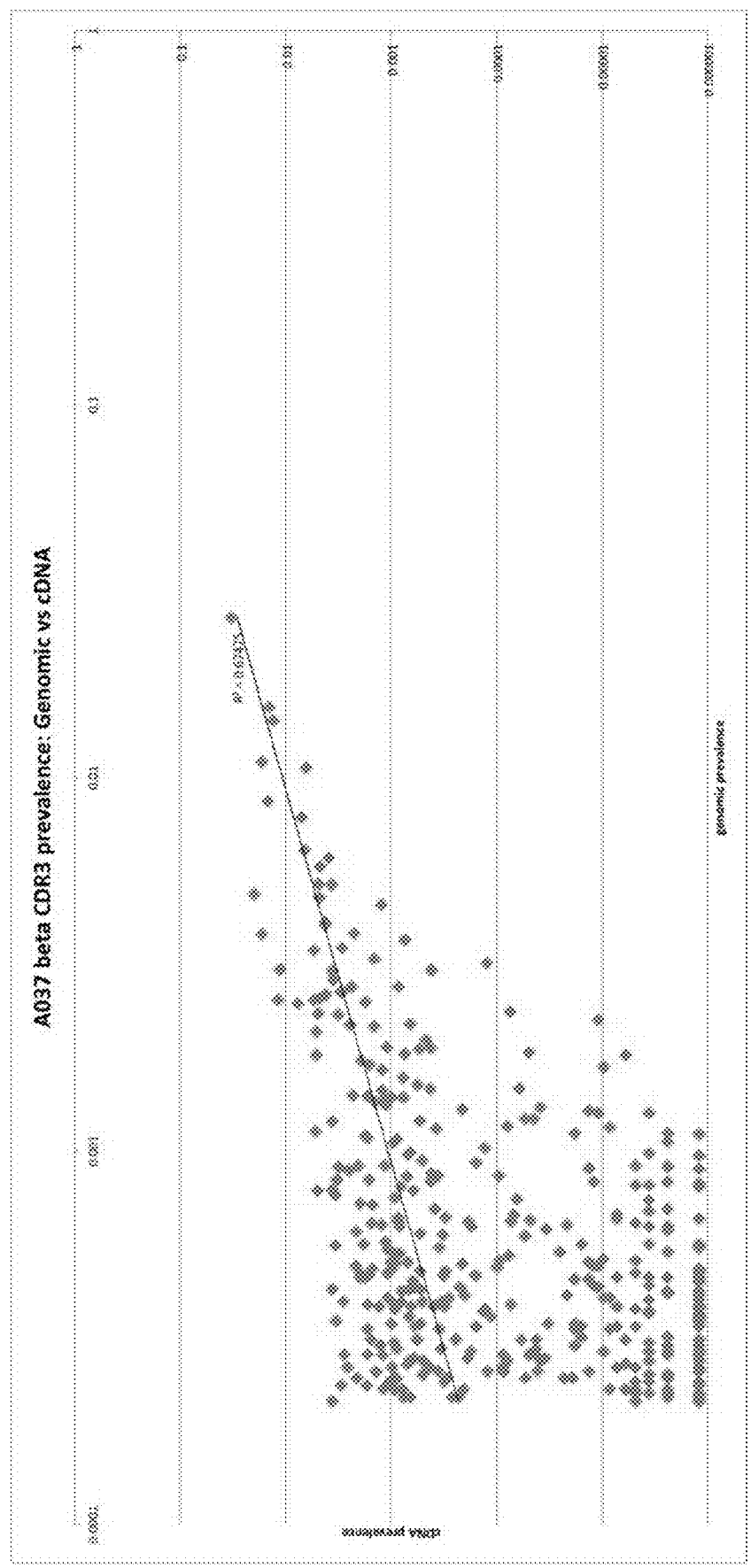
FIG. 13: Prevalence comparison of the top 1000 beta locus CDR3 in the genomic DNA set compared with their prevalences in the cDNA set.

We looked at whether the genomic DNA and cDNA samples were recapitulating the same CDR3 sequences (FIG. 13). For the most prevalent 1000 CDR3 sequences detected from genomic DNA, their correlation with cDNA prevalences had an r squared value of 0.67. Many had similar prevalences however a large number had very low or zero prevalence values in cDNA. This is likely explained by the second group consisting of non-productive rearrangements that are encoded on the alternate chromosome and which are not expressed.

Investigation of Samples from Adoptive Cell Transfer Immunotherapy

Figure 14:
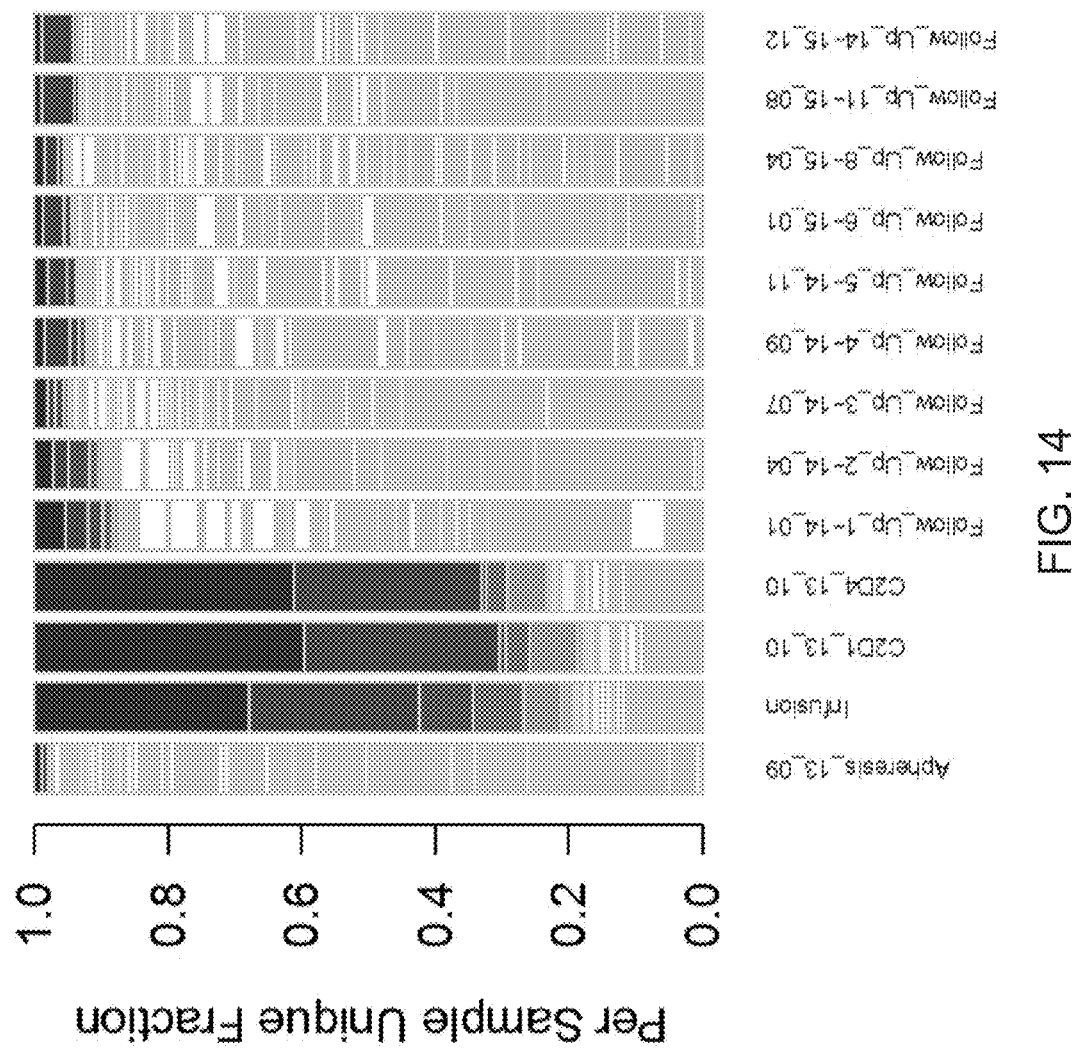
FIG. 14: Beta locus VJ repertoire of an adoptive cell transfer immunotherapy patient over time. Samples are indicated on the X axis ordered by date of sample. VJ clones are ordered in all samples according to prevalence in the TIL infusion product and the top nine most prevalent TIL infusion clones are colored.
Figure 15:
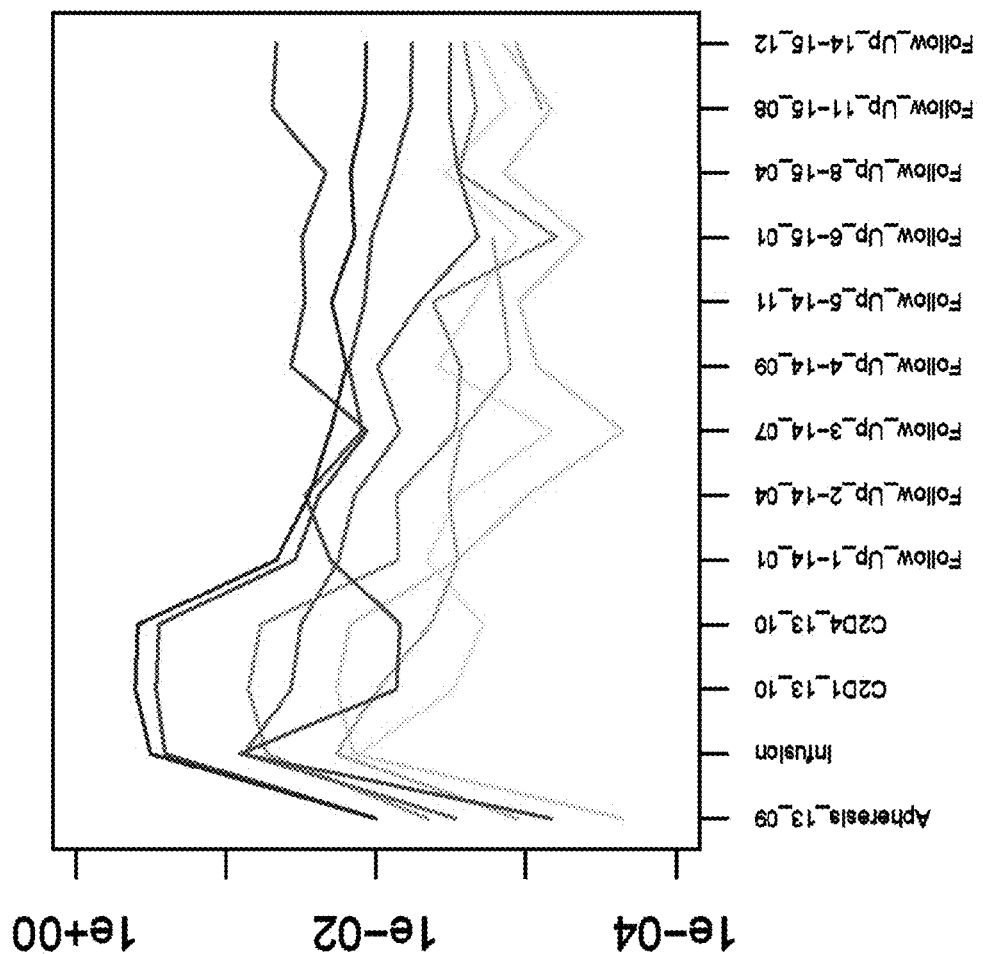
FIG. 15: Nine most prevalent TIL infusion clones at the Beta locus of an adoptive cell transfer immunotherapy patient over time. Samples are indicated on the X axis ordered by date of sample.

We next applied the CapTCR-Seq methodology to samples derived from expanded Tumor Infiltrating Lymphocyte (TIL) infusion populations and PBMCs from serial blood draws from patients undergoing adoptive cell transfer immunotherapy. We wanted to track clones from the TIL culture over time to determine whether they successfully colonized the patient and the extent of their population over time (FIG. 14). Repertoire profiling reveals a polyclonal and diverse baseline repertoire before treatment, a less complex oligoclonal TIL derived culture, less complex oligoclonal repertoires following chemodepletion and transfusion of the TIL infusion, and finally restoration of a more complex polyclonal repertoire over time. When compared to the baseline, highly prevalent clones in the TIL infusion product persist over time albeit in decreasing amounts. The dominant rearrangements decrease in prevalence over time as the native repertoire is reestablished however the TIL product rearrangements persist. We can observe this persistence by graphing the individual profiles for these top nine rearrangements over time (FIG. 15). We can see that while they decrease over time, they remain higher than what was found in the apheresis sample after two years.

Comparison Between Uncaptured and Captured Tumor Samples

We wished to demonstrate the value of this method for interrogating existing cDNA RNA-Seq libraries (data not shown). To do this, Illumina cDNA sequencing libraries were generated from FFPE-derived total RNA and subjected to sequencing followed by analysis using the TCR annotation pipeline to identify unique TCR CDR3 sequences (bulk unique CDR3). Residual library then underwent CapTCR-Seq to identify unique TCR CDR3 sequences (capture unique CDR3). The CapTCR-Seq method yielded a greatly increased number of unique CDR3 sequences (mean: 466 fold, median: 353 fold). When normalized to number of total reads sequenced, we observed a 15fold increase in signal per read sequenced (mean:15.2, median:14.5, n=41).

Investigation of Tumor Repertoires from Different Cancer Types

We next wanted to characterize tumor repertoires and investigate highly prevalent TIL clones in the blood repertoire before and during anti-PDL1 immunotherapy treatment. We selected five patients, each with a different tumor type: Patient A: Head and neck; Patient B: Breast; Patient C: Ovarian; Patient D: Melanoma; Patient E: Cervical. Each patient had three sample types: Tumor tissue (extracted DNA and RNA), pre-treatment blood (extracted PBMC DNA, PBMC RNA, and plasma cfDNA), on-treatment blood (extracted plasma cfDNA).

Figure 16:
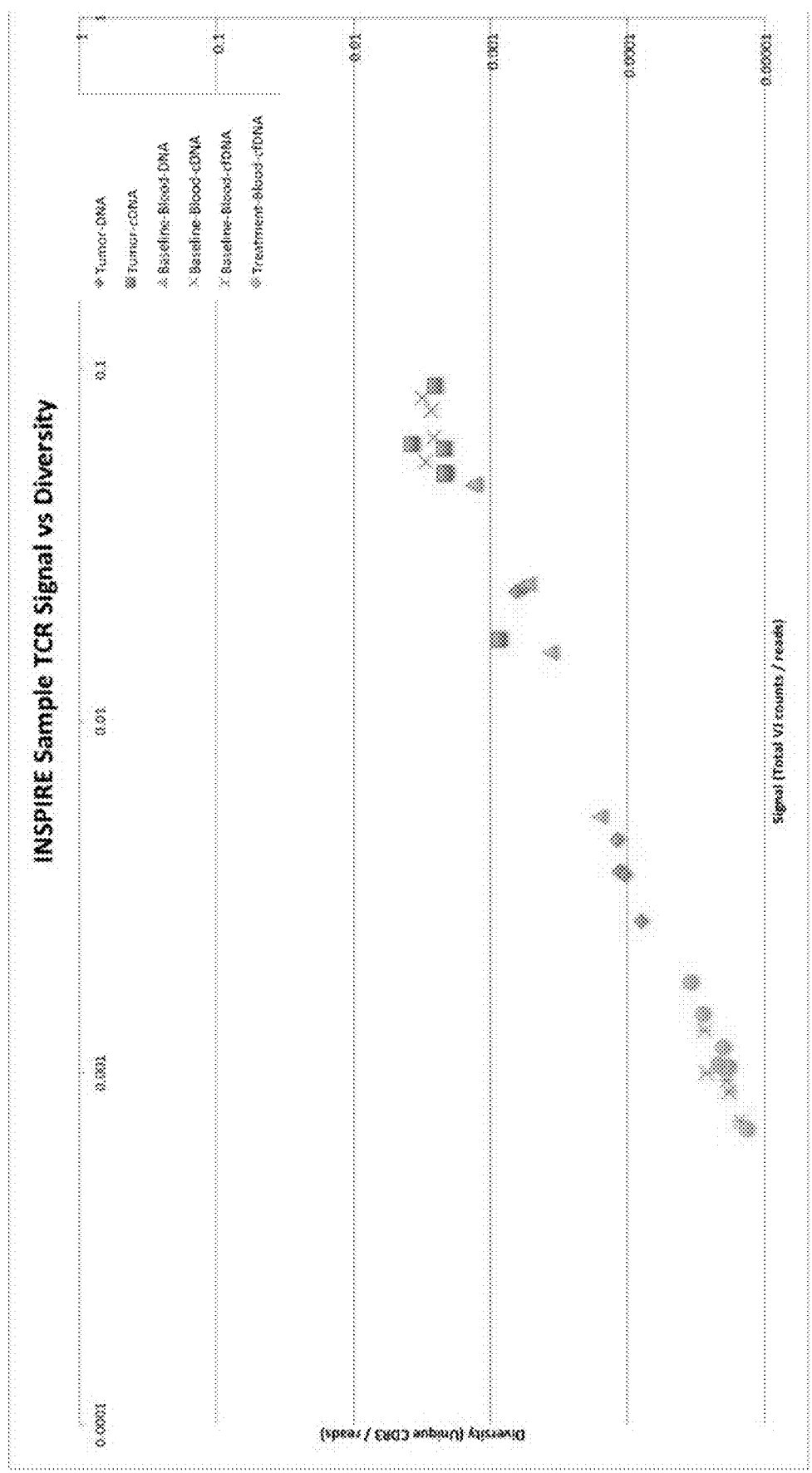
FIG. 16: TCR total signal (VJ counts) and repertoire diversity (unique CDR3 counts) for all samples from five patients.
Figure 17:
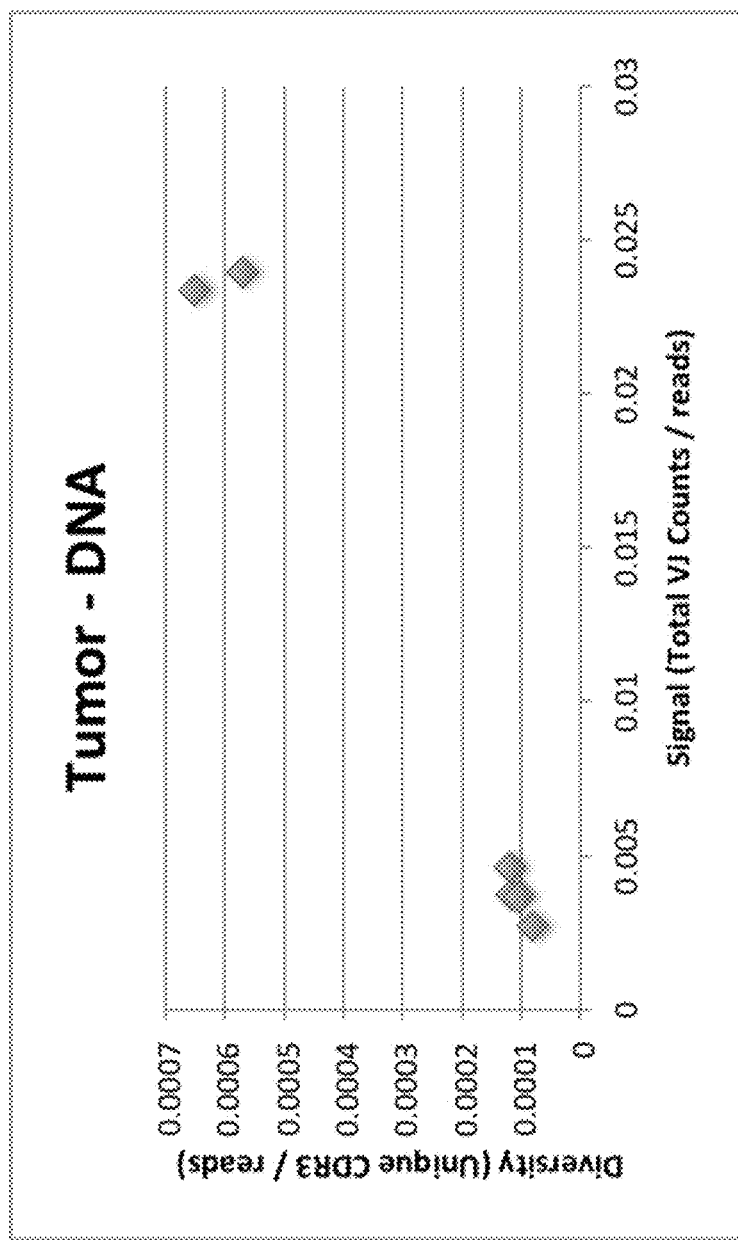
FIG. 17: TCR total signal (VJ counts) and repertoire diversity (unique CDR3 counts) for all tumor samples from five patients.

We first queried the extent of the TCR signal in the tumor samples in terms of infiltration and clonality. TCR signal is defined as the total number of counts of fragments containing both a V and J gene region (non-unique, reads normalized) while diversity is defined as the total number of unique CDR3 sequences detected (unique, reads normalized). Overall, diversity increased with signal (FIG. 16). cfDNA samples had the lowest signal, genomic DNA samples had intermediate signal, while cDNA samples had the highest signal. Blood sample signal and diversity is similar for all five patients, however tumor signal and diversity varied. Two patients had ten-fold higher TCR signal and diversity in their tumors likely reflecting increased infiltration of immune cells (FIG. 17).

Figure 18:
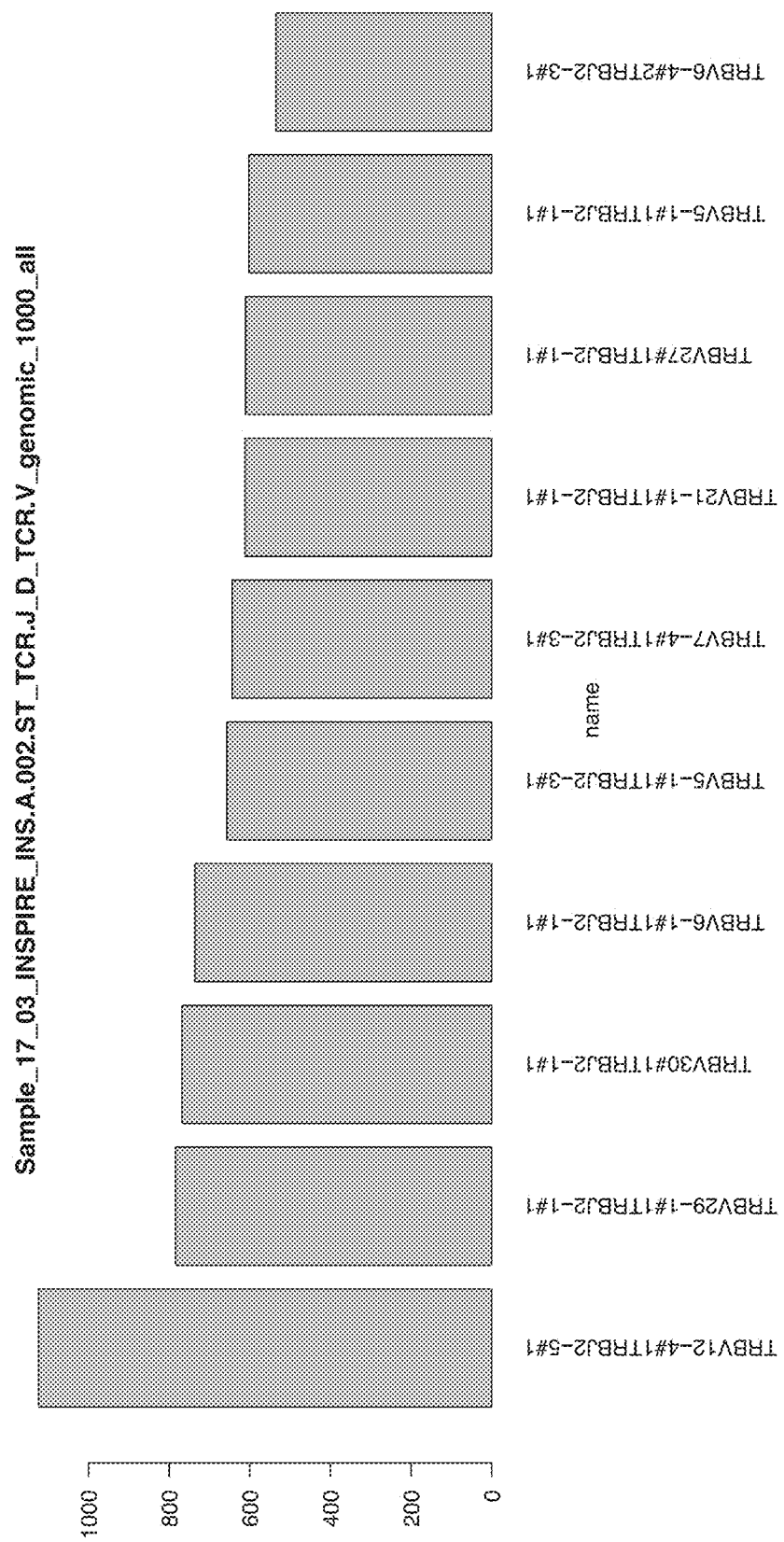
FIG. 18: Top ten most prevalent beta locus rearrangements from patient A tumor.
Figure 19A:
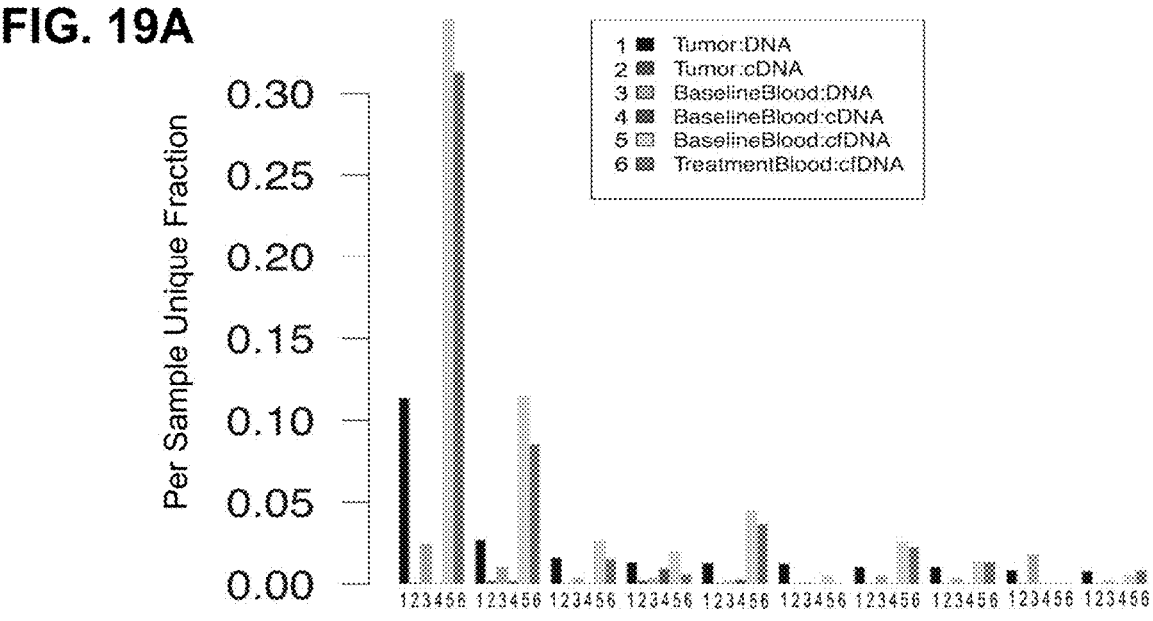
FIG. 19: Sample fractions within all patient A samples for top ten most prevalent VJ rearrangements in tumor. Alpha locus (panel 1), beta locus (panel 2), gamma locus (panel 3), delta locus (panel 4).
Figure 19B:
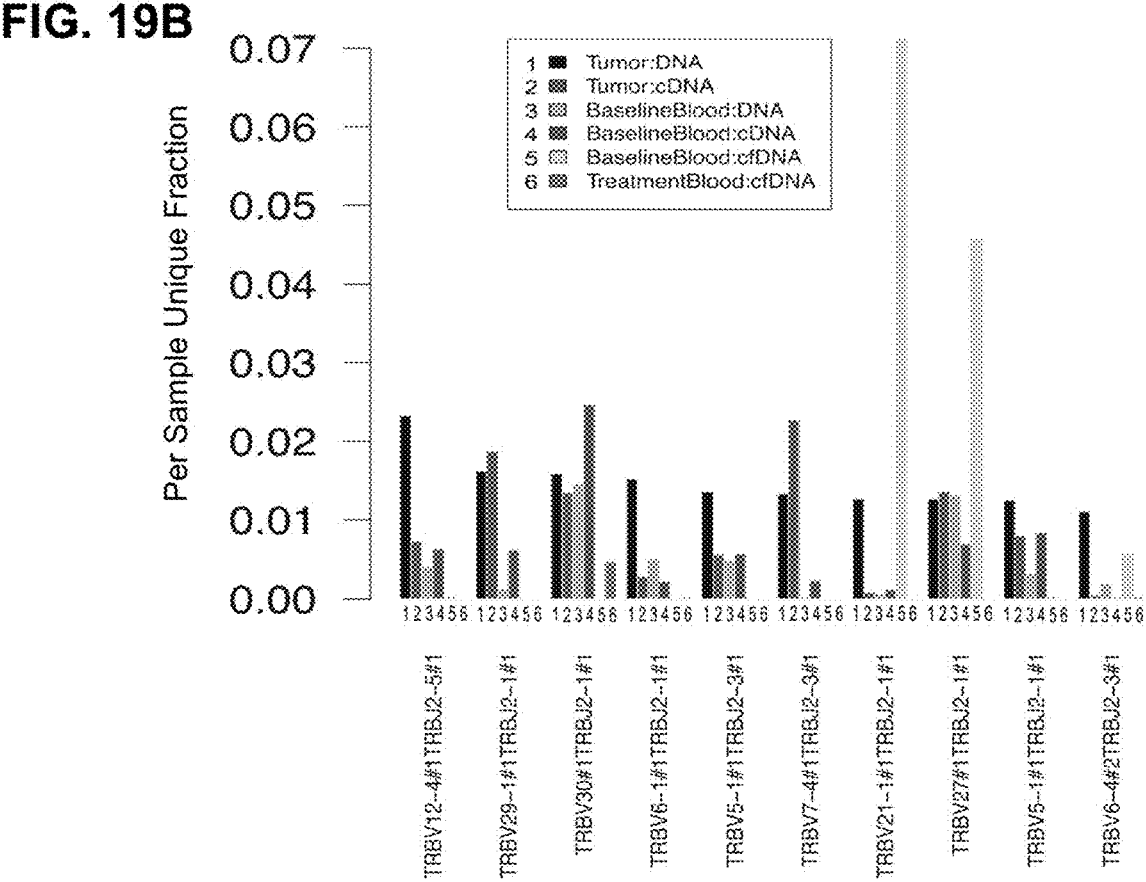
Figure 19C:
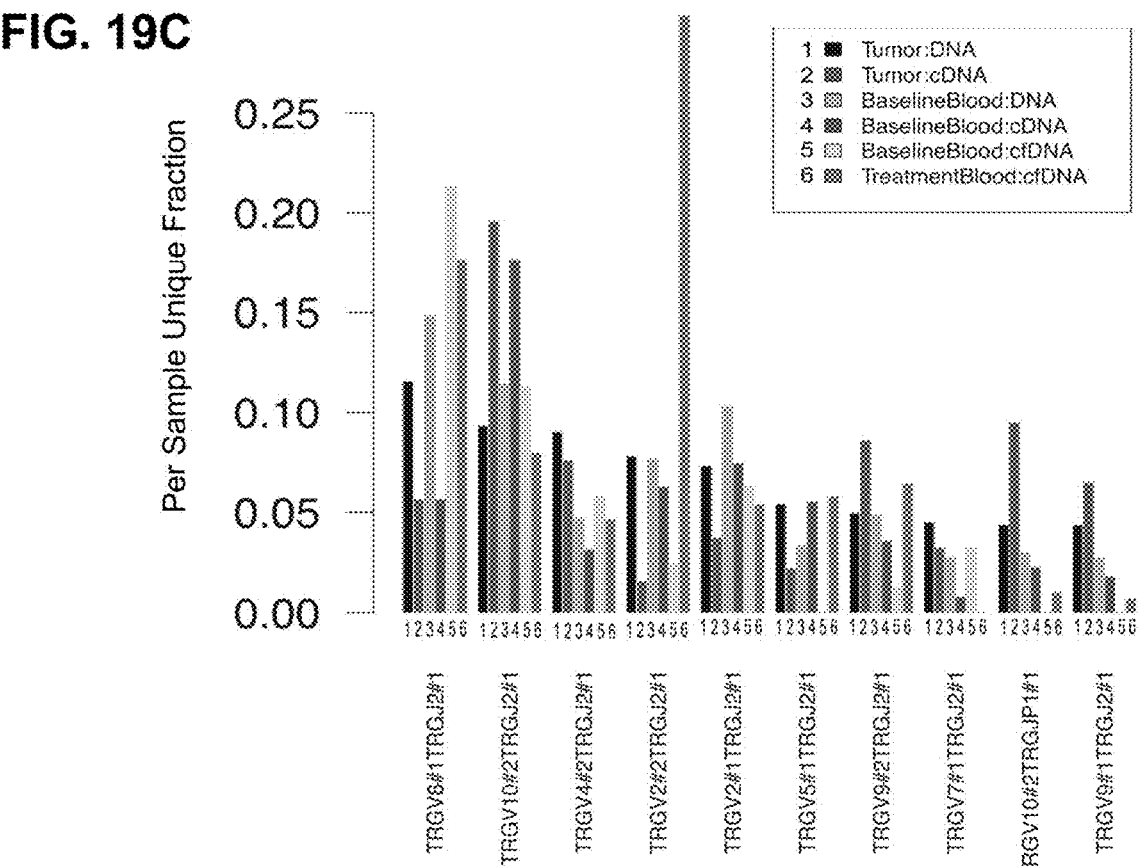
Figure 19D:
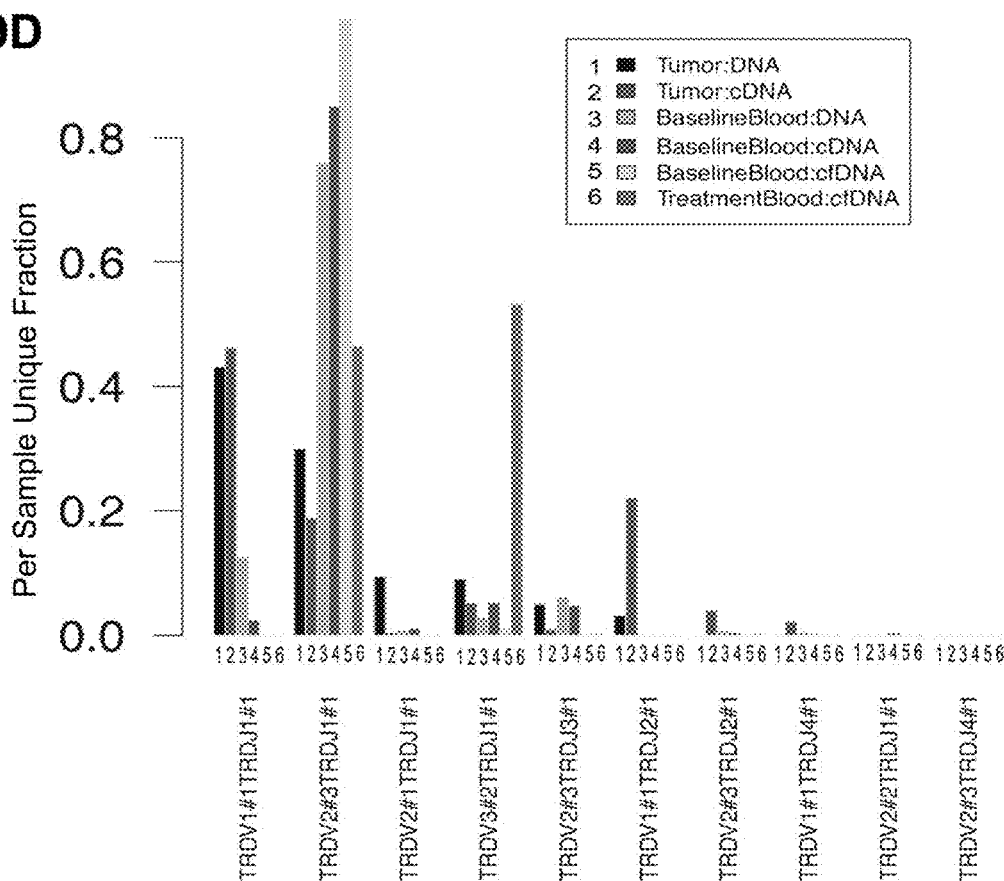

Next we assessed the clonality of the tumor sample TIL repertoire. Tumors with clonal infiltration have a larger than expected population of one or more VJ rearrangements, the population of which are significantly greater than the next most prevalent clone. Patient A appears to have a large alpha rearrangement population in its tumor compared to baseline blood, while the most prevalent beta rearrangement is only slightly enriched (FIG. 18 and data not shown). The tumor sample for patient B showed both greatly enriched top alpha and beta VJ rearrangements compared to baseline blood (data not shown). The tumor sample for patient C showed both greatly enriched top alpha and beta VJ rearrangements compared to baseline blood (data not shown). The tumor sample for patient D showed both greatly enriched top alpha (2) and beta VJ (1) rearrangements compared to baseline blood (data not shown). The tumor sample for patient E showed only a slightly enriched top beta VJ rearrangement compared to baseline blood (data not shown).

Next we assessed how the most prevalent tumor VJ rearrangements differed in terms of prevalence across the other patient samples (FIG. 19 and data not shown). In general, prevalent TIL clones were not prevalent in the blood repertoire demonstrating clonal expansion within the tumor or selective infiltration. However, for a number of the most prevalent TIL clones, we saw very high levels within the plasma samples suggesting that while these clones are actively undergoing cell death. In combination with their high tumor infiltration, this suggests that these are anti-tumor T-cells undergoing active expansion, anti-tumor cytotoxicity and turnover.

Example 4

We performed similar experiments relating to B-cells. Our design targets more than 500 V-regions and 50 J-regions within the IGH, IGK and IGL loci annotated in the IMmunoGeneTics database. This accounts for all known Ig alleles while maximizing depth of coverage in selected regions. A blast-based informatics pipeline calls V(D)J recombinations and an algorithm combining information from large-insert and soft-clipped reads are used to predict candidate rearrangements which are manually verified in Integrated Genome Viewer.

Candidate V(D)J rearrangements and translocations detected through this approach have been validated in three well-characterized cell-lines with publically available whole genome data; an additional 67 MM cell lines have been annotated for V(D)J rearrangements and translocations into IGH, IGL and IGK genes. The limit of detection was established with a cell-line dilution series. We were also able to translate these techniques to cell-free DNA. These methods are applicable to the detection of MRD in mature B-cell malignancies and immunoglobulin repertoire profiling in a many clinical scenarios including cellular immunotherapy and therapeutics with immunomodulatory effects. V(D)J and complex rearrangement annotations in 70 MM cell-lines are highly relevant in further in-vitro studies.

The B-cell V-gene and J-gene capture probes used are shown in Tables B1 and B2 respectively.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCE LIST

References

1. Bertness V, Kirsch I, Hollis G, Johnson B, Bunn P A Jr. T-cell receptor gene rearrangements as clinical markers of human T-cell lymphomas. N Engl J Med. 1985 Aug. 29; 313(9):534-8.
2. Swerdlow S H, Cancer I A for R on, Organization W H. WHO classification of tumours of haematopoietic and lymphoid tissues [Internet]. International Agency for Research on Cancer; 2008. Available from: http://books.google.ca/books?id=WqsTAQAAMAAJ
3. van Dongen J J, Wolvers-Tettero I L. Analysis of immunoglobulin and T cell receptor genes. Part I: Basic and technical aspects. Clin Chim Acta. 1991 April; 198(1-2):1-91.
4. Aisenberg A C. Utility of gene rearrangements in lymphoid malignancies. Annu Rev Med. 1993; 44:75-84.
5. Rezuke W N, Abernathy E C, Tsongalis G J. Molecular diagnosis of B- and T-cell lymphomas: fundamental principles and clinical applications. Clin Chem. 1997 October; 43(10):1814-23.
6. Armitage J O. The aggressive peripheral T-cell lymphomas: 2012 update on diagnosis, risk stratification, and management. Am J Hematol. 2012 May; 87(5):511-9.
7. Abouyabis A N, Shenoy P J, Lechowicz M J, Flowers C R. Incidence and outcomes of the peripheral T-cell lymphoma subtypes in the United States. Leuk Lymphoma. 2008 November; 49(11):2099-107.
8. Criscione V D, Weinstock M A. Incidence of cutaneous T-cell lymphoma in the United States, 1973-2002. Arch Dermatol. 2007 July; 143(7):854-9.
9. Ko O B, Lee D H, Kim S W, Lee J S, Kim S, Huh J, et al. Clinicopathologic characteristics of T-cell non-Hodgkin's lymphoma: a single institution experience. Korean J Intern Med. 2009 June; 24(2):128-34.
10. Luminari S, Cesaretti M, Rashid I, Mammi C, Montanini A, Barbolini E, et al. Incidence, clinical characteristics and survival of malignant lymphomas: a population-based study from a cancer registry in northern Italy. Hematol Oncol. 2007 December; 25(4):189-97.
11. Vazquez A, Khan M N, Blake D M, Sanghvi S, Baredes S, Eloy J A. Extranodal natural killer/T-Cell lymphoma: A population-based comparison of sinonasal and extranasal disease. Laryngoscope. 2014 April; 124(4):888-95.

12. Liao J B, Chuang S S, Chen H C, Tseng H H, Wang J S, Hsieh P P. Clinicopathologic analysis of cutaneous lymphoma in taiwan: a high frequency of extranodal natural killer/t-cell lymphoma, nasal type, with an extremely poor prognosis. Arch Pathol Lab Med. 2010 July; 134(7):996-1002.
13. Mitarnun W, Suwiwat S, Pradutkanchana J. Epstein-Barr virus-associated extranodal non-Hodgkin's lymphoma of the sinonasal tract and nasopharynx in Thailand. Asian Pac J Cancer Prev Apjcp. 2006 January; 7(1):91-4.
14. Shih L Y, Liang D C. Non-Hodgkin's lymphomas in Asia. Hematol—Oncol Clin N Am. 1991 October; 5(5):983-1001.
15. Ai W Z, Chang E T, Fish K, Fu K, Weisenburger D D, Keegan T H. Racial patterns of extranodal natural killer/T-cell lymphoma, nasal type, in California: a population-based study. Br J Haematol. 2012 March; 156(5):626-32.
16. Korgavkar K, Xiong M, Weinstock M. Changing incidence trends of cutaneous T-cell lymphoma. JAMA Dermatol. 2013 November; 149(11):1295-9.
17. Weinstock M A. Epidemiology of mycosis fungoides. Semin Dermatol. 1994 September; 13(3):154-9.
18. Weiss L M, Arber D A, Strickler J G. Nasal T-cell lymphoma. Ann Oncol. 1994; 5 Suppl 1:39-42.
19. Zackheim H S, Vonderheid E C, Ramsay D L, LeBoit P E, Rothfleisch J, Kashani-Sabet M. Relative frequency of various forms of primary cutaneous lymphomas. J Am Acad Dermatol. 2000 November; 43(5 Pt 1):793-6.
20. United Nations D of E and S A Population Division. International Migration Report 2009: A Global Assessment. United Nations, New York; 2011.
21. Cossman J, Uppenkamp M, Andrade R, Medeiros L J. T-cell receptor gene rearrangements and the diagnosis of human T-cell neoplasms. Crit Rev Oncol-Hematol. 1990; 10(3):267-81.
22. Vantourout P, Hayday A. Six-of-the-best: unique contributions of gammadelta T cells to immunology. Nat Rev Immunol. 2013 February; 13(2):88-100.
23. Lefranc M P. TRA (T cell receptor alpha). Atlas Genet Cytogenet Oncol Haematol. 2003; 7(4):245-8.
24. Lefranc M P. TRD (T cell receptor delta). Atlas Genet Cytogenet Oncol Haematol. 2003; 7(4):252-4.
25. Lefranc M P. TRB (T cell receptor beta). Atlas Genet Cytogenet Oncol Haematol. 2003; 7(4):249-51.
26. Lefranc M P. TRG (T cell receptor gamma). Atlas Genet Cytogenet Oncol Haematol. 2003; 7(4):255-6.
27. Bolotin D A, Mamedov I Z, Britanova O V, Zvyagin I V, Shagin D, Ustyugova S V, et al. Next generation sequencing for TCR repertoire profiling: platform-specific features and correction algorithms. Eur J Immunol. 2012 November; 42(11):3073-83.
28. Linnemann C, Heemskerk B, Kvistborg P, Kluin R J, Bolotin D A, Chen X, et al. High-throughput identification of antigen-specific TCRs by TCR gene capture. Nat Med. 2013 November; 19(11):1534-41.
29. van Dongen J J, Langerak A W, Bruggemann M, Evans P A, Hummel M, Lavender F L, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. 2003 December; 17(12):2257-317.
30. Amagai M, Hayakawa K, Amagai N, Kobayashi K, Onodera Y, Shimizu N, et al. T cell receptor gene rearrangement analysis in mycosis fungoides and disseminated lymphocytoma cutis. Dermatologica. 1990; 181(3):193-6.
31. Dosaka N, Tanaka T, Fujita M, Miyachi Y, Horio T, Imamura S. Southern blot analysis of clonal rearrangements of T-cell receptor gene in plaque lesion of mycosis fungoides. J Invest Dermatol. 1989 November; 93(5):626-9.
32. Chan D W, Liang R, Chan V, Kwong Y L, Chan T K. Detection of T-cell receptor delta gene rearrangement by clonal specific polymerase chain reaction. Leukemia. 1997 April; 11 Suppl 3:281-4.
33. Lynch J W Jr, Linoilla I, Sausville E A, Steinberg S M, Ghosh B C, Nguyen D T, et al. Prognostic implications of evaluation for lymph node involvement by T-cell antigen receptor gene rearrangement in mycosis fungoides. Blood. 1992 Jun. 15; 79(12):3293-9.
34. McClure R F, Kaur P, Pagel E, Ouillette P D, Holtegaard C E, Treptow C L, et al. Validation of immunoglobulin gene rearrangement detection by PCR using commercially available BIOMED-2 primers. Leukemia. 2006 January; 20(1):176-9.
35. Bagg A, Braziel R M, Arber D A, Bijwaard K E, Chu A Y. Immunoglobulin heavy chain gene analysis in lymphomas: a multi-center study demonstrating the heterogeneity of performance of polymerase chain reaction assays. J Mol Diagn. 2002 May; 4(2):81-9.
36. Cushman-Vokoun A M, Connealy S, Greiner T C. Assay design affects the interpretation of T-cell receptor gamma gene rearrangements: comparison of the performance of a one-tube assay with the BIOMED-2-based TCRG gene clonality assay. J Mol Diagn. 2010 November; 12(6):787-96.
37. Groenen P J, Langerak A W, van Dongen J J, van Krieken J H. Pitfalls in TCR gene clonality testing: teaching cases. J Hematop. 2008 September; 1(2):97-109.
38. Mamanova L, Coffey A J, Scott C E, Kozarewa I, Turner E H, Kumar A, et al. Target-enrichment strategies for next-generation sequencing. Nat Methods. 2010 February; 7(2):111-8.
39. Bossier AVDV. Chapter 4: Conventional and Real-Time Polymerase Chain Reaction. In: Tubbs R R. S M, editor. Cell and Tissue Based Molecular Pathology. Churchill Livingstone Elsevier; 2009. p. 33-49.
40. Rhodenizer D daSilva C; Skinner N; Hegde, M. One library, many tests: The evolution of Next Generation Sequencing panel testing. In 2014.
41. Bowen D C M; Kautzer, C; Landers, T; Mehta, G; Olivares. Improved Performance of Solution-based Target Enrichment with Spike-in of Individually Synthesized Capture DNA Probes. In 2012.
42. Jarosz M Z Z; Lipson D; Frampton, G; Yalensky, R; Parker A; Cronin, M. High Performance Solution-Based Target Selection Using Individually Synthesized Oligonucleotide Capture Probes. In 2011.
43. Shi W C C; Tang, T; Hipolito, L; Srinivasan, P; Chiang, D; Pend, D; Di Tomaso, E; Tangri, S; Lameh, J; Pollner, R. Development of a Clinical Targeted Next-Generation Sequencing (NGS) Test for Formalin-Fixed Paraffin-Embedded (FFPE) Cancer Samples. In 2014.
44. Schmidt R L, Factor R E. Understanding sources of bias in diagnostic accuracy studies. Arch Pathol Lab Med. 2013 April; 137(4):558-65.
45. Tomaszewski J E, Bear H D, Connally J A, Epstein J I, Feldman M, Foucar K, et al. Consensus conference on second opinions in diagnostic anatomic pathology. Who, What, and When. Am J Clin Pathol. 2000 September; 114(3):329-35.

46. Naaktgeboren C A, Bertens L C, van Smeden M, de Groot J A, Moons K G, Reitsma J B. Value of composite reference standards in diagnostic research. BMJ. 2013; 347:f5605.
47. Duncavage E J, Magrini V, Becker N, Armstrong J R, Demeter R T, Wylie T, et al. Hybrid capture and next-generation sequencing identify viral integration sites from formalin-fixed, paraffin-embedded tissue. J Mol Diagn. 2011 May; 13(3):325-33.
48. Gnirke A, Melnikov A, Maguire J, Rogov P, LeProust E M, Brockman W, et al. Solution hybrid selection with ultra-long oligonucleotides for massively parallel targeted sequencing. Nat Biotechnol. 2009 February; 27(2):182-9.
49. Gilbert M T, Haselkorn T, Bunce M, Sanchez J J, Lucas S B, Jewell L D, et al. The isolation of nucleic acids from fixed, paraffin-embedded tissues-which methods are useful when? PLoS One. 2007; 2(6):e537.
50. Bolotin D A, Poslaysky S, Mitrophanov I, Shugay M, Mamedov I Z, Putintseva E V, et al. MiXCR: software for comprehensive adaptive immunity profiling. Nat Methods. 2015 Apr. 29; 12(5):380-1.
51. Li S, Lefranc M-P, Miles J J, Alamyar E, Giudicelli V, Duroux P, et al. IMGT/HighV QUEST paradigm for T cell receptor IMGT clonotype diversity and next generation repertoire immunoprofiling. Nat Commun [Internet]. 2013 Sep. 2 [cited 2016 Jan. 30]; 4. Available from: http://www.nature.com/doifinder/10.1038/ncomms3333
52. Zhang J, Kobert K, Flouri T, Stamatakis A. PEAR: a fast and accurate Illumine Paired-End reAd mergeR. Bioinforma Oxf Engl. 2014 Mar. 1; 30(5):614-20.
53. Larkin M A, Blackshields G, Brown N P, Chenna R, McGettigan P A, McWilliam H, et al. Clustal W and Clustal X version 2.0. Bioinformatics. 2007 Nov. 1; 23(21):2947-8.
54. Giudicelli V, Chaume D, Lefranc M P. IMGT/GENE-DB: a comprehensive database for human and mouse immunoglobulin and T cell receptor genes. Nucleic Acids Res. 2005 Jan. 1; 33(Database issue):D256-61.
55. Li H D R. Fast and accurate short read alignment with Burrows-Wheeler Transform. Bioinformatics. 2009; 25:1754-60.
56. Brochet X, Lefranc M P, Giudicelli V. IMGT/V-QUEST: the highly customized and integrated system for IG and TR standardized V-J and V-D-J sequence analysis. Nucleic Acids Res. 2008 Jul. 1; 36(Web Server issue): W503-8.
57. Giudicelli V, Lefranc M P. IMGT/junctionanalysis: IMGT standardized analysis of the V-J and V-D-J junctions of the rearranged immunoglobulins (IG) and T cell receptors (TR). Cold Spring Harb Protoc. 2011 June; 2011(6):716-25.
58. Giudicelli V, Brochet X, Lefranc M P. IMGT/V-QUEST: IMGT standardized analysis of the immunoglobulin (IG) and T cell receptor (TR) nucleotide sequences. Cold Spring Harb Protoc. 2011 June; 2011(6):695-715.
59. Yousfi Monod M, Giudicelli V, Chaume D, Lefranc M P. IMGT/JunctionAnalysis: the first tool for the analysis of the immunoglobulin and T cell receptor complex V-J and V-D-J JUNCTIONs. Bioinformatics. 2004 Aug. 4; 20 Suppl 1:i379-85.
60. Smith T F, Waterman M S. Identification of common molecular subsequences. J Mol Biol. 1981 Mar. 25; 147(1):195-7.
61. Krzywinski M, Schein J, Birol I, Connors J, Gascoyne R, Horsman D, et al. Circos: an information aesthetic for comparative genomics. Genome Res. 2009 September; 19(9):1639-45.
62. Lefranc M P. Unique database numbering system for immunogenetic analysis. Immunol Today. 1997 November; 18(11):509.
63. Lefranc M P, Pommie C, Ruiz M, Giudicelli V, Foulquier E, Truong L, et al. IMGT unique numbering for immunoglobulin and T cell receptor variable domains and Ig superfamily V-like domains. Dev Comp Immunol. 2003 January; 27(1):55-77.
64. Altschul S, Erickson B. Optimal sequence alignment using affine gap costs. Bull Math Biol. 1986 Sep. 1; 48(5-6):603-16.
65. Lefranc M P. IMGT-ONTOLOGY and IMGT databases, tools and Web resources for immunogenetics and immunoinformatics. Mol Immunol. 2004 January; 40(10):647-60.
66. Lefranc M P. IMGT databases, web resources and tools for immunoglobulin and T cell receptor sequence analysis, http://imgt.cines.fr. Leukemia. 2003 January; 17(1): 260-6.
67. Sandberg Y, Verhaaf B, van Gastel-Mol E J, Wolvers-Tettero I L, de Vos J, Macleod R A, et al. Human T-cell lines with well-defined T-cell receptor gene rearrangements as controls for the BIOMED-2 multiplex polymerase chain reaction tubes. Leukemia. 2007 February; 21(2):230-7.
68. Ye J, Coulouris G, Zaretskaya I, Cutcutache I, Rozen S, Madden T L. Primer-BLAST: a tool to design target-specific primers for polymerase chain reaction. BMC Bioinformatics. 2012; 13:134.
69. Kent W J. S C. W.; Furey, T. S.; Roskin, K. M.; Pringle, T. H.; Zahler, A. M.; Haussler, D. The human genome browser at UCSC. Genome Res. 2002 June; 12(6):996-1006.
70. Malde K. The effect of sequence quality on sequence alignment. Bioinformatics. 2008 Apr. 1; 24(7):897-900.
71. Davidson J N, Leslie I, White J C. Quantitative studies on the content of nucleic acids in normal and leukaemic cells, from blood and bone marrow. J Pathol Bacteriol. 1951 July; 63(3):471-83.
72. Glen A C. Measurement of DNA and RNA in human peripheral blood lymphocytes. Clin Chem. 1967 April; 13(4):299-313.
73. Metais P, Mandel P. [Percentage of desoxypentose-nucleic acid in leucocytes in normal and pathological conditions]. C R Seances Soc Biol Fil. 1950 February; 144(3-4):277-9.
74. Jones S R, Carley S, Harrison M. An introduction to power and sample size estimation. Emerg Med J. 2003 September; 20(5):453-8.
75. Network NCC. NCCN Clinical Practice Guidelines in Oncology. National Comprehensive Cancer Network, Inc.; 2014.
76. Jaffe E S, Organization W H. Pathology and Genetics of Tumours of Haematopoietic and Lymphoid Tissues [Internet]. IARC Press; 2001. Available from: http://books.google.caJbooks?id=XSKqcy7TUZUC
77. Gazzola A, Mannu C, Rossi M, Laginestra M A, Sapienza M R, Fuligni F, et al. The evolution of clonality testing in the diagnosis and monitoring of hematological malignancies. Ther Adv Hematol. 2014 Apr. 1; 5(2):35-47.
78. Tape T. Interpreting Diagnostic Tests [Internet]. University of Nebraska Medical Center; [cited 2015 Nov. 8]. Available from: http://gim.unmc.edu/dxtests/Default.htm
79. Hu P C, Hegde M R, Lennon P A, editors. Modern clinical molecular techniques. New York: Springer; 2012.436 p.

80. Brunet J-P, Tamayo P, Golub T R, Mesirov J P. Metagenes and molecular pattern discovery using matrix factorization. Proc Natl Acad Sci USA. 2004 Mar. 23; 101(12):4164-9.
81. Tembhare P, Yuan C M, Xi L, Morris J C, Liewehr D, Venzon D, et al. Flow cytometric immunophenotypic assessment of T-cell clonality by VR repertoire analysis: detection of T-cell clonality at diagnosis and monitoring of minimal residual disease following therapy. Am J Clin Pathol. 2011 June; 135(6):890-900.
82. Sufficool K E, Lockwood C M, Abel H J, Hagemann I S, Schumacher J A, Kelley T W, et al. T-cell clonality assessment by next-generation sequencing improves detection sensitivity in mycosis fungoides. J Am Acad Dermatol. 2015 August; 73(2):228-36.e2.
83. Cazzaniga G, Biondi A. Molecular monitoring of childhood acute lymphoblastic leukemia using antigen receptor gene rearrangements and quantitative polymerase chain reaction technology. Haematologica. 2005 March; 90(3):382-90.
84. Lima M, Almeida J, Santos A H, dos Anjos Teixeira M, Alguero M C, Queirós M L, et al. Immunophenotypic analysis of the TCR-Vbeta repertoire in 98 persistent expansions of CD3(+)/TCR-alphabeta(+) large granular lymphocytes: utility in assessing clonality and insights into the pathogenesis of the disease. Am J Pathol. 2001 November; 159(5):1861-8.
85. Miles J J, Douek D C, Price D A. Bias in the αβ T-cell repertoire: implications for disease pathogenesis and vaccination. Immunol Cell Biol. 2011 March; 89(3):375-87.
86. Society C C. Non-Hodgkin Lymphoma Statistics [Internet]. Cancer Information. 2014. Available from: http://www.cancer.ca/en/cancer-information/cancer-type/non-hodgkin-lymphomaistatistics/?region=on
87. Canada S. Population by year, by province and territory [Internet]. 2014 September Available from: www.statcan.gc.ca/tables-tableaux/sum-som/I01/cst01/demo02a-end.htm
88. Information C I for H. DAD Abstracting Manual, 2012-2013 Edition [Internet]. 2012 April Available from: http://sda.chass.utoronto.ca.myaccess.library.utoronto.ca/sdaweb/cihi/2011 to2013/clin/more_doc/DAD_Abstracting_Manual_2012-2013_E.pdf
89. Information C I for H. CIHI Specifications Form for Research Analytical Files [Internet]. 2014 February Available from: http://sda.chass.utoronto.ca.myaccess.library.utoronto.ca/sdaweb/cihi/2011 to2013/clin/more_doc/Specifications-DAD-RAF-EN.pdf
A1. van Dongen, J. J. M. et al. Design and standardization of PCR primers and protocols for detection of clonal immunoglobulin and T-cell receptor gene recombinations in suspect lymphoproliferations: Report of the BIOMED-2 Concerted Action BMH4-CT98-3936. Leukemia 17, 2257-2317 (2003).
A2. Langerak, A. W. et al. EuroClonality/BIOMED-2 guidelines for interpretation and reporting of Ig/TCR clonality testing in suspected lymphoproliferations. Leukemia 26, 2159-2171 (2012).
A3. Han, A., Glanville, J., Hansmann, L. & Davis, M. M. Linking T-cell receptor sequence to functional phenotype at the single-cell level. Nat Biotech 32, 684-692 (2014).
A4. Stubbington, M. J. T. et al. T cell fate and clonality inference from single-cell transcriptomes. Nat Meth 13, 329-332 (2016).
A5. Samorodnitsky, E. et al. Evaluation of Hybridization Capture Versus Amplicon-Based Methods for Whole-Exome Sequencing. Human Mutation 36, 903-914 (2015).
A6. Mamanova, L. et al. Target-enrichment strategies for next-generation sequencing. Nat. Methods 7, 111-118 (2010).
A7. Bodi, K. et al. Comparison of Commercially Available Target Enrichment Methods for Next-Generation Sequencing. J Biomol Tech 24, 73-86 (2013).
A8. Mertes, F. et al. Targeted enrichment of genomic DNA regions for next-generation sequencing. Briefings in Functional Genomics 10, 374-386 (2011).
A9. Giudicelli, V. et al. IMGT/LIGM-DB, the IMGT comprehensive database of immunoglobulin and T cell receptor nucleotide sequences. Nucleic Acids Res. 34, D781-784 (2006).
A10. Bolotin, D. A. et al. MiTCR: software for T-cell receptor sequencing data analysis. Nat Meth 10, 813-814 (2013).
A11. Bolotin, D. A. et al. MiXCR: software for comprehensive adaptive immunity profiling. Nat Meth 12, 380-381 (2015).
A12. Brochet, X., Lefranc, M.-P. & Giudicelli, V. IMGT/V-QUEST: the highly customized and integrated system for IG and TR standardized V-J and V-D-J sequence analysis. Nucleic Acids Res. 36, W503-508 (2008).
A13. Thomas, N., Heather, J., Ndifon, W., Shawe-Taylor, J. & Chain, B. Decombinator: a tool for fast, efficient gene assignment in T-cell receptor sequences using a finite state machine. Bioinformatics 29, 542-550 (2013).
A14. Yu, Y., Ceredig, R. & Seoighe, C. LymAnalyzer: a tool for comprehensive analysis of next generation sequencing data of T cell receptors and immunoglobulins. Nucl. Acids Res. gkv1016 (2015). doi:10.1093/nar/gkv1016
A15. Zhang, W. et al. IMonitor: A Robust Pipeline for TCR and BCR Repertoire Analysis. Genetics 201, 459-472 (2015).
A16. Calis, J. J. A. & Rosenberg, B. R. Characterizing immune repertoires by high throughput sequencing: strategies and applications. Trends Immunol 35, 581-590 (2014).
A17. Sandberg, Y. et al. Human T-cell lines with well-defined T-cell receptor gene rearrangements as controls for the BIOMED-2 multiplex polymerase chain reaction tubes. Leukemia 21, 230-237 (2007).
A18. Zhang, J., Kobert, K., Flouri, T. & Stamatakis, A. PEAR: a fast and accurate Illumina Paired-End reAd mergeR. Bioinformatics 30, 614-620 (2014).
A19. Camacho, C. et al. BLAST+: architecture and applications. BMC Bioinformatics 10, 421 (2009).
B1. Rosenberg, S. A., and Restifo, N. P. (2015). Adoptive cell transfer as personalized immunotherapy for human cancer. Science 348, 62-68.
B2. Hadrup, S., Donia, M., and thor Straten, P. (2013). Effector CD4 and CD8 T Cells and Their Role in the Tumor Microenvironment. Cancer Microenvironment 6, 123-133.
B3. Attaf, M., Huseby, E., and Sewell, A. K. (2015). αβ T cell receptors as predictors of health and disease. Cell. Mol. Immunol. 12, 391-399.
B4. Gubin, M. M., Artyomov, M. N., Mardis, E. R., and Schreiber, R. D. (2015). Tumor neoantigens: building a framework for personalized cancer immunotherapy. Journal of Clinical Investigation 125, 3413-3421.
B5. Clemente, M. J., Przychodzen, B., Jerez, A., Dienes, B. E., Afable, M. G., Husseinzadeh, H., Rajala, H. L. M., Wlodarski, M. W., Mustjoki, S., and Maciejewski, J. P. (2013). Deep sequencing of the T-cell receptor repertoire in CD8+T-large granular lymphocyte leukemia identifies signature landscapes. Blood 122, 4077-4085.

B6. Topalian, S. L., Drake, C. G., and Pardoll, D. M. (2015). Immune checkpoint blockade: a common denominator approach to cancer therapy. Cancer Cell 27, 450-461.

B7. Novosiadly, R., and Kalos, M. (2016). High-content molecular profiling of T-cell therapy in oncology. Molecular Therapy—Oncolytics 3, 16009.

B8. Abbey, J. L., and O'Neill, H. C. (2007). Expression of T-cell receptor genes during early T-cell development. Immunol Cell Biol 86, 166-174.

B9. Emerson, R. O., Sherwood, A. M., Rieder, M. J., Guenthoer, J., Williamson, D. W., Carlson, C. S., Drescher, C. W., Tewari, M., Bielas, J. H., and Robins, H. S. (2013). High-throughput sequencing of T-cell receptors reveals a homogeneous repertoire of tumour-infiltrating lymphocytes in ovarian cancer. J. Pathol. 231, 433-440.

B10. Gerlinger, M., Quezada, S. A., Peggs, K. S., Furness, A. J. S., Fisher, R., Marafioti, T., Shende, V. H., McGranahan, N., Rowan, A. J., Hazell, S., et al. (2013). Ultra-deep T cell receptor sequencing reveals the complexity and intratumour heterogeneity of T cell clones in renal cell carcinomas. J. Pathol. 231, 424-432.

B11. Restifo, N. P., Dudley, M. E., and Rosenberg, S. A. (2012). Adoptive immunotherapy for cancer: harnessing the T cell response. Nat. Rev. Immunol. 12, 269-281.

B12. Silva-Santos, B., Serre, K., and Norell, H. (2015). γδ T cells in cancer. Nat Rev Immunol 15, 683-691.

B13. Tscharke, D. C., Croft, N. P., Doherty, P. C., and La Gruta, N. L. (2015). Sizing up the key determinants of the CD8(+) T cell response. Nat. Rev. Immunol. 15, 705-716.

B14. Wherry, E. J., and Kurachi, M. (2015). Molecular and cellular insights into T cell exhaustion. Nat Rev Immunol 15, 486-499.

TABLE 2

Cell Line Identified VJ Rearrangements

| Cell Line | Internal | Reference Collection # | Alpha | Beta | Gamma | Delta |
|---|---|---|---|---|---|---|
| | | | | Previously Documented/Known TCR Configurations | | |
| CEM | SE14-2035 | ATCC CCL-119 | NA | TRBV3-1*01-TRBD1*01-TRBJ2-3*01 | TRGV3-TRGJ1/TRGJ2 | NA |
| | | | | TRBJ1-5-TRBJ2-1 (partial rearrangement) TRBV9-TRBD2 (partial rearrangement) | TRGV4-TRGJ1/TRGJ2 | |
| | | | Alpha (Counts) | Beta (Counts) | Gamma (Counts) | Delta |
| | | | | Observed | | |
| | | | TRAV27#1TRAJ40#1 (987) | TRBV3-1#1TRBJ2-3#1 (1087) | TRGV4#2TRGJ2#1 (809) | ND |
| | | | TRAV29_DV5#1TRAJ4#1 (765) | TRBV3-2#3TRBJ2-3#1 (512) | TRGV3#2TRGJ2#1 (604) | |
| | | | TRAV29_DV5#3TRAJ4#1 (45) | TRBV3-2#3TRBJ2-4#1 (45) | TRGV3#1TRGJ2#1 (228) | |
| | | | TRAV27#3TRAJ40#1 (3) | TRBV3-1#1TRBJ2-5#1 (8) | TRGV5#1TRGJ2#1 (106) | |
| | | | TRAV27#2TRAJ40#1 (1) TRAV8-6#2TRAJ20#1 (1) | TRBV3-1#1TRBJ2-4#1 (4) TRBV3-1#1TRBJ2-6#1 (2) TRBV3-2#3TRBJ2-6#1 (2) TRBV9#2TRBJ2-1#1 (1) | TRGV4#1TRGJ2#1 (1) | |
| | | | | Previously Documented/Known TCR Configurations | | |
| Jurkat | SE14-2033 | DSMZ ACC-282 | TRAV8-4-TRAJ3 | TRBV12-3-TRBJ1-2 (partial rearrangement) | TRGV8-TRGJ1/TRGJ2 | NA |
| | | | | | TRGV11-TRGJ1/TRGJ2 | |
| | | | | Observed | | |
| | | | TRAV8-4#6TRAJ3#1 (1000) | TRBV12-4#1TRBJ1-2#1 (608) | TRGV8#1TRGJ2#1 (545) | ND |
| | | | TRAV8-4#2TRAJ3#1 (118) | TRBV12-4#2TRBJ1-2#1 (137) | TRGV11#1TRGJ1#1 (272) | |
| | | | TRAV12-3#2TRAJ26#1 (16) | TRBV12-3#1TRBJ1-2#1 (16) | TRGV11#2TRGJ1#1 (202) | |
| | | | TRAV17#1TRAJ24#2 (7) | | TRGV11#1TRGJ2#1 (12) | |
| | | | TRAV17#1TRAJ16#1 (4) TRAV17#1TRAJ29#1 (3) TRAV14_DV4#2TRAJ24#2 (2) TRAV16#1TRAJ29#1 (1) TRAV17#1TRAJ32#1 (1) TRAV29_DVS#1TRAJ4#1 (1) TRAV9-2#1TRAJ29#1 (1) | | TRGV11#2TRGJ2#1 (1) | |
| | | | | Previously Documented/Known TCR Configurations | | |
| MOLT4 | SE14-2034 | ATCC CRL-1582 | NA | TRBV20-1*01-TRBD2*01-TRBJ2-1*01 | TRGV2-TRGJP1 | NA |

TABLE 2-continued

| | | | | TRBV10-3-TRBD1*01-TRBJ2-5 | TRGV2-TRGJP2 | |
|---|---|---|---|---|---|---|
| | | | | Observed | | |
| | | | TRAV1-1#1TRAJ33#1 (799) | TRBV20-1#1TRBJ2-1#1 (937) | TRGV2#1TRGJP2#1 (524) | ND |
| | | | TRAV1-1#1TRAJ24#2 (621) | TRBV10-3#2TRBJ2-5#1 (724) | TRGV2#2TRGJP1#1 (496) | |
| | | | TRAV1-1#2TRAJ24#2 (79) | TRBV20__OR9-2#3TRBJ2-1#1 (384) | TRGV8#1TRGJP1#1 (1) | |
| | | | TRAV1-1#2TRAJ33#1 (1) | TRBV10-3#2TRBJ2-6#1 (91) | | |
| | | | | TRBV20-1#7TRBJ2-1#1 (3) | | |
| | | | | TRBV20__OR9-2#3TRBJ2-2#1 (2) | | |
| | | | | TRBV20-1#1TRBJ2-2#1 (1) | | |
| | | | | TRBV20-1#3TRBJ2-1#1 (1) | | |
| | | | | Previously Documented/Known TCR Configurations | | |
| SUPT1 | SE14-2005 | ATCC CRL-1942 | NA | TRBV9*01-TRBD2*01-TRVJ2-1*01 | TRGV3-TRGJ1/TRGJ2 | NA |
| | | | | | TRGV4-TRGJ1/TRGJ2 | |
| | | | | Observed | | |
| | | | TRAV1-1#1TRAJ12#1 (1110) | TRBV9#2TRBJ2-1#1 (971) | TRGV3#2TRGJ2#1 (683) | ND |
| | | | TRAV1-1#2TRAJ8#1 (836) | TRBV9#1TRBJ2-1#1 (137) | TRGV4#1TRGJ2#1 (449) | |
| | | | TRAV1-1#1TRAJ8#1 (263) | TRBV9#2TRBJ2-2#1 (9) | TRGV4#2TRGJ2#1 (367) | |
| | | | TRAV1-1#2TRAJ12#1 (4) | TRBV5-3#1TRBJ2-5#1 (8) | TRGV3#1TRGJ2#1 (198) | |
| | | | TRAV29__DV5#1TRAJ26#1 (3) | TRBV5-3#2TRBJ2-5#1 (4) | TRGV5#2TRGJ2#1 (156) | |
| | | | TRAV8-4#6TRAJ3#1 (1) | TRBV7-2#4TRBJ2-7#1 (4) | | |
| | | | | TRBV5-3#1TRBJ2-3#1 (2) | | |
| | | | | TRBV9#2TRBJ2-2P#1 (2) | | |
| | | | | TRBV6-3#1TRBJ2-5#1 (1) | | |
| | | | | TRBV7-2#4TRBJ2-2#1 (1) | | |

Unique VJ TCR configurations correspond to sequences recorded at the following IMGT location: http://www.imgt.org/IMGTrepertoire/Probes/Rearrangements%20and%20junctions/human/Hu TRrea.html

TABLE 3

Sanger Sequencing Results

| Primer Combination | Expected PCR Product Size (bp) When Present ¥ | PCR & Electrophoresis Result ‡ | Reads with Detected Primer Combination | Total Number of Rearranged Reads Detected A037 | Reads on Target | Total Number of Input Reads | PCR & Electrophoresis Result ‡ | Reads with Detected Primer Combination | Total Number of Rearranged Reads Detected L2D8 | Reads on Target | Total Number of Input Reads |
|---|---|---|---|---|---|---|---|---|---|---|---|
| TRAV1-1 & TRAJ12 | 275 | Negative | 0 | 877 | 1155401 | 1370124 | Weak | 0 | 1384 | 985843 | 1182258 |
| TRAV1-1 & TRAJ33 | 282 | Weak | 0 | 877 | 1155401 | 1370124 | Weak | 0 | 1384 | 985843 | 1182258 |
| TRAV1-1 & TRAJ49 | 278 | Weak | 0 | 877 | 1155401 | 1370124 | Weak | 0 | 1384 | 985843 | 1182258 |
| TRAV12-2 & TRAJ45 | 285 | Weak | 0 | 877 | 1155401 | 1370124 | Negative | 0 | 1384 | 985843 | 1182258 |
| TRAV17 & TRAJ52 | 103 | Negative | 1 | 877 | 1155401 | 1370124 | Positive | 425 | 1384 | 985843 | 1182258 |
| TRAV27 & TRAJ17 | 326 | Negative | 0 | 877 | 1155401 | 1370124 | Negative | 0 | 1384 | 985843 | 1182258 |
| TRAV27 & TRAJ40 | 327 | Weak | 0 | 877 | 1155401 | 1370124 | Weak | 0 | 1384 | 985843 | 1182258 |
| TRAV29/DV5 & TRAJ26 | 315 | Negative | 0 | 877 | 1155401 | 1370124 | Negative | 0 | 1384 | 985843 | 1182258 |
| TRAV29/DV5 & TRAJ4 | 333 | Negative | 0 | 877 | 1155401 | 1370124 | Positive | 316 | 1384 | 985843 | 1182258 |
| TRAV35 & TRAJ48 | 333 | Negative | 0 | 877 | 1155401 | 1370124 | Negative | 0 | 1384 | 985843 | 1182258 |
| TRAV8-3 & TRAJ42 | 296 | Weak | 0 | 877 | 1155401 | 1370124 | Weak | 0 | 1384 | 985843 | 1182258 |
| TRBV10-3 & TRBJ2-5 | 103 | Negative | 0 | 877 | 1155401 | 1370124 | Negative | 0 | 1384 | 985843 | 1182258 |
| TRBV12-3 & TRBJ1-2 | 264 | Negative | 0 | 877 | 1155401 | 1370124 | Negative | 0 | 1384 | 985843 | 1182258 |
| TRBV18 & TRBJ2-2 | 349 | Positive | 6 | 877 | 1155401 | 1370124 | Negative | 0 | 1384 | 985843 | 1182258 |
| TRBV20-1 & TRBJ12-1 | 133 | Weak | 0 | 877 | 1155401 | 1370124 | Negative | 0 | 1384 | 985843 | 1182258 |
| TRBV5-7 & TRBJ2-2 | 257 | Negative | 0 | 877 | 1155401 | 1370124 | Positive | 315 | 1384 | 985843 | 1182258 |
| TRBV7-8 & TRBJ2-5 | 240 | Weak | 2 | 877 | 1155401 | 1370124 | Negative | 0 | 1384 | 985843 | 1182258 |
| TRBV9 & TRBJ2-1 | 336 | Positive | 2 | 877 | 1155401 | 1370124 | Weak | 0 | 1384 | 985843 | 1182258 |
| TRGV11 & TRGJP2 | 297 | Negative | 8 | 877 | 1155401 | 1370124 | Negative | 0 | 1384 | 985843 | 1182258 |
| TRGV2 & TRGJP2 | 325 | Positive | 13 | 877 | 1155401 | 1370124 | Negative | 0 | 1384 | 985843 | 1182258 |
| TRGV3 & TRGJ1 | 241 | Weak | 3 | 877 | 1155401 | 1370124 | Positive | 161 | 1384 | 985843 | 1182258 |
| TRGV4 & TRGJ1 | 254 | Positive | 17 | 877 | 1155401 | 1370124 | Positive | 4 | 1384 | 985843 | 1182258 |
| TRGV8 & TRGJP1 | 263 | Positive | 8 | 877 | 1155401 | 1370124 | Negative | 0 | 1384 | 985843 | 1182258 |
| TRGV8 & TRGJP1 | 266 | Positive | 2 | 877 | 1155401 | 1370124 | Negative | 0 | 1384 | 985843 | 1182258 |
| TRGV9 & TRGJ1 | 182 | Positive | 9 | 877 | 1155401 | 1370124 | Negative | 0 | 1384 | 985843 | 1182258 |

| Primer Combination | Expected PCR Product Size (bp) When Present ¥ | PCR & Electrophoresis Result ‡ | Reads with Detected Primer Combination | Total Number of Rearranged Reads Detected EZM | Reads on Target | Total Number of Input Reads | PCR & Electrophoresis Result ‡ | Reads with Detected Primer Combination | Total Number of Rearranged Reads Detected TIL2 | Reads on Target | Total Number of Input Reads |
|---|---|---|---|---|---|---|---|---|---|---|---|
| TRAV1-1 & TRAJ12 | 275 | Negative | 0 | 115 | 1377194 | 1595646 | Negative | 0 | 2095 | 926207 | 1145281 |
| TRAV1-1 & TRAJ33 | 282 | Negative | 0 | 115 | 1377194 | 1595646 | Weak | 0 | 2095 | 926207 | 1145281 |
| TRAV1-1 & TRAJ49 | 278 | Negative | 0 | 115 | 1377194 | 1595646 | Weak | 0 | 2095 | 926207 | 1145281 |
| TRAV12-2 & TRAJ45 | 285 | Negative | 1 | 115 | 1377194 | 1595646 | Weak | 0 | 2095 | 926207 | 1145281 |
| TRAV17 & TRAJ52 | 103 | Negative | 0 | 115 | 1377194 | 1595646 | Weak | 0 | 2095 | 926207 | 1145281 |
| TRAV27 & TRAJ17 | 326 | Negative | 0 | 115 | 1377194 | 1595646 | Weak | 0 | 2095 | 926207 | 1145281 |
| TRAV27 & TRAJ40 | 327 | Weak | 0 | 115 | 1377194 | 1595646 | Positive | 37 | 2095 | 926207 | 1145281 |
| TRAV29/DV5 & TRAJ26 | 315 | Negative | 0 | 115 | 1377194 | 1595646 | Negative | 0 | 2095 | 926207 | 1145281 |
| TRAV29/DV5 & TRAJ4 | 333 | Negative | 0 | 115 | 1377194 | 1595646 | Negative | 0 | 2095 | 926207 | 1145281 |
| TRAV35 & TRAJ48 | 333 | Negative | 0 | 115 | 1377194 | 1595646 | Negative | 0 | 2095 | 926207 | 1145281 |
| TRAV8-3 & TRAJ42 | 333 | Negative | 0 | 115 | 1377194 | 1595646 | Negative | 0 | 2095 | 926207 | 1145281 |
| TRBV10-3 & TRBJ2-5 | 296 | Negative | 0 | 115 | 1377194 | 1595646 | Weak | 0 | 2095 | 926207 | 1145281 |

TABLE 3-continued

| Primer Combination | Expected PCR Product Size When Present (bp) ¥ | PCR & Electrophoresis Result ‡ | Reads with Detected Primer Combination | Total Number of Rearranged Reads Detected OV7 | Reads on Target | Total Number of Input Reads | Sanger Sequencing Results PCR & Electrophoresis Result ‡ | Reads with Detected Primer Combination | Total Number of Rearranged Reads Detected STIM1 | Reads on Target | Total Number of Input Reads |
|---|---|---|---|---|---|---|---|---|---|---|---|
| TRBV12-3 & TRBJ1-2 | 103 | Negative | 0 | 115 | 1377194 | 1595646 | Negative | 0 | 2095 | 926207 | 1145281 |
| TRBV18 & TRBJ2-2 | 264 | Negative | 0 | 115 | 1377194 | 1595646 | Negative | 0 | 2095 | 926207 | 1145281 |
| TRBV20-1 & TRBJ2-1 | 349 | Negative | 0 | 115 | 1377194 | 1595646 | Weak | 8 | 2095 | 926207 | 1145281 |
| TRBV5-7 & TRBJ2-2 | 133 | Weak | 0 | 115 | 1377194 | 1595646 | Negative | 0 | 2095 | 926207 | 1145281 |
| TRBV7-8 & TRBJ1-6 | 257 | Negative | 0 | 115 | 1377194 | 1595646 | Negative | 0 | 2095 | 926207 | 1145281 |
| TRBV7-8 & TRBJ2-5 | 240 | Negative | 0 | 115 | 1377194 | 1595646 | Weak | 0 | 2095 | 926207 | 1145281 |
| TRBV9 & TRBJ2-1 | 336 | Weak | 0 | 115 | 1377194 | 1595646 | Negative | 6 | 2095 | 926207 | 1145281 |
| TRGV11 & TRGJ1 | 297 | Negative | 0 | 115 | 1377194 | 1595646 | Negative | 3 | 2095 | 926207 | 1145281 |
| TRGV2 & TRGJP2 | 325 | Positive | 6 | 115 | 1377194 | 1595646 | Positive | 10 | 2095 | 926207 | 1145281 |
| TRGV3 & TRGJ1 | 241 | Positive | 0 | 115 | 1377194 | 1595646 | Positive | 17 | 2095 | 926207 | 1145281 |
| TRGV4 & TRGJ1 | 254 | Positive | 3 | 115 | 1377194 | 1595646 | Positive | 56 | 2095 | 926207 | 1145281 |
| TRGV8 & TRGJ1 | 263 | Positive | 4 | 115 | 1377194 | 1595646 | Positive | 63 | 2095 | 926207 | 1145281 |
| TRGV8 & TRGJP1 | 266 | Weak | 0 | 115 | 1377194 | 1595646 | Positive | 11 | 2095 | 926207 | 1145281 |
| TRGV9 & TRGJ1 | 182 | Weak | 0 | 115 | 1377194 | 1595646 | Positive | | 2095 | 926207 | 1145281 |

| Primer Combination | Expected PCR Product Size When Present (bp) ¥ | PCR & Electrophoresis Result ‡ | Reads with Detected Primer Combination | Total Number of Rearranged Reads Detected OV7 | Reads on Target | Total Number of Input Reads | PCR & Electrophoresis Result ‡ | Reads with Detected Primer Combination | Total Number of Rearranged Reads Detected STIM1 | Reads on Target | Total Number of Input Reads |
|---|---|---|---|---|---|---|---|---|---|---|---|
| TRAV1-1 & TRAJ12 | 275 | Negative | 4 | 2074 | 1379128 | 1675034 | Negative | 0 | 2796 | 1066413 | 1315476 |
| TRAV1-1 & TRAJ33 | 282 | Weak | 0 | 2074 | 1379128 | 1675034 | Negative | 0 | 2796 | 1066413 | 1315476 |
| TRAV1-1 & TRAJ49 | 278 | Weak | 0 | 2074 | 1379128 | 1675034 | Negative | 0 | 2796 | 1066413 | 1315476 |
| TRAV12-2 & TRAJ45 | 285 | Negative | 0 | 2074 | 1379128 | 1675034 | Weak | 238 | 2796 | 1066413 | 1315476 |
| TRAV17 & TRAJ52 | 103 | Weak | 0 | 2074 | 1379128 | 1675034 | Negative | 0 | 2796 | 1066413 | 1315476 |
| TRAV27 & TRAJ17 | 326 | Negative | 0 | 2074 | 1379128 | 1675034 | Negative | 0 | 2796 | 1066413 | 1315476 |
| TRAV27 & TRAJ40 | 327 | Negative | 298 | 2074 | 1379128 | 1675034 | Weak | 0 | 2796 | 1066413 | 1315476 |
| TRAV29/DV5 & TRAJ26 | 327 | Positive | 0 | 2074 | 1379128 | 1675034 | Negative | 2 | 2796 | 1066413 | 1315476 |
| TRAV29/DV5 & TRAJ4 | 315 | Negative | 0 | 2074 | 1379128 | 1675034 | Negative | 0 | 2796 | 1066413 | 1315476 |
| TRAV35 & TRAJ48 | 333 | Negative | 0 | 2074 | 1379128 | 1675034 | Negative | 0 | 2796 | 1066413 | 1315476 |
| TRAV8-3 & TRAJ42 | 333 | Negative | 0 | 2074 | 1379128 | 1675034 | Weak | 185 | 2796 | 1066413 | 1315476 |
| TRBV10-3 & TRBJ2-5 | 296 | Negative | 0 | 2074 | 1379128 | 1675034 | Negative | 0 | 2796 | 1066413 | 1315476 |
| TRBV12-3 & TRBJ1-2 | 103 | Weak | 0 | 2074 | 1379128 | 1675034 | Negative | 0 | 2796 | 1066413 | 1315476 |
| TRBV18 & TRBJ2-2 | 264 | Negative | 1 | 2074 | 1379128 | 1675034 | Negative | 0 | 2796 | 1066413 | 1315476 |
| TRBV20-1 & TRBJ2-1 | 349 | Negative | 0 | 2074 | 1379128 | 1675034 | Negative | 0 | 2796 | 1066413 | 1315476 |
| TRBV5-7 & TRBJ2-2 | 133 | Negative | 0 | 2074 | 1379128 | 1675034 | Negative | 0 | 2796 | 1066413 | 1315476 |
| TRBV7-8 & TRBJ1-6 | 257 | Negative | 0 | 2074 | 1379128 | 1675034 | Negative | 0 | 2796 | 1066413 | 1315476 |
| TRBV7-8 & TRBJ2-5 | 240 | Weak | 85 | 2074 | 1379128 | 1675034 | Negative | 0 | 2796 | 1066413 | 1315476 |
| TRBV9 & TRBJ2-1 | 336 | Positive | 0 | 2074 | 1379128 | 1675034 | Weak | 0 | 2796 | 1066413 | 1315476 |
| TRGV11 & TRGJ1 | 297 | Negative | 0 | 2074 | 1379128 | 1675034 | Negative | 23 | 2796 | 1066413 | 1315476 |
| TRGV2 & TRGJP2 | 325 | Weak | 0 | 2074 | 1379128 | 1675034 | Positive | 11 | 2796 | 1066413 | 1315476 |
| TRGV3 & TRGJ1 | 241 | Negative | 7 | 2074 | 1379128 | 1675034 | Positive | 13 | 2796 | 1066413 | 1315476 |
| TRGV4 & TRGJ1 | 254 | Weak | 5 | 2074 | 1379128 | 1675034 | Positive | 40 | 2796 | 1066413 | 1315476 |
| TRGV8 & TRGJ1 | 263 | Positive | 14 | 2074 | 1379128 | 1675034 | Negative | 24 | 2796 | 1066413 | 1315476 |
| TRGV8 & TRGJP1 | 266 | Positive | 197 | 2074 | 1379128 | 1675034 | Negative | 0 | 2796 | 1066413 | 1315476 |
| TRGV9 & TRGJ1 | 182 | Negative | 15 | 2074 | 1379128 | 1675034 | Positive | 120 | 2796 | 1066413 | 1315476 |

TABLE 3-continued

Sanger Sequencing Results

| Primer Combination | Expected PCR Product Size (bp) ¥ When Present | PCR & Electrophoresis Result ‡ | Reads with Detected Primer Combination SE14-2005 (SUPT1) | Total Number of Rearranged Reads Detected | Reads on Target | Total Number of Input Reads | PCR & Electrophoresis Result ‡ | Reads with Detected Primer Combination SE14-2033 (Jurkat) | Total Number of Rearranged Reads Detected | Reads on Target | Total Number of Input Reads |
|---|---|---|---|---|---|---|---|---|---|---|---|
| TRAV1-1 & TRAJ12 | 275 | Positive | 460 | 2371 | 837044 | 1096080 | Negative | 0 | 1554 | 817921 | 995632 |
| TRAV1-1 & TRAJ33 | 282 | Negative | 0 | 2371 | 837044 | 1096080 | Weak | 0 | 1554 | 817921 | 995632 |
| TRAV1-1 & TRAJ49 | 278 | Weak | 0 | 2371 | 837044 | 1096080 | Negative | 0 | 1554 | 817921 | 995632 |
| TRAV12-2 & TRAJ45 | 285 | Negative | 0 | 2371 | 837044 | 1096080 | Negative | 0 | 1554 | 817921 | 995632 |
| TRAV17 & TRAJ52 | 103 | Negative | 0 | 2371 | 837044 | 1096080 | Negative | 0 | 1554 | 817921 | 995632 |
| TRAV27 & TRAJ17 | 326 | Weak | 0 | 2371 | 837044 | 1096080 | Weak | 0 | 1554 | 817921 | 995632 |
| TRAV27 & TRAJ40 | 327 | Weak | 0 | 2371 | 837044 | 1096080 | Weak | 0 | 1554 | 817921 | 995632 |
| TRAV29/DV5 & TRAJ26 | 327 | Weak | 0 | 2371 | 837044 | 1096080 | Negative | 1 | 1554 | 817921 | 995632 |
| TRAV29/DV5 & TRAJ4 | 315 | Negative | 0 | 2371 | 837044 | 1096080 | Negative | 0 | 1554 | 817921 | 995632 |
| TRAV35 & TRAJ48 | 333 | Negative | 0 | 2371 | 837044 | 1096080 | Negative | 0 | 1554 | 817921 | 995632 |
| TRAV8-3 & TRAJ42 | 333 | Negative | 0 | 2371 | 837044 | 1096080 | Weak | 0 | 1554 | 817921 | 995632 |
| TRAV10-3 & TRBJ2-5 | 296 | Negative | 0 | 2371 | 837044 | 1096080 | Positive | 138 | 1554 | 817921 | 995632 |
| TRAV9 & TRBJ1-2 | 103 | Weak | 0 | 2371 | 837044 | 1096080 | Negative | 0 | 1554 | 817921 | 995632 |
| TRBV18 & TRBJ2-2 | 264 | Negative | 0 | 2371 | 837044 | 1096080 | Negative | 0 | 1554 | 817921 | 995632 |
| TRBV20-1 & TRBJ2-1 | 349 | Negative | 0 | 2371 | 837044 | 1096080 | Negative | 0 | 1554 | 817921 | 995632 |
| TRBV5-7 & TRBJ2-2 | 133 | Weak | 0 | 2371 | 837044 | 1096080 | Negative | 0 | 1554 | 817921 | 995632 |
| TRBV7-8 & TRBJ1-6 | 257 | Negative | 0 | 2371 | 837044 | 1096080 | Negative | 0 | 1554 | 817921 | 995632 |
| TRBV7-8 & TRBJ2-5 | 240 | Negative | 0 | 2371 | 837044 | 1096080 | Negative | 0 | 1554 | 817921 | 995632 |
| TRBV9 & TRBJ2-1 | 336 | Positive | 538 | 2371 | 837044 | 1096080 | Weak | 242 | 1554 | 817921 | 995632 |
| TRGV11 & TRGJ1 | 297 | Negative | 0 | 2371 | 837044 | 1096080 | Negative | 0 | 1554 | 817921 | 995632 |
| TRGV2 & TRGJP2 | 325 | Weak | 0 | 2371 | 837044 | 1096080 | Negative | 0 | 1554 | 817921 | 995632 |
| TRGV3 & TRGJ1 | 241 | Positive | 22 | 2371 | 837044 | 1096080 | Weak | 146 | 1554 | 817921 | 995632 |
| TRGV4 & TRGJ1 | 254 | Positive | 25 | 2371 | 837044 | 1096080 | Negative | 0 | 1554 | 817921 | 995632 |
| TRGV8 & TRGJP1 | 263 | Negative | 0 | 2371 | 837044 | 1096080 | Negative | 0 | 1554 | 817921 | 995632 |
| TRGV8 & TRGJ1 | 266 | Negative | 0 | 2371 | 837044 | 1096080 | Negative | 0 | 1554 | 817921 | 995632 |
| TRGV9 & TRGJ1 | 182 | Weak | 0 | 2371 | 837044 | 1096080 | Negative | 0 | 1554 | 817921 | 995632 |

| Primer Combination | Expected PCR Product Size (bp) ¥ When Present | PCR & Electrophoresis Result ‡ | Reads with Detected Primer Combination SE14-2034 (MOLT4) | Total Number of Rearranged Reads Detected | Reads on Target | Total Number of Input Reads | PCR & Electrophoresis Result ‡ | Reads with Detected Primer Combination SE14-2035 (CEM) | Total Number of Rearranged Reads Detected | Reads on Target | Total Number of Input Reads |
|---|---|---|---|---|---|---|---|---|---|---|---|
| TRAV1-1 & TRAJ12 | 275 | Negative | 0 | 1723 | 741549 | 906513 | Negative | 0 | 1744 | 981779 | 1289677 |
| TRAV1-1 & TRAJ33 | 282 | Positive | 347 | 1723 | 741549 | 906513 | Weak | 0 | 1744 | 981779 | 1289677 |
| TRAV1-1 & TRAJ49 | 278 | Negative | 0 | 1723 | 741549 | 906513 | Negative | 0 | 1744 | 981779 | 1289677 |
| TRAV12-2 & TRAJ45 | 285 | Negative | 0 | 1723 | 741549 | 906513 | Negative | 0 | 1744 | 981779 | 1289677 |
| TRAV17 & TRAJ52 | 103 | Negative | 0 | 1723 | 741549 | 906513 | Positive | 0 | 1744 | 981779 | 1289677 |
| TRAV27 & TRAJ17 | 326 | Negative | 0 | 1723 | 741549 | 906513 | Positive | 506 | 1744 | 981779 | 1289677 |
| TRAV27 & TRAJ40 | 327 | Negative | 0 | 1723 | 741549 | 906513 | Negative | 0 | 1744 | 981779 | 1289677 |
| TRAV29/DV5 & TRAJ26 | 327 | Negative | 0 | 1723 | 741549 | 906513 | Positive | 751 | 1744 | 981779 | 1289677 |
| TRAV29/DV5 & TRAJ4 | 315 | Negative | 0 | 1723 | 741549 | 906513 | Negative | 0 | 1744 | 981779 | 1289677 |
| TRAV35 & TRAJ48 | 333 | Negative | 0 | 1723 | 741549 | 906513 | Negative | 0 | 1744 | 981779 | 1289677 |
| TRAV8-3 & TRAJ42 | 333 | Negative | 0 | 1723 | 741549 | 906513 | Weak | 0 | 1744 | 981779 | 1289677 |
| TRAV10-3 & TRBJ2-5 | 296 | Positive | 379 | 1723 | 741549 | 906513 | Negative | 0 | 1744 | 981779 | 1289677 |
| TRBV12-3 & TRBJ1-2 | 103 | Negative | 0 | 1723 | 741549 | 906513 | Negative | 0 | 1744 | 981779 | 1289677 |
| TRBV18 & TRBJ2-2 | 264 | Negative | 0 | 1723 | 741549 | 906513 | Negative | 0 | 1744 | 981779 | 1289677 |

TABLE 3-continued

Sanger Sequencing Results

| | | | | | | | | | |
|---|---|---|---|---|---|---|---|---|---|
| TRBV20-1 & TRBJ2-1 | 349 | Positive | 1723 | 741549 | 906513 | Negative | 0 | 1744 | 981779 | 1289677 |
| TRBV5-7 & TRBJ2-2 | 133 | Negative | 1723 | 741549 | 906513 | Weak | 0 | 1744 | 981779 | 1289677 |
| TRBV7-8 & TRBJ1-6 | 257 | Negative | 1723 | 741549 | 906513 | Negative | 0 | 1744 | 981779 | 1289677 |
| TRBV7-8 & TRBJ2-5 | 240 | Negative | 1723 | 741549 | 906513 | Negative | 0 | 1744 | 981779 | 1289677 |
| TRBV9 & TRBJ2-1 | 336 | Negative | 1723 | 741549 | 906513 | Positive | 1 | 1744 | 981779 | 1289677 |
| TRGV11 & TRGJ1 | 297 | Negative | 1723 | 741549 | 906513 | Weak | 0 | 1744 | 981779 | 1289677 |
| TRGV2 & TRGJP2 | 325 | Positive | 1723 | 741549 | 906513 | Weak | 0 | 1744 | 981779 | 1289677 |
| TRGV3 & TRGJ1 | 241 | Negative | 1723 | 741549 | 906513 | Positive | 222 | 1744 | 981779 | 1289677 |
| TRGV4 & TRGJ1 | 254 | Negative | 1723 | 741549 | 906513 | Positive | 0 | 1744 | 981779 | 1289677 |
| TRGV8 & TRGJ1 | 263 | Negative | 1723 | 741549 | 906513 | Negative | 0 | 1744 | 981779 | 1289677 |
| TRGV8 & TRGJP1 | 266 | Negative | 1723 | 741549 | 906513 | Negative | 0 | 1744 | 981779 | 1289677 |
| TRGV9 & TRGJ1 | 182 | Negative | 1723 | 741549 | 906513 | Weak | 0 | 1744 | 981779 | 1289677 |

The invention claimed is:

1. A method of capturing a population of T-Cell receptor and/or immunoglobulin sequences with variable regions within a patient sample, said method comprising:
first extracting DNA fragments from the patient sample;
ligating a nucleic acid adapter to the DNA fragments, the nucleic acid adapter suitable for recognition by a preselected nucleic acid probe; and
capturing the extracted DNA fragments existing in the patient sample using a collection of hybrid capture probes, wherein the hybrid capture probes are nucleic acids, wherein the collection of hybrid capture probes is designed to hybridize to all V gene segments and all J gene segments within the T cell receptor genomic loci, immunoglobulin genomic loci, or the combination thereof;
wherein the collection of hybrid capture probes comprises at least 900 unique hybrid capture probes that hybridize to a 3' end of the V gene segments and hybrid capture probes that hybridize to a 5' end of the J gene segments.

2. The method of claim 1, further comprising sequencing the captured DNA fragments to obtain sequences of the captured DNA fragments.

3. The method of claim 2, wherein said sequencing is optimized for short read sequencing.

4. The method of claim 2, further comprising amplifying the captured DNA fragments using nucleic acid amplification probes/oligonucleotides that recognize the adapter prior to said sequencing.

5. The method of claim 1, further comprising fragmenting the extracted DNA fragments from the patient sample to generate the DNA fragments.

6. The method of claim 1, wherein the ligating step is performed before the capturing step.

7. The method of claim 1, wherein the capturing step is performed before the ligating step.

8. The method of claim 1, wherein the patient sample comprises tissue, urine, cerebral spinal fluid, saliva, feces, ascites, pleural effusion, blood or blood plasma.

9. The method of claim 1, wherein the patient sample comprises cell-free nucleic acids in blood plasma.

10. The method of claim 1, wherein the hybrid capture probes are at least 30 bp in length.

11. The method of claim 10, wherein the hybrid capture probes are between 60 bp and 150 bp in length.

12. The method of claim 1, wherein the hybrid capture probes hybridize to at least 30 bp.

13. The method of claim 1, wherein the hybrid capture probes hybridize to at least a portion of the V gene segment.

14. The method of claim 1, wherein each hybrid capture probe is designed to hybridize to the V gene segment and/or the J gene segment within the T cell receptor and/or immunoglobulin genomic loci under stringent conditions.

15. The method of claim 1, wherein the collection of nucleic acid hybrid capture probes captures at least 50% of T-Cell receptor and/or immunoglobulin loci clonotypes.

16. The method of claim 1, wherein the hybrid capture probes are immobilized on an array.

17. The method of claim 1, wherein the hybrid capture probes comprise a label.

18. The method of claim 17, wherein the label is used to distinguish between sequences bound to the hybrid capture probes and unbound double stranded fragments.

19. The method of claim 1, wherein the adapter is designed to permit sequencing of the DNA fragment and/or barcoding of the DNA fragment.

20. The method of claim 1, wherein extracting the DNA fragments comprises extracting RNA from the patient sample and preparing corresponding cDNA.

21. The method of claim 1, further comprising a depletion step, comprising depleting the DNA fragments of non-rearranged sequences using probes that recognize nucleic acid sequences adjacent to V and/or J gene segments in the genome.

22. The method of claim 21, wherein the capturing of DNA fragments using V gene segment and J gene segment hybrid capture probes is performed in separate steps, and wherein the separate steps are separated by the depletion step.

23. A method for characterizing the immune repertoire of a subject, the immune repertoire comprising the subject's T-Cell population, the method comprising the method of claim 2, followed by a method comprising:
 (a) trimming the sequences of the captured DNA fragments to remove any sequences having V gene segments to produce a collection of V-trimmed nucleotide sequences and trimmed V gene segments;
 (b) trimming the V-trimmed nucleotide sequences to remove any sequences having J gene segments to produce VJ-trimmed nucleotide sequences and trimmed J gene segments;
 (c) for each of the VJ-trimmed nucleotide sequences, assembling a composite nucleotide sequence comprising, in linear order, the trimmed V gene segment, any D gene segment comprised in the VJ-trimmed nucleotide sequences, and the trimmed J gene segment;
 (d) extracting a junction nucleotide sequence from the composite nucleotide sequence, the junction nucleotide sequence comprising at least the junction between the trimmed V gene segment and the trimmed J gene segment, including any D gene segment comprised in the VJ-trimmed nucleotide sequence, the junction nucleotide sequence comprising between 18 bp and 140 bp.

24. The method of claim 23, further comprising:
 (e) translating each reading frame of the junction nucleotide sequence and its complementary strand to produce 6 translated sequences; and
 comparing the 6 translated sequences to a library of CDR3 regions of T-Cell receptor and/or immunoglobulin sequences to identify the CDR3 region in the DNA fragments.

* * * * *

UNITED STATES PATENT AND TRADEMARK OFFICE
CERTIFICATE OF CORRECTION

| | | |
|---|---|---|
| PATENT NO. | : 11,149,312 B2 | Page 1 of 1 |
| APPLICATION NO. | : 16/093825 | |
| DATED | : October 19, 2021 | |
| INVENTOR(S) | : Pugh et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 85 days.

Signed and Sealed this
Twenty-ninth Day of November, 2022

Katherine Kelly Vidal
*Director of the United States Patent and Trademark Office*